US012583906B2

(12) United States Patent
Li et al.

(10) Patent No.: US 12,583,906 B2
(45) Date of Patent: Mar. 24, 2026

(54) ACTRII PROTEINS AND USE IN TREATING POST-CAPILLARY PULMONARY HYPERTENSION

(71) Applicant: Acceleron Pharma Inc., Cambridge, MA (US)

(72) Inventors: Gang Li, Cambridge, MA (US); Ravindra Kumar, Cambridge, MA (US); Jonathan Toshi Lu, Cambridge, MA (US); Sachindra Joshi, Cambridge, MA (US); Patrick Andre, Cambridge, MA (US)

(73) Assignee: ACCELERON PHARMA INC., Cambridge, MA (US)

( * ) Notice: Subject to any disclaimer, the term of this patent is extended or adjusted under 35 U.S.C. 154(b) by 0 days.

(21) Appl. No.: 18/953,973

(22) Filed: Nov. 20, 2024

(65) Prior Publication Data

US 2025/0074968 A1 Mar. 6, 2025

Related U.S. Application Data

(63) Continuation of application No. 17/921,810, filed as application No. PCT/US2021/029492 on Apr. 27, 2021.

(60) Provisional application No. 63/159,253, filed on Mar. 10, 2021, provisional application No. 63/016,942, filed on Apr. 28, 2020.

(51) Int. Cl.
*C07K 14/71* (2006.01)
*A61P 9/12* (2006.01)

(52) U.S. Cl.
CPC ................ *C07K 14/71* (2013.01); *A61P 9/12* (2018.01); *C07K 2319/30* (2013.01)

(58) Field of Classification Search
None
See application file for complete search history.

(56) References Cited

U.S. PATENT DOCUMENTS

| | | | |
|---|---|---|---|
| 5,288,931 | A | 2/1994 | Chang et al. |
| 7,112,660 | B1 | 9/2006 | Domingues et al. |
| 7,709,605 | B2 | 5/2010 | Knopf et al. |
| 7,988,973 | B2 | 8/2011 | Sherman |
| 8,293,881 | B2 | 10/2012 | Seehra et al. |
| 8,895,016 | B2 | 11/2014 | Sherman et al. |
| 9,145,433 | B2 | 9/2015 | Bhamidipati et al. |
| 10,550,170 | B2 | 2/2020 | Sherman et al. |
| 10,695,405 | B2 | 6/2020 | Kumar et al. |
| 10,722,558 | B2 | 7/2020 | Kumar et al. |
| 10,946,067 | B2 | 3/2021 | Kumar et al. |
| 10,973,880 | B2 | 4/2021 | Kumar et al. |
| 11,065,303 | B2 | 7/2021 | Kumar et al. |
| 11,219,666 | B2 | 1/2022 | Kumar et al. |
| 11,622,992 | B2 | 4/2023 | Kumar et al. |
| 2003/0045474 | A1 | 3/2003 | Sailer et al. |
| 2003/0144203 | A1 | 7/2003 | Bowen |
| 2005/0239719 | A1 | 10/2005 | Zeldis |
| 2007/0056050 | A1 | 3/2007 | Clokie et al. |
| 2007/0248609 | A1 | 10/2007 | De Kretser et al. |
| 2007/0249022 | A1 | 10/2007 | Knopf et al. |
| 2009/0017019 | A1 | 1/2009 | Shields et al. |
| 2009/0118188 | A1 | 5/2009 | Knopf et al. |
| 2009/0142333 | A1 | 6/2009 | Knopf et al. |
| 2010/0015144 | A1 | 1/2010 | Sherman et al. |
| 2010/0056505 | A1 | 3/2010 | Lee et al. |
| 2010/0267133 | A1 | 10/2010 | Knopf et al. |
| 2011/0182904 | A1 | 7/2011 | Zimmerman et al. |
| 2011/0224236 | A1 | 9/2011 | Rothblatt et al. |
| 2013/0004489 | A1 | 1/2013 | Knopf et al. |
| 2013/0195862 | A1 | 8/2013 | Knopf et al. |
| 2014/0045844 | A1 | 2/2014 | Schafer et al. |
| 2014/0154743 | A1 | 6/2014 | Levy et al. |
| 2014/0271459 | A1 | 9/2014 | Dutzar et al. |
| 2014/0303068 | A1 | 10/2014 | O'Hehir et al. |
| 2014/0322203 | A1 | 10/2014 | Alavattam et al. |
| 2015/0266950 | A1 | 9/2015 | Sung et al. |
| 2015/0283209 | A1 | 10/2015 | Sung et al. |
| 2015/0306150 | A1 | 10/2015 | Zhang et al. |
| 2015/0361163 | A1 | 12/2015 | Kumar et al. |
| 2016/0039922 | A1 | 2/2016 | Attie |
| 2016/0075772 | A1 | 3/2016 | Hatsell |
| 2016/0287664 | A1 | 10/2016 | Yu et al. |
| 2016/0347814 | A1 | 12/2016 | Levine et al. |
| 2017/0202918 | A1 | 7/2017 | Yung et al. |
| 2017/0291935 | A1 | 10/2017 | Sherman et al. |
| 2017/0304397 | A1 | 10/2017 | Hruska et al. |

(Continued)

FOREIGN PATENT DOCUMENTS

| | | | |
|---|---|---|---|
| AU | 2012244215 | A1 | 11/2012 |
| CN | 103920139 | A | 7/2014 |

(Continued)

OTHER PUBLICATIONS

Opitz et al. (2016, J Am Coll Cardiol 68(4):368-378).*
Lepida et al. (2018, Hellenic J Cardiol 58:160-165).*
Humbert et al., 2022, European Heart Journal 43:3618-3731.*
Galiè et al., 2015, Eur. Respir. J. 46:903-975.*
Koller et al., 2017, Heart, Lung & Circulation 26(5):433-441.*
Vachiéry et al., 2018, The European Respiratory Journal 51(2):1701886.*
Cao et al., 2018, International Journal of Cardiology 273:213-220.*
Keros Tropos Topline Data and Restructuring Press Release, 2025.*
Bermejo et al., 2018, European Heart Journal 39(15):1255-1264.*
Alaoui-Ismaili, M. and Falb, D., "Design of second generation therapeutic recombinant bone morphogenetic proteins," Cytokine & Growth Factor Reviews, vol. 20(5-6): 501-507 (2009).

(Continued)

*Primary Examiner* — Vanessa L Ford
(74) *Attorney, Agent, or Firm* — White & Case LLP

(57) ABSTRACT

In some aspects, the disclosure relates to compositions and methods comprising ActRII polypeptides to treat, prevent, or reduce the progression rate and/or severity of post-capillary pulmonary hypertension (PcPH), particularly treating, preventing or reducing the progression rate and/or severity of one or more PcPH-associated complications.

22 Claims, 39 Drawing Sheets

Specification includes a Sequence Listing.

(56) References Cited

U.S. PATENT DOCUMENTS

| | | | |
|---|---|---|---|
| 2018/0008672 | A1 | 1/2018 | Chalothorn et al. |
| 2018/0050089 | A1* | 2/2018 | Kumar .................... A61P 11/00 |
| 2018/0125928 | A1 | 5/2018 | Attie |
| 2018/0179279 | A1 | 6/2018 | Bebbington et al. |
| 2018/0327477 | A1 | 11/2018 | Kumar et al. |
| 2019/0365844 | A1 | 12/2019 | Kumar et al. |
| 2020/0109193 | A1 | 4/2020 | Attie |
| 2020/0197367 | A1 | 6/2020 | Lindblad et al. |
| 2020/0384080 | A1 | 12/2020 | Kumar et al. |
| 2020/0397865 | A1 | 12/2020 | Kumar et al. |
| 2020/0407415 | A1 | 12/2020 | Seehra et al. |
| 2023/0226146 | A1 | 7/2023 | de Oliveira Pena et al. |

FOREIGN PATENT DOCUMENTS

| | | | |
|---|---|---|---|
| CN | 107709357 | A | 2/2018 |
| EP | 2594280 | A1 | 5/2013 |
| KR | 20150115961 | A | 10/2015 |
| WO | WO-94/11502 | A2 | 5/1994 |
| WO | WO-2003/006057 | | 1/2003 |
| WO | WO-2005/084699 | A1 | 9/2005 |
| WO | WO-2006/012627 | A2 | 2/2006 |
| WO | WO-2007/062188 | A2 | 5/2007 |
| WO | WO-2008/052734 | | 5/2008 |
| WO | WO-2008/073351 | A2 | 6/2008 |
| WO | WO-2008/073928 | A1 | 6/2008 |
| WO | WO-2008/076437 | A2 | 6/2008 |
| WO | WO-2008/094708 | A2 | 8/2008 |
| WO | WO-2008/097541 | A2 | 8/2008 |
| WO | WO-2008/100384 | A2 | 8/2008 |
| WO | WO2008/109167 | | 9/2008 |
| WO | WO-2009/038745 | A1 | 3/2009 |
| WO | WO-2009/133070 | | 11/2009 |
| WO | WO-2009/134428 | A2 | 11/2009 |
| WO | WO-2009/158033 | A2 | 12/2009 |
| WO | WO-2009/158035 | A2 | 12/2009 |
| WO | WO-2010/019261 | A1 | 2/2010 |
| WO | WO-2010/062640 | A1 | 6/2010 |
| WO | WO-2010/083034 | A1 | 7/2010 |
| WO | WO-2010/114860 | A1 | 10/2010 |
| WO | WO-2011/056497 | A1 | 5/2011 |
| WO | WO-2011/115922 | A1 | 9/2011 |
| WO | WO-2012/051559 | A2 | 4/2012 |
| WO | WO-2013/009140 | | 1/2013 |
| WO | WO-2014/071158 | A1 | 5/2014 |
| WO | WO-2014/055955 | | 10/2014 |
| WO | WO-2014/160336 | A1 | 10/2014 |
| WO | WO-2015/017576 | A1 | 2/2015 |
| WO | WO-2015/148654 | | 10/2015 |
| WO | WO-2015/161220 | A1 | 10/2015 |
| WO | WO-2015/192111 | A1 | 12/2015 |
| WO | WO-2016/039796 | | 3/2016 |
| WO | WO-2016/069234 | | 5/2016 |
| WO | WO-2016/164089 | A2 | 10/2016 |
| WO | WO-2016/164497 | A1 | 10/2016 |
| WO | WO-2016/164501 | A1 | 10/2016 |
| WO | WO 2016/171948 | A1 | 10/2016 |
| WO | WO 2016/182813 | | 11/2016 |
| WO | WO-2016/183280 | A1 | 11/2016 |
| WO | WO-2016/187378 | A1 | 11/2016 |
| WO | WO2016205370 | | 12/2016 |
| WO | WO-2017/015622 | A2 | 1/2017 |
| WO | WO 2017/156488 | | 9/2017 |
| WO | WO-2018/013936 | A1 | 1/2018 |
| WO | WO2018/075747 | | 4/2018 |
| WO | WO-2018/116201 | A1 | 6/2018 |
| WO | WO-2018/144968 | A1 | 8/2018 |
| WO | WO 2018/175460 | A1 * | 9/2018 |
| WO | WO-2018195338 | | 10/2018 |
| WO | WO-2019/140283 | | 7/2019 |
| WO | WO 2019/217715 | A1 * | 11/2019 |
| WO | WO-2021/092079 | | 5/2021 |
| WO | WO-2021/158675 | A1 | 8/2021 |
| WO | WO 2021/158695 | A1 | 8/2021 |
| WO | WO 2021/262718 | | 12/2021 |
| WO | WO 2022/150590 | | 7/2022 |
| WO | WO-2022/192420 | | 9/2022 |
| WO | WO 2022/261436 | | 12/2022 |
| WO | WO 2022/271571 | | 12/2022 |
| WO | WO2024/186418 | | 9/2024 |
| WO | WO2024/186990 | | 9/2024 |
| WO | WO2024/238263 | | 11/2024 |

OTHER PUBLICATIONS

Attie et al., "A phase I study of ACE-536, a regulator of erythroid differentiation, in healthy volunteers," American Journal of Hematology, vol. 89(7): 766-770 (2014).

Bernier et al., "Pharmacological chaperone action on G-protein-coupled receptors," Current Opinions in Pharmacology, vol. 4(5): 528-533 (2004).

Bhattacharya et al., "Impact of genetic variation on three dimensional structure and function of proteins," PLoS One, vol. 12(3): e0171355.

Biosis Accession No. 2015:276893 & Piga, A. et al., 'ACE-536 Increases Hemoglobin and Decreases Transfusion Burden and Serum Ferritin in Adults with Beta-Thalassemia: Preliminary Results from a Phase 2 Study', Blood, vol. 124(21): p. 53 (2014).

Cappellini et al., "A Phase 2a, Open-Label, Dose-Finding Study to Determine the Safety and Tolerability of Sotatercept (ACE-011) in Adults with Beta(?)-Thalassemia: Interim Results," Blood, vol. 122(21): 3448 (2013).

Carrancio et al., "An activin receptor IIA ligand trap promotes erythropoiesis resulting in a rapid induction of red blood cells and haemoglobin," British Journal of Haematology, vol. 165:870-882 (2014).

Castonguay et al., "Soluble endoglin specifically binds bone morphongenetic proteins 9 and 10 via its orphan domain, inhibits blood vessel formation, and suppress tumor growth," The Journal of Biological Chemistry, vol. 286(34): 30034-30046 (2011).

"Efficacy Versus Potency", https://step1.medbullets.com/pharmacology/107007/efficacy-vs-patency, accessed Jan. 2, 2019.

Fenton, et al., "Rheostat positions: A new classification of protein positions relevant to pharmacogenomics", Medicinal Chemistry Research 29: 1133-1146 (2020).

Fox et al., "Pulmonary arterial hypertension: classification, diagnosis and contemporary management," Postgrad Medicine J, vol. 82:717-722 (2006).

Guazzi et al., "Pulmonary Hypertension Due to Left Heart Disease," Circulation, vol. 126(8):975-990 (2012).

Guo et al., "Protein tolerance to random amino acid change," Proceedings of the National Academy of Sciences, vol. 101(25): 9205-9210 (2004).

Hill et al., "Postoperative Pulmonary Hypertension: Etiology and Treatment of a Dangerous Complication," Respiratory Care, vol. 54(7): 958-968 (2009).

Humbert, Marc et al., "Pathology and pathobiology of pulmonary hypertension: state of the art and research perspectives," The European Respiratory Journal, vol. 53: 1801887, 1-14 (2019).

Humbert, M., "Update in Pulmonary Hypertension 2008," American Journal of Respiratory Critical Care Medicine, vol. 179: 650-656 (2009).

ISR PCT/US2021/029492 dated Jul. 13, 2021 (6 pages).

Joshi, Sachindra R. et al., "Sotatercept analog improves cardiopulmonary remodeling and pulmonary hypertension in experimental left heart failure," Frontiers in Cardiovascular Medicine, vol. 10, 1064290, 1-14 (2023).

Kohno et al., "Binding Characteristics of Tumor Necrosis Factor Receptor-FC Fusion Proteins vs Anti-Tumor Necrosis Factor mAbs," J. Investigative Dermatology, vol. 12(1): 5-8 (2007).

Lai, Y.C. et al., "SIRT3-AMPK-Activation by Nitrite and Metformin Improves Hyperglycemia and Normalizes Pulmonary Hypertension Associated with Heart Failure With Preserved Ejection Fraction (PH-HF-pEF)", Circulation, vol. 133(8): 717-731 (2016).

Lis et al., "Tumor necrosis factor inhibitors—state of knowledge," Arch Med Sci. vol. 10(6): 1175-1185 (2014).

(56) References Cited

OTHER PUBLICATIONS

Long et al., "Selective enhancement of endothelial BMPR-II with BMP9 reverses pulmonary arterial hypertension," Nature Medicine, vol. 21(7): 777-785 (2015).
Montani, David et al., Pulmonary arterial hypertension, Orphanet Journal of Rare Diseases, vol. 8:97, 1-58 (2013).
Myllarniemi et al., "Upregulation of activin-B and follistatin in pulmonary fibrosis—a translational study using human biopsies and a specific inhibior in mouse fibrosis models," BMC Pulmonary Medicine, vol. 14(170): (14 pages) (2014).
Oba et al., "Pulmonary hypertension associated with left ventricular disease," Medical Progress, vol. 255(1): 89-93 (2015).
Optiz, Christian F. et al., "Pre-Capillary, Combined, and Post-Cappillary Pulmonary Hypertension A Pathophysiological Continuum," Journal of the American College of Cardiology, Elsevier, Amsterdam, NL, vol. 68(4): 368-378 (2016).
Pietra, et al., "Pathologic Assessment of Vasculopathies in Pulmonary Hypertension," Journal of the American College of Cardiology, vol. 43(12) Suppl S: 25S-32S (2004).
Project Information No. 5R01HL074352-07 "BMPR2 and the Pathogenesis of Pulmonary Hypertension", NIH RePorter—NIH Research Portfolio Online Reporting Tool Expenditures and Results (Feb. 20, 2020) 2 pages.
National Organization for Rare Disorders, "Pulmonary Arterial Hypertension", The website downloaded Nov. 2, 2020 from https://rarediseases.org/rare-disease/pulmonary-arterial-hypertensin/; 13 pages (2020).
Rose-Jones et al., "Pulmonary Hypertension: Types and Treatments," Current Cardiology Reviews, vol. 11:73-79 (2015).
Rubin, L.J., "Diagnosis and Management of Pulmonary Arterial Hypertension: ACCP Evidence-Based Clinical Practice Guidelines," Chest, vol. 126(1): 7S-10S (2004).
Sugimura et al., "Pulmonary hypertension associated with left ventricular disease," Angiology Frontier, vol. 14(2): 117-122 (2015).
Simonneau et al., "Updated Clinical Classification of Pulmonary Hypertension," Journal of the American College of Cardiology, vol. 54(1) Suppl S: S43-S54 (2009).
Sotatercept (https://www.genome.jp/dbget-bin/www_bget?dr:D09670; accessed Feb. 1, 2022).
Spiess et al., "Alternative molecular formats and therapeutic applications for bispecific antibodies," Molecular Immunology, vol. 67: 95-106 (2015).
Supplementary EP Search Report No. EP 21 79 7514, dated Mar. 28, 2024 (2 pages).
Tokuriki et al., "Stability effects of mutations and protein evolvability," Current Opinions in Structural Biology, vol. 19(5): 596-604 (2009).
Todd et al., "Current Understanding of Circulating Biomarkers in Pulmonary Hypertension Due to Left Heart Disease," Frontiers in Medicine, vol. 7:570016: 1-12 (2020).
Ulloa-Aguirre et al., "Pharmacologic rescue of conformationally-defective proteins: implications for the treatment of human disease," Traffic, vol. 5(11): 821-837 (2004).
Vachiéry et al., Pulmonary hypertension due to left heart disease, Eur. Respir. Journal, vol. 53:1801897: pp. 1-12 (2019).
Yndestad et al., Elevated levels of activin A in clinical and experimental pulmonary hypertension, J. Applied Physiology, vol. 106(4): 1356-1364 (2009).
Yung et al., "ACTRIIA-Fc rebalances activin/GDF versus BMP signaling in pulmonary hypertension," Science Translational Medicine, vol. 12(543): 5660 (2020).
Cappellini et al. (Sotatercept, a novel transforming growth factor B ligand trap, improves anemia in B-thalassemia: a phase II, open-label, dose-finding study Haematologica 104:477-484. (2018).
Hoeper et al. "Phase 3 Trial of Sotatercept for Treatment of Pulmonary Arterial Hypertension" New Engl. J. Med. 388: 1478-1490. (2023).
Kenny, Jane R. et al., "Therapeutic Protein Drug-Drug Interactions: Navigating the Knowledge Gaps-Highlights from the 2012 AAPS NBC Roundtable and IQ Consortium/FDA Workshop", The AAPS Journal, vol. 15(4): 933-940 (2013).
Maron et al., "Pulmonary hypertension associated with left heart disease", European Respiratory Journal, vol. 64:2401344 (22 pages) (2024).
Rath et al., "Fc-fusion proteins and FcRn: structural insights for longer-lasting and more effective therapeutics," Critical Reviews in Biotechnology, vol. 35(2): 235-254 (2015).
Tyagi et al., "Chemical modification and chemical cross-linking for protein/enzyme stabilization", Biochemistry (Mosc)P. vol. 63(3): 334-344 (1998).
Sunamura et al., "Different Roles of myocardial ROCK1 and ROCK2 in cardiac dysfunction and postcapillary pulmonary hypertension in mice," PNAS, vol. 115:30: E7129-E7138 (2018).
Acceleron Pharma: A Study of Sotatercept for the Treatment of Pulmonary Arterial Hypertension (Pah) (Pulsar), retrieved from the Internet: https://clinicaltrials.gov/study/NCT03496207 (2018).
Badesch, David "Pulsar: A phase 2, randomized, double-blind, placebo-controlled study to assess the efficacy and safety of sotatercept (ACE-11) when added to standard of care (SOC) for treatment of pulmonary arterial hypertension (PAH)", Pulmonary Hypertension, page PA4750 (2019).
Cottin, et al., "Pulmonary hypertension in patients with combined pulmonary fibrosis and emphysema syndrome", Eur. Respir J., vol. 35:105-111; (2010).
Guo, Wen et al., Administration of an activin receptor IIB ligand trap protects male juvenile rhesus macaques from simian immunodeficiency virus-associated bone loss, Bone, vol. 97:209-215 (2017).
Humbert, Marc et al.: Sotatercept for the Treatment of Pulmonary /Arterial Hypertension, The New England Journal of Medicine, vol. 384(13); 1204-1215 (2021).
Joshi, S. R., et al. "ACTRIIA-Fc (Sotatercept) Reverses Pulmonary Vascular Remodeling to Attenuate Pulmonary Arterial Hypertension (PAH) by Rebalancing TGF-b/BMP Signaling in a Preclinical Model" American Journal of Respiratory and Critical Care Medicine, vol. 199, Abstract 4395 (2019).
Joshi, S. R., et al. "Rap-011, a Murine Ortholog of ActRIIA-Fc (Sotatercept), Improves Pulmonary Hemodynamics and Restores Right Ventricular Structure and Function in a Preclinical Model of Severe Angio-Obliterative Pulmonary Arterial Hypertension." Circulation, vol. 138, No. Suppl_1, Abstract 16179 (2018).
Karnati et al., "Chronic Obstructive Pulmonary Disease and the Cardiovascular System: Vascular Repair and Regeneration as a Therapeutic Target," Frontiers in Cardiovascular Medicine, vol. 8(649512): 1-26 (2021).
Liu, Shao-Fei et al., "Animal models of pulmonary hypertension due to left heart disease", Animal Models and Experimental Medicine, vol. 5(3): 197-206 (2022).
Lombardi, Sandra et al., "Titration of pulmonary arterial hypertension therapeutics: Experience-based recommendations," Respiratory Medicine, vol. 143: 139-156 (2018).
Naeije, Robert et al., "Differentiating Precapillary From Postcapillary Pulmonary Hypertension: Pulmonary Artery Wedge Pressure Versus Left Ventricular End-Diastolic Pressure", Circulation, vol. 140(9): 712-714 (2019).
Oliviera et al., "Idiopathic Interstitial pneumonias: review of the latest American Thoracic Society/European Respiratory Society classification," Radiologia Brasileira, vol. 51(5): 321-327 (2018).
Patel, Nina M. et al., "Pulmonary hypertension in idopathic pulmonary fibrosis", Chest, Elsevier, vol. 132(3): 998-1006 (2007).
Roh, Jason D., et al., "Activin type II receptor signaling in cardiac aging and heart failure," Sci. Transl. Med., vol. 11(482) (2019).
Saito et al., "TGF-beta Signaling in Lung Health and Disease," International Journal of Molecular Sciences, vol. 19(2460): 1-18 (2018).
Schroll et al., "Improvement of bleomycin-induced pulmonary hypertension and pulmonary fibrosis by the endothelin receptor antagonist", Bosentan. Respir Physiol Neurobiol; vol. 170(1): 32-36 (2010).
Shah, Sanjiv J., "Pulmonary Hypertension," JAMA, vol. 308(13): 1366-1374 (2012).

(56) References Cited

OTHER PUBLICATIONS

Simonneau et al., "Updated Clinical Classification of Pulmonary Hypertension," Journal of the American College of Cardiology, vol. 62(52) Suppl D: D34-D41 (2013).
Waxman et.al., "SPECTRA Phase 2b Study: Impact of Sotatercept on Exercise Tolerance and Right Ventricular Function in Pulmonary Arterial Hypertension", Circulation: Heart Failure, vol. 17:3011227: 391-402 (2024).
Xiong et al., "Models and Molecular Mechanisms of World Health Organization Group 2 to 4 Pulmonary Hypertension", Hypertension, vol. 71(1): 34-55 (2018).
Yung, Lai-Ming et al., "ACTRIIA-Fc rebalances activin/GDF versus BMP signaling in pulmonary hypertension", Science Translational Medicine, vol. 12(543) (2020) (25 pages).
Yung, L. M., et al. "ActRIIA-Fc Rebalances Activin/GDF and BMP9 Signaling to Attenuate Experimental Pulmonary Hypertension." Circulation, vol. 138, No. Suppl_1, Abstract 17217 (2018).
Yung et al., "ACTRIIA-Fc rebalances activin/GDF versus BMP signaling in pulmonary hypertension", Science Translational Medicine, vol. 12, (543) 5660, pp. 1-12 (2020).
Zu, L. et al., "Evidence for a Role of Immunoproteasomes in Regulating Cardiac Muscle Mass in Diabetic Mice", Journal Mol. Cell Cardiol, vol. 49(1): 5-15 (2010).
Supplementary EP Search Report EP 17 82 8540, dated Feb. 27, 2020 (2 pages).
Supplementary EP Search Report EP 21 16 3839, dated Oct. 31, 2021 (2 pages).
Supplementary EP Search Report EP 22 73 7173, dated Oct. 7, 2024.
Supplementary EP Search Report (EP 22 82 1107) dated Mar. 4, 2025 (3 pages).
Supplementary EP Search Report No. EP 22 84 6466 dated Mar. 26, 2025.
Supplementary EP Search Report EP 21 82 8310, dated May 23, 2024 (2 pages).
Supplementary EP Search Report EP 22 82 9068, dated Mar. 25, 2025 (3 pages).
International Search Report PCT/US2021/038482 dated Sep. 16, 2021.
ISR PCT/US2022/037479, dated Oct. 31, 2022 (4 pages).
ISR PCT/US2022/034090, dated Sep. 14, 2022 (4 pages).
ISR PCT/US22/33007 dated Nov. 22, 2022 (8 pages).
ISR PCT/US2017/042157, dated Sep. 27, 2017 (9 pages).
ISR/PCT2022/011619 dated Mar. 29, 2022 (5 pages).

* cited by examiner

```
ActRIIa    ILGRSETQEC LFFNANWEKD RTNQTGVEPC YGDKDKRRHC FATWKNISGS
ActRIIb    GRGEAETREC IYYNANWELE RTNQSGLERC EGEQDKRLHC YASWRNSSGT

           IEIVKQGCWL DDINCYDRTD CVEKKDSPEV YFCCCEGNMC NEKFSYFPEM
           IELVKKGCWL DDFNCYDRQE CVATEENPQV YFCCCEGNFC NERFTHLPEA

           EVTQPTSNPV TPKPPT  (SEQ ID NO: 42)
           GGPEVTYEPP PTAPT   (SEQ ID NO: 31)
```

FIGURE 1

```
         .........10 .........20 .........30 .........40 .........50
human    ILGRSETQEC LFFNANWEKD RTNQTGVEPC YGDKDKRRHC FATWKNISGS
sheep    ILGRSETQEC IFYNANWERD RTNRTGVESC YGDKDKRRHC FATWKNISGS
mole     ILGRSETQEC LFFNANWERD RTNQTGVEPC YGDKDKRRHC FATWKNISGS
mouse    ILGRSETQEC LFFNANWERD RTNQTGVEPC YGDKDKRRHC FATWKNISGS
chicken  ILGRSETQEC IYYNANWEKD KTNRSGIEPC YGDKDKRRHC FATWKNISGS
cow      ILGRSETQEC IFYNANWERD RTNRTGVESC YGDKDKRRHC FATWKNISGS
owl      ILGRSETQEC IYYNANWEKD KTNRSGIEPC YGDKDKRRHC FATWKNISGS
bat      ILGRSETQEC IFYNANWERD KTNRTGVELC YGDKDKRRHC FATWKNISGS

         .........60 .........70 .........80 .........90 .........100
human    IEIVKQGCWL DDINCYDRTD CVEKKDSPEV YFCCCEGNMC NEKFSYFPEM
sheep    IEIVKQGCWL DDINCYDRTD CIEKKDSPEV YFCCCEGNMC NERFSYFPEM
mole     IEIVKQGCWL DDINCYDRTD CIEKKDSPEV YFCCCEGNMC NEKFSYFPEM
mouse    IEIVKQGCWL DDINCYDRTD CIEKKDSPEV YFCCCEGNMC NEKFSYFPEM
chicken  IEIVKQGCWL DDINCYDRND CIEKKDSPEV FFCCCEGNMC NERFFYFPEM
cow      IEIVKQGCWL DDINCYDRTD CIEKKDSPEV YFCCCEGNMC NERFSYFPEM
owl      IEIVKQGCWL DDINCYDRND CIEKKDSPEV FFCCCEGNMC NERFFYFPEM
bat      IEIVKQGCWL DDINCYDRTD CIEKKDSPEV YFCCCEGNMC NERFSYFPEM

         .........110.....
human    EVTQPTSNPV TPKPP (SEQ ID NO: 6)
sheep    EVTQPTSNPV TPKPP (SEQ ID NO: 7)
mole     EVTQPTSNPV TPKAP (SEQ ID NO: 8)
mouse    EVTQPTSNPV TPKPP (SEQ ID NO: 9)
chicken  EVTQPTSNPV TPKPP (SEQ ID NO: 10)
cow      EVTQPTSNPV TPKPP (SEQ ID NO: 36)
owl      EVTQPTSNPV TPKPP (SEQ ID NO: 37)
bat      EVTQPTSNPV TPKPP (SEQ ID NO: 38)
```

Figure 2

```
IgG1   -------THTCPPCPAPELLGGPSVFLFPPKPKDTLMISRTPEVTCVVVDVSHEDPEVKF  53
IgG4   ---ESKYGPPCPSCPAPEFLGGPSVFLFPPKPKDTLMISRTPEVTCVVVDVSQEDPEVQF  57
IgG2   --------VECPPCPAPPVAG-PSVFLFPPKPKDTLMISRTPEVTCVVVDVSHEDPEVQF  51
IgG3   EPKSCDTPPPCPRCPAPELLGGPSVFLFPPKPKDTLMISRTPEVTCVVVDVSHEDPEVQF  60
                 ** ****  .* ******************************:*****:*

IgG1   NWYVDGVEVHNAKTKPREEQYNSTYRVVSVLTVLHQDWLNGKEYKCKVSNKALPAPIEKT  113
IgG4   NWYVDGVEVHNAKTKPREEQFNSTYRVVSVLTVLHQDWLNGKEYKCKVSNKGLPSSIEKT  117
IgG2   NWYVDGVEVHNAKTKPREEQFNSTFRVVSVLTVVHQDWLNGKEYKCKVSNKGLPAPIEKT  111
IgG3   KWYVDGVEVHNAKTKPREEQYNSTFRVVSVLTVLHQDWLNGKEYKCKVSNKALPAPIEKT  120
       :*******************:***:********:*****************.**::****

IgG1   ISKAKGQPREPQVYTLPPSREEMTKNQVSLTCLVKGFYPSDIAVEWESNGQPENNYKTTP  173
IgG4   ISKAKGQPREPQVYTLPPSQEEMTKNQVSLTCLVKGFYPSDIAVEWESNGQPENNYKTTP  177
IgG2   ISKTKGQPREPQVYTLPPSREEMTKNQVSLTCLVKGFYPSDIAVEWESNGQPENNYKTTP  171
IgG3   ISKTKGQPREPQVYTLPPSREEMTKNQVSLTCLVKGFYPSDIAVEWESSGQPENNYNTTP  180
       ***:***************:****************************.*******:***

IgG1   PVLDSDGSFFLYSKLTVDKSRWQQGNVFSCSVMHEALHNHYTQKSLSLSPGK  225  (SEQ ID NO: 32)
IgG4   PVLDSDGSFFLYSRLTVDKSRWQEGNVFSCSVMHEALHNHYTQKSLSLSLGK  229  (SEQ ID NO: 35)
IgG2   PMLDSDGSFFLYSKLTVDKSRWQQGNVFSCSVMHEALHNHYTQKSLSLSPGK  223  (SEQ ID NO: 33)
IgG3   PMLDSDGSFFLYSKLTVDKSRWQQGNIFSCSVMHEALHNRFTQKSLSLSPGK  232  (SEQ ID NO: 34)
       *:***********:*********:**:***********::********* **
```

Figure 3

A.
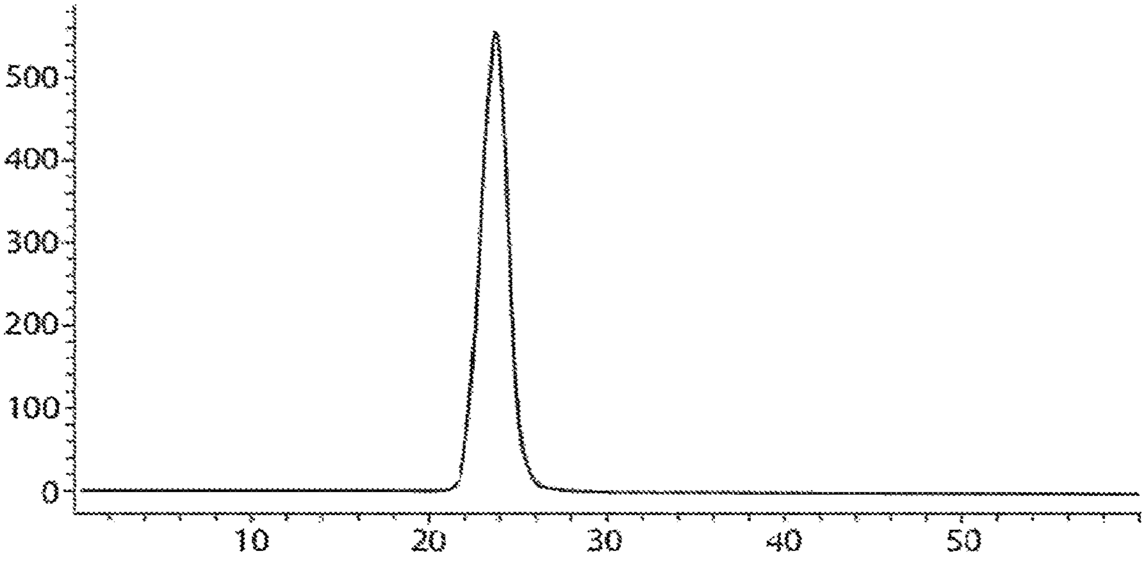
B.
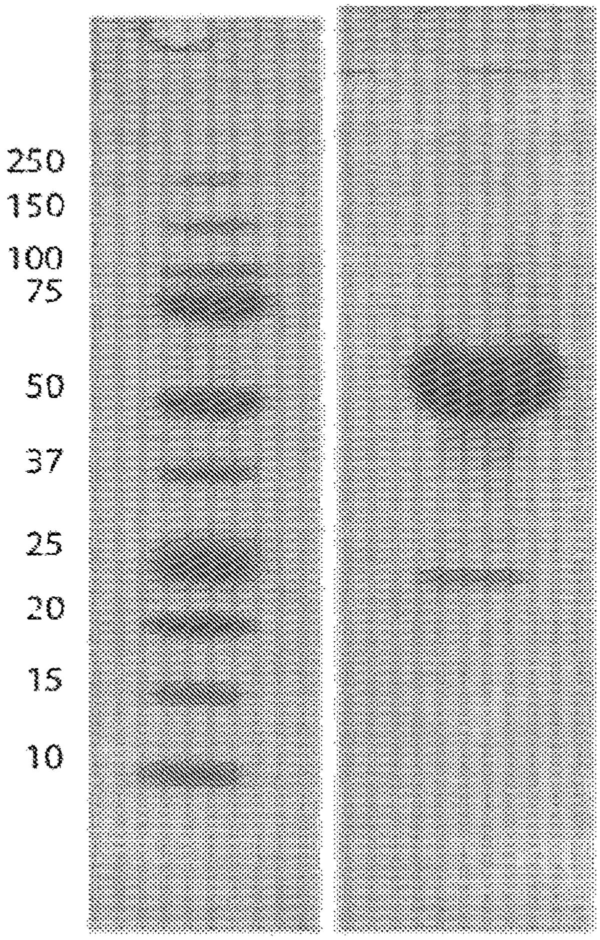
FIGURE 4

A.
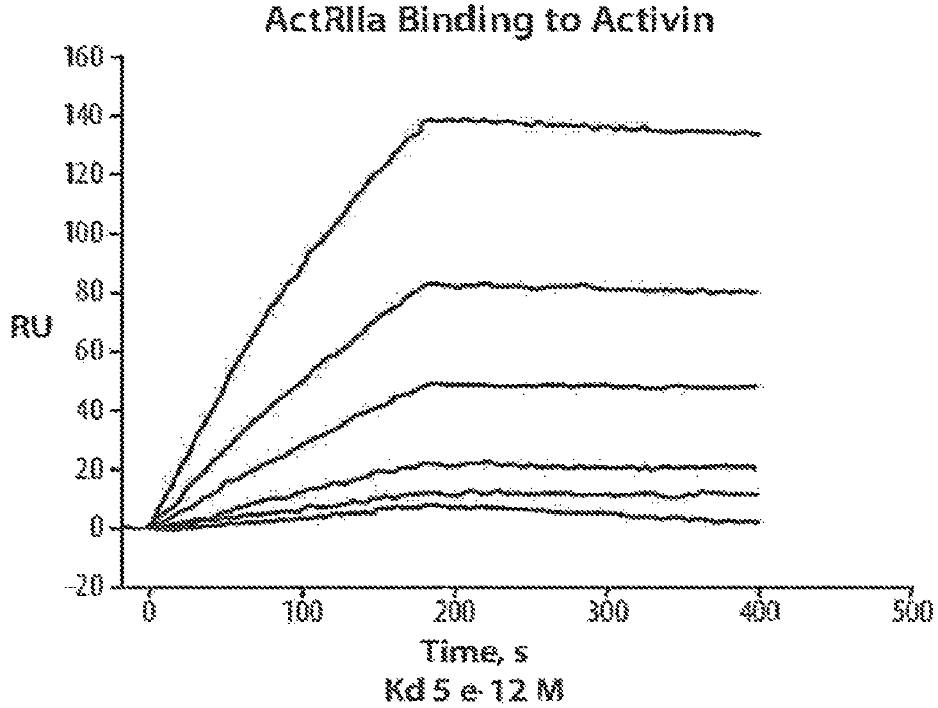
B.
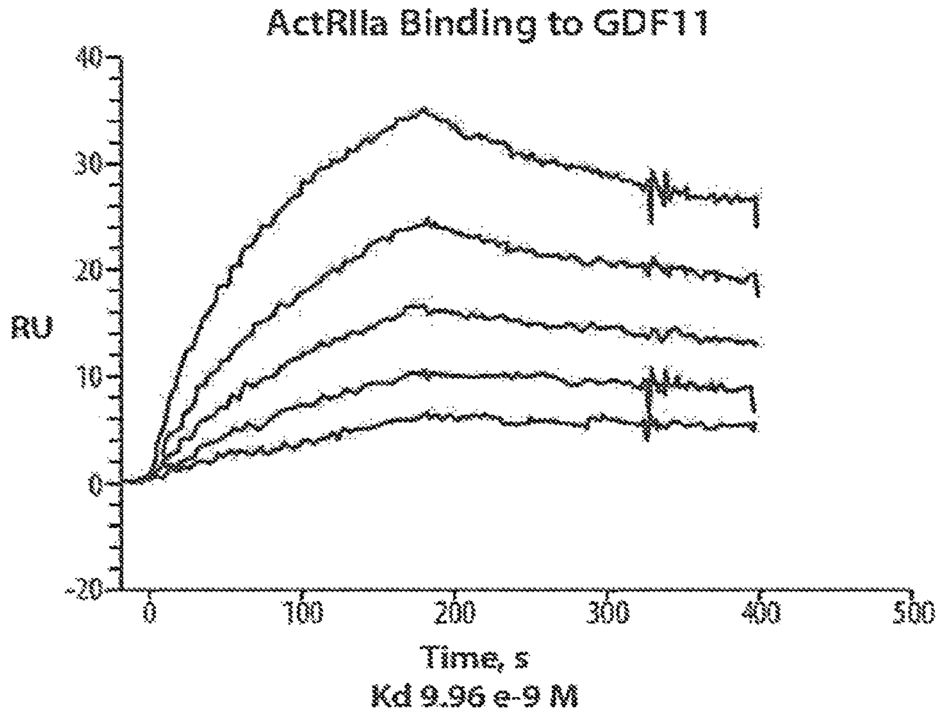
FIGURE 5

Combined post- and pre-capillary PH (CpcPH)
mPAP > 20 mmHg
PAWP > 15 mmHg
PVR ≥ 3 WU
DPG ≥ 7 mmHg VC  RA  RV    PA        PC        PV      LA  Lv  AO Rx: ActRIIA-mFc s.c., 3 and 10mpk, BIW

ACTRII PROTEINS AND USE IN TREATING POST-CAPILLARY PULMONARY HYPERTENSION

CROSS-REFERENCE TO RELATED APPLICATIONS

This application is a continuation application of U.S. application Ser. No. 17/921,810 filed Oct. 27, 2022 which is a national stage filing under 35 U.S.C. § 371 of International Application No. PCT/US2021/029492, filed on Apr. 27, 2021, which claims the benefit of priority from U.S. Provisional Application No. 63/016,942, filed on Apr. 28, 2020 and from U.S. Provisional Application No. 63/159,253, filed on Mar. 10, 2021. The specifications of the foregoing applications are incorporated herein by reference in their entirety.

SEQUENCE LISTING

The instant application contains a Sequence Listing which has been submitted electronically in XML format and is hereby incorporated by reference in its entirety. Said XML copy, created on Nov. 20, 2024, is named 1848179-0002-141-302_SL.xml and is 53,413 bytes in size.

BACKGROUND OF THE INVENTION

Pulmonary hypertension (PH) is a disease characterized by high blood pressure in lung vasculature, including pulmonary arteries, pulmonary veins, and pulmonary capillaries. In general, PH is defined as a mean pulmonary arterial pressure (mPAP) ≥20 mm Hg at rest or ≥30 mm Hg with exercise [Hill et al., Respiratory Care 54(7):958-68 (2009)]. One of the main PH symptoms is difficulty in breathing or shortness of breath, and other symptoms include fatigue, dizziness, fainting, peripheral edema (swelling in foot, legs or ankles), bluish lips and skin, chest pain, angina pectoris, light-headedness during exercise, non-productive cough, racing pulse and palpitations. PH can be a severe disease causing heart failure, which is one of the most common causes of death in people who have pulmonary hypertension. Postoperative pulmonary hypertension may complicate many types of surgeries or procedures, and present a challenge associated with a high mortality.

PH may be grouped based on different manifestations of the disease sharing similarities in pathophysiologic mechanisms, clinical presentation, and therapeutic approaches [Simonneau et al., JACC 54(1):S44-54 (2009)]. Clinical classification of PH was first proposed in 1973, and a recent updated clinical classification was endorsed by the World Health Organization (WHO) in 2018. According to the updated PH clinical classification, there are five main groups of PH: pulmonary arterial hypertension (PAH), characterized by a pulmonary arterial wedge pressure (PAWP)≤15 mm Hg; PH due to left heart disease (also known as pulmonary venous hypertension or congestive heart failure), characterized by a PAWP >15 mm Hg; PH due to lung diseases and/or hypoxia; PH due to pulmonary artery obstructions; and PH with unclear and/or multifactorial mechanisms [Simonneau (2019) Eur Respir J: 53:1801913]. PH due to left heart disease is further classified into PH due to heart failure with preserved left ventricular ejection fraction; PH due to heart failure with reduced left ventricular ejection fraction; valvular heart disease; and congenital/acquired cardiovascular conditions leading to post-capillary PH [Simonneau (2019) Eur Respir J: 53:1801913]. Diagnosis of various types of PH typically requires a series of tests.

In general, PH treatment depends on the cause or classification of PH. Where PH is caused by a known medicine or medical condition, it is known as a secondary PH, and its treatment is usually directed at the underlying disease. Treatment of Group 2 pulmonary hypertension (e.g., venous hypertension) generally involves optimizing left ventricular function by administering diuretics, beta blockers, angiotensin receptor-neprilysin inhibitors (ARNI), and ACE inhibitors, cardiac resynchronization therapy, or repairing or replacing a mitral valve or aortic valve.

There is a high, unmet need for effective therapies for treating pulmonary hypertension. Accordingly, it is an object of the present disclosure to provide methods for treating, preventing, or reducing the progression rate and/or severity of PH, particularly treating, preventing or reducing the progression rate and/or severity of one or more PH-associated complications.

SUMMARY OF THE INVENTION

In some embodiments, the disclosure provides for a method of treating post-capillary pulmonary hypertension (PcPH), comprising administering to a patient in need thereof an effective amount of a polypeptide comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 21, 22, 23, 24, 25, 26, 27, 28, 29, or 30 of SEQ ID NO: 1 and ends at any one of amino acids 110, 111, 112, 113, 114, 115, 116, 117, 118, 119, 120, 121, 122, 123, 124, 125, 126, 127, 128, 129, 130, 131, 132, 133, 134, or 135 of SEQ ID NO: 1. In some embodiments, the disclosure provides for a method of treating, preventing, or reducing the progression rate and/or severity of one or more complications of post-capillary pulmonary hypertension (e.g., WHO Group 2 and/or Group 5 PH), comprising administering to a patient in need thereof an effective amount of a polypeptide comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 21, 22, 23, 24, 25, 26, 27, 28, 29, or 30 of SEQ ID NO: 1 and ends at any one of amino acids 110, 111, 112, 113, 114, 115, 116, 117, 118, 119, 120, 121, 122, 123, 124, 125, 126, 127, 128, 129, 130, 131, 132, 133, 134, or 135 of SEQ ID NO: 1. In some embodiments, the one or more complications of post-capillary pulmonary hypertension is selected from the group consisting of: smooth muscle and/or endothelial cell proliferation in the pulmonary artery, angiogenesis in the pulmonary artery, dyspnea, chest pain, pulmonary vascular remodeling, right ventricular hypertrophy, left ventricular hypertrophy, left atrium dilation, left ventricular fibrosis, right ventricular fibrosis, and pulmonary fibrosis. In some embodiments, the PcPH is isolated post-capillary pulmonary hypertension (IpcPH). In some embodiments, the PcPH is combined post- and pre-capillary PH (CpcPH).

In some embodiments, the patient has Group 2 pulmonary hypertension as recognized by the World Health Organization (WHO). In some embodiments, the patient has pulmonary hypertension due to heart failure with preserved left ventricular ejection fraction (LVEF). In some embodiments, the patient has pulmonary hypertension due to heart failure with reduced left ventricular ejection fraction (LVEF). In some embodiments, the patient has valvular heart disease. In some embodiments, the patient has congenital/acquired cardiovascular conditions leading to post-capillary PH. In some embodiments, the patient has Group 5 pulmonary hypertension as recognized by the WHO. In some embodiments, the patient has pulmonary hypertension with unclear and/or multifactorial mechanisms. In some embodiments, the valvular heart disease is aortic regurgitation. In some embodiments, the valvular heart disease is aortic stenosis. In some embodiments, the valvular heart disease is mitral valve regurgitation. In some embodiments, the valvular heart disease is mitral valve stenosis.

In some embodiments, the patient has a mean pulmonary arterial pressure (mPAP) selected from the group consisting of an mPAP of at least 20 mmHg; an mPAP of at least 25 mmHg; an mPAP of at least 30 mmHg; an mPAP of at least 35 mmHg; an mPAP of at least 40 mmHg; an mPAP of at least 45 mmHg; and an mPAP of at least 50 mmHg. In some embodiments, the method reduces mPAP in the patient. In some embodiments, the method reduces the mPAP in the patient by at least 10% (e.g., 10%, 15%, 20%, 25%, 30%, 35%, 40%, 45%, 50%, 55%, 60%, 65%, 70%, 75%, or at least 80%). In some embodiments, the method reduces the mPAP by at least 3 mmHg (e.g., at least 3, 5, 7, 10, 12, 15, 20, or 25 mm Hg) in the patient.

In some embodiments, the patient has a pulmonary arterial wedge pressure (PAWP) of greater than 15 mmHg. In some embodiments, the method decreases the PAWP in the patient. In some embodiments, the method reduces the PAWP in the patient by at least 10% (e.g., 10%, 15%, 20%, 25%, 30%, 35%, 40%, 45%, 50%, 55%, 60%, 65%, 70%, 75%, or at least 80%). In some embodiments, the patient has a left ventricular end diastolic pressure (LVEDP) of greater than 15 mmHg. In some embodiments, the method decreases the LVEDP in the patient. In some embodiments, the method reduces the LVEDP in the patient by at least 10% (e.g., 10%, 15%, 20%, 25%, 30%, 35%, 40%, 45%, or at least 50%). In some embodiments, the patient has a diastolic pressure gradient (DPG) of less than 7 mmHg. In some embodiments, the patient has a DPG of at least 7 mmHg. In some embodiments, the method decreases the DPG in the patient. In some embodiments, the method reduces the DPG in the patient by at least 10% (e.g., 10%, 15%, 20%, 25%, 30%, 35%, 40%, 45%, 50%, 55%, 60%, 65%, 70%, 75%, or at least 80%). In some embodiments, the patient has a transpulmonary pressure gradient (TPG) of less than or equal to 12 mm Hg. In some embodiments, the patient has a TPG of greater than 12 mm Hg. In some embodiments, the method decreases the TPG in the patient. In some embodiments, the method reduces the TPG in the patient by at least 10% (e.g., 10%, 15%, 20%, 25%, 30%, 35%, 40%, 45%, 50%, 55%, 60%, 65%, 70%, 75%, or at least 80%). In some embodiments, the patient has a pulmonary vascular resistance (PVR) greater than or equal to 3 Wood Units. In some embodiments, the method decreases the PVR in the patient. In some embodiments, the method reduces the PVR in the patient by at least 10% (e.g., 10%, 15%, 20%, 25%, 30%, 35%, 40%, 45%, 50%, 55%, 60%, 65%, 70%, 75%, or at least 80%).

In some embodiments, the method prevents the progression of IpcPH to CpcPH. In some embodiments, the method reduces the development of a pre-capillary component of PH. In some embodiments, the patient has preserved left ventricular ejection fraction. In some embodiments, the preserved left ventricular ejection fraction is greater than 45%. In some embodiments, the patient has reduced left ventricular ejection fraction. In some embodiments, the reduced left ventricular fraction is less than 45%. In some embodiments, the preserved left ventricular fraction is measured using echocardiography. In some embodiments, the patient has diastolic dysfunction of the left ventricle. In some embodiments, the patient has systolic dysfunction of the left ventricle. In some embodiments, the method decreases right ventricular hypertrophy in the patient. In some embodiments, the method decreases right ventricular hypertrophy in the patient by at least 10% (e.g., 10%, 15%, 20%, 25%, 30%, 35%, 40%, 45%, 50%, 55%, 60%, 65%, 70%, 75%, or at least 80%). In some embodiments, the method decreases left ventricular hypertrophy in the patient. In some embodiments, the method decreases left ventricular hypertrophy in the patient by at least 10% (e.g., 10%, 15%, 20%, 25%, 30%, 35%, 40%, 45%, 50%, 55%, 60%, 65%, 70%, 75%, or at least 80%). In some embodiments, the method decreases smooth muscle hypertrophy in the patient. In some embodiments, the method decreases smooth muscle hypertrophy in the patient by at least 10% (e.g., 10%, 15%, 20%, 25%, 30%, 35%, 40%, 45%, 50%, 55%, 60%, 65%, 70%, 75%, or at least 80%). In some embodiments, the method decreases pulmonary arteriole muscularity in the patient. In some embodiments, the method decreases pulmonary arteriole muscularity in the patient by at least 10% (e.g., 10%, 15%, 20%, 25%, 30%, 35%, 40%, 45%, 50%, 55%, 60%, 65%, 70%, 75%, or at least 80%).

In some embodiments, the patient has a right ventricular systolic pressure (RVSP) of greater than 35 mmHg. In some embodiments, the method decreases the RVSP in the patient. In some embodiments, the method reduces the RVSP in the patient by at least 10% (e.g., 10%, 15%, 20%, 25%, 30%, 35%, 40%, 45%, or at least 50%). In some embodiments, the patient has left ventricular fibrosis. In some embodiments, the method decreases the left ventricular fibrosis in the patient. In some embodiments, the method reduces the left ventricular fibrosis in the patient by at least 10% (e.g., 10%, 15%, 20%, 25%, 30%, 35%, 40%, 45%, or at least 50%). In some embodiments, the patient has right ventricular fibrosis. In some embodiments, the method decreases the right ventricular fibrosis in the patient. In some embodiments, the method reduces the right ventricular fibrosis in the patient by at least 10% (e.g., 10%, 15%, 20%, 25%, 30%, 35%, 40%, 45%, or at least 50%). In some embodiments, the patient has pulmonary fibrosis. In some embodiments, the method decreases the pulmonary fibrosis in the patient. In some embodiments, the method reduces the pulmonary fibrosis in the patient by at least 10% (e.g., 10%, 15%, 20%, 25%, 30%, 35%, 40%, 45%, or at least 50%).

In some embodiments, the patient has a comorbidity selected from the group consisting of systemic hypertension, diabetes mellitus, obesity, coronary artery disease (CAD), heart failure, and anemia. In some embodiments, the method further comprises administering to the patient an additional active agent and/or supportive therapy. In some embodiments, the additional active agent and/or supportive therapy is selected from the group consisting of: beta-blockers, angiotensin-converting enzyme inhibitors (ACE inhibitors), angiotensin receptor blockers (ARBs), neprilysin inhibitors, angiotensin receptor-neprilysin inhibitors (ARNI), mineralocorticoid receptor antagonists (MRA), hyperpolarization-activated cyclic nucleotide-gated (HCN) channel blockers, diuretic agents, lipid-lowering medications, endothelin blockers, PDE5 inhibitors, prostacyclins, cardiac resynchronization therapy, valve replacement, valve repair, implantable cardioverter-defibrillator (ICD), or a left ventricular assist device (LVAD). In some embodiments, the additional active agent and/or supportive therapy is selected from the group consisting of: prostacyclin and derivatives thereof (e.g., epoprostenol, treprostinil, and iloprost); prostacyclin receptor agonists (e.g., selexipag); endothelin receptor antagonists (e.g., thelin, ambrisentan, macitentan, and bosentan); calcium channel blockers (e.g., amlodipine, diltiazem, and nifedipine; anticoagulants (e.g., warfarin); diuretics; oxygen therapy; atrial septostomy; pulmonary thromboendarterectomy; phosphodiesterase type 5 inhibitors (e.g., sildenafil and tadalafil); activators of soluble guanylate cyclase (e.g., cinaciguat and riociguat); ASK-1 inhibitors (e.g., CIIA; SCH79797; GS-4997; MSC2032964A; 3H-naphtho[1,2,3-de]quiniline-2,7-diones, NQDI-1; 2-thioxo-thiazolidines, 5-bromo-3-(4-oxo-2-thioxo-thiazolidine-5-ylidene)-1,3-dihydro-indol-2-one); NF-κB antagonists (e.g., dh404, CDDO-epoxide; 2,2-difluoropropionamide; C28 imidazole (CDDO-Im); 2-cyano-3,12-dioxoolean-1,9-dien-28-oic acid (CDDO); 3-Acetyloleanolic Acid; 3-Triflouroacetyloleanolic Acid; 28-Methyl-3-acetyloleanane; 28-Methyl-3-trifluoroacetyloleanane; 28-Methyloxyoleanolic Acid; SZC014; SCZ015; SZC017; PEGylated derivatives of oleanolic acid; 3-O-(beta-D-glucopyranosyl) oleanolic acid; 3-O-[beta-D-glucopyranosyl-(1-->3)-beta-D-glucopyranosyl]oleanolic acid; 3-O-[beta-D-glucopyranosyl-(1-->2)-beta-D-glucopyranosyl]oleanolic acid; 3-O-[beta-D-glucopyranosyl-(1-->3)-beta-D-glucopyranosyl]oleanolic acid 28-O-beta-D-glucopyranosyl ester; 3-O-[beta-D-glucopyranosyl-(1-->2)-beta-D-glucopyranosyl]oleanolic acid 28-O-beta-D-glucopyranosyl ester; 3-O-[a-L-rhamnopyranosyl-(1-->3)-beta-D-glucuronopyranosyl]oleanolic acid; 3-O-[alpha-L-rhamnopyranosyl-(1-->3)-beta-D-glucuronopyranosyl] oleanolic acid 28-O-beta-D-glucopyranosyl ester; 28-O-β-D-glucopyranosyl-oleanolic acid; 3-O-β-D-glucopyranosyl (1--3)-β-D-glucopyranosiduronic acid (CS1); oleanolic acid 3-O-β-D-glucopyranosyl (1->3)-β-D-glucopyranosiduronic acid (CS2); methyl 3,11-dioxoolean-12-en-28-olate (DIOXOL); $ZCVI_4$-2; Benzyl 3-dehydr-oxy-1,2,5-oxadiazolo [3',4':2,3]oleanolate); eplerenone, spironolactone, ivabradine, implantable cardioverter-defibrillator (ICD), a left ventricular assist device (LVAD), or lung and/or heart transplantation.

In some embodiments, the patient has elevated brain natriuretic peptide (BNP) levels as compared to a healthy patient. In some embodiments, the patient has a BNP level of at least 100 pg/mL (e.g., 100, 150, 200, 300, 400, 500, 1000, 3000, 5000, 10,000, 15,000, or 20,000 pg/mL). In some embodiments, the method decreases BNP levels in the patient by at least 10% (e.g., 10%, 15%, 20%, 25%, 30%, 35%, 40%, 45%, 50%, 55%, 60%, 65%, 70%, 75%, or at least 80%). In some embodiments, the method decreases BNP levels to normal levels (i.e., <100 pg/ml). In some embodiments, the method decreases NT-proBNP levels in the patient. In some embodiments, the method decreases NT-proBNP levels in the patient by at least 10% (e.g., 10%, 15%, 20%, 25%, 30%, 35%, 40%, 45%, 50%, 55%, 60%, 65%, 70%, 75%, or at least 80%). In some embodiments, the method decreases NT-proBNP levels in the patient by at least 30%. In some embodiments, the method decreases NT-proBNP levels to normal levels. In some embodiments, the normal level of NT-proBNP is <100 pg/ml. In some embodiments, the method increases exercise capacity of the patient. In some embodiments, the patient has a 6-minute walk distance from 150 to 400 meters. In some embodiments, the patient has a 6-minute walk distance from 150 to 550 meters. In some embodiments, the method increases the patient's 6-minute walk distance. In some embodiments, the method increases the patient's 6-minute walk distance by at least 10 meters (e.g., at least 10, 20, 30, 40, 50, 60, 70, 80, 90, 100, 125, 150, 175, 200, 250, 300, or more than 400 meters). In some embodiments, the method reduces the patient's Borg dyspnea index (BDI). In some embodiments, the method reduces the patient's BDI by at least 0.5 index points (e.g., at least 0.5, 1, 1.5, 2, 2.5, 3, 3.5, 4, 4.5, 5, 5.5, 6, 6.5, 7, 7.5, 8, 8.5, 9, 9.5, or 10 index points).

In some embodiments, the patient has decreased renal function. In some embodiments, the method further improves renal function. In some embodiments, the patient has Functional Class II or Class III pulmonary hypertension in accordance with the World Health Organization's functional classification system for pulmonary hypertension. In some embodiments, the patient has Functional Class I, Class II, Class III, or Class IV pulmonary hypertension as recognized by the World Health Organization. In some embodiments, the method prevents or delays pulmonary hypertension Functional Class progression (e.g., prevents or delays progression from Functional Class I to Class II, Class II to Class III, or Class III to Class IV pulmonary hypertension as recognized by the World Health Organization). In some embodiments, the method promotes or increases pulmonary hypertension Functional Class regression (e.g., promotes or increases regression from Class IV to Class III, Class III to Class II, or Class II to Class I pulmonary hypertension as recognized by the World Health Organization). In some embodiments, the patient has Functional Class II or Class III pulmonary hypertension in accordance with the New York Heart Association's functional classification system for pulmonary hypertension. In some embodiments, the patient has Functional Class I, Class II, Class III, or Class IV pulmonary hypertension as recognized by the New York Heart Association. In some embodiments, the method prevents or delays pulmonary hypertension Functional Class progression (e.g., prevents or delays progression from Functional Class I to Class II, Class II to Class III, or Class III to Class IV pulmonary hypertension as recognized by the New York Heart Association). In some embodiments, the method promotes or increases pulmonary hypertension Functional Class regression (e.g., promotes or increases regression from Class IV to Class III, Class III to Class II, or Class II to Class I pulmonary hypertension as recognized by the New York Heart Association). In some embodiments, the method delays clinical worsening of PcPH. In some embodiments, the method delays clinical worsening of PcPH in accordance with the World Health Organization's functional classification system for pulmonary hypertension. In some embodiments, the method delays clinical worsening of PcPH in accordance with the New York Heart Association's functional classification system for pulmonary hypertension. In some embodiments, the method reduces the risk of hospitalization for one or more complications associated with PcPH. In some embodiments, the patient has a hemoglobin level from >8 and <15 g/dl.

In some embodiments, the patient has been treated with one or more vasodilators. In some embodiments, the patient has been treated with one or more agents selected from the group consisting of: phosphodiesterase type 5 inhibitors, soluble guanylate cyclase stimulators, prostacyclin receptor agonist, and endothelin receptor antagonists. In some embodiments, the one or more agents is selected from the group consisting of: bosentan, sildenafil, beraprost, macitentan, selexipag, epoprostenol, treprostinil, iloprost, ambrisentan, and tadalafil. In some embodiments, the method further comprises administration of one or more vasodilators. In some embodiments, the method further comprises administration of one or more agents selected from the group consisting of: phosphodiesterase type 5 inhibitors, soluble guanylate cyclase stimulators, prostacyclin receptor agonist, and endothelin receptor antagonists. In some embodiments, the one or more agents is selected from the group consisting of: bosentan, sildenafil, beraprost, macitentan, selexipag, epoprostenol, treprostinil, iloprost, ambrisentan, and tadalafil.

In some embodiments, the ActRII polypeptide comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the sequence of amino acids corresponding to residues 30-110 of SEQ ID NO: 1. In some embodiments, the ActRII polypeptide comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence SEQ ID NO: 2. In some embodiments, the ActRII polypeptide comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of SEQ ID NO: 3. In some embodiments, the ActRII polypeptide is a fusion protein further comprising an Fc domain of an immunoglobulin. In some embodiments, the Fc domain of the immunoglobulin is an Fc domain of an IgG1 immunoglobulin. In some embodiments, the Fc fusion protein further comprises a linker domain positioned between the ActRII polypeptide domain and the Fc domain of the immunoglobulin. In some embodiments, the linker domain is selected from the group consisting of: TGGG (SEQ ID NO: 20), TGGGG (SEQ ID NO: 18), SGGGG (SEQ ID NO: 19), GGGGS (SEQ ID NO: 22), GGG (SEQ ID NO: 16), GGGG (SEQ ID NO: 17), and SGGG (SEQ ID NO: 21). In some embodiments, the ActRII polypeptide comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of SEQ ID NO: 23. In some embodiments, the polypeptide comprises an amino acid sequence that is at least 90% identical to an amino acid sequence corresponding to residues 30-110 of SEQ ID NO: 1, wherein the polypeptide binds to activin and/or GDF11. In some embodiments, the polypeptide comprises an amino acid sequence that is at least 90% identical to an amino acid sequence corresponding to residues 21-135 of SEQ ID NO: 1, wherein the polypeptide binds to activin and/or GDF11. In some embodiments, the polypeptide is lyophilized. In some embodiments, the polypeptide is soluble. In some embodiments, the polypeptide is administered using subcutaneous injection. In some embodiments, the polypeptide is administered every 4 weeks. In some embodiments, the polypeptide is part of a homodimer protein complex. In some embodiments, the polypeptide is glycosylated. In some embodiments, the polypeptide has a glycosylation pattern obtainable by expression in a Chinese hamster ovary cell. In some embodiments, the ActRII polypeptide binds to one or more ligands selected from the group consisting of: activin A, activin B, and GDF11. In some embodiments, the ActRII polypeptide further binds to one or more ligands selected from the group consisting of: BMP10, GDF8, and BMP6.

In certain aspects, the disclosure relates to a kit comprising a lyophilized polypeptide and an injection device, wherein the polypeptide is an ActRII polypeptide comprising an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence that begins at any one of amino acids 21, 22, 23, 24, 25, 26, 27, 28, 29, or 30 of SEQ ID NO: 1 and ends at any one of amino acids 110, 111, 112, 113, 114, 115, 116, 117, 118, 119, 120, 121, 122, 123, 124, 125, 126, 127, 128, 129, 130, 131, 132, 133, 134, or 135 of SEQ ID NO: 1. In some embodiments, the polypeptide is a polypeptide comprising an amino acid sequence that is at least 90% identical to an amino acid sequence corresponding to residues 30-110 of SEQ ID NO: 1. In some embodiments, the polypeptide is a polypeptide comprising an amino acid sequence that is at least 95% identical to the amino acid sequence corresponding to residues 30-110 of SEQ ID NO: 1. In some embodiments, the polypeptide is a polypeptide comprising an amino acid sequence that is at least 99% identical to the amino acid sequence corresponding to residues 30-110 of SEQ ID NO: 1. In some embodiments, the polypeptide is a polypeptide comprising the amino acid sequence corresponding to residues 30-110 of SEQ ID NO: 1. In some embodiments, the polypeptide is a polypeptide consisting of the amino acid sequence corresponding to residues 30-110 of SEQ ID NO: 1. In some embodiments, the polypeptide is a polypeptide comprising an amino acid sequence that is at least 90% identical to the amino acid sequence corresponding to residues 21-135 of SEQ ID NO: 1. In some embodiments, the polypeptide is a polypeptide comprising an amino acid sequence that is at least 95% identical to the amino acid sequence corresponding to residues 21-135 of SEQ ID NO: 1.

In some embodiments, the polypeptide is a polypeptide comprising an amino acid sequence that is at least 99% identical to the amino acid sequence corresponding to residues 21-135 of SEQ ID NO: 1. In some embodiments, the polypeptide is a polypeptide comprising the amino acid sequence corresponding to residues 21-135 of SEQ ID NO: 1. In some embodiments, the polypeptide is a polypeptide consisting of the amino acid sequence corresponding to residues 21-135 of SEQ ID NO: 1. In some embodiments, the polypeptide is a polypeptide comprising an amino acid sequence that is at least 90% identical to the amino acid sequence of SEQ ID NO: 2. In some embodiments, the polypeptide is a polypeptide comprising an amino acid sequence that is at least 95% identical to the amino acid sequence of SEQ ID NO: 2. In some embodiments, the polypeptide is a polypeptide comprising an amino acid sequence that is at least 99% identical to the amino acid sequence of SEQ ID NO: 2. In some embodiments, the polypeptide is a polypeptide comprising the amino acid sequence of SEQ ID NO: 2. In some embodiments, the polypeptide is a polypeptide consisting of the amino acid sequence of SEQ ID NO: 2. In some embodiments, the polypeptide is a polypeptide comprising an amino acid sequence that is at least 90% identical to the amino acid sequence of SEQ ID NO: 3. In some embodiments, the polypeptide is a polypeptide comprising an amino acid sequence that is at least 95% identical to the amino acid sequence of SEQ ID NO: 3. In some embodiments, the polypeptide is a polypeptide comprising an amino acid sequence that is at least 99% identical to the amino acid sequence of SEQ ID NO: 3. In some embodiments, the polypeptide is a polypeptide comprising the amino acid sequence of SEQ ID NO: 3. In some embodiments, the polypeptide is a polypeptide consisting of the amino acid sequence of SEQ ID NO: 3.

In some embodiments, the polypeptide is a fusion protein further comprising an Fc domain of an immunoglobulin. In some embodiments, the immunoglobulin is an Fc domain of an IgG1 immunoglobulin. In some embodiments, the fusion protein further comprises a linker domain positioned between the polypeptide domain and the Fc domain of the immunoglobulin. In some embodiments, the linker domain is selected from the group consisting of: TGGG (SEQ ID NO: 20), TGGGG (SEQ ID NO: 18), SGGGG (SEQ ID NO: 19), GGGGS (SEQ ID NO: 22), GGG, GGGG (SEQ ID NO: 17), and SGGG (SEQ ID NO: 21). In some embodiments, the linker domain comprises TGGG (SEQ ID NO: 20). In some embodiments, the ActRII polypeptide comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of SEQ ID NO: 23. In some embodiments, the ActRII polypeptide comprises the amino acid sequence of SEQ ID NO: 23. In some embodiments, the ActRII polypeptide consists of the amino acid sequence of SEQ ID NO: 23. In some embodiments, the polypeptide is part of a homodimer protein complex. In some embodiments, the polypeptide is glycosylated. In some embodiments, the polypeptide binds to one or more ligands selected from the group consisting of: activin A, activin B, and GDF11. In some embodiments, the polypeptide further binds to one or more ligands selected from the group consisting of: BMP10, GDF8, and BMP6. In some embodiments, the polypeptide binds to activin and/or GDF11.

In some embodiments, the kit comprises one or more vials containing the lyophilized polypeptide. In some embodiments, the injection device comprises a pre-filled syringe. In some embodiments, the injection device comprises a pump apparatus. In some embodiments, the pump apparatus comprises an electromechanical pumping assembly. In some embodiments, the pump apparatus is a wearable pump apparatus. In some embodiments, the pre-filled syringe comprises a reconstitution solution. In some embodiments, the reconstitution solution comprises a pharmaceutically acceptable carrier and/or excipient. In some embodiments, the pharmaceutically acceptable carrier is selected from saline solution, purified water, or sterile water for injection. In some embodiments, the pharmaceutically acceptable excipient is selected from a buffering agent [e.g., citric acid (monohydrate) and/or trisodium citrate (dehydrate)], a surfactant (e.g., polysorbate 80), a stabilizer (e.g., sucrose), and a lyoprotectant (e.g., sucrose).

In some embodiments, the injection device comprises a vial adapter. In some embodiments, the vial adapter is capable of attaching to a vial. In some embodiments, the vial adapter is capable of attaching to a pre-filled syringe. In some embodiments, the pre-filled syringe and the vial are attached to opposite ends of the vial adapter. In some embodiments, the reconstitution solution is transferred from the pre-filled syringe to the vial. In some embodiments, the lyophilized polypeptide is reconstituted into a sterile injectable solution. In some embodiments, the lyophilized polypeptide is reconstituted into a sterile injectable solution prior to use. In some embodiments, the sterile injectable solution is sterile water for injection.

In some embodiments, the sterile injectable solution is administered parenterally. In some embodiments, the injection device is used to administer the sterile injectable solution parenterally. In some embodiments, the sterile injectable solution is administered via subcutaneous injection. In some embodiments, the sterile injectable solution is administered via intradermal injection. In some embodiments, the sterile injectable solution is administered via intramuscular injection. In some embodiments, the sterile injectable solution is administered via intravenous injection. In some embodiments, the sterile injectable solution is self-administered. In some embodiments, the sterile injectable solution comprises a therapeutically effective dose. In some embodiments, the therapeutically effective dose comprises a weight based dose. In some embodiments, the lyophilized polypeptide is administered every 4 weeks.

In some embodiments, the kit is used to treat post-capillary pulmonary hypertension (PcPH). In some embodiments, the PcPH is isolated post-capillary pulmonary hypertension (IpcPH). In some embodiments, the PcPH is combined post- and pre-capillary PH (CpcPH). In some embodiments, the patient has Group 2 pulmonary hypertension as recognized by the WHO. In some embodiments, the patient has pulmonary hypertension due to heart failure with preserved left ventricular ejection fraction (LVEF). In some embodiments, the patient has pulmonary hypertension due to heart failure with reduced left ventricular ejection fraction (LVEF). In some embodiments, the patient has valvular heart disease. In some embodiments, the patient has congenital/acquired cardiovascular conditions leading to post-capillary PH. In some embodiments, the patient has Group 5 pulmonary hypertension as recognized by the WHO. In some embodiments, the patient has pulmonary hypertension with unclear and/or multifactorial mechanisms. In some embodiments, the shelf life of the lyophilized polypeptide is at least 1, 1.5, 2, 2.5, or 3 years. In some embodiments, the lyophilized polypeptide is reconstituted. In some embodiments, the reconstituted polypeptide has a shelf life of at least 2 hrs, 3 hrs, or 4 hrs.

BRIEF DESCRIPTION OF THE DRAWINGS

FIG. 1 shows an alignment of extracellular domains of human ActRIIB (SEQ ID NO: 31) and human ActRIIA (SEQ ID NO: 42) with the residues that are deduced herein, based on composite analysis of multiple ActRIIB and ActRIIA crystal structures, to directly contact ligand indicated with boxes.

FIG. 2 shows a multiple sequence alignment of various vertebrate ActRIIA proteins and human ActRIIA (SEQ ID NOs: 6-10 and 36-38).

FIG. 3 shows multiple sequence alignment of Fc domains from human IgG isotypes using Clustal 2.1. Hinge regions are indicated by dotted underline. Double underline indicates examples of positions engineered in IgG1 Fc (SEQ ID NO: 32) to promote asymmetric chain pairing and the corresponding positions with respect to other isotypes IgG2 (SEQ ID NO: 33), IgG3 (SEQ ID NO: 34) and IgG4 (SEQ ID NO: 35).

FIGS. 4A and 4B show the purification of ActRIIA-hFc expressed in CHO cells. The protein purifies as a single, well-defined peak as visualized by sizing column (FIG. 4A) and Coomassie stained SDS-PAGE (FIG. 4B) (left lane: molecular weight standards; right lane: ActRIIA-hFc).

FIGS. 5A and 5B show the binding of ActRIIA-hFc to activin (FIG. 5A) and GDF-11 (FIG. 5B), as measured by Biacore™ assay.

FIGS. 10-14 show endpoints for left ventricle function, including changes in cardiac hypertrophy heart weight/body weight (HW/BW) (FIG. 10), LV function parameters fractional shorting (FIG. 11) and LV ejection fraction (FIG. 12); and LV diastolic function parameters E/E'[Ratio of mitrial inflow velocity (E) to mitrial annular velocity (E')](FIG. 13) and isovolumetric relaxation time (IVRT) (FIG. 14). Relative to “TAC-PH/PBS” treated mice, “TAC-PH/ActRIIA-mFc” treated mice demonstrated a significant effect of ActRIIA-mFc in reducing cardiac hypertrophy and improving cardiac function. Statistical significance (p value) is depicted as *p<0.05, p<0.01, *p<0.001, and ****p<0.0001 for comparison between “Sham” and sample “TAC-PH/PBS”. Statistical significance (p value) is depicted as #p<0.05, ##p<0.01, ###p<0.001, and ####p<0.0001 for comparison between “Sham” and sample “TAC-PH/ActRIIA-mFc”. Statistical significance (p value) is depicted as @p<0.05, @@p<0.01, @@@p<0.001, and @@@@p<0.0001 for comparison between sample “TAC-PH/PBS” and sample “TAC-PH/ActRIIA-mFc”.

FIGS. 15-18 show endpoints for right ventricle function, including RV remodeling parameter right ventricular free wall thickness (RVFWT) (FIG. 15), RV remodeling and function parameter tricuspid annular plane systolic excursion (TAPSE) (FIG. 16), and RV function parameters RV stroke work (FIG. 17) and RV contractility (dP/dT) (FIG. 18). Relative to “TAC-PH/PBS” treated mice, “TAC-PH/ActRIIA-mFc” treated mice demonstrated a significant effect of ActRIIA-mFc in improving right heart remodeling and function. Statistical significance (p value) is depicted as *p<0.05, p<0.01, *p<0.001, and ****p<0.0001 for comparison between “Sham” and sample “TAC-PH/PBS”. Statistical significance (p value) is depicted as #p<0.05, ##p<0.01, ###p<0.001, and ####p<0.0001 for comparison between “Sham” and sample “TAC-PH/ActRIIA-mFc”. Statistical significance (p value) is depicted as @p<0.05, @@p<0.01, @@@p<0.001, and @@@@p<0.0001 for comparison between sample “TAC-PH/PBS” and sample “TAC-PH/ActRIIA-mFc”.

FIGS. 19 and 20 show endpoints for lung remodeling, including ratio of lung weight to tibia length (LW/TL) (FIG. 19) and lung fibrosis percentage (FIG. 20). Relative to “TAC-PH/PBS” treated mice, “TAC-PH/ActRIIA-mFc” treated mice demonstrated a significant effect of ActRIIA-mFc in reducing pulmonary remodeling and fibrosis. Statistical significance (p value) is depicted as *p<0.05, p<0.01, *p<0.001, and ****p<0.0001 for comparison between “Sham” and sample “TAC-PH/PBS”. Statistical significance (p value) is depicted as #p<0.05, ##p<0.01, ###p<0.001, and ####p<0.0001 for comparison between “Sham” and sample “TAC-PH/ActRIIA-mFc”. Statistical significance (p value) is depicted as @p<0.05, @@p<0.01, @@@p<0.001, and @@@@p<0.0001 for comparison between sample “TAC-PH/PBS” and sample “TAC-PH/ActRIIA-mFc”.

FIGS. 23-25 show endpoints for left ventricular function, including the left ventricular ejection fraction (FIG. 23); LV diastolic function parameters E/E' [Ratio of mitrial inflow velocity (E) to mitrial annular velocity (E')] (FIG. 24); and isovolumetric relaxation time (IVRT) (FIG. 25). Statistical significance (p value) is depicted as $*p<0.05$, $p<0.01$, and $*p<0.001$.

FIGS. 26-28 show endpoints for left heart remodeling, including changes in ratio of heart weight to tibia length (HW/TL) (FIG. 26); interventricular septal dimension at diastole (IVSd) (FIG. 27); and left ventricular mass (LVM) (FIG. 28). Statistical significance (p value) is depicted as $*p<0.05$, $p<0.01$, and $*p<0.001$.

FIGS. 29-31 show endpoints for right ventricular function, including changes in right ventricular free wall thickness (FIG. 29); pulmonary artery acceleration time (PAAT) (FIG. 30); and right ventricular systolic pressure (RVSP) (FIG. 31). Statistical significance (p value) is depicted as $*p<0.05$ and $**p<0.01$.

FIGS. 32-34 show a reduction in fibrosis, including changes in left ventricular fibrosis (FIG. 32); right ventricular fibrosis (FIG. 33); and lung fibrosis (FIG. 34). Statistical significance (p value) is depicted as $*p<0.05$ and $**p<0.01$.

FIGS. 35-38 show endpoints for hyperglycemia and glucose intolerance, including changes in body weight (FIG. 35); fasting glucose (FIG. 36); blood glucose (FIG. 37); and glucose/creatine ratio (FIG. 38). Statistical significance (p value) is depicted as $*p<0.05$, $p<0.01$, and $*p<0.001$.

FIGS. 40-43 show endpoints for left ventricle function, including changes in cardiac hypertrophy heart weight/tibia length (HW/TL) (FIG. 41), LV function parameters such as LV ejection fraction (FIG. 40), LV diastolic function parameters E/E' [Ratio of mitral inflow velocity (E) to mitral annular velocity (E')](FIG. 42) and isovolumetric relaxation time (IVRT) (FIG. 43). Relative to "TAC PBS" treated mice, "TAC ActRIIA-mFc" treated mice demonstrated a significant effect of ActRIIA-mFc in inhibiting cardiac remodeling and improving LV function. Statistical significance (p value) is depicted as $*p<0.05$, $p<0.01$, $*p<0.001$, and $****p<0.0001$ for comparison between "TAC PBS" and sample "TAC ActRIIA-mFc". Statistical significance (p value) is depicted as $\#p<0.05$, $\#\#p<0.01$, $\#\#\#p<0.001$, and $\#\#\#\#p<0.0001$ for comparison between "Sham" and sample "TAC PBS."

FIGS. 44-46 show endpoints for right ventricle function including right ventricular systolic pressure (RVSP) (FIG. 44), right ventricular free wall thickness (RVFWT) (FIG. 45), and pulmonary artery acceleration time (PAAT) (FIG. 46). Relative to "TAC PBS" treated mice, "TAC ActRIIA-mFc" mice treated with either 3 mpk and 10 mpk demonstrated a significant effect of ActRIIA-mFc in reducing RVSP and improving RV function. Statistical significance (p value) is depicted as $*p<0.05$, $p<0.01$, $*p<0.001$, and $****p<0.0001$ for comparison between "TAC PBS" and sample "TAC ActRIIA-mFc." Statistical significance (p value) is depicted as $\#p<0.05$, $\#\#p<0.01$, $\#\#\#p<0.001$, and $\#\#\#\#p<0.0001$ for comparison between "Sham" and sample "TAC PBS."

FIGS. 47-49 show endpoints for fibrosis in the left ventricle (LV) (FIG. 47), right ventricle (RV) (FIG. 48), and lung (FIG. 49). Relative to "TAC PBS" treated mice, "TAC ActRIIA-mFc" mice treated with either 3 mpk or 10 mpk demonstrated a significant effect of ActRIIA-mFc in reducing fibrosis in the LV (FIG. 47), RV (FIG. 48), and lung (FIG. 49). Statistical significance (p value) is depicted as $*p<0.05$, $p<0.01$, $*p<0.001$, and $****p<0.0001$ for comparison between "TAC PBS" and sample "TAC ActRIIA-mFc." Statistical significance (p value) is depicted as $\#p<0.05$, $\#\#p<0.01$, $\#\#\#p<0.001$, and $\#\#\#\#p<0.0001$ for comparison between "Sham" and sample "TAC PBS."

FIGS. 51-55 show endpoints for right ventricular function, including changes in pulmonary artery acceleration time (PAAT) (FIG. 51); right ventricular systolic pressure (RVSP) (FIG. 52); right ventricular wall thickness (RVWT) (FIG. 53); tricuspid annular plane systolic excursion (TAPSE) (FIG. 54); and Fulton index, calculated as the ratio of right ventricular weight (RV) to weight of the combined left ventricle and septum (LV+S) (FIG. 55). Statistical significance (p value) is depicted as $*p<0.05$, $p<0.01$, $*p<0.001$, and $****p<0.0001$.

DETAILED DESCRIPTION

1. Overview

Figure 6:
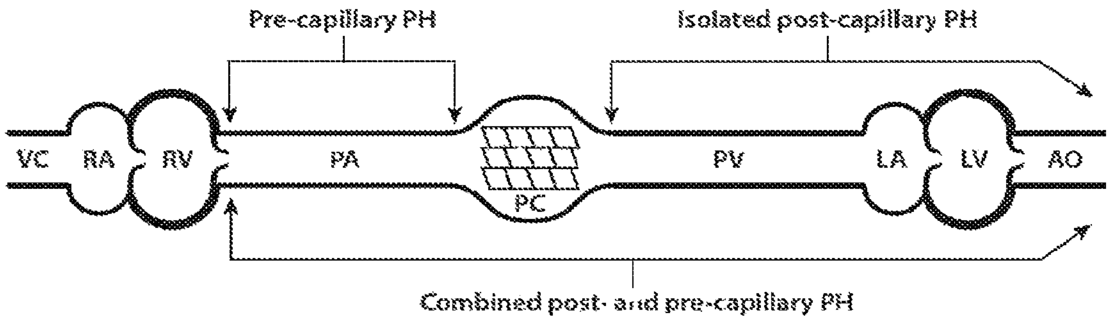
FIG. 6 shows a schematic image of a linearized version of cardiopulmonary circulation and the regions associated with various types of PH. The difference between pre-capillary pulmonary hypertension, isolated post-capillary pulmonary hypertension, and combined post- and pre-capillary pulmonary hypertension are based on pulmonary hemodynamic parameters and the involvement of various regions of the cardiopulmonary system (pre and/or post capillary regions). Abbreviations are as follows: VC—vena cava; RA—right atrium; RV—right ventricle; PA—pulmonary artery; PC—pulmonary capillaries; PV—pulmonary ventricles; LA—left atrium; LV—left ventricle; AO—Aorta. See, e.g., Aras M A, et al. Curr Cardiol Rep. 2019; 21(7):62 and Galib N. et al. Eur Heart J. 2018; 39(15):1265-1268.
Figure 7:
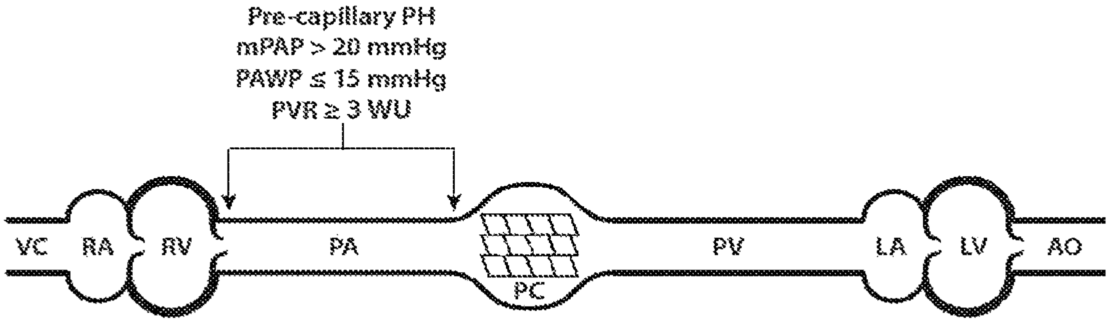
FIG. 7 shows a schematic image of a linearized version of cardiopulmonary circulation and the hemodynamic parameters associated with pre-capillary PH. Abbreviations are as follows: VC—vena cava; RA—right atrium; RV—right ventricle; PA—pulmonary artery; PC—pulmonary capillaries; PV—pulmonary ventricles; LA—left atrium; LV—left ventricle; AO—Aorta; mPAP—mean pulmonary arterial pressure; PAWP—pulmonary arterial wedge pressure; PVR—pulmonary vascular resistance. Id.
Figure 8:
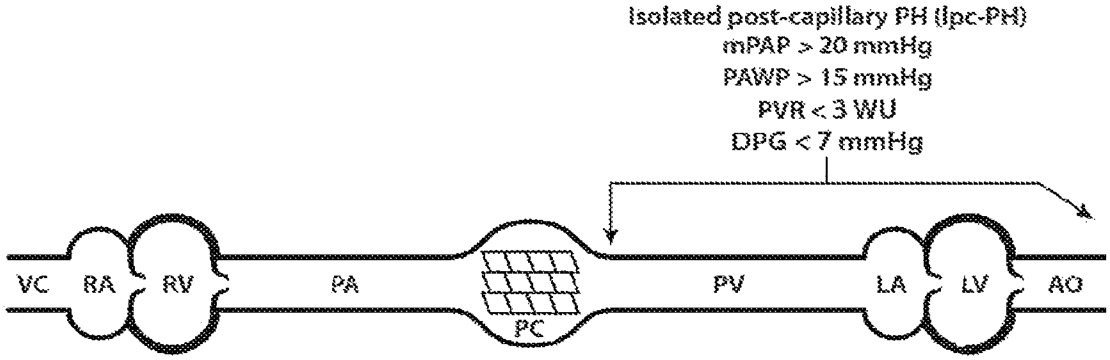
FIG. 8 shows a schematic image of a linearized version of cardiopulmonary circulation and the hemodynamic parameters associated with isolated post-capillary PH (IpcPH). Abbreviations are as follows: VC—vena cava; RA—right atrium; RV—right ventricle; PA—pulmonary artery; PC—pulmonary capillaries; PV—pulmonary ventricles; LA—left atrium; LV—left ventricle; AO—Aorta; mPAP—mean pulmonary arterial pressure; PAWP—pulmonary arterial wedge pressure; PVR—pulmonary vascular resistance. Id.
Figure 9:
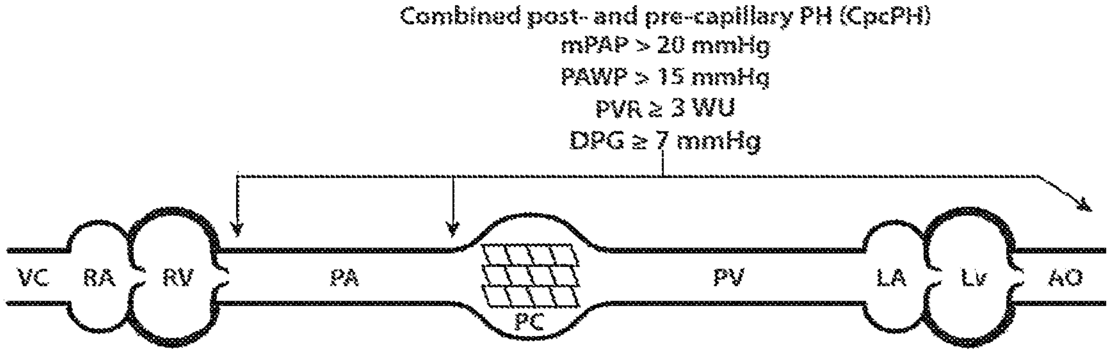
FIG. 9 shows a schematic image of a linearized version of cardiopulmonary circulation and the hemodynamic parameters associated with combined post- and pre-capillary PH (CpcPH). Abbreviations are as follows: VC—vena cava; RA—right atrium; RV—right ventricle; PA—pulmonary artery; PC—pulmonary capillaries; PV—pulmonary ventricles; LA—left atrium; LV—left ventricle; AO—Aorta; mPAP—mean pulmonary arterial pressure; PAWP—pulmonary arterial wedge pressure; PVR—pulmonary vascular resistance. Id.

The present disclosure relates to compositions and methods of treating post-capillary pulmonary hypertension (e.g., WHO Group 2 and/or Group 5 PH) comprising administering to a patient in need thereof an effective amount of an ActRII polypeptide as described herein. In certain embodiments, the present disclosure provides methods of treating or preventing post-capillary pulmonary hypertension (PcPH) in an individual in need thereof through administering to the individual a therapeutically effective amount of an ActRII polypeptide as described herein. In certain embodiments, the present disclosure provides methods of treating or preventing combined post- and pre-capillary PH in an individual in need thereof through administering to the individual a therapeutically effective amount of an ActRII polypeptide as described herein.

Pulmonary hypertension due to left heart disease (PH-LHD) (also known as WHO Group 2 PH) is a complex pathophenotype that, when present, may result in an increased susceptibility to adverse events and a worse clinical outcome. Among those patients with PH-LHD, two phenotypes have been described: 1) a group of isolated post-capillary (IpcPH) or "passive" PH in which elevated pulmonary pressures are reversible and in proportion to increases in left atrial pressure, and 2) a group with "pre-capillary" component [combined post-capillary and pre-capillary PH (CpcPH)] whose pulmonary hypertension is worse than can be fully explained by passive elevation secondary to elevated left atrial pressure. This latter group, CpcPH, may have comorbid pulmonary vascular remodeling and therefore may demonstrate persistent PH after interventions to lower left sided filling pressures.

PH-LHD is sometimes defined as patients having a pulmonary capillary wedge pressure (PCWP) >15 mmHg and a mean pulmonary artery pressure (mPAP) ≥25 mmHg (or a mean pulmonary artery pressure (mPAP) ≥20 mmHg under updated guidelines). PH-LHD occurs as a consequence of the backward transmission of high left sided filling pressures, mainly driven by LV diastolic function, directly to the post-capillary pulmonary vessels and, thereby, to the rest of the pulmonary circulation. In some embodiments, PH-LHD is driven by both systolic and diastolic dysfunction. PH-LHD may be associated with or caused by PH due to heart failure with preserved left ventricle ejection fraction (LVEF) [also known as HFpEF], PH due to heart failure with reduced LVEF (also known as HFrEF), valvular heart disease, or congenital/acquired cardiovascular conditions leading to post-capillary PH. Compared with PAH, patients with PH-LHD are often older, female, with a higher prevalence of cardiovascular co-morbidities and most, if not all, of the features of metabolic syndrome.

For WHO Group 2 (PH-LHD) and Group 5 PH patients, there are no approved specific therapies available beyond treatment of the underlying disease. Most PH-LHD therapies target the underlying condition (e.g., repair of valvular heart disease) rather than specifically treating PH. The lack of specific therapies is particularly problematic because PH-LHD is the most common cause of PH in western countries and its presence commonly results in adverse course of the disease. Specifically, the presence of PH-LHD can result in more severe symptoms in LHD, worse exercise tolerance, and a negative impact on outcome. Accordingly, there is a high unmet need for new treatments for post-capillary pulmonary hypertension (e.g., WHO Group 2 and/or Group 5 PH) and these treatments would have the potential to positively affect large numbers of patients.

The terms used in this specification generally have their ordinary meanings in the art, within the context of this disclosure and in the specific context where each term is used. Certain terms are discussed below or elsewhere in the specification to provide additional guidance to the practitioner in describing the compositions and methods of the disclosure and how to make and use them. The scope or meaning of any use of a term will be apparent from the specific context in which it is used.

The term "sequence similarity," in all its grammatical forms, refers to the degree of identity or correspondence between nucleic acid or amino acid sequences that may or may not share a common evolutionary origin.

"Percent (%) sequence identity" with respect to a reference polypeptide (or nucleotide) sequence is defined as the percentage of amino acid residues (or nucleic acids) in a candidate sequence that are identical to the amino acid residues (or nucleic acids) in the reference polypeptide (nucleotide) sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid (nucleic acid) sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

"Agonize", in all its grammatical forms, refers to the process of activating a protein and/or gene (e.g., by activating or amplifying that protein's gene expression or by inducing an inactive protein to enter an active state) or increasing a protein's and/or gene's activity.

"Antagonize", in all its grammatical forms, refers to the process of inhibiting a protein and/or gene (e.g., by inhibiting or decreasing that protein's gene expression or by inducing an active protein to enter an inactive state) or decreasing a protein's and/or gene's activity.

The terms "about" and "approximately" as used in connection with a numerical value throughout the specification and the claims denotes an interval of accuracy, familiar and acceptable to a person skilled in the art. In general, such interval of accuracy is ±10%. Alternatively, and particularly in biological systems, the terms "about" and "approximately" may mean values that are within an order of magnitude, preferably ≤5-fold and more preferably ≤2-fold of a given value.

Numeric ranges disclosed herein are inclusive of the numbers defining the ranges.

The terms "a" and "an" include plural referents unless the context in which the term is used clearly dictates otherwise. The terms "a" (or "an"), as well as the terms "one or more," and "at least one" can be used interchangeably herein. Furthermore, "and/or" where used herein is to be taken as specific disclosure of each of the two or more specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Throughout this specification, the word "comprise" or variations such as "comprises" or "comprising" will be understood to imply the inclusion of a stated integer or groups of integers but not the exclusion of any other integer or group of integers.

2. ActRII Polypeptides

In certain aspects, the disclosure relates to ActRII polypeptides and uses thereof (e.g., of treating, preventing, or reducing the progression rate and/or severity of post-capillary pulmonary hypertension (PcPH) or one or more complications of PcPH). As used herein, the term "ActRII" refers to the family of type II activin receptors. This family includes activin receptor type IIA (ActRIIA) and activin receptor type IIB (ActRIIB).

In certain embodiments, the present disclosure relates to ActRII polypeptides having an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence as set forth in anyone of SEQ ID NOs: 1, 2, 3, 23, 27, 30, and 41. In other embodiments, the present disclosure relates to ActRII polypeptides having an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to an amino acid sequence as set forth in anyone of SEQ ID NOs: 31, 39, and 40. As used herein, the term "ActRII" refers to a family of activin receptor type IIA (ActRIIA) proteins, a family of activin receptor type IIB (ActRIIB) proteins, or combinations and/or variants thereof. The ActRII polypeptides can be derived from any species and include variants derived from such ActRII proteins by mutagenesis or other modification. Reference to ActRII herein is understood to be a reference to any one of the currently identified forms. Members of the ActRII family are generally transmembrane proteins, composed of a ligand-binding extracellular domain comprising a cysteine-rich region, a transmembrane domain, and a cytoplasmic domain with predicted serine/threonine kinase activity.

The term ActRII polypeptide includes polypeptides comprising any naturally occurring polypeptide of an ActRII family member as well as any variants thereof (including mutants, fragments, fusions, and peptidomimetic forms) that retain a useful activity. Examples of such variant ActRII polypeptides are provided throughout the present disclosure as well as in International Patent Application Publication Nos. WO 2006/012627, WO 2007/062188, WO 2008/097541, WO 2010/151426, and WO 2011/020045, which are incorporated herein by reference in their entirety. Numbering of amino acids for all ActRII-related polypeptides described herein is based on the numbering of the human ActRII precursor protein sequence provided below (SEQ ID NO: 1), unless specifically designated otherwise.

The canonical human ActRII precursor protein sequence is as follows:

```
                                                  (SEQ ID NO: 1)
1     MGAAAKLAFA VFLISCSSGA ILGRSETQEC LFFNANWEKD RTNQTGVEPC
51    YGDKDKRRHC FATWKNISGS IEIVKQGCWL DDINCYDRTD CVEKKDSPEV
101   YFCCCEGNMC NEKFSYFPEM EVTQPTSNPV TPKPPYYNIL LYSLVPLMLI
151   AGIVICAFWV YRHHKMAYPP VLVPTQDPGP PPPSPLLGLK PLQLLEVKAR
201   GRFGCVWKAQ LLNEYVAVKI FPIQDKQSWQ NEYEVYSLPG MKHENILQFI
251   GAEKRGTSVD VDLWLITAFH EKGSLSDFLK ANVVSWNELC HIAETMARGL
301   AYLHEDIPGL KDGHKPAISH RDIKSKNVLL KNNLTACIAD FGLALKFEAG
351   KSAGDTHGQV GTRRYMAPEV LEGAINFQRD AFLRIDMYAM GLVLWELASR
401   CTAADGPVDE YMLPFEEEIG QHPSLEDMQE VVVHKKKRPV LRDYWQKHAG
451   MAMLCETIEE CWDHDAEARL SAGCVGERIT QMQRLTNIIT TEDIVTVVTM
501   VTNVDFPPKE SSL
```

The signal peptide is indicated by a single underline; the extracellular domain is indicated in bold font; and the potential, endogenous N-linked glycosylation sites are indicated by a double underline.

A processed (mature) extracellular human ActRII polypeptide sequence is as follows:

```
                                                  (SEQ ID NO: 2)
ILGRSETQECLFFNANWEKDRTNQTGVEPCYGDKDKRRHCFATWKNISG
SIEIVKQGCWLDDINCYDRTDCVEKKDSPEVYFCCCEGNMCNEKFSYFP
EMEVTQPTSNPVTPKPP
```

The C-terminal "tail" of the extracellular domain is indicated by single underline. The sequence with the "tail" deleted (a Δ15 sequence) is as follows:

```
                                                  (SEQ ID NO: 3)
ILGRSETQECLFFNANWEKDRTNQTGVEPCYGDKDKRRHCFATWKNISG
SIEIVKQGCWLDDINCYDRTDCVEKKDSPEVYFCCCEGNMCNEKFSYFP
EM
```

The nucleic acid sequence encoding human ActRII precursor protein is shown below (SEQ ID NO: 4), as follows nucleotides 159-1700 of Genbank Reference Sequence NM_001616.4. The signal sequence is underlined.

(SEQ ID NO: 4)

```
   1 ATGGGAGCTG CTGCAAAGTT GGCGTTTGCC GTCTTTCTTA TCTCCTGTTC
  51 TTCAGGTGCT ATACTTGGTA GATCAGAAAC TCAGGAGTGT CTTTTCTTTA
 101 ATGCTAATTG GGAAAAAGAC AGAACCAATC AAACTGGTGT TGAACCGTGT
 151 TATGGTGACA AAGATAAACG GCGGCATTGT TTTGCTACCT GGAAGAATAT
 201 TTCTGGTTCC ATTGAAATAG TGAAACAAGG TTGTTGGCTG GATGATATCA
 251 ACTGCTATGA CAGGACTGAT TGTGTAGAAA AAAAAGACAG CCCTGAAGTA
 301 TATTTTTGTT GCTGTGAGGG CAATATGTGT AATGAAAAGT TTTCTTATTT
 351 TCCGGAGATG GAAGTCACAC AGCCCACTTC AAATCCAGTT ACACCTAAGC
 401 CACCCTATTA CAACATCCTG CTCTATTCCT TGGTGCCACT TATGTTAATT
 451 GCGGGGATTG TCATTTGTGC ATTTTGGGTG TACAGGCATC ACAAGATGGC
 501 CTACCCTCCT GTACTTGTTC CAACTCAAGA CCCAGGACCA CCCCCACCTT
 551 CTCCATTACT AGGTTTGAAA CCACTGCAGT TATTAGAAGT GAAAGCAAGG
 601 GGAAGATTTG GTTGTGTCTG GAAAGCCCAG TTGCTTAACG AATATGTGGC
 651 TGTCAAAATA TTTCCAATAC AGGACAAACA GTCATGGCAA AATGAATACG
 701 AAGTCTACAG TTTGCCTGGA ATGAAGCATG AGAACATATT ACAGTTCATT
 751 GGTGCAGAAA AACGAGGCAC CAGTGTTGAT GTGGATCTTT GGCTGATCAC
 801 AGCATTTCAT GAAAAGGGTT CACTATCAGA CTTTCTTAAG GCTAATGTGG
 851 TCTCTTGGAA TGAACTGTGT CATATTGCAG AAACCATGGC TAGAGGATTG
 901 GCATATTTAC ATGAGGATAT ACCTGGCCTA AAAGATGGCC ACAAACCTGC
 951 CATATCTCAC AGGGACATCA AAAGTAAAAA TGTGCTGTTG AAAAACAACC
1001 TGACAGCTTG CATTGCTGAC TTTGGGTTGG CCTTAAAATT TGAGGCTGGC
1051 AAGTCTGCAG GCGATACCCA TGGACAGGTT GGTACCCGGA GGTACATGGC
1101 TCCAGAGGTA TTAGAGGGTG CTATAAACTT CCAAAGGGAT GCATTTTTGA
1151 GGATAGATAT GTATGCCATG GGATTAGTCC TATGGGAACT GGCTTCTCGC
1201 TGTACTGCTG CAGATGGACC TGTAGATGAA TACATGTTGC CATTTGAGGA
1251 GGAAATTGGC CAGCATCCAT CTCTTGAAGA CATGCAGGAA GTTGTTGTGC
1301 ATAAAAAAAA GAGGCCTGTT TTAAGAGATT ATTGGCAGAA ACATGCTGGA
1351 ATGGCAATGC TCTGTGAAAC CATTGAAGAA TGTTGGGATC ACGACGCAGA
1401 AGCCAGGTTA TCAGCTGGAT GTGTAGGTGA AAGAATTACC CAGATGCAGA
1451 GACTAACAAA TATTATTACC ACAGAGGACA TTGTAACAGT GGTCACAATG
1501 GTGACAAATG TTGACTTTCC TCCCAAAGAA TCTAGTCTA
```

The nucleic acid sequence encoding processed soluble (extracellular) human ActRII polypeptide is as follows:

(SEQ ID NO: 5)

```
   1 ATACTTGGTA GATCAGAAAC TCAGGAGTGT CTTTTCTTTA ATGCTAATTG
  51 GGAAAAAGAC AGAACCAATC AAACTGGTGT TGAACCGTGT TATGGTGACA
 101 AAGATAAACG GCGGCATTGT TTTGCTACCT GGAAGAATAT TTCTGGTTCC
 151 ATTGAAATAG TGAAACAAGG TTGTTGGCTG GATGATATCA ACTGCTATGA
 201 CAGGACTGAT TGTGTAGAAA AAAAAGACAG CCCTGAAGTA TATTTTTGTT
```

-continued

```
251  GCTGTGAGGG CAATATGTGT AATGAAAAGT TTTCTTATTT TCCGGAGATG

301  GAAGTCACAC AGCCCACTTC AAATCCAGTT ACACCTAAGC CACCC
```

ActRII is well-conserved among vertebrates, with large stretches of the extracellular domain completely conserved. For example, FIG. 2 depicts a multi-sequence alignment of a human ActRII extracellular domain compared to various ActRII orthologs. Many of the ligands that bind to ActRII are also highly conserved. Accordingly, from these alignments, it is possible to predict key amino acid positions within the ligand-binding domain that are important for normal ActRII-ligand binding activities as well as to predict amino acid positions that are likely to be tolerant to substitution without significantly altering normal ActRII-ligand binding activities. Therefore, an active, human ActRII variant polypeptide useful in accordance with the presently disclosed methods may include one or more amino acids at corresponding positions from the sequence of another vertebrate ActRII, or may include a residue that is similar to that in the human or other vertebrate sequences.

An alignment of the amino acid sequences of human ActRIIA extracellular domain and human ActRIIB extracellular domain are illustrated in FIG. 1. This alignment indicates amino acid residues within both receptors that are believed to directly contact ActRII ligands. For example, the composite ActRII structures indicated that the ActRIIA-ligand binding pocket is defined, in part, by residues F31, N33, N35, K38 through T41, E47, Y50, K53 through K55, R57, H58, F60, T62, K74, W78 through N83, Y85, R87, E92, and K94 through F101. At these positions, it is expected that conservative mutations will be tolerated.

Without meaning to be limiting, the following examples illustrate this approach to defining an active ActRII variant. As illustrated in FIG. 2, F13 in the human extracellular domain is Y in *Ovis aries* (SEQ ID NO: 7), *Gallus gallus* (SEQ ID NO: 10), *Bos Taurus* (SEQ ID NO: 36), *Tyto alba* (SEQ ID NO: 37), and *Myotis davidii* (SEQ ID NO: 38) ActRII, indicating that aromatic residues are tolerated at this position, including F, W, and Y. Q24 in the human extracellular domain is R in *Bos Taurus* ActRII, indicating that charged residues will be tolerated at this position, including D, R, K, H, and E. S95 in the human extracellular domain is F in *Gallus gallus* and *Tyto alba* ActRII, indicating that this site may be tolerant of a wide variety of changes, including polar residues, such as E, D, K, R, H, S, T, P, G, Y, and probably hydrophobic residue such as L, I, or F. E52 in the human extracellular domain is D in *Ovis aries* ActRII, indicating that acidic residues are tolerated at this position, including D and E. P29 in the human extracellular domain is relatively poorly conserved, appearing as S in *Ovis aries* ActRII and L in *Myotis davidii* ActRII, thus essentially any amino acid should be tolerated at this position.

Moreover, as discussed above, ActRII proteins have been characterized in the art in terms of structural/functional characteristics, particularly with respect to ligand binding [Attisano et al. (1992) Cell 68(1):97-108; Greenwald et al. (1999) Nature Structural Biology 6(1): 18-22; Allendorph et al. (2006) PNAS 103(20: 7643-7648; Thompson et al. (2003) The EMBO Journal 22(7): 1555-1566; as well as U.S. Pat. Nos. 7,709,605, 7,612,041, and 7,842,663]. For example, a defining structural motif known as a three-finger toxin fold is important for ligand binding by type I and type II receptors and is formed by conserved cysteine residues located at varying positions within the extracellular domain of each monomeric receptor [Greenwald et al. (1999) Nat Struct Biol 6:18-22; and Hinck (2012) FEBS Lett 586:1860-1870]. In addition to the teachings herein, these references provide amply guidance for how to generate ActRII variants that retain one or more desired activities (e.g., ligand-binding activity).

For example, a defining structural motif known as a three-finger toxin fold is important for ligand binding by type I and type II receptors and is formed by conserved cysteine residues located at varying positions within the extracellular domain of each monomeric receptor [Greenwald et al. (1999) Nat Struct Biol 6:18-22; and Hinck (2012) FEBS Lett 586:1860-1870]. Accordingly, the core ligand-binding domains of human ActRII, as demarcated by the outermost of these conserved cysteines, corresponds to positions 30-110 of SEQ ID NO: 1 (ActRII precursor). Therefore, the structurally less-ordered amino acids flanking these cysteine-demarcated core sequences can be truncated by about 1, 2, 3, 4, 5, 6, 7, 8, 9, 10, 11, 12, 13, 14, 15, 16, 17, 18, 19, 20, 21, 22, 23, 24, 25, 26, 27, 28, or 29 residues at the N-terminus and by about 1, 2, 3, 4, 5, 6, 7, 8, 9, 10, 11, 12, 13, 14, 15, 16, 17, 18, 19, 20, 21, 22, 23, 24, or 25 residues at the C-terminus without necessarily altering ligand binding. Exemplary ActRII extracellular domains truncations include SEQ ID NOs: 2 and 3.

Accordingly, a general formula for an active portion (e.g., ligand binding) of ActRII is a polypeptide that comprises, consists essentially of, or consists of amino acids 30-110 of SEQ ID NO: 1. Therefore ActRII polypeptides may, for example, comprise, consists essentially of, or consists of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRII beginning at a residue corresponding to any one of amino acids 21-30 (e.g., beginning at any one of amino acids 21, 22, 23, 24, 25, 26, 27, 28, 29, or 30) of SEQ ID NO: 1 and ending at a position corresponding to any one amino acids 110-135 (e.g., ending at any one of amino acids 110, 111, 112, 113, 114, 115, 116, 117, 118, 119, 120, 121, 122, 123, 124, 125, 126, 127, 128, 129, 130, 131, 132, 133, 134, or 135) of SEQ ID NO: 1. Other examples include constructs that begin at a position selected from 21-30 (e.g., beginning at any one of amino acids 21, 22, 23, 24, 25, 26, 27, 28, 29, or 30), 22-30 (e.g., beginning at any one of amino acids 22, 23, 24, 25, 26, 27, 28, 29, or 30), 23-30 (e.g., beginning at any one of amino acids 23, 24, 25, 26, 27, 28, 29, or 30), 24-30 (e.g., beginning at any one of amino acids 24, 25, 26, 27, 28, 29, or 30) of SEQ ID NO: 1, and end at a position selected from 111-135 (e.g., ending at any one of amino acids 111, 112, 113, 114, 115, 116, 117, 118, 119, 120, 121, 122, 123, 124, 125, 126, 127, 128, 129, 130, 131, 132, 133, 134 or 135), 112-135 (e.g., ending at any one of amino acids 112, 113, 114, 115, 116, 117, 118, 119, 120, 121, 122, 123, 124, 125, 126, 127, 128, 129, 130, 131, 132, 133, 134 or 135), 113-135 (e.g., ending at any one of amino acids 113, 114, 115, 116, 117, 118, 119, 120, 121, 122, 123, 124, 125, 126, 127, 128, 129, 130, 131, 132, 133, 134 or 135), 120-135 (e.g., ending at any one of amino acids 120, 121, 122, 123, 124, 125, 126, 127, 128, 129, 130, 131, 132, 133, 134 or 135), 130-135 (e.g., ending at any one of amino acids 130, 131, 132, 133, 134 or 135), 111-134 (e.g., ending at any one of amino acids 110, 111, 112, 113, 114, 115, 116, 117, 118, 119, 120, 121, 122, 123, 124, 125, 126, 127, 128, 129, 130, 131, 132, 133, or 134), 111-133 (e.g., ending at any one of amino acids 110, 111, 112, 113, 114, 115, 116, 117, 118, 119, 120, 121, 122, 123, 124, 125, 126, 127, 128, 129, 130, 131, 132, or 133), 111-132 (e.g., ending at any one of amino acids 110, 111, 112, 113, 114, 115, 116, 117, 118, 119, 120, 121, 122, 123, 124, 125, 126, 127, 128, 129, 130, 131, or 132), or 111-131 (e.g., ending at any one of amino acids 110, 111, 112, 113, 114, 115, 116, 117, 118, 119, 120, 121, 122, 123, 124, 125, 126, 127, 128, 129, 130, or 131) of SEQ ID NO: 1. Variants within these ranges are also contemplated, particularly those comprising, consisting essentially of, or consisting of an amino acid sequence that has at least 70%, 75%, 80%, 85%, 86%, 87%, 88%, 89%, 90%, 91%, 92%, 93%, 94%, 95%, 96%, 97%, 98%, 99%, or 100% identity to the corresponding portion of SEQ ID NO: 1. Thus, in some embodiments, an ActRII polypeptide may comprise, consists essentially of, or consist of a polypeptide that is at least 70%, 75%, 80%, 85%, 86%, 87%, 88%, 89%, 90%, 91%, 92%, 93%, 94%, 95%, 96%, 97%, 98%, 99%, or 100% identical to amino acids 30-110 of SEQ ID NO: 1. Optionally, ActRII polypeptides comprise a polypeptide that is at least 70%, 75%, 80%, 85%, 86%, 87%, 88%, 89%, 90%, 91%, 92%, 93%, 94%, 95%, 96%, 97%, 98%, 99%, or 100% identical to amino acids 30-110 of SEQ ID NO: 1, and comprising no more than 1, 2, 5, 10 or 15 conservative amino acid changes in the ligand-binding pocket.

In certain embodiments, the disclosure relates to an ActRII polypeptide, which includes fragments, functional variants, and modified forms thereof as well as uses thereof (e.g., treating, preventing, or reducing the post-capillary pulmonary hypertension). Preferably, ActRII polypeptides are soluble (e.g., an extracellular domain of ActRII). In some embodiments, ActRII polypeptides inhibit (e.g., Smad signaling) of one or more GDF/BMP ligands [e.g., GDF11, GDF8, activin A, activin B, GDF3, BMP4, BMP6, BMP10, and/or BMP15]. In some embodiments, ActRII polypeptides bind to one or more GDF/BMP ligands [e.g., GDF11, GDF8, activin A, activin B, GDF3, BMP4, BMP6, BMP10, and/or BMP15]. In some embodiments, ActRII polypeptide of the disclosure comprise, consist essentially of, or consist of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of ActRII beginning at a residue corresponding to amino acids 21-30 (e.g., beginning at any one of amino acids 21, 22, 23, 24, 25, 26, 27, 28, 29, or 30) of SEQ ID NO: 1 and ending at a position corresponding to any one amino acids 110-135 (e.g., ending at any one of amino acids 110, 111, 112, 113, 114, 115, 116, 117, 118, 119, 120, 121, 122, 123, 124, 125, 126, 127, 128, 129, 130, 131, 132, 133, 134 or 135) of SEQ ID NO: 1. In some embodiments, ActRII polypeptides comprise, consist, or consist essentially of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 30-110 of SEQ ID NO: 1. In certain embodiments, ActRII polypeptides comprise, consist, or consist essentially of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical amino acids 21-135 of SEQ ID NO: 1. In some embodiments, ActRII polypeptides comprise, consist, or consist essentially of an amino acid sequence that is at least 70%, 75%, 80%, 85%, 86%, 87%, 88%, 89%, 90%, 91%, 92%, 93%, 94%, 95%, 97%, 98%, 99%, or 100% identical to the amino acid sequence of any one of SEQ ID NOs: 1, 2, 3, 23, 27, 30, and 41.

In some embodiments, ActRII polypeptides comprise, consist, or consist essentially of an amino acid sequence that is at least 70%, 75%, 80%, 85%, 86%, 87%, 88%, 89%, 90%, 91%, 92%, 93%, 94%, 95%, 97%, 98%, 99%, or 100% identical to the amino acid sequence of SEQ ID NO: 23. In some alternative embodiments, the ActRII polypeptide (e.g., SEQ ID NO: 23) may lack the C-terminal lysine. In some embodiments, the ActRII polypeptide lacking the C-terminal lysine is SEQ ID NO: 41. In some embodiments, the ActRII polypeptides comprise, consist, or consist essentially of an amino acid sequence that is at least 70%, 75%, 80%, 85%, 86%, 87%, 88%, 89%, 90%, 91%, 92%, 93%, 94%, 95%, 97%, 98%, 99%, or 100% identical to the amino acid sequence of SEQ ID NO: 41. In some embodiments, a patient is administered an ActRII polypeptide comprising, consisting, or consisting essentially of an amino acid sequence that is at least 70%, 75%, 80%, 85%, 86%, 87%, 88%, 89%, 90%, 91%, 92%, 93%, 94%, 95%, 97%, 98%, 99%, or 100% identical to the amino acid sequence of SEQ ID NO: 23. In some embodiments, a patient is administered an ActRII polypeptide comprising, consisting, or consisting essentially of an amino acid sequence that is at least 70%, 75%, 80%, 85%, 86%, 87%, 88%, 89%, 90%, 91%, 92%, 93%, 94%, 95%, 97%, 98%, 99%, or 100% identical to the amino acid sequence of SEQ ID NO: 41. In some embodiments, a patient is administered a combination of SEQ ID NO: 23 and SEQ ID NO: 41.

In certain aspects, the present disclosure relates to ActRII polypeptides. In some embodiments, ActRII traps of the present disclosure are variant ActRII polypeptides (e.g., ActRIIA polypeptides, ActRIIB polypeptides, or combinations thereof) that comprise one or more mutations (e.g., amino acid additions, deletions, substitutions, and combinations thereof) in the extracellular domain (also referred to as the ligand-binding domain) of an ActRII polypeptide (e.g., a "wild-type" or unmodified ActRII polypeptide) such that the variant ActRII polypeptide has one or more altered ligand-binding activities than the corresponding wild-type ActRII polypeptide. In preferred embodiments, variant ActRII polypeptides of the present disclosure retain at least one similar activity as a corresponding wild-type ActRII polypeptide. For example, preferable ActRII polypeptides bind to and inhibit (e.g. antagonize) the function of GDF11 and/or GDF8. In some embodiments, ActRII polypeptides of the present disclosure further bind to and inhibit one or more of ligand of the GDF/BMP [e.g., GDF11, GDF8, activin A, activin B, GDF3, BMP4, BMP6, BMP10, and/or BMP15]. Accordingly, the present disclosure provides ActRII polypeptides that have an altered binding specificity for one or more ActRII ligands.

To illustrate, one or more mutations may be selected that increase the selectivity of the altered ligand-binding domain for GDF11 and/or GDF8 over one or more ActRII-binding ligands such as activins (activin A or activin B), particularly activin A. Optionally, the altered ligand-binding domain has a ratio of $K_d$ for activin binding to $K_d$ for GDF11 and/or GDF8 binding that is at least 2-, 5-, 10-, 20-, 50-, 100- or even 1000-fold greater relative to the ratio for the wild-type ligand-binding domain. Optionally, the altered ligand-binding domain has a ratio of $IC_{50}$ for inhibiting activin to $IC_{50}$ for inhibiting GDF11 and/or GDF8 that is at least 2-, 5-, 10-, 20-, 50-, 100- or even 1000-fold greater relative to the wild-type ligand-binding domain. Optionally, the altered ligand-binding domain inhibits GDF11 and/or GDF8 with an $IC_{50}$ at least 2-, 5-, 10-, 20-, 50-, 100- or even 1000-times less than the $IC_{50}$ for inhibiting activin.

In certain embodiments, the present disclosure contemplates specific mutations of an ActRII polypeptide so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine or asparagine-X-serine (where "X" is any amino acid) which is specifically recognized by appropriate cellular glycosylation enzymes. The alteration may also be made by the addition of, or substitution by, one or more serine or threonine residues to the sequence of the polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on a polypeptide is by chemical or enzymatic coupling of glycosides to the polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. Removal of one or more carbohydrate moieties present on a polypeptide may be accomplished chemically and/or enzymatically. Chemical deglycosylation may involve, for example, exposure of a polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Enzymatic cleavage of carbohydrate moieties on polypeptides can be achieved by the use of a variety of endo- and exo-glycosidases as described by Thotakura et al. [Meth. Enzymol. (1987) 138:350]. The sequence of a polypeptide may be adjusted, as appropriate, depending on the type of expression system used, as mammalian, yeast, insect, and plant cells may all introduce differing glycosylation patterns that can be affected by the amino acid sequence of the peptide. In general, polypeptides of the present disclosure for use in humans may be expressed in a mammalian cell line that provides proper glycosylation, such as HEK293 or CHO cell lines, although other mammalian expression cell lines are expected to be useful as well.

The present disclosure further contemplates a method of generating mutants, particularly sets of combinatorial mutants of an ActRII polypeptide as well as truncation mutants. Pools of combinatorial mutants are especially useful for identifying functionally active (e.g., GDF/BMP ligand binding) ActRII sequences. The purpose of screening such combinatorial libraries may be to generate, for example, polypeptides variants, which have altered properties, such as altered pharmacokinetic or altered ligand binding. A variety of screening assays are provided below, and such assays may be used to evaluate variants. For example, ActRII variants may be screened for ability to bind to one or more GDF/BMP ligands [e.g., GDF11, GDF8, activin A, activin B, GDF3, BMP4, BMP6, BMP10, and/or BMP15], to prevent binding of a GDF/BMP ligand to an ActRII polypeptide, as well as heteromultimers thereof, and/or to interfere with signaling caused by an GDF/BMP ligand.

The activity of ActRII polypeptides or variants thereof may also be tested in a cell-based or in vivo assay. For example, the effect of an ActRII polypeptide on the expression of genes involved in PcPH pathogenesis may be assessed. This may, as needed, be performed in the presence of one or more recombinant ligand proteins [e.g., GDF11, GDF8, activin A, activin B, GDF3, BMP4, BMP6, BMP10, and/or BMP15], and cells may be transfected so as to produce an ActRII polypeptide, and optionally, an GDF/BMP ligand. Likewise, an ActRII polypeptide may be administered to a mouse or other animal and effects on PcPH pathogenesis may be assessed using art-recognized methods. Similarly, the activity of an ActRII polypeptide or variant thereof may be tested in blood cell precursor cells for any effect on growth of these cells, for example, by the assays as described herein and those of common knowledge in the art. A SMAD-responsive reporter gene may be used in such cell lines to monitor effects on downstream signaling.

Combinatorial-derived variants can be generated which have increased selectivity or generally increased potency relative to a reference ActRII polypeptide. Such variants, when expressed from recombinant DNA constructs, can be used in gene therapy protocols. Likewise, mutagenesis can give rise to variants which have intracellular half-lives dramatically different than the corresponding unmodified ActRII polypeptide. For example, the altered protein can be rendered either more stable or less stable to proteolytic degradation or other cellular processes which result in destruction, or otherwise inactivation, of an unmodified polypeptide. Such variants, and the genes which encode them, can be utilized to alter polypeptide complex levels by modulating the half-life of the polypeptide. For instance, a short half-life can give rise to more transient biological effects and, when part of an inducible expression system, can allow tighter control of recombinant polypeptide complex levels within the cell. In an Fc fusion protein, mutations may be made in the linker (if any) and/or the Fc portion to alter the half-life of the ActRII polypeptide.

A combinatorial library may be produced by way of a degenerate library of genes encoding a library of polypeptides which each include at least a portion of potential ActRII polypeptide sequences. For instance, a mixture of synthetic oligonucleotides can be enzymatically ligated into gene sequences such that the degenerate set of potential ActRII encoding nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes can then be ligated into an appropriate vector for expression. The synthesis of degenerate oligonucleotides is well known in the art [Narang, SA (1983) Tetrahedron 39:3; Itakura et al. (1981) Recombinant DNA, Proc. 3rd Cleveland Sympos. Macromolecules, ed. AG Walton, Amsterdam: Elsevier pp 273-289; Itakura et al. (1984) Annu. Rev. Biochem. 53:323; Itakura et al. (1984) Science 198:1056; and Ike et al. (1983) Nucleic Acid Res. 11:477]. Such techniques have been employed in the directed evolution of other proteins [Scott et al., (1990) Science 249:386-390; Roberts et al. (1992) PNAS USA 89:2429-2433; Devlin et al. (1990) Science 249: 404-406; Cwirla et al., (1990) PNAS USA 87: 6378-6382; as well as U.S. Pat. Nos. 5,223,409, 5,198,346, and 5,096,815].

Alternatively, other forms of mutagenesis can be utilized to generate a combinatorial library. For example, ActRII polypeptides of the disclosure can be generated and isolated from a library by screening using, for example, alanine scanning mutagenesis [Ruf et al. (1994) Biochemistry 33:1565-1572; Wang et al. (1994) J. Biol. Chem. 269:3095-3099; Balint et al. (1993) Gene 137:109-118; Grodberg et al. (1993) Eur. J. Biochem. 218:597-601; Nagashima et al. (1993) J. Biol. Chem. 268:2888-2892; Lowman et al. (1991) Biochemistry 30:10832-10838; and Cunningham et al. (1989) Science 244:1081-1085], by linker scanning mutagenesis [Gustin et al. (1993) Virology 193:653-660; and Brown et al. (1992) Mol. Cell Biol. 12:2644-2652; McKnight et al. (1982) Science 232:316], by saturation mutagenesis [Meyers et al., (1986) Science 232:613]; by PCR mutagenesis [Leung et al. (1989) Method Cell Mol Biol 1:11-19]; or by random mutagenesis, including chemical mutagenesis [Miller et al. (1992) A Short Course in Bacterial Genetics, CSHL Press, Cold Spring Harbor, NY; and Greener et al. (1994) Strategies in Mol Biol 7:32-34]. Linker scanning mutagenesis, particularly in a combinatorial setting, is an attractive method for identifying truncated (bioactive) forms of ActRII polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of ActRII polypeptides. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include ligand [e.g., GDF11, GDF8, activin A, activin B, GDF3, BMP4, BMP6, BMP10, and/or BMP15] binding assays and/or ligand-mediated cell signaling assays.

As will be recognized by one of skill in the art, most of the described mutations, variants or modifications described herein may be made at the nucleic acid level or, in some cases, by post-translational modification or chemical synthesis. Such techniques are well known in the art and some of which are described herein. In part, the present disclosure identifies functionally active portions (fragments) and variants of ActRII polypeptides that can be used as guidance for generating and using other variant ActRII polypeptides within the scope of the disclosure provided herein.

In certain embodiments, functionally active fragments of ActRII polypeptides of the present disclosure can be obtained by screening polypeptides recombinantly produced from the corresponding fragment of the nucleic acid encoding an ActRII polypeptide. In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function as antagonists (inhibitors) of ActRII receptors and/or one or more ligands [e.g., GDF11, GDF8, activin A, activin B, GDF3, BMP4, BMP6, BMP10, and/or BMP15].

In certain embodiments, ActRII polypeptides of the present disclosure may further comprise post-translational modifications in addition to any that are naturally present in the ActRII polypeptide. Such modifications include, but are not limited to, acetylation, carboxylation, glycosylation, phosphorylation, lipidation, and acylation. As a result, the ActRII polypeptide may contain non-amino acid elements, such as polyethylene glycols, lipids, polysaccharide or monosaccharide, and phosphates. Effects of such non-amino acid elements on the functionality of a ligand trap polypeptide may be tested as described herein for other ActRII variants. When a polypeptide of the disclosure is produced in cells by cleaving a nascent form of the polypeptide, post-translational processing may also be important for correct folding and/or function of the protein. Different cells (e.g., CHO, HeLa, MDCK, 293, W138, NIH-3T3 or HEK293) have specific cellular machinery and characteristic mechanisms for such post-translational activities and may be chosen to ensure the correct modification and processing of the ActRII polypeptides.

In certain aspects, ActRII polypeptides of the present disclosure include fusion proteins having at least a portion (domain) of an ActRII polypeptide and one or more heterologous portions (domains). Well-known examples of such fusion domains include, but are not limited to, polyhistidine, Glu-Glu, glutathione S-transferase (GST), thioredoxin, protein A, protein G, an immunoglobulin heavy-chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with ($HIS_6$ (SEQ ID NO: 43)) fusion partners. As another example, a fusion domain may be selected so as to facilitate detection of the ActRII polypeptide. Examples of such detection domains include the various fluorescent proteins (e.g., GFP) as well as "epitope tags," which are usually short peptide sequences for which a specific antibody is available. Well-known epitope tags for which specific monoclonal antibodies are readily available include FLAG, influenza virus haemagglutinin (HA), and c-myc tags. In some cases, the fusion domains have a protease cleavage site, such as for Factor Xa or thrombin, which allows the relevant protease to partially digest the fusion proteins and thereby liberate the recombinant proteins therefrom. The liberated proteins can then be isolated from the fusion domain by subsequent chromatographic separation. Other types of fusion domains that may be selected include multimerizing (e.g., dimerizing, tetramerizing) domains and functional domains (that confer an additional biological function) including, for example constant domains from immunoglobulins (e.g., Fc domains).

In certain aspects, ActRII polypeptides of the present disclosure contain one or more modifications that are capable of "stabilizing" the polypeptides. By "stabilizing" is meant anything that increases the in vitro half-life, serum half-life, regardless of whether this is because of decreased destruction, decreased clearance by the kidney, or other pharmacokinetic effect of the agent. For example, such modifications enhance the shelf-life of the polypeptides, enhance circulatory half-life of the polypeptides, and/or reduce proteolytic degradation of the polypeptides. Such stabilizing modifications include, but are not limited to, fusion proteins (including, for example, fusion proteins comprising an ActRII polypeptide domain and a stabilizer domain), modifications of a glycosylation site (including, for example, addition of a glycosylation site to a polypeptide of the disclosure), and modifications of carbohydrate moiety (including, for example, removal of carbohydrate moieties from a polypeptide of the disclosure). As used herein, the term "stabilizer domain" not only refers to a fusion domain (e.g., an immunoglobulin Fc domain) as in the case of fusion proteins, but also includes nonproteinaceous modifications such as a carbohydrate moiety, or nonproteinaceous moiety, such as polyethylene glycol. In certain preferred embodiments, an ActRII polypeptide is fused with a heterologous domain that stabilizes the polypeptide (a "stabilizer" domain), preferably a heterologous domain that increases stability of the polypeptide in vivo. Fusions with a constant domain of an immunoglobulin (e.g., a Fc domain) are known to confer desirable pharmacokinetic properties on a wide range of proteins. Likewise, fusions to human serum albumin can confer desirable properties.

An example of a native amino acid sequence that may be used for the Fc portion of human IgG1 (G1Fc) is shown below (SEQ ID NO: 11). Dotted underline indicates the hinge region, and solid underline indicates positions with naturally occurring variants. In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NO: 11. Naturally occurring variants in G1Fc would include E134D and M136L according to the numbering system used in SEQ ID NO: 11 (see Uniprot P01857).

(SEQ ID NO: 11)

```
  1 THTCPPCPAP ELLGGPSVFL FPPKPKDTLM ISRTPEVTCV VVDVSHEDPE
 51 VKFNWYVDGV EVHNAKTKPR EEQYNSTYRV VSVLTVLHQD WLNGKEYKCK
101 VSNKALPAPI EKTISKAKGQ PREPQVYTLP PSREEMTKNQ VSLTCLVKGF
151 YPSDIAVEWE SNGQPENNYK TTPPVLDSDG SFFLYSKLTV DKSRWQQGNV
201 FSCSVMHEAL HNHYTQKSLS LSPGK
```

Optionally, the IgG1 Fc domain has one or more mutations at residues such as Asp-265, lysine 322, and Asn-434. In certain cases, the mutant IgG1 Fc domain having one or more of these mutations (e.g., Asp-265 mutation) has reduced ability of binding to the Fcγ receptor relative to a wild-type Fc domain. In other cases, the mutant Fc domain having one or more of these mutations (e.g., Asn-434 mutation) has increased ability of binding to the MHC class I-related Fc-receptor (FcRN) relative to a wild-type IgG1 Fc domain.

An example of a native amino acid sequence that may be used for the Fc portion of human IgG2 (G2Fc) is shown below (SEQ ID NO: 12). Dotted underline indicates the hinge region and double underline indicates positions where there are data base conflicts in the sequence (according to UniProt P01859). In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NO: 12.

(SEQ ID NO:12)

```
  1 VECPPCPAPP VAGPSVFLFP PKPKDTLMIS RTPEVTCVVV DVSHEDPEVQ
 51 FNWYVDGVEV HNAKTKPREE QFNSTFRVVS VLTVVHQDWL NGKEYKCKVS
101 NKGLPAPIEK TISKTKGQPR EPQVYTLPPS REEMTKNQVS LTCLVKGFYP
151 SDIAVEWESN GQPENNYKTT PPMLDSDGSF FLYSKLTVDK SRWQQGNVFS
201 CSVMHEALHN HYTQKSLS LSPGK
```

Two examples of amino acid sequences that may be used for the Fc portion of human IgG3 (G3Fc) are shown below. The hinge region in G3Fc can be up to four times as long as in other Fc chains and contains three identical 15-residue segments preceded by a similar 17-residue segment. The first G3Fc sequence shown below (SEQ ID NO: 13) contains a short hinge region consisting of a single 15-residue segment, whereas the second G3Fc sequence (SEQ ID NO: 14) contains a full-length hinge region. In each case, dotted underline indicates the hinge region, and solid underline indicates positions with naturally occurring variants according to UniProt P01859. In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NOs: 13 and 14.

(SEQ ID NO: 13)

```
  1 EPKSCDTPPP CPRCPAPELL GGPSVFLFPP KPKDTLMISR TPEVTCVVVD
 51 VSHEDPEVQF KWYVDGVEVH NAKTKPREEQ YNSTFRVVSV LTVLHQDWLN
101 GKEYKCKVSN KALPAPIEKT ISKTKGQPRE PQVYTLPPSR EEMTKNQVSL
151 TCLVKGFYPS DIAVEWESSG QPENNYNTTP PMLDSDGSFF LYSKLTVDKS
201 RWQQGNIFSC SVMHEALHNR FTQKSLSLSP GK
```

(SEQ ID NO: 14)

```
  1 ELKTPLGDTT HTCPRCPEPK SCDTPPPCPR CPEPKSCDTP PPCRCPEPK
 51 SCDTPPPCPR CPAPELLGGP SVFLFPPKPK DTLMISRTPE VTCVVVDVSH
101 EDPEVQFKWY VDGVEVHNAK TKPREEQYNS TFRVVSVLTV LHQDWLNGKE
151 YKCKVSNKAL PAPIEKTISK TKGQPREPQV YTLPPSREEM TKNQVSLTCL
```

-continued

```
201 VKGFYPSDIA VEWESSGQPE NNYNTTPPML DSDGSFFLYS KLTVDKSRWQ

251 QGNIFSCSVM HEALHNRFTQ KSLSLSPGK
```

Naturally occurring variants in G3Fc (for example, see Uniprot P01860) include E68Q, P76L, E79Q, Y81F, D97N, N100D, T124A, S169N, S169del, F221Y when converted to the numbering system used in SEQ ID NO: 13, and the present disclosure provides fusion proteins comprising G3Fc domains containing one or more of these variations. In addition, the human immunoglobulin IgG3 gene (IGHG3) shows a structural polymorphism characterized by different hinge lengths [see Uniprot P01859]. Specifically, variant WIS is lacking most of the V region and all of the CH1 region. It has an extra interchain disulfide bond at position 7 in addition to the 11 normally present in the hinge region. Variant ZUC lacks most of the V region, all of the CH1 region, and part of the hinge. Variant OMM may represent an allelic form or another gamma chain subclass. The present disclosure provides additional fusion proteins comprising G3Fc domains containing one or more of these variants.

An example of a native amino acid sequence that may be used for the Fc portion of human IgG4 (G4Fc) is shown below (SEQ ID NO: 15). Dotted underline indicates the hinge region. In part, the disclosure provides polypeptides comprising, consisting essential of, or consisting of amino acid sequences with 70%, 75%, 80%, 85%, 86%, 87%, 88%, 89%, 90%, 91%, 92%, 93%, 94%, 95%, 96%, 97%, 98%, 99%, or 100% identity to SEQ ID NO: 15.

```
                                              (SEQ ID NO: 15)
  1 ESKYGPPCPS CPAPEFLGGP SVFLFPPKPK DTLMISRTPE VTCVVVDVSQ

 51 EDPEVQFNWY VDGVEVHNAK TKPREEQFNS TYRVVSVLTV LHQDWLNGKE

101 YKCKVSNKGL PSSIEKTISK AKGQPREPQV YTLPPSQEEM TKNQVSLTCL

151 VKGFYPSDIA VEWESNGQPE NNYKTTPPVL DSDGSFFLYS RLTVDKSRWQ

201 EGNVFSCSVM HEALHNHYTQ KSLSLSLGK
```

A variety of engineered mutations in the Fc domain are presented herein with respect to the G1Fc sequence (SEQ ID NO: 11), and analogous mutations in G2Fc, G3Fc, and G4Fc can be derived from their alignment with G1Fc in FIG. 4. Due to unequal hinge lengths, analogous Fc positions based on isotype alignment (FIG. 4) possess different amino acid numbers in SEQ ID NOs: 11, 12, 13, 14, and 15. It can also be appreciated that a given amino acid position in an immunoglobulin sequence consisting of hinge, $C_H2$, and $C_H3$ regions (e.g., SEQ ID NOs: 11, 12, 13, 14, and 15) will be identified by a different number than the same position when numbering encompasses the entire IgG1 heavy-chain constant domain (consisting of the $C_H1$, hinge, $C_H2$, and $C_H3$ regions) as in the Uniprot database. For example, correspondence between selected $C_H3$ positions in a human G1Fc sequence (SEQ ID NO: 11), the human IgG1 heavy chain constant domain (Uniprot P01857), and the human IgG1 heavy chain is as follows.

Correspondence of $C_H3$ Positions in Different Numbering Systems

| G1Fc (Numbering begins at first threonine in hinge region) | IgG1 heavy chain constant domain (Numbering begins at $C_H1$) | IgG1 heavy chain (EU numbering scheme of Kabat et al., 1991*) |
|---|---|---|
| Y127 | Y232 | Y349 |
| S132 | S237 | S354 |
| E134 | E239 | E356 |
| T144 | T249 | T366 |
| L146 | L251 | L368 |
| K170 | K275 | K392 |
| D177 | D282 | D399 |
| Y185 | Y290 | Y407 |
| K187 | K292 | K409 |

*Kabat et al. (eds) 1991; pp. 688-696 in Sequences of Proteins of Immunological Interest, 5th ed., Vol. 1, NIH, Bethesda, MD.

Various methods are known in the art that increase desired pairing of Fc-containing fusion polypeptide chains in a single cell line to produce a preferred asymmetric fusion protein at acceptable yields [Klein et al (2012) mAbs 4:653-663; and Spiess et al (2015) Molecular Immunology 67(2A): 95-106]. Methods to obtain desired pairing of Fc-containing chains include, but are not limited to, charge-based pairing (electrostatic steering), "knobs-into-holes" steric pairing, SEEDbody pairing, and leucine zipper-based pairing [Ridgway et al (1996) Protein Eng 9:617-621; Merchant et al (1998) Nat Biotech 16:677-681; Davis et al (2010) Protein Eng Des Sel 23:195-202; Gunasekaran et al (2010); 285:19637-19646; Wranik et al (2012) J Biol Chem 287:43331-43339; U.S. Pat. No. 5,932,448; WO 1993/011162; WO 2009/089004, and WO 2011/034605].

It is understood that different elements of the fusion proteins (e.g., immunoglobulin Fc fusion proteins) may be arranged in any manner that is consistent with desired functionality. For example, an ActRII polypeptide domain may be placed C-terminal to a heterologous domain, or alternatively, a heterologous domain may be placed C-terminal to an ActRII polypeptide domain. The ActRII polypeptide domain and the heterologous domain need not be adjacent in a fusion protein, and additional domains or amino acid sequences may be included C- or N-terminal to either domain or between the domains.

For example, an ActRII receptor fusion protein may comprise an amino acid sequence as set forth in the formula A-B-C. The B portion corresponds to an ActRII polypeptide domain. The A and C portions may be independently zero, one, or more than one amino acid, and both the A and C portions when present are heterologous to B. The A and/or C portions may be attached to the B portion via a linker sequence. A linker may be rich in glycine (e.g., 2-10, 2-5, 2-4, 2-3 glycine residues) or glycine and proline residues and may, for example, contain a single sequence of threonine/serine and glycines or repeating sequences of threonine/serine and/or glycines, e.g., GGG GGGG (SEQ ID NO: 17), TGGGG (SEQ ID NO: 18), SGGGG (SEQ ID NO: 19), TGGG (SEQ ID NO: 20), SGGG (SEQ ID NO: 21), or GGGGS (SEQ ID NO: 22) singlets, or repeats. In certain embodiments, an ActRII fusion protein comprises an amino acid sequence as set forth in the formula A-B-C, wherein A is a leader (signal) sequence, B consists of an ActRII polypeptide domain, and C is a polypeptide portion that enhances one or more of in vivo stability, in vivo half-life, uptake/administration, tissue localization or distribution, formation of protein complexes, and/or purification. In certain embodiments, an ActRII fusion protein comprises an amino acid sequence as set forth in the formula A-B-C, wherein A is a TPA leader sequence, B consists of an ActRII receptor polypeptide domain, and C is an immunoglobulin Fc domain. Preferred fusion proteins comprise the amino acid sequence set forth in any one of SEQ ID NOs: 23, 27, 30, and 41.

In preferred embodiments, ActRII polypeptides to be used in accordance with the methods described herein are isolated polypeptides. As used herein, an isolated protein or polypeptide is one which has been separated from a component of its natural environment. In some embodiments, a polypeptide of the disclosure is purified to greater than 95%, 96%, 97%, 98%, or 99% purity as determined by, for example, electrophoretic (e.g., SDS-PAGE, isoelectric focusing (IEF), capillary electrophoresis) or chromatographic (e.g., ion exchange or reverse phase HPLC). Methods for assessment of purity are well known in the art [see, e.g., Flatman et al., (2007) J. Chromatogr. B 848:79-87]. In some embodiments, ActRII polypeptides to be used in accordance with the methods described herein are recombinant polypeptides.

ActRII polypeptides of the disclosure can be produced by a variety of art-known techniques. For example, polypeptides of the disclosure can be synthesized using standard protein chemistry techniques such as those described in Bodansky, M. Principles of Peptide Synthesis, Springer Verlag, Berlin (1993) and Grant G. A. (ed.), Synthetic Peptides: A User's Guide, W. H. Freeman and Company, New York (1992). In addition, automated peptide synthesizers are commercially available (e.g., Advanced ChemTech Model 396; Milligen/Biosearch 9600). Alternatively, the polypeptides of the disclosure, including fragments or variants thereof, may be recombinantly produced using various expression systems [e.g., *E. coli*, Chinese Hamster Ovary (CHO) cells, COS cells, baculovirus] as is well known in the art. In a further embodiment, the modified or unmodified polypeptides of the disclosure may be produced by digestion of recombinantly produced full-length ActRII polypeptides by using, for example, a protease, e.g., trypsin, thermolysin, chymotrypsin, pepsin, or paired basic amino acid converting enzyme (PACE). Computer analysis (using commercially available software, e.g., MacVector, Omega, PCGene, Molecular Simulation, Inc.) can be used to identify proteolytic cleavage sites. Alternatively, such polypeptides may be produced from recombinantly generated full-length ActRII polypeptides using chemical cleavage (e.g., cyanogen bromide, hydroxylamine, etc.).

3. Nucleic Acids Encoding ActRII Polypeptides

In certain embodiments, the present disclosure provides isolated and/or recombinant nucleic acids encoding ActRII polypeptides (including fragments, functional variants, and fusion proteins thereof).

As used herein, isolated nucleic acid(s) refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

In certain embodiments, nucleic acids encoding ActRII polypeptides of the disclosure are understood to include nucleic acids that are variants of any one of SEQ ID NOs: 4, 5, or 28. Variant nucleotide sequences include sequences that differ by one or more nucleotide substitutions, additions, or deletions including allelic variants, and therefore, will include coding sequence that differ from the nucleotide sequence designated in any one of SEQ ID NOs: 4, 5, or 28.

In certain embodiments, ActRII polypeptides of the disclosure are encoded by isolated and/or recombinant nucleic acid sequences that are at least 70%, 75%, 80%, 85%, 90%, 91%, 92%, 93%, 94% 95%, 96%, 97%, 98%, 99%, or 100% identical to any one of SEQ ID NOs: 4, 5, or 28. One of ordinary skill in the art will appreciate that nucleic acid sequences that are at least 70%, 75%, 80%, 85%, 90%, 91%, 92%, 93%, 94% 95%, 96%, 97%, 98%, 99%, or 100% identical to the sequences complementary to SEQ ID NOs: 4, 5, or 28, and variants thereof, are also within the scope of the present disclosure. In further embodiments, the nucleic acid sequences of the disclosure can be isolated, recombinant, and/or fused with a heterologous nucleotide sequence, or in a DNA library.

In other embodiments, nucleic acids of the present disclosure also include nucleotide sequences that hybridize under highly stringent conditions to the nucleotide sequence designated in SEQ ID NOs: 4, 5, or 28, complement sequences of SEQ ID NOs: 4, 5, or 28, or fragments thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by awash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the disclosure provides nucleic acids which hybridize under low stringency conditions of 6×SSC at room temperature followed by awash at 2×SSC at room temperature.

Isolated nucleic acids which differ from the nucleic acids as set forth in SEQ ID NOs: 4, 5, or 28 to degeneracy in the genetic code are also within the scope of the disclosure. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this disclosure.

In certain embodiments, the recombinant nucleic acids of the present disclosure may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art and can be used in a variety of host cells. Typically, one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the disclosure. The promoters may be either naturally occurring promoters, or hybrid promoters that combine elements of more than one promoter. An expression construct may be present in a cell on an episome, such as a plasmid, or the expression construct may be inserted in a chromosome. In some embodiments, the expression vector contains a selectable marker gene to allow the selection of transformed host cells. Selectable marker genes are well known in the art and can vary with the host cell used.

In certain aspects, the subject nucleic acid disclosed herein is provided in an expression vector comprising a nucleotide sequence encoding an ActRII polypeptide and operably linked to at least one regulatory sequence. Regulatory sequences are art-recognized and are selected to direct expression of the ActRII polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, CA (1990). For instance, any of a wide variety of expression control sequences that control the expression of a DNA sequence when operatively linked to it may be used in these vectors to express DNA sequences encoding an ActRII polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the present disclosure can be produced by ligating the cloned gene, or a portion thereof, into a vector suitable for expression in either prokaryotic cells, eukaryotic cells (yeast, avian, insect or mammalian), or both. Expression vehicles for production of a recombinant ActRII polypeptide include plasmids and other vectors. For instance, suitable vectors include plasmids of the following types: pBR322-derived plasmids, pEMBL-derived plasmids, pEX-derived plasmids, pBTac-derived plasmids and pUC-derived plasmids for expression in prokaryotic cells, such as *E. coli.*

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, e.g., Molecular Cloning A Laboratory Manual, 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of the subject ActRII polypeptides in CHO cells, such as a Pcmv-Script vector (Stratagene, La Jolla, Calif), pcDNA4 vectors (Invitrogen, Carlsbad, Calif) and pCI-neo vectors (Promega, Madison, Wisc.). As will be apparent, the subject gene constructs can be used to cause expression of the subject ActRII polypeptides in cells propagated in culture, e.g., to produce proteins, including fusion proteins or variant proteins, for purification.

This disclosure also pertains to a host cell transfected with a recombinant gene including a coding sequence for one or more of the subject ActRII polypeptides. The host cell may be any prokaryotic or eukaryotic cell. For example, an ActRII polypeptide of the disclosure may be expressed in bacterial cells such as *E. coli*, insect cells (e.g., using a baculovirus expression system), yeast, or mammalian cells [e.g. a Chinese hamster ovary (CHO) cell line]. Other suitable host cells are known to those skilled in the art.

Accordingly, the present disclosure further pertains to methods of producing the subject ActRII polypeptides. For example, a host cell transfected with an expression vector encoding an ActRII polypeptide can be cultured under appropriate conditions to allow expression of the ActRII polypeptide to occur. The polypeptide may be secreted and isolated from a mixture of cells and medium containing the polypeptide. Alternatively, the ActRII polypeptide may be retained cytoplasmically or in a membrane fraction and the cells harvested, lysed and the protein isolated. A cell culture includes host cells, media and other byproducts. Suitable media for cell culture are well known in the art. The subject polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the ActRII polypeptides, and affinity purification with an agent that binds to a domain fused to the ActRII polypeptide (e.g., a protein A column may be used to purify an ActRII-Fc fusion proteins). In some embodiments, the ActRII polypeptide is a fusion protein containing a domain which facilitates its purification.

In some embodiments, purification is achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. An ActRII protein may be purified to a purity of >90%, >95%, >96%, >98%, or >99% as determined by size exclusion chromatography and >90%, >95%, >96%, >98%, or >99% as determined by SDS PAGE. The target level of purity should be one that is sufficient to achieve desirable results in mammalian systems, particularly non-human primates, rodents (mice), and humans.

In another embodiment, a fusion gene coding for a purification leader sequence, such as a poly-(His)/enterokinase cleavage site sequence at the N-terminus of the desired portion of the recombinant ActRII polypeptide, can allow purification of the expressed fusion protein by affinity chromatography using a $Ni^{2+}$ metal resin. The purification leader sequence can then be subsequently removed by treatment with enterokinase to provide the purified ActRII polypeptide. See, e.g., Hochuli et al. (1987) *J. Chromatography* 411:177; and Janknecht et al. (1991) *PNAS USA* 88:8972.

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence. See, e.g., Current Protocols in Molecular Biology, eds. Ausubel et al., John Wiley & Sons: 1992.

4. Methods of Use

In part, the present disclosure relates to methods of treating post-capillary pulmonary hypertension (PcPH) (e.g., WHO Group 2 and/or Group 5 PH) comprising administering to a patient in need thereof an effective amount of an ActRII polypeptide as described herein. In some embodiments, the PcPH is combined post- and pre-capillary PH. In certain embodiments, the present disclosure provides methods of treating or preventing post-capillary pulmonary hypertension (PcPH) in an individual in need thereof through administering to the individual a therapeutically effective amount of an ActRII polypeptide as described herein. These methods are particularly aimed at therapeutic and prophylactic treatments of animals, and more particularly, humans. The terms "subject," an "individual," or a "patient" are interchangeable throughout the specification and and refer to either a human or a non-human animal. These terms include mammals, such as humans, non-human primates, laboratory animals, livestock animals (including bovines, porcines, camels, etc.), companion animals (e.g., canines, felines, other domesticated animals, etc.) and rodents (e.g., mice and rats). In particular embodiments, the patient, subject or individual is a human.

The terms "treatment", "treating", "alleviating" and the like are used herein to generally mean obtaining a desired pharmacologic and/or physiologic effect, and may also be used to refer to improving, alleviating, and/or decreasing the severity of one or more clinical complication of a condition being treated (e.g., WHO Group 2 and/or Group 5 PH). The effect may be prophylactic in terms of completely or partially delaying the onset or recurrence of a disease, condition, or complications thereof, and/or may be therapeutic in terms of a partial or complete cure for a disease or condition and/or adverse effect attributable to the disease or condition. "Treatment" as used herein covers any treatment of a disease or condition of a mammal, particularly a human. As used herein, a therapeutic that "prevents" a disorder or condition refers to a compound that, in a statistical sample, reduces the occurrence of the disorder or condition in a treated sample relative to an untreated control sample, or delays the onset of the disease or condition, relative to an untreated control sample.

In general, treatment or prevention of a disease or condition as described in the present disclosure (e.g., WHO Group 2 and/or Group 5 PH) is achieved by administering one or more ActRII polypeptides of the present disclosure in an "effective amount". An effective amount of an agent refers to an amount effective, at dosages and for periods of time necessary, to achieve the desired therapeutic or prophylactic result. A "therapeutically effective amount" of an agent of the present disclosure may vary according to factors such as the disease state, age, sex, and weight of the individual, and the ability of the agent to elicit a desired response in the individual. A "prophylactically effective amount" refers to an amount effective, at dosages and for periods of time necessary, to achieve the desired prophylactic result.

In certain aspects, the disclosure contemplates the use of an ActRII polypeptide, in combination with one or more additional active agents or other supportive therapy for treating or preventing a disease or condition (e.g., WHO Group 2 and/or Group 5 PH). As used herein, "in combination with", "combinations of", "combined with", or "conjoint" administration refers to any form of administration such that additional active agents or supportive therapies (e.g., second, third, fourth, etc.) are still effective in the body (e.g., multiple compounds are simultaneously effective in the patient for some period of time, which may include synergistic effects of those compounds). Effectiveness may not correlate to measurable concentration of the agent in blood, serum, or plasma. For example, the different therapeutic compounds can be administered either in the same formulation or in separate formulations, either concomitantly or sequentially, and on different schedules. Thus, a subject who receives such treatment can benefit from a combined effect of different active agents or therapies. One or more ActRII polypeptides of the disclosure can be administered concurrently with, prior to, or subsequent to, one or more other additional agents or supportive therapies, such as those disclosed herein. In general, each active agent or therapy will be administered at a dose and/or on a time schedule determined for that particular agent. The particular combination to employ in a regimen will take into account compatibility of the ActRII polypeptide of the present disclosure with the additional active agent or therapy and/or the desired effect.

WHO Classification Outline

A pulmonary hypertension condition treated by methods describe herein, can comprise any one or more of the conditions recognized according to the World Health Organization (WHO). See, e.g., Simonneau (2019) Eur Respir J: 53:1801913.

TABLE 1

| Clinical Classification of Pulmonary Hypertension |
|---|
| Group 1: Pulmonary arterial hypertension (PAH) |
| 1.1 Idiopathic PAH |
| 1.2 Heritable PAH |
| 1.2.1 BMPR2 |
| 1.2 2 ALK-1, ENG, SMAD9, CAV1, KCNK3 |
| 1.2.3 Unknown |
| 1.3 Drug and toxin induced PAH |
| 1.4 Associated with: |
| 1.4.1 Connective tissue disease |
| 1.4.2 HIV infection |
| 1.4.3 Portal hypertension |
| 1.4.4 Congenital heart diseases |
| 1.4.5 Schistosomiasis |
| 1.5 PAH long-term responders to calcium channel blockers |
| 1.6 PAH with overt features of venous/capillaries (PVOD/PCH) involvement |
| 1.7 Persistent PH of the newborn syndrome |
| Group 2: Pulmonary hypertension due to left heart disease |
| 2.1 PH due to heart failure with preserved LVEF[1] (HFpEF) |
| 2.2 PH due to heart failure with reduced LVEF (HFrEF) |
| 2.3 Valvular heart disease |
| 2.4 Congenital/acquired cardiovascular conditions leading to post-capillary PH |
| Group 3: Pulmonary hypertension due to lung disease and/or hypoxia |
| 3.1 Obstructive lung disease |
| 3.2 Restrictive lung disease |
| 3.3 Other lung disease with mixed restrictive/obstructive pattern |
| 3.4 Hypoxia without lung disease |
| 3.5 Developmental lung disorders |
| Group 4: Pulmonary hypertension due to pulmonary artery obstructions |
| 4.1 Chronic thromboembolic PH |
| 4.2 Other pulmonary artery obstructions |
| 4.2.1 Sarcoma (high or intermediate grade) or angiosarcoma |
| 4.2.2 Other malignant tumours |
| Renal carcinoma |
| Uterine carcinoma |
| Germ cell tumours of the testis |
| Other tumours |
| 4.2.3 Non-malignant tumours |
| Uterine leiomyoma |
| 4.2.4 Arteritis without connective tissue disease |
| 4.2.5 Congenital pulmonary artery stenoses |
| 4.2.6 Parasites |
| Hydatidosis |
| Group 5: Pulmonary hypertension with unclear and/or multifactorial mechanisms. |
| 5.1 Hematological disorders (e.g., Chronic hemolytic anaemia and myeloproliferative disorders) |
| 5.2 Systemic and metabolic disorders (e.g., Pulmonary Langerhans cell histiocytosis, Gaucher disease, Glycogen storage disease, Neurofibromatosis, and Sarcoidosis) |
| 5.3 Others (e.g., Chronic renal failure with or without haemodialysis and Fibrosing mediastinitis) |
| 5.4 Complex congenital heart disease |

[1]Left ventricular ejection fraction

The clinical purpose of the classification of PH is to categorize clinical conditions associated with PH into five groups according to their pathophysiological mechanisms, clinical presentation, hemodynamic characteristics, and treatment strategy. This clinical classification may be updated when new data are available on the above features or when additional clinical entities are considered.

Pulmonary hypertension (PH) has been previously classified as primary or secondary PH. The term primary pulmonary hypertension has now been replaced by idiopathic PAH or familial PAH depending on the absence or presence of genetic information; the term secondary pulmonary hypertension has been abandoned.

As used herein, the term “pulmonary hemodynamic parameter” refers to any parameter used to describe or evaluate the blood flow through the heart and pulmonary vasculature. Examples of pulmonary hemodynamic parameters include, but are not limited to, mean pulmonary artery pressure (mPAP), diastolic pulmonary artery pressure (dPAP) [also known as pulmonary artery diastolic pressure (PADP)], systolic pulmonary artery pressure (sPAP) [also known as pulmonary artery systolic pressure (PASP)], mean right atrial pressure (mRAP), pulmonary capillary wedge pressure (PCWP) [also known as pulmonary artery wedge pressure (PAWP)], left ventricular end-diastolic pressure (LVEDP), diastolic pressure gradient (DPG) [also known as diastolic pressure difference (DPD)], left atrial pressure (LAP), transpulmonary gradient (TPG), pulmonary vascular resistance (PVR) and cardiac output (CO).

Many of the pulmonary hemodynamic parameters described above are interrelated. For example, PCWP is often used as a more convenient, less invasive approximation of LAP.

As another example, PVR is related to mPAP, PCWP and CO according to the following equation:

$$PVR=(mPAP-PCWP)/CO\text{[Woods Units]}$$

The PVR measures the resistance to flow imposed by the pulmonary vasculature without the influence of the left-sided filling pressure. PVR can also be measured according to the following equations:

$$PVR=TPG\times 80/CO[\text{unit: dynes}-sec-\text{cm}^{-5}]\text{ OR}$$

$$PVR=(mPAP-PCWP)\times 80/CO[\text{unit: dynes}-sec-\text{cm}^{-5}]$$

In some embodiments, the total PVR can be measured using the following equation:

$$TPR=mPAP/CO$$

According to some embodiments, a pre-capillary pulmonary arterial contribution to PH may be reflected by an elevated PVR. In some embodiments, the normal PVR is 20-130 dynes-sec-$cm^{-5}$ or 0.5-1.1 Wood units. According to some embodiments, an elevated PVR may refer to a PVR above 2 Wood units, above 2.5 Wood units, above 3 Wood units or above 3.5 Wood units.

As yet another example, TPG is the difference between mPAP and left atrial pressure (PLA; commonly estimated by pulmonary capillary wedge pressure: PCWP) as shown by the following equation: TPG=mPAP-PCWP The TPG is influenced by all the determinants of mPAP, including flow, resistance and left heart filling pressure. A pre-capillary pulmonary arterial contribution to PH may be reflected by an increased trans-pulmonary gradient (TPG). According to some embodiments, an increased TPG may refer to an mPAP-PCWP that exceeds 12-15 mmHg.

DPG (defined as diastolic PAP–mean PAWP) appears to best approach the characteristics required to determine pulmonary vascular disease. In some embodiments, the DPG is synonymous with diastolic pressure difference (DPD). In normal subjects, DPG generally lies in the 1-3 mmHg range, and in patients evaluated for cardiac disease (excluding shunts), DPG remains ≤5 mmHg in most cases.

As a further example, mPAP is related to dPAP and sPAP according to the following equation: mPAP=(⅔)dPAP+(⅓) sPAP Furthermore, dPAP and sPAP can be used to calculate the pulse pressure (mmHg) using the following equation: pulse pressure=sPAP–dPAP Pulse pressure can be used to calculate the pulmonary artery compliance using the following equation: pulmonary artery compliance (mI·$mmHg^{-1}$)=stroke volume/pulse pressure. In some embodiments, the pulmonary hemodynamic parameters are measured directly, such as during a right heart catheterization. In other embodiments, the pulmonary hemodynamic parameters are estimated and/or evaluated through other techniques such as magnetic resonance imaging (MRI) or echocardiography.

Exemplary pulmonary hemodynamic parameters include mPAP, PAWP, TPG, DPG, and PVR. The one or more pulmonary hemodynamic parameters may be measured by any appropriate procedures, such as by utilizing a right heart catheterization or echocardiography. Various hemodynamic types of PH are shown in Table 2 together with their corresponding clinical classification (Table 1).

TABLE 2

Hemodynamic Types of Pulmonary Hypertension (PH)

| Hemodynamic Type | Hemodynamic Subtype | Characteristics | WHO PH Classification |
|---|---|---|---|
| Pulmonary Hypertension | — | mPAP > 20 mmHg | All (Groups 1-5) |
| Pre-Capillary PH | — | mPAP > 20 mmHg<br>PAWP ≤ 15 mmHg<br>PVR ≥ 3 Wood units | Group 1: Pulmonary arterial hypertension<br>Group 3: PH due to lung disease and/or hypoxia<br>Group 4: PH due to pulmonary artery obstructions<br>Group 5: PH with unclear and/or multifactorial mechanisms. |
| Post-Capillary PH | Isolated Post-Capillary PH | mPAP > 20 mmHg<br>PAWP > 15 mmHg<br>PVR < 3 Wood units<br>DPG < 7 mmHg | Group 2: PH due to left heart disease<br>Group 5: PH with unclear and/or multifactorial mechanisms. |
| | Combined Pre- and Post-Capillary PH | mPAP > 20 mmHg<br>PAWP > 15 mmHg<br>PVR ≥ 3 Wood units<br>DPG ≥ 7 mmHg | |

The types of PH and the difference between pre-capillary pulmonary hypertension and post-capillary pulmonary hypertension are based on pulmonary hemodynamic parameters. As used herein, the term "pre-capillary pulmonary hypertension" includes WHO clinical Groups 1, 3, 4, and 5. In general, pre-capillary pulmonary hypertension is characterized using the pulmonary hemodynamic parameters shown in Table 2 (i.e., an mPAP >20 mmHg or in some embodiments an mPAP >25 mmHg). As used herein, the term "post-capillary pulmonary hypertension" (PcPH) includes both isolated post-capillary pulmonary hypertension (IpcPH) and combined pre- and post-capillary pulmonary hypertension (CpcPH), both within WHO clinical Groups 2 and 5. In some embodiments, IpcPH is characterized using the pulmonary hemodynamic parameters shown in Table 2 (i.e., one or more of the following pulmonary hemodynamic parameters: mPAP >20 mmHg, PAWP >15 mmHg, PVR <3 Wood units, and/or DPG <7 mmHg). In some embodiments, CpcPH is characterized using the pulmonary hemodynamic parameters shown in Table 2 (i.e., one or more of the following pulmonary hemodynamic parameters: mPAP >20 mmHg, PAWP >15 mmHg, PVR≥3 Wood units, and/or DPG≥7 mmHg). In some embodiments, CpcPH is characterized as comprising one or more of the following hemodynamic parameters: mPAP ≥25 mmHg; PAWP >15 mmHg; and PVR >3 WU.

The clinical classification or hemodynamic types of PH described herein and the associated diagnostic parameters may be updated or varied based on the availability of new or existing sources of data or when additional clinical entities are considered.

Characteristics of PH

The diagnosis of PH, including WHO PH class and functional group, can be determined based on symptoms and physical examination using a review of a comprehensive set of parameters to determine if the hemodynamic and other criteria are met. Some of the criteria which may considered include the patient's clinical presentation (e.g., shortness of breath, fatigue, weakness, angina, syncope, dry-couch, exercise-induced nausea and vomiting), electrocardiogram (ECG) results, chest radiograph results, pulmonary function tests, arterial blood gases, echocardiography results, ventilation/perfusion lung scan results, high-resolution computed tomography results, contrast-enhanced computed tomography results, pulmonary angiography results, cardiac magnetic resonance imaging, blood tests (e.g., biomarkers such as BNP or NT-proBNP), immunology, abdominal ultrasound scan, right heart catherization (RHC), vasoreactivity, and genetic testing. See, e.g., Galie N., et al Euro Heart J. (2016) 37, 67-119.

In some embodiments, a biomarker may be used to determine the diagnosis of PH. For instance, in some embodiments, the biomarker is a marker of vascular dysfunction (e.g., asymmetric dimethylarginine (ADMA), endothelin-1, angiopoeitins, or von Willebrand factor). In some embodiments, the biomarker is a marker of inflammation (C-reactive protein, interleukin 6, chemokines). In some embodiments, the biomarker is a marker of myocardial stress (e.g., (atrial natriuretic peptide, brain natriuretic peptide (BNP)/NT-proBNP, or troponins). In some embodiments, the biomarker is a marker of low CO and/or tissue hypoxia (e.g., pCO2, uric acid, growth differentiation factor 15 (GDF15), or osteopontin). In some embodiments, the biomarker is a marker of secondary organ damage (e.g., creatinine or bilirubin). See, e.g., Galie N., et al Euro Heart J. (2016) 37, 67-119.

Group 1 PH

Pulmonary arterial hypertension (WHO Group 1 PH) is a serious, progressive and life-threatening disease of the pulmonary vasculature, characterized by profound vasoconstriction and an abnormal proliferation of smooth muscle cells in the walls of the pulmonary arteries. Severe constriction of the blood vessels in the lungs leads to very high pulmonary arterial pressures. These high pressures make it difficult for the heart to pump blood through the lungs to be oxygenated. Patients with PAH suffer from extreme shortness of breath as the heart struggles to pump against these high pressures. Patients with PAH typically develop significant increases in PVR and sustained elevations in mPAP, which ultimately lead to right ventricular failure and death. Patients diagnosed with PAH have a poor prognosis and equally compromised quality of life, with a mean life expectancy of 2 to 5 years from the time of diagnosis if untreated.

A variety of factors contribute to the pathogenesis of pulmonary hypertension including proliferation of pulmonary cells which can contribute to vascular remodeling (i.e., hyperplasia). For example, pulmonary vascular remodeling occurs primarily by proliferation of arterial endothelial cells and smooth muscle cells of patients with pulmonary hypertension. Overexpression of various cytokines is believed to promote pulmonary hypertension. Further, it has been found that pulmonary hypertension may rise from the hyperproliferation of pulmonary arterial smooth cells and pulmonary endothelial cells. Still further, advanced PAH may be characterized by muscularization of distal pulmonary arterioles, concentric intimal thickening, and obstruction of the vascular lumen by proliferating endothelial cells. Pietra et al., J. Am. Coll. Cardiol., 43:255-325 (2004).

PAH can be diagnosed based on a mean pulmonary artery pressure of above 25 mmHg (or above 20 mmHg under updated guidelines) at rest, with a normal pulmonary artery capillary wedge pressure. PAH can lead to shortness of breath, dizziness, fainting, and other symptoms, all of which are exacerbated by exertion. PAH can be a severe disease with a markedly decreased exercise tolerance and heart failure. Two major types of PAH include idiopathic PAH (e.g., PAH in which no predisposing factor is identified) and heritable PAH (e.g., PAH associated with a mutation in BMPR2, ALK1, ENG, SMAD9, CAV1, KCNK3, or EIF2AK4). In 70% of familial PAH cases, mutations are located in the BMPR2 gene. Risk factors for the development of PAH include family history of PAH, drug and toxin use (e.g., methamphetamine or cocaine use), infection (e.g., HIV infection or schistosomiasis), cirrhosis of the liver, congenital heart abnormalities, portal hypertension, pulmonary veno-occlusive disease, pulmonary capillary hemangiomatosis, or connective tissue/autoimmune disorders (e.g., scleroderma or lupus). PAH may be associated with long term responders to calcium channel blockers, overt features of venous/capillaries (PVOD/PCH) involvement, and persistent PH of the newborn syndrome.

Group 2 PH

Pulmonary hypertension due to left heart disease (PH-LHD) (WHO Group 2 PH) is a complex pathophenotype that, when present, may result in an increased susceptibility to adverse events and worse clinical outcome. PH-LHD is sometimes defined as patients having a pulmonary capillary wedge pressure (PCWP) >15 mmHg and a mean pulmonary artery pressure (mPAP) ≥25 mmHg (or a mean pulmonary artery pressure (mPAP) ≥20 mmHg under updated guidelines). PH-LHD occurs as a consequence of the backward transmission of high left sided filling pressures, mainly driven by LV diastolic function, directly to the post-capillary pulmonary vessels and, thereby, to the rest of the pulmonary circulation. PH-LHD may be associated with or caused by PH due to heart failure with preserved left ventricle ejection fraction (LVEF) [also known as HFpEF], PH due to heart failure with reduced LVEF (also known as HFrEF), valvular heart disease (VHD), or congenital/acquired cardiovascular conditions leading to post-capillary PH. Compared with PAH, patients with PH-LHD are often older, female, with a higher prevalence of cardiovascular co-morbidities and most, if not all, of the features of metabolic syndrome.

Valvular heart disease (VHD) associated with pulmonary hypertension may result from multiple mechanisms such as an increase in PVR, pulmonary blood flow, or pulmonary venous pressure. The chronic rise in PAP frequently leads to RV pressure overload and subsequent RV failure. Clinical signs and symptoms of left-sided VHD with PH are orthopnea and paroxysmal nocturnal dyspnea. In advanced stages of diseases, signs of RV failure including peripheral edema, ascites, and syncope are frequently observed. There are four valvular heart disease subtypes which include mitral valve stenosis, mitral valve regurgitation, aortic stenosis, and aortic regurgitation.

Mitral valve stenosis occurs when the heart's mitral valve is narrowed due to the valve becoming stiff or scarred, or the valve flaps partially joining together. This results in the valve not opening as widely as it should, which causes poor blood flow and may result in blood backing up into the lungs. Left untreated, mitral valve stenosis can lead to serious heart complications. Common causes of mitral valve stenosis include rheumatic heart disease, radiation, and mitral annulus calcification. Typical interventions for mitral stenosis include balloon vavuloplasty, commisurrotomy, and surgical valve replacement.

Mitral valve regurgitation (also called mitral insufficiency) occurs when the flaps (leaflets) of the mitral valve do not close tightly, allowing blood to flow backward in the heart. As a result, blood can't move through the heart or to the rest of the body as efficiently, resulting in fatigue or shortness of breath. Additionally, the reduced flow increases pressure in the left atrium and lung vasculature. In moderate to severe cases, surgery may be recommended to either repair or replace the damaged valve. Left untreated, severe mitral valve regurgitation can cause heart failure or serious heart rhythm problems. Common causes of mitral valve regurgitation include degenerative mitral disease such as mitral valve prolapse and mitral annulus calcification. Typical interventions for mitral valve regurgitation include transcatheter mitral valve repair, surgical repair, or replacement.

In aortic stenosis, the aortic valve does not open fully. This decreases blood flow from the heart. As the aortic valve becomes more narrow, the pressure increases inside the left heart ventricle. This causes the left heart ventricle to become thicker, which decreases blood flow and can lead to chest pain. As the pressure continues to rise, blood may back up into the lungs causing dyspnea. Severe forms of aortic stenosis prevent enough blood from reaching the brain and rest of the body. Common causes of aortic stenosis include calcification of the aortic valve or the presence of a bicuspid aortic valve. Typical interventions include transcatheter aortic valve replacement (percutaneous valve replacement) and surgical valve replacement.

Aortic regurgitation (also known as aortic insufficiency) occurs when the aortic valve is unable to fully close. The valve leaks, resulting in reduced blood flow. As a result, the heart has to work harder to make up for the reduced blood flow, and over time it will weaken. Because of this, the amount of blood that flows from the heart to the rest of the body is reduced. Common causes of aortic regurgitation include aortic root dilatation and presence of a bicuspid aortic valve.

Among those patients with PH-LHD, two phenotypes have been described: 1) a group of isolated post-capillary (IpcPH) or "passive" PH in which elevated pulmonary pressures are reversible and in proportion to increases in left atrial pressure, and 2) a group with an added "pre-capillary" component [combined post-capillary and pre-capillary PH (CpcPH)]. This latter group, CpcPH, may have comorbid pulmonary vascular remodeling and therefore may demonstrate persistent PH after interventions to lower left sided filling pressures.

In some embodiments, a combination of mPAP, PAWP, PVR, or DPG may be used to define the different subtypes of PH-LHD, i.e., IpcPH and CpcPH (see, e.g., Table 2). In some embodiments, patients with CpcPH are characterized as having a TPG >12-15 mmHg and a PVR >2.5-3 Wood units (WU). In some embodiments, CpcPH is distinguished from IpcPH using the DPG. In some embodiments, a patient with CpcPH has a DPG ≥7 mmHg. In some embodiments, a patient with IpcPH has a DPG <7 mmHg.

In some embodiments, a combination of DPG and PVR may be used to define the different types of PH-LHD. For instance, in some embodiments, IpcPH patients have a DPG <7 mmHg and/or a PVR of ≤3 WU. In some embodiments, CpcPH patients have a DPG ≥7 mmHg and/or a PVR >3 WU.

The clinical classification or hematological classification described herein and the associated diagnostic parameters may be updated when new data are available or when additional clinical entities are considered. For instance, at the $5^{th}$ World Symposium on Pulmonary Hypertension (WSPH), a new terminology was adopted to distinguish IpcPH from CpcPH, based on the diastolic pressure difference/gradient (DPG) between the dPAP and PAWP. However, this definition was found to be too restrictive and exposed to interpretation, leading to controversies about whether the DPG would or would not predict outcome in patients with group 2 PH. Accordingly, at the $6^{th}$ WSPH, pulmonary vascular resistance (PVR) was subsequently reintroduced to better reflect the impact of the right ventricle on patient outcome. See, e.g., Vachiery J. L., et al. Eur Respir J 2019 Jan. 24; 53(1).

Therapies for treating PH-LHD primarily include treatment of the underlying condition (i.e., COPD, sleep apnea syndrome, CTEPH) prior to considering specific measures to treat the PH itself. Some therapies include repair of valvular heart disease (if indicated). Non-specific vasodilators such as nitrates and hydralazine may also be used. In some embodiments, an LV assist device (LVAD) may be used to lower pulmonary pressure. The lack of specific therapies is particularly problematic because PH-LHD is the most common cause of PH in western countries and its presence commonly results in adverse course of the disease. Specifically, the presence of PH-LHD can result in more severe symptoms in LHD, worse exercise tolerance, and a negative impact on outcome.

Group 3 PH

Pulmonary hypertension due to lung disease and/or hypoxia (WHO Group 3 PH) refers to a form of pulmonary hypertension that is due to lung disease or chronic hypoxia. This form of PH is also known as "hypoxic PH" or "hypoxic pulmonary hypertension." Hypoxic PH may be associated with or caused by chronic obstructive pulmonary disease (e.g., emphysema), interstitial lung disease, sleep-disordered breathing (e.g., sleep apnea), lung disease (e.g., pulmonary fibrosis), alveolar hypoventilation disorders, chronic exposure to high altitude, or developmental abnormalities.

Group 4 PH

Pulmonary hypertension due to pulmonary artery obstructions (WHO Group 4 PH) is a form of pulmonary hypertension that is related to chronic arterial obstruction (e.g., blood clots). There may be multiple pathophysiological mechanisms driving development of PH in Group 4 including chronic thromboembolic PH, sarcoma (high or intermediate grade) or angiosarcoma, other malignant tumors (e.g., renal carcinoma, uterine carcinoma, germ cell tumors of the testis, or other tumors), non-malignant tumors (e.g., uterine leiomyoma), arteritis without connective tissue disease, congenital pulmonary artery stenosis, or parasites (e.g., hydatidosis).

Various pulmonary hemodynamic parameters are associated with Group 4 PH. For instance, in patients with PH due to pulmonary artery obstructions, those with severe PH (>40 mmHg) often have a marked increase in PVR (around 10 WU); more often these patients may have a mild PH (mPAP 20-30 mmHg), associated with lower PVR but remaining generally >3 WU. See, e.g., Simonneau (2019) Eur Respir J: 53:1801913. In these different chronic lung diseases, even a modest elevation in mPAP (20-29 mmHg) can be associated with a poor prognosis. Furthermore, in chronic thromboembolism, patients may have severe pre-capillary PH with a mPAP of about 47 mmHg and a mean PVR of about 8.9 WU. Id. In this setting, even in patients with mild elevation of mPAP (20-24 mmHg), PVR is generally >3 WU.

Group 5 PH

Pulmonary hypertension with unclear and/or multifactorial mechanisms (WHO Group 5 PH) is a group which contains less-studied forms of PH in comparison with the other groups. However, many of the PH forms currently in group 5 represent a significant part of the PH burden. The diseases within Group 5 PH are characterized by having no identified predominant mechanism driving the development of PH. There may be multiple pathophysiological mechanisms driving development of PH, including hematological disorders (e.g., chronic hemolytic anemia or myeloproliferative disorders), systemic and metabolic disorders (e.g., Pulmonary Langerhans cell histiocytosis, Gaucher disease, glycogen storage disease, neurofibromatosis, or sarcoidosis), others (e.g., chronic renal failure with or without hemodialysis or fibrosing mediastinitis), or complex congenital heart disease.

Measurements of PH

In certain aspects, the disclosure relates to methods of treating, preventing, or reducing the progression rate and/or severity of PcPH (e.g., treating, preventing, or reducing the progression rate and/or severity of one or more complications of post-capillary pulmonary hypertension in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to treating PcPH patients that have IpcPH. In some embodiments, the method relates to treating PcPH patients that have CpcPH. In some embodiments, the method relates to treating PcPH patients that have pulmonary hypertension due to left heart disease (PH-LHD). In some embodiments, the method relates to treating PcPH patients that have Group 2 PH as classified by the WHO. In some embodiments, the method relates to treating PcPH patients that have pulmonary hypertension due to heart failure with preserved LVEF (HFpEF). In some embodiments, the method relates to treating PcPH patients that have pulmonary hypertension due to heart failure with reduced LVEF (HFrEF). In some embodiments, the method relates to treating PcPH patients that have valvular heart disease. In some embodiments, the valvular heart disease is aortic regurgitation. In some embodiments, the valvular heart disease is aortic stenosis. In some embodiments, the valvular heart disease is mitral valve disease. In some embodiments, the valvular heart disease is mitral valve regurgitation. In some embodiments, the valvular heart disease is mitral valve stenosis. In some embodiments, the method relates to treating CpcPH patients who have PH due to valvular heart disease. In some embodiments, the method relates to treating IpcPH patients who have PH due to valvular heart disease. In some embodiments, the method relates to treating PcPH patients that have congenital/acquired cardiovascular conditions leading to post-capillary PH. In some embodiments, the method relates to treating PcPH patients that have pulmonary hypertension with unclear and/or multifactorial mechanisms. In some embodiments, the method relates to treating PcPH patients that have Group 5 PH as classified by the WHO.

In some embodiments, the disclosure relates to methods of treating, preventing, or reducing the progression rate and/or severity of pulmonary hypertension in combinations of certain patient populations. Each of the patient populations described herein can be combined and reorganized accordingly. For instance, in some embodiments, the method relates to treating CpcPH patients who have PH due to heart failure with preserved LVEF (HFpEF). In some embodiments, the method relates to treating CpcPH patients who have PH due to heart failure with reduced LVEF (HFrEF). In some embodiments, the method relates to treating CpcPH patients who have PH due to valvular heart disease. In some embodiments, the method relates to treating IpcPH patients who have PH due to heart failure with preserved LVEF (HFpEF). In some embodiments, the method relates to treating IpcPH patients who have PH due to heart failure with reduced LVEF (HFrEF). In some embodiments, the method relates to treating IpcPH patients who have PH due to valvular heart disease.

In some embodiments, the method relates to pulmonary hypertension patients that have pulmonary hypertension with unclear and/or multifactorial mechanisms. In some embodiments, the method relates to patients that have a hematological disorder (e.g., chronic hemolytic anemia and myeloproliferative disorders). In some embodiments, the method relates to patients that have a systemic and/or metabolic disorder (e.g., pulmonary langerhans cell histiocytosis, Gaucher disease, glycogen storage disease, neurofibromatosis, and sarcoidosis). In some embodiments, the method relates to pulmonary hypertension patients that have other disorders with unclear and/or multifactorial mechanisms (e.g., chronic renal failure with or without hemodialysis or fibrosing mediastinitis). In some embodiments, the method relates to patients that have complex congenital heart disease.

mPAP

In certain aspects, the disclosure relates to methods of treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has resting mean pulmonary arterial pressure (mPAP) of at least 20 mmHg (e.g., 20, 25, 30, 35, 40, 45, or 50 mmHg). As used herein, the terms "mean pulmonary arterial pressure" and mean pulmonary artery pressure are used interchangeably. In some embodiments, the method relates to patients having a resting mPAP of at least 20 mmHg. In some embodiments, the method relates to patients having a resting mPAP of at least 25 mmHg. In some embodiments, the method relates to patients having a resting mPAP of at least 30 mmHg. In some embodiments, the method relates to patients having a resting mPAP of at least 35 mmHg. In some embodiments, the method relates to patients having a resting mPAP of at least 40 mmHg. In some embodiments, the method relates to patients having a resting mPAP of at least 45 mmHg. In some embodiments, the method relates to patients having a resting mPAP of at least 50 mmHg.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to improving the pulmonary arterial pressure in the patient. In some embodiments, the improvement in pulmonary arterial pressure is a reduction in the mean pulmonary arterial pressure (mPAP). In some embodiments, the method relates to reducing mPAP. In some embodiments, the method relates to reducing the patient's mPAP by at least 1 mmHg. In some embodiments, the method relates to reducing the patient's mPAP by at least 2 mmHg. In some embodiments, the method relates to reducing the patient's mPAP by at least 3 mmHg. In certain embodiments, the method relates to reducing the patient's mPAP by at least 5 mmHg. In certain embodiments, the method relates to reducing the patient's mPAP by at least 7 mmHg. In certain embodiments, the method relates to reducing the patient's mPAP by at least 10 mmHg. In certain embodiments, the method relates to reducing the patient's mPAP by at least 12 mmHg. In certain embodiments, the method relates to reducing the patient's mPAP by at least 15 mmHg. In certain embodiments, the method relates to reducing the patient's mPAP by at least 20 mmHg. In certain embodiments, the method relates to reducing the patient's mPAP by at least 25 mmHg.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to decreasing the patient's mPAP by least 1% (e.g., 1, 5, 10, 15, 20, 25, 30, 35, 40, 45, 50, 55, 60, 65, 70, 75, 80, 85, 90, 95, or 100%). In some embodiments, the method relates to decreasing the patient's mPAP by at least 1%. In some embodiments, the method relates to decreasing the patient's mPAP by at least 5%. In some embodiments, the method relates to decreasing the patient's mPAP by at least 10%. In some embodiments, the method relates to decreasing the patient's mPAP by at least 15%. In some embodiments, the method relates to decreasing the patient's mPAP by at least 20%. In some embodiments, the method relates to decreasing the patient's mPAP by at least 25%. In some embodiments, the method relates to decreasing the patient's mPAP by at least 30%. In some embodiments, the method relates to decreasing the patient's mPAP by at least 35%. In some embodiments, the method relates to decreasing the patient's mPAP by at least 40%. In some embodiments, the method relates to decreasing the patient's mPAP by at least 45%. In some embodiments, the method relates to decreasing the patient's mPAP by at least 50%. In some embodiments, the method relates to decreasing the patient's mPAP by at least 55%. In some embodiments, the method relates to decreasing the patient's mPAP by at least 60%. In some embodiments, the method relates to decreasing the patient's mPAP by at least 65%. In some embodiments, the method relates to decreasing the patient's mPAP by at least 70%. In some embodiments, the method relates to decreasing the patient's mPAP by at least 75%. In some embodiments, the method relates to decreasing the patient's mPAP by at least 80%. In some embodiments, the method relates to decreasing the patient's mPAP by at least 85%. In some embodiments, the method relates to decreasing the patient's mPAP by at least 90%. In some embodiments, the method relates to decreasing the patient's mPAP by at least 95%. In some embodiments, the method relates to decreasing the patient's mPAP by at least 100%.

mRAP

In some patients, increased pulmonary vascular resistance to blood flow leads to increased right atrial pressure (RAP) and right heart failure. Patients with right heart failure typically have an increased ratio of RAP and pulmonary artery wedge pressure (PAWP). In certain aspects, the disclosure relates to methods of treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has resting mean right atrial pressure (mRAP) of at least 5 mmHg (e.g., 5, 6, 7, 8, 9, 10, 11, 12, 13, 14, 15, 16, 17, 18, 18, 20, 21, 22, 23, 24, or 25 mmHg). In some embodiments, the method relates to a patient having a resting mRAP of at least 5 mmHg. In some embodiments, the method relates to a patient having a resting mRAP of at least 6 mmHg. In some embodiments, the method relates to a patient having a resting mRAP of at least 7 mmHg. In some embodiments, the method relates to a patient having a resting mRAP of at least 8 mmHg. In some embodiments, the method relates to a patient having a resting mRAP of at least 9 mmHg. In some embodiments, the method relates to a patient having a resting mRAP of at least 10 mmHg. In some embodiments, the method relates to a patient having a resting mRAP of at least 11 mmHg. In some embodiments, the method relates to a patient having a resting mRAP of at least 12 mmHg. In some embodiments, the method relates to a patient having a resting mRAP of at least 13 mmHg. In some embodiments, the method relates to a patient having a resting mRAP of at least 14 mmHg. In some embodiments, the method relates to a patient having a resting mRAP of at least 15 mmHg. In some embodiments, the method relates to a patient having a resting mRAP of at least 16 mmHg. In some embodiments, the method relates to a patient having a resting mRAP of at least 17 mmHg. In some embodiments, the method relates to a patient having a resting mRAP of at least 18 mmHg. In some embodiments, the method relates to a patient having a resting mRAP of at least 19 mmHg. In some embodiments, the method relates to a patient having a resting mRAP of at least 20 mmHg. In some embodiments, the method relates to a patient having a resting mRAP of at least 21 mmHg. In some embodiments, the method relates to a patient having a resting mRAP of at least 22 mmHg. In some embodiments, the method relates to a patient having a resting mRAP of at least 23 mmHg. In some embodiments, the method relates to a patient having a resting mRAP of at least 24 mmHg. In some embodiments, the method relates to a patient having a resting mRAP of at least 25 mmHg.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to improving the mean right atrial pressure in the patient. In some embodiments, the improvement in the mean right atrial pressure (mRAP) is a reduction in the mRAP. In some embodiments, the method relates to reducing mRAP. In some embodiments, the method relates to reducing the patient's mRAP by at least 1 mmHg. In some embodiments, the method relates to reducing the patient's mRAP by at least 2 mmHg. In some embodiments, the method relates to reducing the patient's mRAP by at least 3 mmHg. In some embodiments, the method relates to reducing the patient's mRAP by at least 4 mmHg. In certain embodiments, the method relates to reducing the patient's mRAP by at least 5 mmHg. In some embodiments, the method relates to reducing the patient's mRAP by at least 6 mmHg. In certain embodiments, the method relates to reducing the patient's mRAP by at least 7 mmHg. In some embodiments, the method relates to reducing the patient's mRAP by at least 8 mmHg. In some embodiments, the method relates to reducing the patient's mRAP by at least 9 mmHg. In certain embodiments, the method relates to reducing the patient's mRAP by at least 10 mmHg. In some embodiments, the method relates to reducing the patient's mRAP by at least 11 mmHg. In certain embodiments, the method relates to reducing the patient's mRAP by at least 12 mmHg. In some embodiments, the method relates to reducing the patient's mRAP by at least 13 mmHg. In some embodiments, the method relates to reducing the patient's mRAP by at least 14 mmHg. In certain embodiments, the method relates to reducing the patient's mRAP by at least 15 mmHg. In some embodiments, the method relates to reducing the patient's mRAP by at least 16 mmHg. In some embodiments, the method relates to reducing the patient's mRAP by at least 17 mmHg. In some embodiments, the method relates to reducing the patient's mRAP by at least 18 mmHg. In some embodiments, the method relates to reducing the patient's mRAP by at least 19 mmHg. In certain embodiments, the method relates to reducing the patient's mRAP by at least 20 mmHg.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to decreasing the patient's mRAP by least 1% (e.g., 1, 5, 10, 15, 20, 25, 30, 35, 40, 45, 50, 55, 60, 65, 70, 75, 80, 85, 90, 95, or 100%). In some embodiments, the method relates to decreasing the patient's mRAP by at least 1%. In some embodiments, the method relates to decreasing the patient's mRAP by at least 5%. In some embodiments, the method relates to decreasing the patient's mRAP by at least 10%. In some embodiments, the method relates to decreasing the patient's mRAP by at least 15%. In some embodiments, the method relates to decreasing the patient's mRAP by at least 20%. In some embodiments, the method relates to decreasing the patient's mRAP by at least 25%. In some embodiments, the method relates to decreasing the patient's mRAP by at least 30%. In some embodiments, the method relates to decreasing the patient's mRAP by at least 35%. In some embodiments, the method relates to decreasing the patient's mRAP by at least 40%. In some embodiments, the method relates to decreasing the patient's mRAP by at least 45%. In some embodiments, the method relates to decreasing the patient's mRAP by at least 50%. In some embodiments, the method relates to decreasing the patient's mRAP by at least 55%. In some embodiments, the method relates to decreasing the patient's mRAP by at least 60%. In some embodiments, the method relates to decreasing the patient's mRAP by at least 65%. In some embodiments, the method relates to decreasing the patient's mRAP by at least 70%. In some embodiments, the method relates to decreasing the patient's mRAP by at least 75%. In some embodiments, the method relates to decreasing the patient's mRAP by at least 80%. In some embodiments, the method relates to decreasing the patient's mRAP by at least 85%. In some embodiments, the method relates to decreasing the patient's mRAP by at least 90%. In some embodiments, the method relates to decreasing the patient's mRAP by at least 95%. In some embodiments, the method relates to decreasing the patient's mRAP by at least 100%.

PVR

In certain aspects, the disclosure relates to methods of treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has a pulmonary vascular resistance (PVR) of at least 2.5 Woods Units (e.g., 2.5, 3, 4, 5, 6, 7, 8, 9, 10, 12, 14, 16, 18, or 20 Woods Units). In some embodiments, the method relates to patients having a PVR of at least 2.5 Woods Units. In some embodiments, the method relates to patients having a PVR of at least 3 Woods Units. In some embodiments, the method relates to patients having a PVR of at least 4 Woods Units. In some embodiments, the method relates to patients having a PVR of at least 5 Woods Units. In some embodiments, the method relates to patients having a PVR of at least 6 Woods Units. In some embodiments, the method relates to patients having a PVR of at least 7 Woods Units. In some embodiments, the method relates to patients having a PVR of at least 8 Woods Units. In some embodiments, the method relates to patients having a PVR of at least 9 Woods Units. In some embodiments, the method relates to patients having a PVR of at least 10 Woods Units. In some embodiments, the method relates to patients having a PVR of at least 12 Woods Units. In some embodiments, the method relates to patients having a PVR of at least 14 Woods Units. In some embodiments, the method relates to patients having a PVR of at least 16 Woods Units. In some embodiments, the method relates to patients having a PVR of at least 18 Woods Units. In some embodiments, the method relates to patients having a PVR of at least 20 Woods Units.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to reducing the patient's PVR. In some embodiments, the reduction in the patient's PVR is a result of a decrease in the patient's mean pulmonary arterial pressure (mPAP). In some embodiments, the method relates to reducing the patient's PVR by at least 0.5 Wood Units. In some embodiments, the method relates to reducing the patient's PVR by at least 1 Wood Units. In some embodiments, the method relates to reducing the patient's PVR by at least 2 Wood Units. In some embodiments, the method relates to reducing the patient's PVR by at least 4 Wood Units. In some embodiments, the method relates to reducing the patient's PVR by at least 6 Wood Units. In some embodiments, the method relates to reducing the patient's PVR by at least 8 Wood Units. In some embodiments, the method relates to reducing the patient's PVR by at least 10 Wood Units.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to decreasing the patient's PVR. In some embodiments, the reduction in the patient's PVR is a result of a decrease in the patient's mean pulmonary arterial pressure (mPAP). In some embodiments, the method relates to decreasing the patient's PVR by least 1% (e.g., 1%, 5, 10, 15, 20, 25, 30, 35, 40, 45, 50, 55, 60, 65, 70, 75, 80, 85, 90, 95, or 100%). In some embodiments, the method relates to decreasing the patient's PVR by at least 1%. In some embodiments, the method relates to decreasing the patient's PVR by at least 5%. In some embodiments, the method relates to decreasing the patient's PVR by at least 10%. In some embodiments, the method relates to decreasing the patient's PVR by at least 15%. In some embodiments, the method relates to decreasing the patient's PVR by at least 20%. In some embodiments, the method relates to decreasing the patient's PVR by at least 25%. In some embodiments, the method relates to decreasing the patient's PVR by at least 30%. In some embodiments, the method relates to decreasing the patient's PVR by at least 35%. In some embodiments, the method relates to decreasing the patient's PVR by at least 40%. In some embodiments, the method relates to decreasing the patient's PVR by at least 45%. In some embodiments, the method relates to decreasing the patient's PVR by at least 50%. In some embodiments, the method relates to decreasing the patient's PVR by at least 55%. In some embodiments, the method relates to decreasing the patient's PVR by at least 60%. In some embodiments, the method relates to decreasing the patient's PVR by at least 65%. In some embodiments, the method relates to decreasing the patient's PVR by at least 70%. In some embodiments, the method relates to decreasing the patient's PVR by at least 75%. In some embodiments, the method relates to decreasing the patient's PVR by at least 80%. In some embodiments, the method relates to decreasing the patient's PVR by at least 85%. In some embodiments, the method relates to decreasing the patient's PVR by at least 90%. In some embodiments, the method relates to decreasing the patient's PVR by at least 95%. In some embodiments, the method relates to decreasing the patient's PVR by at least 100%.

PAWP

In certain aspects, the disclosure relates to methods of treating, preventing, or reducing the progression rate and/or severity of PcPH (e.g., treating, preventing, or reducing the progression rate and/or severity of one or more complications of PcPH WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has pulmonary arterial wedge pressure (PAWP) of at least 12 mmHg (e.g., 12, 15, 20, 25, 30, 35, 40, 45, or 50 mmHg). In some embodiments, the method relates to patients having a PAWP of at least 15 mmHg. In some embodiments, the method relates to patients having a PAWP of at least 20 mmHg. In some embodiments, the method relates to patients having a PAWP of at least 25 mmHg. In some embodiments, the method relates to patients having a PAWP of at least 30 mmHg. In some embodiments, the method relates to patients having a PAWP of at least 35 mmHg. In some embodiments, the method relates to patients having a PAWP of at least 40 mmHg. In some embodiments, the method relates to patients having a PAWP of at least 45 mmHg. In some embodiments, the method relates to patients having a PAWP of at least 50 mmHg. In some embodiments, the method relates to patients having a PCWP between 15 to 30 mmHg.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to reducing the patient's PAWP by at least 1 mmHg. In some embodiments, the method relates to reducing the patient's PAWP by at least 2 mmHg. In some embodiments, the method relates to reducing the patient's PAWP by at least 4 mmHg. In some embodiments, the method relates to reducing the patient's PAWP by at least 6 mmHg. In some embodiments, the method relates to reducing the patient's PAWP by at least 10 mmHg. In some embodiments, the method relates to reducing the patient's PAWP by at least 15 mmHg. In some embodiments, the method relates to reducing the patient's PAWP by at least 20 mmHg. In some embodiments, the method relates to reducing the patient's PAWP by at least 25 mmHg. In some embodiments, the method relates to reducing the patient's PAWP by at least 30 mmHg.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to decreasing the patient's PAWP by least 1% (e.g., 1, 5, 10, 15, 20, 25, 30, 35, 40, 45, 50, 55, 60, 65, 70, 75, 80, 85, 90, 95, or 100%). In some embodiments, the method relates to decreasing the patient's PAWP by at least 1%. In some embodiments, the method relates to decreasing the patient's PAWP by at least 5%. In some embodiments, the method relates to decreasing the patient's PAWP by at least 10%. In some embodiments, the method relates to decreasing the patient's PAWP by at least 15%. In some embodiments, the method relates to decreasing the patient's PAWP by at least 20%. In some embodiments, the method relates to decreasing the patient's PAWP by at least 25%. In some embodiments, the method relates to decreasing the patient's PAWP by at least 30%. In some embodiments, the method relates to decreasing the patient's PAWP by at least 35%. In some embodiments, the method relates to decreasing the patient's PAWP by at least 40%. In some embodiments, the method relates to decreasing the patient's PAWP by at least 45%. In some embodiments, the method relates to decreasing the patient's PAWP by at least 50%. In some embodiments, the method relates to decreasing the patient's PAWP by at least 55%. In some embodiments, the method relates to decreasing the patient's PAWP by at least 60%. In some embodiments, the method relates to decreasing the patient's PAWP by at least 65%. In some embodiments, the method relates to decreasing the patient's PAWP by at least 70%. In some embodiments, the method relates to decreasing the patient's PAWP by at least 75%. In some embodiments, the method relates to decreasing the patient's PAWP by at least 80%. In some embodiments, the method relates to decreasing the patient's PAWP by at least 85%. In some embodiments, the method relates to decreasing the patient's PAWP by at least 90%. In some embodiments, the method relates to decreasing the patient's PAWP by at least 95%. In some embodiments, the method relates to decreasing the patient's PAWP by at least 100%.

LVEDP

In certain aspects, the disclosure relates to methods of treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has left ventricular end diastolic pressure (LVEDP) of at least 12 mmHg (e.g., 12, 15, 20, 25, 30, 35, 40, 45, or 50 mmHg). In some embodiments, the method relates to patients having a LVEDP of at least 15 mmHg. In some embodiments, the method relates to patients having a LVEDP of at least 20 mmHg. In some embodiments, the method relates to patients having a LVEDP of at least 25 mmHg. In some embodiments, the method relates to patients having a LVEDP of at least 30 mmHg. In some embodiments, the method relates to patients having a LVEDP of at least 35 mmHg. In some embodiments, the method relates to patients having a LVEDP of at least 40 mmHg. In some embodiments, the method relates to patients having a LVEDP of at least 45 mmHg. In some embodiments, the method relates to patients having a LVEDP of at least 50 mmHg.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to reducing the patient's LVEDP by at least 1 mmHg. In some embodiments, the method relates to reducing the patient's LVEDP by at least 2 mmHg. In some embodiments, the method relates to reducing the patient's LVEDP by at least 4 mmHg. In some embodiments, the method relates to reducing the patient's LVEDP by at least 6 mmHg. In some embodiments, the method relates to reducing the patient's LVEDP by at least 10 mmHg. In some embodiments, the method relates to reducing the patient's LVEDP by at least 15 mmHg. In some embodiments, the method relates to reducing the patient's LVEDP by at least 20 mmHg. In some embodiments, the method relates to reducing the patient's LVEDP by at least 25 mmHg. In some embodiments, the method relates to reducing the patient's LVEDP by at least 30 mmHg.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to decreasing the patient's LVEDP by least 1% (e.g., 1, 5, 10, 15, 20, 25, 30, 35, 40, 45, 50, 55, 60, 65, 70, 75, 80, 85, 90, 95, or 100%). In some embodiments, the method relates to decreasing the patient's LVEDP by at least 1%. In some embodiments, the method relates to decreasing the patient's LVEDP by at least 5%. In some embodiments, the method relates to decreasing the patient's LVEDP by at least 10%. In some embodiments, the method relates to decreasing the patient's LVEDP by at least 15%. In some embodiments, the method relates to decreasing the patient's LVEDP by at least 20%. In some embodiments, the method relates to decreasing the patient's LVEDP by at least 25%. In some embodiments, the method relates to decreasing the patient's LVEDP by at least 30%. In some embodiments, the method relates to decreasing the patient's LVEDP by at least 35%. In some embodiments, the method relates to decreasing the patient's LVEDP by at least 40%. In some embodiments, the method relates to decreasing the patient's LVEDP by at least 45%. In some embodiments, the method relates to decreasing the patient's LVEDP by at least 50%. In some embodiments, the method relates to decreasing the patient's LVEDP by at least 55%. In some embodiments, the method relates to decreasing the patient's LVEDP by at least 60%. In some embodiments, the method relates to decreasing the patient's LVEDP by at least 65%. In some embodiments, the method relates to decreasing the patient's LVEDP by at least 70%. In some embodiments, the method relates to decreasing the patient's LVEDP by at least 75%. In some embodiments, the method relates to decreasing the patient's LVEDP by at least 80%. In some embodiments, the method relates to decreasing the patient's LVEDP by at least 85%. In some embodiments, the method relates to decreasing the patient's LVEDP by at least 90%. In some embodiments, the method relates to decreasing the patient's LVEDP by at least 95%. In some embodiments, the method relates to decreasing the patient's LVEDP by at least 100%.

DPG

In certain aspects, the disclosure relates to methods of treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has resting diastolic pressure gradient (DPG) of at least 5 mmHg (e.g., 5, 6, 7, 8, 9, 10, 15, 20, 25, 30, 35, 40, or 45 mmHg). In some embodiments, the method relates to patients having a DPG of at least 5 mmHg. In some embodiments, the method relates to patients having a DPG of at least 6 mmHg. In some embodiments, the method relates to patients having a DPG of at least 7 mmHg. In some embodiments, the method relates to patients having a DPG of at least 8 mmHg. In some embodiments, the method relates to patients having a DPG of at least 9 mmHg. In some embodiments, the method relates to patients having a DPG of at least 10 mmHg. In some embodiments, the method relates to patients having a DPG of at least 15 mmHg. In some embodiments, the method relates to patients having a DPG of at least 20 mmHg. In some embodiments, the method relates to patients having a DPG of at least 25 mmHg. In some embodiments, the method relates to patients having a DPG of at least 30 mmHg. In some embodiments, the method relates to patients having a DPG of at least 35 mmHg. In some embodiments, the method relates to patients having a DPG of at least 40 mmHg. In some embodiments, the method relates to patients having a DPG of at least 45 mmHg.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to reducing the patient's DPG by at least 1 mmHg. In some embodiments, the method relates to reducing the patient's DPG by at least 2 mmHg. In some embodiments, the method relates to reducing the patient's DPG by at least 4 mmHg. In some embodiments, the method relates to reducing the patient's DPG by at least 6 mmHg. In some embodiments, the method relates to reducing the patient's DPG by at least 10 mmHg. In some embodiments, the method relates to reducing the patient's DPG by at least 15 mmHg. In some embodiments, the method relates to reducing the patient's DPG by at least 20 mmHg. In some embodiments, the method relates to reducing the patient's DPG by at least 25 mmHg. In some embodiments, the method relates to reducing the patient's DPG by at least 30 mmHg.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to decreasing the patient's DPG by least 1% (e.g., 1, 5, 10, 15, 20, 25, 30, 35, 40, 45, 50, 55, 60, 65, 70, 75, 80, 85, 90, 95, or 100%). In some embodiments, the method relates to decreasing the patient's DPG by at least 1%. In some embodiments, the method relates to decreasing the patient's DPG by at least 5%. In some embodiments, the method relates to decreasing the patient's DPG by at least 10%. In some embodiments, the method relates to decreasing the patient's DPG by at least 15%. In some embodiments, the method relates to decreasing the patient's DPG by at least 20%. In some embodiments, the method relates to decreasing the patient's DPG by at least 25%. In some embodiments, the method relates to decreasing the patient's DPG by at least 30%. In some embodiments, the method relates to decreasing the patient's DPG by at least 35%. In some embodiments, the method relates to decreasing the patient's DPG by at least 40%. In some embodiments, the method relates to decreasing the patient's DPG by at least 45%. In some embodiments, the method relates to decreasing the patient's DPG by at least 50%. In some embodiments, the method relates to decreasing the patient's DPG by at least 55%. In some embodiments, the method relates to decreasing the patient's DPG by at least 60%. In some embodiments, the method relates to decreasing the patient's DPG by at least 65%. In some embodiments, the method relates to decreasing the patient's DPG by at least 70%. In some embodiments, the method relates to decreasing the patient's DPG by at least 75%. In some embodiments, the method relates to decreasing the patient's DPG by at least 80%. In some embodiments, the method relates to decreasing the patient's DPG by at least 85%. In some embodiments, the method relates to decreasing the patient's DPG by at least 90%. In some embodiments, the method relates to decreasing the patient's DPG by at least 95%. In some embodiments, the method relates to decreasing the patient's DPG by at least 100%.

TPG

In certain aspects, the disclosure relates to methods of treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has a transpulmonary gradient (TPG) of at least 10 mmHg (e.g., 10, 11, 12, 13, 14, 15, 20, 25, 30, 35, 40, 45, or 50 mmHg). In some embodiments, the method relates to patients having a TPG of at least 10 mmHg. In some embodiments, the method relates to patients having a TPG of at least 11 mmHg. In some embodiments, the method relates to patients having a TPG of at least 12 mmHg. In some embodiments, the method relates to patients having a TPG of at least 13 mmHg. In some embodiments, the method relates to patients having a TPG of at least 14 mmHg. In some embodiments, the method relates to patients having a TPG of at least 15 mmHg. In some embodiments, the method relates to patients having a TPG of at least 20 mmHg. In some embodiments, the method relates to patients having a TPG of at least 25 mmHg. In some embodiments, the method relates to patients having a TPG of at least 30 mmHg. In some embodiments, the method relates to patients having a TPG of at least 35 mmHg. In some embodiments, the method relates to patients having a TPG of at least 40 mmHg. In some embodiments, the method relates to patients having a TPG of at least 45 mmHg. In some embodiments, the method relates to patients having a TPG of at least 50 mmHg.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to reducing the patient's TPG by at least 1 mmHg. In some embodiments, the method relates to reducing the patient's TPG by at least 2 mmHg. In some embodiments, the method relates to reducing the patient's TPG by at least 4 mmHg. In some embodiments, the method relates to reducing the patient's TPG by at least 6 mmHg. In some embodiments, the method relates to reducing the patient's TPG by at least 10 mmHg. In some embodiments, the method relates to reducing the patient's TPG by at least 15 mmHg. In some embodiments, the method relates to reducing the patient's TPG by at least 20 mmHg. In some embodiments, the method relates to reducing the patient's TPG by at least 25 mmHg. In some embodiments, the method relates to reducing the patient's TPG by at least 30 mmHg. In some embodiments, the method relates to reducing the patient's TPG by at least 40 mmHg.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to decreasing the patient's TPG by least 1% (e.g., 1, 5, 10, 15, 20, 25, 30, 35, 40, 45, 50, 55, 60, 65, 70, 75, 80, 85, 90, 95, or 100%). In some embodiments, the method relates to decreasing the patient's TPG by at least 1%. In some embodiments, the method relates to decreasing the patient's TPG by at least 5%. In some embodiments, the method relates to decreasing the patient's TPG by at least 10%. In some embodiments, the method relates to decreasing the patient's TPG by at least 15%. In some embodiments, the method relates to decreasing the patient's TPG by at least 20%. In some embodiments, the method relates to decreasing the patient's TPG by at least 25%. In some embodiments, the method relates to decreasing the patient's TPG by at least 30%. In some embodiments, the method relates to decreasing the patient's TPG by at least 35%. In some embodiments, the method relates to decreasing the patient's TPG by at least 40%. In some embodiments, the method relates to decreasing the patient's TPG by at least 45%. In some embodiments, the method relates to decreasing the patient's TPG by at least 50%. In some embodiments, the method relates to decreasing the patient's TPG by at least 55%. In some embodiments, the method relates to decreasing the patient's TPG by at least 60%. In some embodiments, the method relates to decreasing the patient's TPG by at least 65%. In some embodiments, the method relates to decreasing the patient's TPG by at least 70%. In some embodiments, the method relates to decreasing the patient's TPG by at least 75%. In some embodiments, the method relates to decreasing the patient's TPG by at least 80%. In some embodiments, the method relates to decreasing the patient's TPG by at least 85%. In some embodiments, the method relates to decreasing the patient's TPG by at least 90%. In some embodiments, the method relates to decreasing the patient's TPG by at least 95%. In some embodiments, the method relates to decreasing the patient's TPG by at least 100%.

BNP

Both BNP and NT-proBNP are markers of atrial and ventricular distension due to increased intracardiac pressure. The New York Heart Association (NYHA) developed a 4-stage functional classification system for congestive heart failure (CHF) based on the severity of symptoms. Studies have demonstrated that the measured concentrations of circulating BNP and NT-proBNP increase with the severity of CHF based on the NYHA classification. In certain aspects, the disclosure relates to methods of treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has a brain natriuretic peptide (BNP) level of at least 100 pg/mL (e.g., 100, 150, 200, 300, 400, 500, 600, 700, 800, 900 1000, 3000, 5000, 10,000, 15,000, or 20,000 pg/mL). In some embodiments, the method relates to patient's having a BNP level of at least 100 pg/mL. In some embodiments, the method relates to patient's having a BNP level of at least 150 pg/mL. In some embodiments, the method relates to patient's having a BNP level of at least 200 pg/mL. In some embodiments, the method relates to patient's having a BNP level of at least 300 pg/mL. In some embodiments, the method relates to patient's having a BNP level of at least 400 pg/mL. In some embodiments, the method relates to patient's having a BNP level of at least 500 pg/mL. In some embodiments, the method relates to patient's having a BNP level of at least 600 pg/mL. In some embodiments, the method relates to patient's having a BNP level of at least 700 pg/mL. In some embodiments, the method relates to patient's having a BNP level of at least 800 pg/mL. In some embodiments, the method relates to patient's having a BNP level of at least 900 pg/mL. In some embodiments, the method relates to patient's having a BNP level of at least 1000 pg/mL. In some embodiments, the method relates to patient's having a BNP level of at least 5000 pg/mL. In some embodiments, the method relates to patient's having a BNP level of at least 10,000 pg/mL. In some embodiments, the method relates to patient's having a BNP level of at least 15,000 pg/mL. In some embodiments, the method relates to patient's having a BNP level of at least 20,000 pg/mL. In some embodiments, the method relates to treatment of a patient who has elevated BNP levels as compared to a healthy patient.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to reducing the patient's BNP levels by at least 10 pg/mL. In some embodiments, the method relates to reducing the patient's BNP levels by at least 50 pg/mL. In some embodiments, the method relates to reducing the patient's BNP levels by at least 100 pg/mL. In some embodiments, the method relates to reducing the patient's BNP levels by at least 200 pg/mL. In some embodiments, the method relates to reducing the patient's BNP levels by at least 300 pg/mL. In some embodiments, the method relates to reducing the patient's BNP levels by at least 400 pg/mL. In some embodiments, the method relates to reducing the patient's BNP levels by at least 500 pg/mL. In some embodiments, the method relates to reducing the patient's BNP levels by at least 600 pg/mL. In some embodiments, the method relates to reducing the patient's BNP levels by at least 700 pg/mL. In some embodiments, the method relates to reducing the patient's BNP levels by at least 800 pg/mL. In some embodiments, the method relates to reducing the patient's BNP levels by at least 900 pg/mL. In some embodiments, the method relates to reducing the patient's BNP levels by at least 1000 pg/mL. In some embodiments, the method relates to reducing the patient's BNP levels by at least 5000 pg/mL. In some embodiments, the method relates to reducing the patient's BNP levels to normal levels. In some embodiments, normal levels correspond to levels of <100 pg/mL.

In some embodiments, the method relates to reducing the patient's BNP by at least 5% (e.g., 5, 10, 15, 20, 25, 30, 35, 40, 45, 50, 55, 60, 65, 70, 75, 80, 85, 90, 95, or 100%). In some embodiments, the method relates to reducing the patient's BNP by at least 5%. In some embodiments, the method relates to reducing the patient's BNP by at least 10%. In some embodiments, the method relates to reducing the patient's BNP by at least 15%. In some embodiments, the method relates to reducing the patient's BNP by at least 20%. In some embodiments, the method relates to reducing the patient's BNP by at least 25%. In some embodiments, the method relates to reducing the patient's BNP by at least 30%. In some embodiments, the method relates to reducing the patient's BNP by at least 35%. In some embodiments, the method relates to reducing the patient's BNP by at least 40%. In some embodiments, the method relates to reducing the patient's BNP by at least 45%. In some embodiments, the method relates to reducing the patient's BNP by at least 50%. In some embodiments, the method relates to reducing the patient's BNP by at least 55%. In some embodiments, the method relates to reducing the patient's BNP by at least 60%. In some embodiments, the method relates to reducing the patient's BNP by at least 65%. In some embodiments, the method relates to reducing the patient's BNP by at least 70%. In some embodiments, the method relates to reducing the patient's BNP by at least 75%. In some embodiments, the method relates to reducing the patient's BNP by at least 80%. In some embodiments, the method relates to reducing the patient's BNP by at least 85%. In some embodiments, the method relates to reducing the patient's BNP by at least 90%. In some embodiments, the method relates to reducing the patient's BNP by at least 95%. In some embodiments, the method relates to reducing the patient's BNP by at least 100%.

NT-proBNP

In certain aspects, the disclosure relates to methods of treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has a NT-proBNP level of at least 100 pg/mL (e.g., 100, 150, 200, 300, 400, 500, 600, 700, 800, 900, 1000, 3000, 5000, 10,000, 15,000, 20,000, 25,000, or 30,000 pg/mL). In some embodiments, the method relates to patient's having a NT-proBNP level of at least 100 pg/mL. In some embodiments, the method relates to patient's having a NT-proBNP level of at least 150 pg/mL. In some embodiments, the method relates to patient's having a NT-proBNP level of at least 200 pg/mL. In some embodiments, the method relates to patient's having a NT-proBNP level of at least 300 pg/mL. In some embodiments, the method relates to patient's having a NT-proBNP level of at least 400 pg/mL. In some embodiments, the method relates to patient's having a NT-proBNP level of at least 500 pg/mL. In some embodiments, the method relates to patient's having a NT-proBNP level of at least 600 pg/mL. In some embodiments, the method relates to patient's having a NT-proBNP level of at least 700 pg/mL. In some embodiments, the method relates to patient's having a NT-proBNP level of at least 800 pg/mL. In some embodiments, the method relates to patient's having a NT-proBNP level of at least 900 pg/mL. In some embodiments, the method relates to patient's having a NT-proBNP level of at least 1000 pg/mL. In some embodiments, the method relates to patient's having a NT-proBNP level of at least 5000 pg/mL. In some embodiments, the method relates to patient's having a NT-proBNP level of at least 10,000 pg/mL. In some embodiments, the method relates to patient's having a NT-proBNP level of at least 15,000 pg/mL. In some embodiments, the method relates to patient's having a NT-proBNP level of at least 20,000 pg/mL. In some embodiments, the method relates to patient's having a NT-proBNP level of at least 25,000 pg/mL. In some embodiments, the method relates to patient's having a NT-proBNP level of at least 30,000 pg/mL. In some embodiments, the method relates to treatment of a patient who has elevated NT-proBNP levels as compared to a healthy patient.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to reducing the patient's NT-proBNP levels. In some embodiments, the method relates to reducing the patient's NT-proBNP by at least 10 pg/mL. In some embodiments, the method relates to reducing the patient's NT-proBNP by at least 50 pg/mL. In some embodiments, the method relates to reducing the patient's NT-proBNP by at least 100 pg/mL. In some embodiments, the method relates to reducing the patient's NT-proBNP by at least 200 pg/mL. In some embodiments, the method relates to reducing the patient's NT-proBNP by at least 300 pg/mL. In some embodiments, the method relates to reducing the patient's NT-proBNP by at least 400 pg/mL. In some embodiments, the method relates to reducing the patient's NT-proBNP by at least 500 pg/mL. In some embodiments, the method relates to reducing the patient's NT-proBNP by at least 600 pg/mL. In some embodiments, the method relates to reducing the patient's NT-proBNP by at least 700 pg/mL. In some embodiments, the method relates to reducing the patient's NT-proBNP by at least 800 pg/mL. In some embodiments, the method relates to reducing the patient's NT-proBNP by at least 900 pg/mL. In some embodiments, the method relates to reducing the patient's NT-proBNP by at least 1000 pg/mL. In some embodiments, the method relates to reducing the patient's NT-proBNP by at least 5000 pg/mL. In some embodiments, the method relates to reducing the patient's NT-proBNP by at least 10,000 pg/mL. In some embodiments, the method relates to reducing the patient's NT-proBNP by at least 15,000 pg/mL. In some embodiments, the method relates to reducing the patient's NT-proBNP by at least 20,000 pg/mL. In some embodiments, the method relates to reducing the patient's NT-proBNP by at least 25,000 pg/mL.

In some embodiments, the method relates to decreasing the patient's NT-proBNP levels to a normal level and maintaining their normal NT-proBNP levels. In some embodiments, the disclosure relates to methods of maintaining one or more hemodynamic parameters in the PcPH patient at a normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to maintaining the patient's NT-proBNP levels at a normal level. In some embodiments, the method relates to maintaining the patient's NT-proBNP level at less than 100 pg/mL. In some embodiments, the method relates to maintaining the patient's NT-proBNP level at less than 200 pg/mL. In some embodiments, the method relates to maintaining the patient's NT-proBNP level at less than 300 pg/mL. In some embodiments, the method relates to maintaining the patient's NT-proBNP level at less than 400 pg/mL.

In some embodiments, the method relates to reducing the patient's NT-proBNP by at least 5% (e.g., 5, 10, 15, 20, 25, 30, 35, 40, 45, 50, 55, 60, 65, 70, 75, 80, 85, 90, 95, or 100%). In some embodiments, the method relates to reducing the patient's NT-proBNP by at least 5%. In some embodiments, the method relates to reducing the patient's NT-proBNP by at least 10%. In some embodiments, the method relates to reducing the patient's NT-proBNP by at least 15%. In some embodiments, the method relates to reducing the patient's NT-proBNP by at least 20%. In some embodiments, the method relates to reducing the patient's NT-proBNP by at least 25%. In some embodiments, the method relates to reducing the patient's NT-proBNP by at least 30%. In some embodiments, the method relates to reducing the patient's NT-proBNP by at least 35%. In some embodiments, the method relates to reducing the patient's NT-proBNP by at least 40%. In some embodiments, the method relates to reducing the patient's NT-proBNP by at least 45%. In some embodiments, the method relates to reducing the patient's NT-proBNP by at least 50%. In some embodiments, the method relates to reducing the patient's NT-proBNP by at least 55%. In some embodiments, the method relates to reducing the patient's NT-proBNP by at least 60%. In some embodiments, the method relates to reducing the patient's NT-proBNP by at least 65%. In some embodiments, the method relates to reducing the patient's NT-proBNP by at least 70%. In some embodiments, the method relates to reducing the patient's NT-proBNP by at least 75%. In some embodiments, the method relates to reducing the patient's NT-proBNP by at least 80%. In some embodiments, the method relates to reducing the patient's NT-proBNP by at least 85%. In some embodiments, the method relates to reducing the patient's NT-proBNP by at least 90%. In some embodiments, the method relates to reducing the patient's NT-proBNP by at least 95%. In some embodiments, the method relates to reducing the patient's NT-proBNP by at least 100%. In some embodiments, the method relates to reducing the patient's NT-proBNP levels to normal levels. In some embodiments, normal levels of NT-proBNP is <100 pg/ml. In some embodiments, the method relates to reducing the patient's NT-proBNP levels to less than 300 ng/L.

Smooth Muscle Hypertrophy

In certain aspects, the disclosure relates to methods of treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has smooth muscle hypertrophy. In some embodiments, the disclosure relates to methods of adjusting one or more parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to decreasing smooth muscle hypertrophy in the patient. In some embodiments, the method relates to decreasing the patient's smooth muscle hypertrophy by least 1% (e.g., 1, 5, 10, 15, 20, 25, 30, 35, 40, 45, 50, 55, 60, 65, 70, 75, 80, 85, 90, 95, or 100%). In some embodiments, the method relates to decreasing the patient's smooth muscle hypertrophy by at least 1%. In some embodiments, the method relates to decreasing the patient's smooth muscle hypertrophy by at least 5%. In some embodiments, the method relates to decreasing the patient's smooth muscle hypertrophy by at least 10%. In some embodiments, the method relates to decreasing the patient's smooth muscle hypertrophy by at least 15%. In some embodiments, the method relates to decreasing the patient's smooth muscle hypertrophy by at least 20%. In some embodiments, the method relates to decreasing the patient's smooth muscle hypertrophy by at least 25%. In some embodiments, the method relates to decreasing the patient's smooth muscle hypertrophy by at least 30%. In some embodiments, the method relates to decreasing the patient's smooth muscle hypertrophy by at least 35%. In some embodiments, the method relates to decreasing the patient's smooth muscle hypertrophy by at least 40%. In some embodiments, the method relates to decreasing the patient's smooth muscle hypertrophy by at least 45%. In some embodiments, the method relates to decreasing the patient's smooth muscle hypertrophy by at least 50%. In some embodiments, the method relates to decreasing the patient's smooth muscle hypertrophy by at least 55%. In some embodiments, the method relates to decreasing the patient's smooth muscle hypertrophy by at least 60%. In some embodiments, the method relates to decreasing the patient's smooth muscle hypertrophy by at least 65%. In some embodiments, the method relates to decreasing the patient's smooth muscle hypertrophy by at least 70%. In some embodiments, the method relates to decreasing the patient's smooth muscle hypertrophy by at least 75%. In some embodiments, the method relates to decreasing the patient's smooth muscle hypertrophy by at least 80%. In some embodiments, the method relates to decreasing the patient's smooth muscle hypertrophy by at least 85%. In some embodiments, the method relates to decreasing the patient's smooth muscle hypertrophy by at least 90%. In some embodiments, the method relates to decreasing the patient's smooth muscle hypertrophy by at least 95%. In some embodiments, the method relates to decreasing the patient's smooth muscle hypertrophy by at least 100%.

Pulmonary Arteriole Muscularity

In certain aspects, the disclosure relates to methods of treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has increased pulmonary arteriole muscularity. In some embodiments, the disclosure relates to methods of adjusting one or more parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to decreasing pulmonary arteriole muscularity in the patient. In some embodiments, the method relates to decreasing the patient's pulmonary arteriole muscularity by least 1% (e.g., 1, 5, 10, 15, 20, 25, 30, 35, 40, 45, 50, 55, 60, 65, 70, 75, 80, 85, 90, 95, or 100%). In some embodiments, the method relates to decreasing the patient's pulmonary arteriole muscularity by at least 1%. In some embodiments, the method relates to decreasing the patient's pulmonary arteriole muscularity by at least 5%. In some embodiments, the method relates to decreasing the patient's pulmonary arteriole muscularity by at least 10%. In some embodiments, the method relates to decreasing the patient's pulmonary arteriole muscularity by at least 15%. In some embodiments, the method relates to decreasing the patient's pulmonary arteriole muscularity by at least 20%. In some embodiments, the method relates to decreasing the patient's pulmonary arteriole muscularity by at least 25%. In some embodiments, the method relates to decreasing the patient's pulmonary arteriole muscularity by at least 30%. In some embodiments, the method relates to decreasing the patient's pulmonary arteriole muscularity by at least 35%. In some embodiments, the method relates to decreasing the patient's pulmonary arteriole muscularity by at least 40%. In some embodiments, the method relates to decreasing the patient's pulmonary arteriole muscularity by at least 45%. In some embodiments, the method relates to decreasing the patient's pulmonary arteriole muscularity by at least 50%. In some embodiments, the method relates to decreasing the patient's pulmonary arteriole muscularity by at least 55%. In some embodiments, the method relates to decreasing the patient's pulmonary arteriole muscularity by at least 60%. In some embodiments, the method relates to decreasing the patient's pulmonary arteriole muscularity by at least 65%. In some embodiments, the method relates to decreasing the patient's pulmonary arteriole muscularity by at least 70%. In some embodiments, the method relates to decreasing the patient's pulmonary arteriole muscularity by at least 75%. In some embodiments, the method relates to decreasing the patient's pulmonary arteriole muscularity by at least 80%. In some embodiments, the method relates to decreasing the patient's pulmonary arteriole muscularity by at least 85%. In some embodiments, the method relates to decreasing the patient's pulmonary arteriole muscularity by at least 90%. In some embodiments, the method relates to decreasing the patient's pulmonary arteriole muscularity by at least 95%. In some embodiments, the method relates to decreasing the patient's pulmonary arteriole muscularity by at least 100%.

Rate of Hospitalization

In certain aspects, the disclosure relates to methods of treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the method reduces the patient's hospitalization rate by at least 1% (e.g., 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100%. In some embodiments, the method relates to reducing the patient's hospitalization rate by at least 1%. In some embodiments, the method relates to reducing the patient's hospitalization rate by at least 2%. In some embodiments, the method relates to reducing the patient's hospitalization rate by at least 3%. In some embodiments, the method relates to reducing the patient's hospitalization rate by at least 4%. In some embodiments, the method relates to reducing the patient's hospitalization rate by at least 5%. In some embodiments, the method relates to reducing the patient's hospitalization rate by at least 10%. In some embodiments, the method relates to reducing the patient's hospitalization rate by at least 15%. In some embodiments, the method relates to reducing the patient's hospitalization rate by at least 20%. In some embodiments, the method relates to reducing the patient's hospitalization rate by at least 25%. In some embodiments, the method relates to reducing the patient's hospitalization rate by at least 30%. In some embodiments, the method relates to reducing the patient's hospitalization rate by at least 35%. In some embodiments, the method relates to reducing the patient's hospitalization rate by at least 40%. In some embodiments, the method relates to reducing the patient's hospitalization rate by at least 45%. In some embodiments, the method relates to reducing the patient's hospitalization rate by at least 50%. In some embodiments, the method relates to reducing the patient's hospitalization rate by at least 55%. In some embodiments, the method relates to reducing the patient's hospitalization rate by at least 60%. In some embodiments, the method relates to reducing the patient's hospitalization rate by at least 65%. In some embodiments, the method relates to reducing the patient's hospitalization rate by at least 70%. In some embodiments, the method relates to reducing the patient's hospitalization rate by at least 75%. In some embodiments, the method relates to reducing the patient's hospitalization rate by at least 80%. In some embodiments, the method relates to reducing the patient's hospitalization rate by at least 85%. In some embodiments, the method relates to reducing the patient's hospitalization rate by at least 90%. In some embodiments, the method relates to reducing the patient's hospitalization rate by at least 95%. In some embodiments, the method relates to reducing the patient's hospitalization rate by at least 100%. In some embodiments, the method reduces the risk of hospitalization for one or more complications associated with PcPH.

Quality of Life

In certain aspects, the disclosure relates to methods of treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the method increases the patient's quality of life by at least 1% (e.g., 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100%). In some embodiments, the method relates to increasing the patient's quality of life by at least 1%. In some embodiments, the method relates to increasing the patient's quality of life by at least 2%. In some embodiments, the method relates to increasing the patient's quality of life by at least 3%. In some embodiments, the method relates to increasing the patient's quality of life by at least 4%. In some embodiments, the method relates to increasing the patient's quality of life by at least 5%. In some embodiments, the method relates to increasing the patient's quality of life by at least 10%. In some embodiments, the method relates to increasing the patient's quality of life by at least 15%. In some embodiments, the method relates to increasing the patient's quality of life by at least 20%. In some embodiments, the method relates to increasing the patient's quality of life by at least 25%. In some embodiments, the method relates to increasing the patient's quality of life by at least 30%. In some embodiments, the method relates to increasing the patient's quality of life by at least 35%. In some embodiments, the method relates to increasing the patient's quality of life by at least 40%. In some embodiments, the method relates to increasing the patient's quality of life by at least 45%. In some embodiments, the method relates to increasing the patient's quality of life by at least 50%. In some embodiments, the method relates to increasing the patient's quality of life by at least 55%. In some embodiments, the method relates to increasing the patient's quality of life by at least 60%. In some embodiments, the method relates to increasing the patient's quality of life by at least 65%. In some embodiments, the method relates to increasing the patient's quality of life by at least 70%. In some embodiments, the method relates to increasing the patient's quality of life by at least 75%. In some embodiments, the method relates to increasing the patient's quality of life by at least 80%. In some embodiments, the method relates to increasing the patient's quality of life by at least 85%. In some embodiments, the method relates to increasing the patient's quality of life by at least 90%. In some embodiments, the method relates to increasing the patient's quality of life by at least 95%. In some embodiments, the method relates to increasing the patient's quality of life by at least 100%.

In some embodiments, the patient's quality of life is measured using the Cambridge Pulmonary Hypertension Outcome Review (CAMPHOR). In some embodiments, the patient's quality of life is measured using PAH-SYMPACT®. In some embodiments, the patient's quality of life is measured using the Medical Outcomes Survey Short Form-36 (SF-36). In some embodiments, the patient's quality of life is measured using the Euro Quality of Life (EuroQol). In some embodiments, the patient's quality of life is measured using the Euro Quality of Life-5 dimensions (EQ-5D). In some embodiments, the patient's quality of life is measured using the Euro Quality of Life-5 dimensions 5-levels (EQ-5D-5L). In some embodiments, the patient's quality of life is measured using the Kansas City Cardiomyopathy Questionnaire (KCCQ).

Diastolic Function

In certain aspects, the disclosure relates to methods of treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the method increases the patient's LV diastolic function by at least 5% (e.g., 5, 10, 15, 20, 25, 30, 35, 40, 45, 50, 55, 60, 65, 70, 75, 80, 85, 90, 95, or 100%). In some embodiments, the method relates to increasing the patient's LV diastolic function by at least 5%. In some embodiments, the method relates to increasing the patient's LV diastolic function by at least 10%. In some embodiments, the method relates to increasing the patient's LV diastolic function by at least 15%. In some embodiments, the method relates to increasing the patient's LV diastolic function by at least 20%. In some embodiments, the method relates to increasing the patient's LV diastolic function by at least 25%. In some embodiments, the method relates to increasing the patient's LV diastolic function by at least 30%. In some embodiments, the method relates to increasing the patient's LV diastolic function by at least 35%. In some embodiments, the method relates to increasing the patient's LV diastolic function by at least 40%. In some embodiments, the method relates to increasing the patient's LV diastolic function by at least 45%. In some embodiments, the method relates to increasing the patient's LV diastolic function by at least 50%. In some embodiments, the method relates to increasing the patient's LV diastolic function by at least 55%. In some embodiments, the method relates to increasing the patient's LV diastolic function by at least 60%. In some embodiments, the method relates to increasing the patient's LV diastolic function by at least 65%. In some embodiments, the method relates to increasing the patient's LV diastolic function by at least 70%. In some embodiments, the method relates to increasing the patient's LV diastolic function by at least 75%. In some embodiments, the method relates to increasing the patient's LV diastolic function by at least 80%. In some embodiments, the method relates to increasing the patient's LV diastolic function by at least 85%. In some embodiments, the method relates to increasing the patient's LV diastolic function by at least 90%. In some embodiments, the method relates to increasing the patient's LV diastolic function by at least 95%. In some embodiments, the method relates to increasing the patient's LV diastolic function by at least 100%.

Ejection Fraction

In certain aspects, the disclosure relates to methods of treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has an ejection fraction of less than 10% (e.g., 10, 15, 20, 25, 30, 35, 40, or 45%). In some embodiments, the method relates to patient's having an ejection fraction of less than 10%. In some embodiments, the method relates to patient's having an ejection fraction of less than 15%. In some embodiments, the method relates to patient's having an ejection fraction of less than 20%. In some embodiments, the method relates to patient's having an ejection fraction of less than 25%. In some embodiments, the method relates to patient's having an ejection fraction of less than 30%. In some embodiments, the method relates to patient's having an ejection fraction of less than 35%. In some embodiments, the method relates to patient's having an ejection fraction of less than 40%. In some embodiments, the method relates to patient's having an ejection fraction of less than 45%. In some embodiments, the method relates to patient's having an ejection fraction of less than 50%. In some embodiments, the method relates to patient's having an ejection fraction of less than 55%.

In certain aspects, the disclosure relates to methods of treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has an ejection fraction of at least 35% (e.g., 35, 40, 45, 50, or 55%). In some embodiments, the method relates to patient's having an ejection fraction of at least 35%. In some embodiments, the method relates to patient's having an ejection fraction of at least 40%. In some embodiments, the method relates to patient's having an ejection fraction of at least 45%. In some embodiments, the method relates to patient's having an ejection fraction of at least 50%. In some embodiments, the method relates to patient's having an ejection fraction of at least 55%. In some embodiments, the ejection fraction is the right ventricular ejection fraction. In some embodiments, the ejection fraction is the left ventricular ejection fraction (LVEF). In some embodiments, the ejection fraction is measured using an echocardiogram. In some embodiments, the patient has a preserved left ventricular ejection fraction.

In some embodiments, the disclosure relates to methods of adjusting one or more hemodynamic parameters in the PcPH patient toward a more normal level (e.g., >50% ejection fraction), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to increasing the patient's ejection fraction by least 1%. In some embodiments, the method relates to increasing the patient's ejection fraction by at least 5%. In some embodiments, the method relates to increasing the patient's ejection fraction by at least 10%. In some embodiments, the method relates to increasing the patient's ejection fraction by at least 15%. In some embodiments, the method relates to increasing the patient's ejection fraction by at least 20%. In some embodiments, the method relates to increasing the patient's ejection fraction by at least 25%. In some embodiments, the method relates to increasing the patient's ejection fraction by at least 30%. In some embodiments, the method relates to increasing the patient's ejection fraction by at least 35%. In some embodiments, the method relates to increasing the patient's ejection fraction by at least 40%. In some embodiments, the method relates to increasing the patient's ejection fraction by at least 45%. In some embodiments, the method relates to increasing the patient's ejection fraction by at least 50%. In some embodiments, the method relates to increasing the patient's ejection fraction by at least 55%. In some embodiments, the method relates to increasing the patient's ejection fraction by at least 60%. In some embodiments, the method relates to increasing the patient's ejection fraction by at least 65%. In some embodiments, the method relates to increasing the patient's ejection fraction by at least 70%. In some embodiments, the method relates to increasing the patient's ejection fraction by at least 75%. In some embodiments, the method relates to increasing the patient's ejection fraction by at least 80%. In some embodiments, the method relates to increasing the patient's ejection fraction by at least 85%. In some embodiments, the method relates to increasing the patient's ejection fraction by at least 90%. In some embodiments, the method relates to increasing the patient's ejection fraction by at least 95%. In some embodiments, the method relates to increasing the patient's ejection fraction by at least 100%.

Ventricular Function

In certain aspects, the disclosure relates to methods of improving or maintaining ventricular function (e.g., left ventricular function or right ventricular function) in PcPH comprising administering to a patient in need thereof an effective amount of an ActRII polypeptide (e.g., an amino acid sequence that is at least 90% identical to an amino acid sequence corresponding to residues 30-110 of SEQ ID NO: 1). Echocardiography is a useful noninvasive screening tool for determining the severity of pulmonary hypertension in a patient. Improvement or maintenance of ventricular function (e.g., left ventricular function or right ventricular function) can be assessed by many echocardiographic measurements. One such quantitative approach to assess ventricular function is the measurement of the tricuspid annular plane systolic excursion (TAPSE). The TAPSE estimates RV systolic function by measuring the level of systolic excursion of the lateral tricuspid valve annulus towards the apex. Other echocardiographic measurements that may be used to assess maintenance and/or improvements in ventricular function include, but are not limited to, right ventricular fractional area change (RVFAC), right ventricular end-diastolic area (RVEDA), right ventricular end-systolic area (RVESA), right ventricular free wall thickness (RVFWT), right ventricular ejection fraction (RVEF), right ventricular-pulmonary artery (RV-PA) coupling, pulmonary arterial systolic pressure (PASP), right ventricular systolic pressure (RVSP), pulmonary artery acceleration time (PAAT), tricuspid regurgitation velocity (TRV), left ventricular hypertrophy, and right ventricular hypertrophy.

TAPSE

The tricuspid annular plane systolic excursion (TAPSE) can be obtained using echocardiography and represents a measure of RV longitudinal function. The TAPSE has previously been shown to have good correlations with parameters estimating RV global systolic function. A TAPSE <17 mm is highly suggestive of RV systolic dysfunction. In some embodiments, an improvement or maintenance of right ventricular function in a PcPH patient is measured as an increase in TAPSE. In some embodiments, a PcPH patient with an improvement or maintenance of right ventricular function has a TAPSE between 20 mm-28 mm. In some embodiments, a PcPH patient with an improvement or maintenance of right ventricular function has a TAPSE of at least 20 mm. In some embodiments, a PcPH patient with an improvement or maintenance of right ventricular function has a TAPSE of at least 22 mm. In some embodiments, a PcPH patient with an improvement or maintenance of right ventricular function has a TAPSE of at least 24 mm. In some embodiments, a PcPH patient with an improvement or maintenance of right ventricular function has a TAPSE of at least 26 mm. In some embodiments, a PcPH patient with an improvement or maintenance of right ventricular function has a TAPSE of at least 28 mm. In some embodiments, the TAPSE is measured using echocardiography.

In some embodiments, a PcPH patient with an improvement or maintenance of right ventricular function has a TAPSE between 16 mm-30 mm. In some embodiments, a PcPH patient with an improvement or maintenance of right ventricular function has a TAPSE between 18 mm-28 mm. In some embodiments, a PcPH patient with an improvement or maintenance of right ventricular function has a TAPSE of at least 18 mm. In some embodiments, the TAPSE is measured using echocardiography.

PASP and RVSP

In certain aspects, the disclosure relates to methods of treating, preventing, or reducing the progression rate and/or severity of PcPH comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has a pulmonary arterial systolic pressure (PASP) of at least 30 mmHg (e.g., 30, 35, 40, 45, 50, 55, 60, 65, 70, 75, or 80 mmHg). In some embodiments, the method relates to patients having a PASP of at least 30 mmHg. In some embodiments, the method relates to patients having a PASP of at least 35 mmHg. In some embodiments, the method relates to patients having a PASP of at least 40 mmHg. In some embodiments, the method relates to patients having a PASP of at least 45 mmHg. In some embodiments, the method relates to patients having a PASP of at least 50 mmHg. In some embodiments, the method relates to patients having a PASP of at least 55 mmHg. In some embodiments, the method relates to patients having a PASP of at least 60 mmHg. In some embodiments, the method relates to patients having a PASP of at least 65 mmHg. In some embodiments, the method relates to patients having a PASP of at least 70 mmHg. In some embodiments, the method relates to patients having a PASP of at least 75 mmHg. In some embodiments, the method relates to patients having a PASP of at least 80 mmHg. In some embodiments, the PASP is a resting PASP. In some embodiments, the PASP is determined using the tricuspid regurgitation velocity (TRV) and right arterial (RA) pressure. In some embodiments, the PASP is determined using the following formula:

$$PASP = TRV^2 \times 4 + RA \text{ pressure}$$

TRV has been shown to correlate with PASP at rest and with exercise. The pressure gradient between the right ventricle and the right atrium can be calculated using the modified Bernoulli equation ($\Delta p=4V^2$).

In some embodiments, the right ventricular systolic pressure (RVSP) is equal to PASP. In some embodiments, the RVSP is measured in the absence of right ventricular outflow tract obstruction. In some embodiments, the RVSP is determined using the following formula:

$$RVSP = 4V^2 + RAP$$

In the above formula, V represents the peak tricuspid regurgitant jet velocity and RAP is the mean right atrial pressure. RVSP is frequently used for estimating PASP.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to improving the pulmonary arterial systolic pressure (PASP) in the patient. In some embodiments, the method relates to reducing PASP. In some embodiments, the method relates to reducing the patient's PASP by at least 1 mmHg (e.g., 1, 2, 3, 5, 7, 10, 12, 15, 20, 25, 30, or 35 mmHg). In some embodiments, the method relates to reducing the patient's PASP by at least 2 mmHg. In some embodiments, the method relates to reducing the patient's PASP by at least 3 mmHg. In certain embodiments, the method relates to reducing the patient's PASP by at least 5 mmHg. In certain embodiments, the method relates to reducing the patient's PASP by at least 7 mmHg. In certain embodiments, the method relates to reducing the patient's PASP by at least 10 mmHg. In certain embodiments, the method relates to reducing the patient's PASP by at least 12 mmHg. In certain embodiments, the method relates to reducing the patient's PASP by at least 15 mmHg. In certain embodiments, the method relates to reducing the patient's PASP by at least 20 mmHg. In certain embodiments, the method relates to reducing the patient's PASP by at least 25 mmHg. In certain embodiments, the method relates to reducing the patient's PASP by at least 30 mmHg. In certain embodiments, the method relates to reducing the patient's PASP by at least 35 mmHg.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to reducing the patient's PASP by least 1% (e.g., 1, 5, 10, 15, 20, 25, 30, 35, 40, 45, 50, 55, 60, 65, 70, 75, 80, 85, 90, 95, or 100%). In some embodiments, the method relates to reducing the patient's PASP by at least 1%. In some embodiments, the method relates to reducing the patient's PASP by at least 5%. In some embodiments, the method relates to reducing the patient's PASP by at least 10%. In some embodiments, the method relates to reducing the patient's PASP by at least 15%. In some embodiments, the method relates to reducing the patient's PASP by at least 20%. In some embodiments, the method relates to reducing the patient's PASP by at least 25%. In some embodiments, the method relates to reducing the patient's PASP by at least 30%. In some embodiments, the method relates to reducing the patient's PASP by at least 35%. In some embodiments, the method relates to reducing the patient's PASP by at least 40%. In some embodiments, the method relates to reducing the patient's PASP by at least 45%. In some embodiments, the method relates to reducing the patient's PASP by at least 50%. In some embodiments, the method relates to reducing the patient's PASP by at least 55%. In some embodiments, the method relates to reducing the patient's PASP by at least 60%. In some embodiments, the method relates to reducing the patient's PASP by at least 65%. In some embodiments, the method relates to reducing the patient's PASP by at least 70%. In some embodiments, the method relates to reducing the patient's PASP by at least 75%. In some embodiments, the method relates to reducing the patient's PASP by at least 80%. In some embodiments, the method relates to reducing the patient's PASP by at least 85%. In some embodiments, the method relates to reducing the patient's PASP by at least 90%. In some embodiments, the method relates to reducing the patient's PASP by at least 95%. In some embodiments, the method relates to reducing the patient's PASP by at least 100%.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to improving the right ventricular systolic pressure (RVSP) in the patient. In some embodiments, the method relates to reducing RVSP. In some embodiments, the method relates to reducing the patient's RVSP by at least 1 mmHg (e.g., 1, 2, 3, 5, 7, 10, 12, 15, 20, 25, 30, or 35 mmHg). In some embodiments, the method relates to reducing the patient's RVSP by at least 2 mmHg. In some embodiments, the method relates to reducing the patient's RVSP by at least 3 mmHg. In certain embodiments, the method relates to reducing the patient's RVSP by at least 5 mmHg. In certain embodiments, the method relates to reducing the patient's RVSP by at least 7 mmHg. In certain embodiments, the method relates to reducing the patient's RVSP by at least 10 mmHg. In certain embodiments, the method relates to reducing the patient's RVSP by at least 12 mmHg. In certain embodiments, the method relates to reducing the patient's RVSP by at least 15 mmHg. In certain embodiments, the method relates to reducing the patient's RVSP by at least 20 mmHg. In certain embodiments, the method relates to reducing the patient's RVSP by at least 25 mmHg. In certain embodiments, the method relates to reducing the patient's RVSP by at least 30 mmHg. In certain embodiments, the method relates to reducing the patient's RVSP by at least 35 mmHg.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to reducing the patient's RVSP by least 1% (e.g., 1, 5, 10, 15, 20, 25, 30, 35, 40, 45, 50, 55, 60, 65, 70, 75, 80, 85, 90, 95, or 100%). In some embodiments, the method relates to reducing the patient's RVSP by at least 5%. In some embodiments, the method relates to reducing the patient's RVSP by at least 10%. In some embodiments, the method relates to reducing the patient's RVSP by at least 15%. In some embodiments, the method relates to reducing the patient's RVSP by at least 20%. In some embodiments, the method relates to reducing the patient's RVSP by at least 25%. In some embodiments, the method relates to reducing the patient's RVSP by at least 30%. In some embodiments, the method relates to reducing the patient's RVSP by at least 35%. In some embodiments, the method relates to reducing the patient's RVSP by at least 40%. In some embodiments, the method relates to reducing the patient's RVSP by at least 45%. In some embodiments, the method relates to reducing the patient's RVSP by at least 50%. In some embodiments, the method relates to reducing the patient's RVSP by at least 55%. In some embodiments, the method relates to reducing the patient's RVSP by at least 60%. In some embodiments, the method relates to reducing the patient's RVSP by at least 65%. In some embodiments, the method relates to reducing the patient's RVSP by at least 70%. In some embodiments, the method relates to reducing the patient's RVSP by at least 75%. In some embodiments, the method relates to reducing the patient's RVSP by at least 80%. In some embodiments, the method relates to reducing the patient's RVSP by at least 85%. In some embodiments, the method relates to reducing the patient's RVSP by at least 90%. In some embodiments, the method relates to reducing the patient's RVSP by at least 95%. In some embodiments, the method relates to reducing the patient's RVSP by at least 100%.

RV-PA Coupling

Right ventricular dysfunction can occur in PcPH and is a factor affecting prognosis. Energy transfer between ventricle contractility and arterial afterload is termed coupling. Energy transfer specifically between the right ventricle (RV) and pulmonary artery is termed right ventricle-pulmonary artery (RV-PA) coupling. In some embodiments, right ventricular dysfunction is due to a decrease in RV-PA coupling. RV-PA coupling can be estimated non-invasively as a ratio of TAPSE/PASP values. In some embodiments, a TAPSE/PASP ratio of ≥0.31 mm/mm Hg may be associated with a better prognosis and reduced risk of clinical worsening. In some embodiments, the improvement in RV-PA coupling is due to an improvement in PASP. In some embodiments, the calculation of RV-PA coupling is dependent upon paired results for three parameters (e.g., TRV, RAP, and TAPSE).

In certain aspects, the disclosure relates to methods of treating, preventing, or reducing the progression rate and/or severity of PcPH comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has a TAPSE/PASP ratio less than 0.31 mm/mmHg (e.g., 0.3, 0.25, 0.2, 0.15, or 0.1 mm/mmHg). In some embodiments, the method relates to patients having a TAPSE/PASP ratio less than 0.31 mm/mmHg. In some embodiments, the method relates to patients having a TAPSE/PASP ratio less than 0.3 mm/mmHg. In some embodiments, the method relates to patients having a TAPSE/PASP ratio less than 0.25 mm/mmHg. In some embodiments, the method relates to patients having a TAPSE/PASP ratio less than 0.2 mm/mmHg. In some embodiments, the method relates to patients having a TAPSE/PASP ratio less than 0.15 mm/mmHg. In some embodiments, the method relates to patients having a TAPSE/PASP ratio less than 0.1 mm/mmHg. In some embodiments, the method relates to patients having a decreased TAPSE/PASP ratio as compared to a normal TAPSE/PASP ratio.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to improving or maintaining the right ventricular function in the patient. In some embodiments, a PcPH patient with an improvement or maintenance of right ventricular function has a TAPSE/PASP ratio greater than 0.3 mm/mmHg (e.g., greater than 0.31, 0.32, 0.33, 0.34, or 0.35 mm/mmHg). In some embodiments, a PcPH patient with an improvement or maintenance of right ventricular function has a TAPSE/PASP ratio greater than 0.31 mm/mmHg. In some embodiments, a PcPH patient with an improvement or maintenance of right ventricular function has a TAPSE/PASP ratio greater than 0.32 mm/mmHg. In some embodiments, a PcPH patient with an improvement or maintenance of right ventricular function has a TAPSE/PASP ratio greater than 0.33 mm/mmHg. In some embodiments, a PcPH patient with an improvement or maintenance of right ventricular function has a TAPSE/PASP ratio greater than 0.34 mm/mmHg. In some embodiments, a PcPH patient with an improvement or maintenance of right ventricular function has a TAPSE/PASP ratio greater than 0.35 mm/mmHg. In some embodiments, the improvement in right ventricular function is an increase in TAPSE/PASP ratio. In some embodiments, the method relates to increasing the TAPSE/PASP ratio. In some embodiments, the method relates to increasing the patient's TAPSE/PASP ratio by at least 0.05 mm/mmHg. In some embodiments, the method relates to increasing the patient's TAPSE/PASP ratio by at least 0.07 mm/mmHg. In some embodiments, the method relates to increasing the patient's TAPSE/PASP ratio by at least 0.10 mm/mmHg. In some embodiments, the method relates to increasing the patient's TAPSE/PASP ratio by at least 0.12 mm/mmHg. In some embodiments, the method relates to increasing the patient's TAPSE/PASP ratio by at least 0.15 mm/mmHg. In some embodiments, the method relates to increasing the patient's TAPSE/PASP ratio by at least 0.18 mm/mmHg. In some embodiments, the method relates to increasing the patient's TAPSE/PASP ratio by at least 0.20 mm/mmHg.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO:

1). In some embodiments, the method relates to increasing the patient's TAPSE/PASP ratio by least 1% (e.g., 1, 5, 10, 15, 20, 25, 30, 35, 40, 45, 50, 55, 60, 65, 70, 75, 80, 85, 90, 95, or 100%). In some embodiments, the method relates to increasing the patient's TAPSE/PASP ratio by at least 5%. In some embodiments, the method relates to increasing the patient's TAPSE/PASP ratio by at least 10%. In some embodiments, the method relates to increasing the patient's TAPSE/PASP ratio by at least 15%. In some embodiments, the method relates to increasing the patient's TAPSE/PASP ratio by at least 20%. In some embodiments, the method relates to increasing the patient's TAPSE/PASP ratio by at least 25%. In some embodiments, the method relates to increasing the patient's TAPSE/PASP ratio by at least 30%. In some embodiments, the method relates to increasing the patient's TAPSE/PASP ratio by at least 35%. In some embodiments, the method relates to increasing the patient's TAPSE/PASP ratio by at least 40%. In some embodiments, the method relates to increasing the patient's TAPSE/PASP ratio by at least 45%. In some embodiments, the method relates to increasing the patient's TAPSE/PASP ratio by at least 50%. In some embodiments, the method relates to increasing the patient's TAPSE/PASP ratio by at least 55%. In some embodiments, the method relates to increasing the patient's TAPSE/PASP ratio by at least 60%. In some embodiments, the method relates to increasing the patient's TAPSE/PASP ratio by at least 65%. In some embodiments, the method relates to increasing the patient's TAPSE/PASP ratio by at least 70%. In some embodiments, the method relates to increasing the patient's TAPSE/PASP ratio by at least 75%. In some embodiments, the method relates to increasing the patient's TAPSE/PASP ratio by at least 80%. In some embodiments, the method relates to increasing the patient's TAPSE/PASP ratio by at least 85%. In some embodiments, the method relates to increasing the patient's TAPSE/PASP ratio by at least 90%. In some embodiments, the method relates to increasing the patient's TAPSE/PASP ratio by at least 100%.

RVFAC, RVEDA, and RVESA

Right ventricular fractional area change (RVFAC) is a non-invasive quantitative measure of right ventricular function. RVFAC can be calculated using the formula [(RVEDA-RVESA)/RVEDA]*100. In some embodiments, the RVFAC is measured using echocardiography. In some embodiments, normal RVFAC is approximately 47.5±8.6% in men and approximately 50.9±8.0% in women. See, e.g., Kou S, et al. European Heart Journal—Cardiovascular Imaging. 2014 Jun. 1; 15(6):680-90. In some embodiments, PcPH patients have a decrease in RVFAC.

In certain aspects, the disclosure relates to methods of treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has a RVFAC of less than 20% (e.g., 20, 25, 30, 35, or 40%). In some embodiments, the method relates to patients having a RVFAC of less than 25%. In some embodiments, the method relates to patients having a RVFAC of less than 30%. In some embodiments, the method relates to patients having a RVFAC of less than 35%. In some embodiments, the method relates to patients having a RVFAC of less than 40%.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to improving or maintaining the right ventricular function in the patient. In some embodiments, the improvement or maintenance of right ventricular function is due to an increase in right ventricular fractional area change (RVFAC). In some embodiments, a PcPH patient with an improvement or maintenance of right ventricular function has a RVFAC between 32-56%. In some embodiments, a PcPH patient with an improvement or maintenance of right ventricular function has a RVFAC of at least 32%. In some embodiments, a PcPH patient with an improvement or maintenance of right ventricular function has a RVFAC of at least 34%. In some embodiments, a PcPH patient with an improvement or maintenance of right ventricular function has a RVFAC of at least 35%. In some embodiments, a PcPH patient with an improvement or maintenance of right ventricular function has a RVFAC of at least 36%. In some embodiments, a PcPH patient with an improvement or maintenance of right ventricular function has a RVFAC of at least 38%. In some embodiments, a PcPH patient with an improvement or maintenance of right ventricular function has a RVFAC of at least 40%. In some embodiments, a PcPH patient with an improvement or maintenance of right ventricular function has a RVFAC of at least 42%. In some embodiments, a PcPH patient with an improvement or maintenance of right ventricular function has a RVFAC of at least 44%. In some embodiments, a PcPH patient with an improvement or maintenance of right ventricular function has a RVFAC of at least 46%. In some embodiments, a PcPH patient with an improvement or maintenance of right ventricular function has a RVFAC of at least 48%. In some embodiments, a PcPH patient with an improvement or maintenance of right ventricular function has a RVFAC of at least 50%. In some embodiments, a PcPH patient with an improvement or maintenance of right ventricular function has a RVFAC of at least 52%. In some embodiments, a PcPH patient with an improvement or maintenance of right ventricular function has a RVFAC of at least 54%. In some embodiments, a PcPH patient with an improvement or maintenance of right ventricular function has a RVFAC of at least 56%.

In some embodiments, the disclosure relates to methods of adjusting one or more echocardiogram parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to decreasing the patient's RVEDA by least 1% (e.g., 1, 2, 3, 4, 5, 6, 7, 8, 9, 10, 12, 14, 16, 18, or 20%). In some embodiments, the method relates to increasing the patient's RVFAC by least 2%. In some embodiments, the method relates to increasing the patient's RVFAC by least 3%. In some embodiments, the method relates to increasing the patient's RVFAC by least 4%. In some embodiments, the method relates to increasing the patient's RVFAC by least 5%. In some embodiments, the method relates to increasing the patient's RVFAC by least 6%. In some embodiments, the method relates to increasing the patient's RVFAC by least 7%. In some embodiments, the method relates to increasing the patient's RVFAC by least 8%. In some embodiments, the method relates to increasing the patient's RVFAC by least 9%. In some embodiments, the method relates to increasing the patient's RVFAC by least 10%. In some embodiments, the method relates to increasing the patient's RVFAC by least 12%. In some embodiments, the method relates to increasing the patient's RVFAC by least 14%. In some embodiments, the method relates to increasing the patient's RVFAC by least 16%. In some embodiments, the method relates to increasing the patient's RVFAC by least 18%. In some embodiments, the method relates to increasing the patient's RVFAC by least 20%.

In some embodiments, the improvement in right ventricular function is due to an increase in ejection fraction. In some embodiments, the improvement in right ventricular function is due to an increase in ejection fraction and an increase in the patient's RVFAC.

The right ventricular end-diastolic area (RVEDA) can be measured using echocardiography. In some embodiments, normal RVEDA is approximately 18.2±4.3 $cm^2$ in men and approximately 14.8±3.5 $cm^2$ in women. See, e.g., Kou S, et al. European Heart Journal—Cardiovascular Imaging. 2014 Jun. 1; 15(6):680-90.

In certain aspects, the disclosure relates to methods of treating, preventing, or reducing the progression rate and/or severity of PcPH comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has a RVEDA of at least 22 $cm^2$ (e.g., 22, 24, 26, 28, 30, 32, or 34 $cm^2$). In some embodiments, the method relates to patients having a RVEDA of at least 24 $cm^2$. In some embodiments, the method relates to patients having a RVEDA of at least 26 $cm^2$. In some embodiments, the method relates to patients having a RVEDA of at least 28 $cm^2$. In some embodiments, the method relates to patients having a RVEDA of at least 30 $cm^2$. In some embodiments, the method relates to patients having a RVEDA of at least 32 $cm^2$. In some embodiments, the method relates to patients having a RVEDA of at least 34 $cm^2$. In some embodiments, the method relates to patients having increased RVEDA as compared to normal RVEDA.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to improving or maintaining the right ventricular function in the patient. In some embodiments, a patient with an improvement or maintenance of right ventricular function has a RVEDA of 14-22 $cm^2$. In some embodiments, the improvement in right ventricular function is a reduction in RVEDA. In some embodiments, the method relates to reducing the RVEDA. In some embodiments, the method relates to reducing the patients RVEDA by at least 1 $cm^2$. In some embodiments, the method relates to reducing the patients RVEDA by at least 2 $cm^2$. In some embodiments, the method relates to reducing the patients RVEDA by at least 3 $cm^2$. In some embodiments, the method relates to reducing the patients RVEDA by at least 4 $cm^2$. In some embodiments, the method relates to reducing the patients RVEDA by at least 5 $cm^2$. In some embodiments, the method relates to reducing the patients RVEDA by at least 6 $cm^2$. In some embodiments, the method relates to reducing the patients RVEDA by at least 7 $cm^2$. In some embodiments, the method relates to reducing the patients RVEDA by at least 8 $cm^2$. In some embodiments, the method relates to reducing the patients RVEDA by at least 9 $cm^2$. In some embodiments, the method relates to reducing the patients RVEDA by at least 10 $cm^2$.

In some embodiments, the disclosure relates to methods of adjusting one or more echocardiogram parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to decreasing the patient's RVEDA by least 1% (e.g., 1, 5, 10, 15, 20, 25, 30, 35, or 40%). In some embodiments, the method relates to decreasing the patient's RVEDA by at least 5%. In some embodiments, the method relates to decreasing the patient's RVEDA by at least 10%. In some embodiments, the method relates to decreasing the patient's RVEDA by at least 15%. In some embodiments, the method relates to decreasing the patient's RVEDA by at least 20%. In some embodiments, the method relates to decreasing the patient's RVEDA by at least 25%. In some embodiments, the method relates to decreasing the patient's RVEDA by at least 30%. In some embodiments, the method relates to decreasing the patient's RVEDA by at least 35%. In some embodiments, the method relates to decreasing the patient's RVEDA by at least 40%.

The right ventricular end-systolic area (RVESA) can be measured using echocardiography. In some embodiments, normal RVESA is approximately 9.6±2.8 $cm^2$ in men and approximately 7.3±2.3 $cm^2$ in women. See, e.g., Kou S, et al. European Heart Journal—Cardiovascular Imaging. 2014 Jun. 1; 15(6):680-90.

In certain aspects, the disclosure relates to methods of treating, preventing, or reducing the progression rate and/or severity of PcPH comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has a RVESA of at least 12 $cm^2$ (e.g., 12, 14, 16, 18, 20, 22, 24, 26, 28, 30, or 32 $cm^2$). In some embodiments, the method relates to patients having a RVESA of at least 14 $cm^2$. In some embodiments, the method relates to patients having a RVESA of at least 16 $cm^2$. In some embodiments, the method relates to patients having a RVESA of at least 18 $cm^2$. In some embodiments, the method relates to patients having a RVESA of at least 20 $cm^2$. In some embodiments, the method relates to patients having a RVESA of at least 22 $cm^2$. In some embodiments, the method relates to patients having a RVESA of at least 24 $cm^2$. In some embodiments, the method relates to patients having a RVESA of at least 26 $cm^2$. In some embodiments, the method relates to patients having a RVESA of at least 28 $cm^2$. In some embodiments, the method relates to patients having a RVESA of at least 30 $cm^2$. In some embodiments, the method relates to patients having a RVESA of at least 32 $cm^2$. In some embodiments, the method relates to patients having increased RVESA as compared to normal RVESA.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to improving or maintaining the right ventricular function in the patient. In some embodiments, a patient with an improvement or maintenance of right ventricular function has a RVESA of 7-20 $cm^2$. In some embodiments, the improvement in right ventricular function is a reduction in RVESA. In some embodiments, the method relates to reducing the RVESA. In some embodiments, the method relates to reducing the patient's RVESA by at least 1 $cm^2$. In some embodiments, the method relates to reducing the patient's RVESA by at least 2 $cm^2$. In some embodiments, the method relates to reducing the patient's RVESA by at least 3 $cm^2$. In some embodiments, the method relates to reducing the patient's RVESA by at least 4 $cm^2$. In some embodiments, the method relates to reducing the patient's RVESA by at least 5 $cm^2$. In some embodiments, the method relates to reducing the patient's RVESA by at least 6 $cm^2$. In some embodiments, the method relates to reducing the patient's RVESA by at least 7 $cm^2$. In some embodiments, the method relates to reducing the patient's RVESA by at least 8 $cm^2$. In some embodiments, the method relates to reducing the patient's RVESA by at least 9 $cm^2$. In some embodiments, the method relates to reducing the patient's RVESA by at least 10 $cm^2$.

In some embodiments, the disclosure relates to methods of adjusting one or more echocardiogram parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to decreasing the patient's RVESA by least 1% (e.g., 1, 2, 3, 4, 5, 10, 15, 20, 25, 30, 35, or 40%). In some embodiments, the method relates to decreasing the patient's RVESA by at least 2%. In some embodiments, the method relates to decreasing the patient's RVESA by at least 3%. In some embodiments, the method relates to decreasing the patient's RVESA by at least 4%. In some embodiments, the method relates to decreasing the patient's RVESA by at least 5%. In some embodiments, the method relates to decreasing the patient's RVESA by at least 10%. In some embodiments, the method relates to decreasing the patient's RVESA by at least 15%. In some embodiments, the method relates to decreasing the patient's RVESA by at least 20%. In some embodiments, the method relates to decreasing the patient's RVESA by at least 25%. In some embodiments, the method relates to decreasing the patient's RVESA by at least 30%. In some embodiments, the method relates to decreasing the patient's RVESA by at least 35%. In some embodiments, the method relates to decreasing the patient's RVESA by at least 40%.

RVFWT

In patients with pulmonary hypertension, the right ventricle dilates in response to increased PAP and right ventricular remodeling. As the disease progresses right ventricular hypertrophy develops, resulting in increased right ventricle free wall thickness. In some embodiments, the right ventricular free wall thickness (RVFWT) can be measured using echocardiography. In some embodiments, normal RVFWT is approximately 0.22-0.42 cm in women and approximately 0.24-0.42 cm in men. See, e.g., Lang R M, J Am Soc Echocardiogr. 2015; 28(1):1-39.e14.

In certain aspects, the disclosure relates to methods of treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has a RVFWT of at least 0.42 cm (e.g., 0.42, 0.44, 0.46, 0.48, 0.50, 0.52, 0.54, 0.56, 0.58, or 0.60 cm). In some embodiments, the method relates to patients having a RVFWT of at least 0.44 cm. In some embodiments, the method relates to patients having a RVFWT of at least 0.46 cm. In some embodiments, the method relates to patients having a RVFWT of at least 0.48 cm. In some embodiments, the method relates to patients having a RVFWT of at least 0.50 cm. In some embodiments, the method relates to patients having a RVFWT of at least 0.52 cm. In some embodiments, the method relates to patients having a RVFWT of at least 0.54 cm. In some embodiments, the method relates to patients having a RVFWT of at least 0.56 cm. In some embodiments, the method relates to patients having a RVFWT of at least 0.58 cm. In some embodiments, the method relates to patients having a RVFWT of at least 0.60 cm. In some embodiments, the method relates to patients having increased RVFWT as compared to normal RVFWT.

In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to improving or maintaining the right ventricular function in the patient. In some embodiments, a patient with an improvement or maintenance of right ventricular function has a RVFWT of between 0.22-0.42 cm. In some embodiments, the improvement in right ventricular function is a reduction in RVFWT. In some embodiments, the method relates to reducing the RVFWT. In some embodiments, the method relates to reducing the patients RVFWT by at least 0.05 cm (e.g., 0.05, 0.1, 0.15, 0.2, 0.25, 0.3, 0.35, or 0.4 cm). In some embodiments, the method relates to reducing the patients RVFWT by at least 0.1 cm. In some embodiments, the method relates to reducing the patients RVFWT by at least 0.15 cm. In some embodiments, the method relates to reducing the patients RVFWT by at least 0.2 cm. In some embodiments, the method relates to reducing the patients RVFWT by at least 0.25 cm. In some embodiments, the method relates to reducing the patients RVFWT by at least 0.3 cm. In some embodiments, the method relates to reducing the patients RVFWT by at least 0.35 cm. In some embodiments, the method relates to reducing the patients RVFWT by at least 0.4 cm.

In some embodiments, the disclosure relates to methods of adjusting the RVFWT in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to decreasing the patient's RVFWT by least 1% (e.g., 1, 5, 10, 15, 20, 25, 30, 35, 40, 45, 50, 55, 60, 65, 70, or 75%). In some embodiments, the method relates to decreasing the patient's RVFWT by at least 5%. In some embodiments, the method relates to decreasing the patient's RVFWT by at least 10%. In some embodiments, the method relates to decreasing the patient's RVFWT by at least 15%. In some embodiments, the method relates to decreasing the patient's RVFWT by at least 20%. In some embodiments, the method relates to decreasing the patient's RVFWT by at least 25%. In some embodiments, the method relates to decreasing the patient's RVFWT by at least 30%. In some embodiments, the method relates to decreasing the patient's RVFWT by at least 35%. In some embodiments, the method relates to decreasing the patient's RVFWT by at least 40%. In some embodiments, the method relates to decreasing the patient's RVFWT by at least 45%. In some embodiments, the method relates to decreasing the patient's RVFWT by at least 50%. In some embodiments, the method relates to decreasing the patient's RVFWT by at least 55%. In some embodiments, the method relates to decreasing the patient's RVFWT by at least 60%. In some embodiments, the method relates to decreasing the patient's RVFWT by at least 65%. In some embodiments, the method relates to decreasing the patient's RVFWT by at least 70%. In some embodiments, the method relates to decreasing the patient's RVFWT by at least 75%.

RVEF

Right ventricular ejection fraction is a global measure of RV systolic performance. RVEF can be calculated using the RV end-diastolic volume (RVEDV) and RV end systolic volume (RVESV). Specifically, RVEF can be calculated using the following formula: RVEF (%)=((RVEDV−RVESV)/RVEDV)*100. Normal RVEF is approximately 56-65% in men and 60-71% in women. See, e.g., Lang R M, J Am Soc Echocardiogr. 2015; 28(1):1-39.e14. In some embodiments, the RVEF is measured using echocardiography. In some embodiments, the disclosure relates to methods of adjusting one or more hemodynamic parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to improving or maintaining the right ventricular function in the patient. In some embodiments, a patient with an improvement or maintenance of right ventricular function has a RVEF of 45-71%. In some embodiments, a patient with an improvement or maintenance of right ventricular function has a RVEF of at least 45%. In some embodiments, a patient with an improvement or maintenance of right ventricular function has a RVEF of at least 50%. In some embodiments, a patient with an improvement or maintenance of right ventricular function has a RVEF of at least 55%. In some embodiments, a patient with an improvement or maintenance of right ventricular function has a RVEF of at least 60%. In some embodiments, a patient with an improvement or maintenance of right ventricular function has a RVEF of at least 65%. In some embodiments, a patient with an improvement or maintenance of right ventricular function has a RVEF of at least 70%.

In some embodiments, the disclosure relates to methods of adjusting one or more echocardiogram parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to increasing the patient's RVEF by least 2%. In some embodiments, the method relates to increasing the patient's RVEF by least 3%. In some embodiments, the method relates to increasing the patient's RVEF by least 4%. In some embodiments, the method relates to increasing the patient's RVEF by least 5%. In some embodiments, the method relates to increasing the patient's RVEF by least 6%. In some embodiments, the method relates to increasing the patient's RVEF by least 7%. In some embodiments, the method relates to increasing the patient's RVEF by least 8%. In some embodiments, the method relates to increasing the patient's RVEF by least 9%. In some embodiments, the method relates to increasing the patient's RVEF by least 10%. In some embodiments, the method relates to increasing the patient's RVEF by least 11%. In some embodiments, the method relates to increasing the patient's RVEF by least 12%. In some embodiments, the method relates to increasing the patient's RVEF by least 13%. In some embodiments, the method relates to increasing the patient's RVEF by least 14%. In some embodiments, the method relates to increasing the patient's RVEF by least 15%.

Right Ventricular Hypertrophy

In certain aspects, the improvement in right ventricular function is measured as a decrease in right ventricular hypertrophy. In some embodiment, the right ventricular hypertrophy is measured using the Fulton Index (RV/(LV+S)).

In certain aspects, the disclosure relates to methods of treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has right ventricular hypertrophy. In some embodiments, the disclosure relates to methods of adjusting one or more parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the right ventricular hypertrophy is measured using the Fulton index (RV/(LV+S)). In some embodiments, the method relates to decreasing the patient's right ventricular hypertrophy by least 1% (e.g., 1, 5, 10, 15, 20, 25, 30, 35, 40, 45, 50, 55, 60, 65, 70, 75, 80, 85, 90, 95, or 100%). In some embodiments, the method relates to decreasing the patient's right ventricular hypertrophy by at least 1%. In some embodiments, the method relates to decreasing the patient's right ventricular hypertrophy by at least 5%. In some embodiments, the method relates to decreasing the patient's right ventricular hypertrophy by at least 10%. In some embodiments, the method relates to decreasing the patient's right ventricular hypertrophy by at least 15%. In some embodiments, the method relates to decreasing the patient's right ventricular hypertrophy by at least 20%. In some embodiments, the method relates to decreasing the patient's right ventricular hypertrophy by at least 25%. In some embodiments, the method relates to decreasing the patient's right ventricular hypertrophy by at least 30%. In some embodiments, the method relates to decreasing the patient's right ventricular hypertrophy by at least 35%. In some embodiments, the method relates to decreasing the patient's right ventricular hypertrophy by at least 40%. In some embodiments, the method relates to decreasing the patient's right ventricular hypertrophy by at least 45%. In some embodiments, the method relates to decreasing the patient's right ventricular hypertrophy by at least 50%. In some embodiments, the method relates to decreasing the patient's right ventricular hypertrophy by at least 55%. In some embodiments, the method relates to decreasing the patient's right ventricular hypertrophy by at least 60%. In some embodiments, the method relates to decreasing the patient's right ventricular hypertrophy by at least 65%. In some embodiments, the method relates to decreasing the patient's right ventricular hypertrophy by at least 70%. In some embodiments, the method relates to decreasing the patient's right ventricular hypertrophy by at least 75%. In some embodiments, the method relates to decreasing the patient's right ventricular hypertrophy by at least 80%. In some embodiments, the method relates to decreasing the patient's right ventricular hypertrophy by at least 85%. In some embodiments, the method relates to decreasing the patient's right ventricular hypertrophy by at least 90%. In some embodiments, the method relates to decreasing the patient's right ventricular hypertrophy by at least 95%. In some embodiments, the method relates to decreasing the patient's right ventricular hypertrophy by at least 100%.

Left Ventricular Hypertrophy

In certain aspects, the disclosure relates to methods of treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has left ventricular hypertrophy. In some embodiments, the disclosure relates to methods of adjusting one or more parameters in the PcPH patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to decreasing the patient's left ventricular hypertrophy by least 1% (e.g., 1, 5, 10, 15, 20, 25, 30, 35, 40, 45, 50, 55, 60, 65, 70, 75, 80, 85, 90, 95, or 100%). In some embodiments, the method relates to decreasing the patient's left ventricular hypertrophy by at least 10%. In some embodiments, the method relates to decreasing the patient's left ventricular hypertrophy by at least 5%. In some embodiments, the method relates to decreasing the patient's left ventricular hypertrophy by at least 10%. In some embodiments, the method relates to decreasing the patient's left ventricular hypertrophy by at least 15%. In some embodiments, the method relates to decreasing the patient's left ventricular hypertrophy by at least 20%. In some embodiments, the method relates to decreasing the patient's left ventricular hypertrophy by at least 25%. In some embodiments, the method relates to decreasing the patient's left ventricular hypertrophy by at least 30%. In some embodiments, the method relates to decreasing the patient's left ventricular hypertrophy by at least 35%. In some embodiments, the method relates to decreasing the patient's left ventricular hypertrophy by at least 40%. In some embodiments, the method relates to decreasing the patient's left ventricular hypertrophy by at least 45%. In some embodiments, the method relates to decreasing the patient's left ventricular hypertrophy by at least 50%. In some embodiments, the method relates to decreasing the patient's left ventricular hypertrophy by at least 55%. In some embodiments, the method relates to decreasing the patient's left ventricular hypertrophy by at least 60%. In some embodiments, the method relates to decreasing the patient's left ventricular hypertrophy by at least 65%. In some embodiments, the method relates to decreasing the patient's left ventricular hypertrophy by at least 70%. In some embodiments, the method relates to decreasing the patient's left ventricular hypertrophy by at least 75%. In some embodiments, the method relates to decreasing the patient's left ventricular hypertrophy by at least 80%. In some embodiments, the method relates to decreasing the patient's left ventricular hypertrophy by at least 85%. In some embodiments, the method relates to decreasing the patient's left ventricular hypertrophy by at least 90%. In some embodiments, the method relates to decreasing the patient's left ventricular hypertrophy by at least 95%. In some embodiments, the method relates to decreasing the patient's left ventricular hypertrophy by at least 100%.

Cardiac Output

Cardiac output is the volume of blood the heart pumps per minute. Cardiac output is calculated by multiplying the stroke volume by the heart rate. In general, normal cardiac output at rest is about 4 to 8 L/min. The cardiac index is an assessment of the cardiac output value based on the patient's size. To find the cardiac index, the cardiac output is divided by the person's body surface area (BSA). The normal range for CI is 2.5 to 4 L/min/$m^2$. Cardiac output can decline by almost 40% without deviating from the normal limits. A low cardiac index of less than about 2.5 L/min/$m^2$ usually indicates a disturbance in cardiovascular performance. The cardiac output can be utilized to calculate the cardiac index (e.g., cardiac index=cardiac output/body surface area). The cardiac output can also be utilized to calculate the stroke volume (e.g., stroke volume=CO/heart rate). In certain aspects, the disclosure relates to methods of treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the method increases the patient's cardiac output by at least 5% (e.g., 5, 10, 15, 20, 25, 30, 35, 40, 45, 50, 55, 60, 65, 70, 75, 80, 85, 90, 95, or 100%). In some embodiments, the method relates to increasing the patient's cardiac output by at least 5%. In some embodiments, the method relates to increasing the patient's cardiac output by at least 10%. In some embodiments, the method relates to increasing the patient's cardiac output by at least 15%. In some embodiments, the method relates to increasing the patient's cardiac output by at least 20%. In some embodiments, the method relates to increasing the patient's cardiac output by at least 25%. In some embodiments, the method relates to increasing the patient's cardiac output by at least 30%. In some embodiments, the method relates to increasing the patient's cardiac output by at least 35%. In some embodiments, the method relates to increasing the patient's cardiac output by at least 40%. In some embodiments, the method relates to increasing the patient's cardiac output by at least 45%. In some embodiments, the method relates to increasing the patient's cardiac output by at least 50%. In some embodiments, the method relates to increasing the patient's cardiac output by at least 55%. In some embodiments, the method relates to increasing the patient's cardiac output by at least 60%. In some embodiments, the method relates to increasing the patient's cardiac output by at least 65%. In some embodiments, the method relates to increasing the patient's cardiac output by at least 70%. In some embodiments, the method relates to increasing the patient's cardiac output by at least 75%. In some embodiments, the method relates to increasing the patient's cardiac output by at least 80%. In some embodiments, the method relates to increasing the patient's cardiac output by at least 85%. In some embodiments, the method relates to increasing the patient's cardiac output by at least 90%. In some embodiments, the method relates to increasing the patient's cardiac output by at least 95%. In some embodiments, the method relates to increasing the patient's cardiac output by at least 100%. In some embodiments, the method relates to increasing the patient's cardiac index to at least 4.2 L/min/$m^2$. In some embodiments, the cardiac index is measured at rest. In some embodiments, the method relates to increasing the patient's cardiac output to at least 4 L/min. In some embodiments, the cardiac output is measured at rest. In some embodiments, the cardiac output is using a right heart catheter. In some embodiments, cardiac output is measured by thermodilution. In some embodiments, cardiac output is measured using the Fick method.

Progression of IpcPH to CpcPH

The predominant mechanism underlying PcPH (e.g., WHO Group 2 and/or Group 5 PH) is elevated left-side filling pressure (i.e., left atrial pressure). Sustained elevations in left atrial pressure may cause passive pulmonary venous congestion with elevation of pulmonary pressures. In some patients, transmission of venous congestion to the pulmonary capillaries results in leakage and damage, ultimately leading to the creation of an obstructive vasculopathy such that higher pulmonary pressures are needed to sustain forward flow. This is sometimes referred to as the development of a "pre-capillary" component of PH. In certain aspects, the disclosure relates to methods of treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the method reduces the development of a pre-capillary component of PH by at least 1% (e.g., 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100%. In some embodiments, the method relates to reducing the development of a pre-capillary component of PH in a patient by at least 1%. In some embodiments, the method relates to reducing the development of a pre-capillary component of PH in a patient by at least 2%. In some embodiments, the method relates to reducing the development of a pre-capillary component of PH in a patient by at least 3%. In some embodiments, the method relates to reducing the development of a pre-capillary component of PH in a patient by at least 4%. In some embodiments, the method relates to reducing the development of a pre-capillary component of PH in a patient by at least 5%. In some embodiments, the method relates to reducing the development of a pre-capillary component of PH in a patient by at least 10%. In some embodiments, the method relates to reducing the development of a pre-capillary component of PH in a patient by at least 15%. In some embodiments, the method relates to reducing the development of a pre-capillary component of PH in a patient by at least 20%. In some embodiments, the method relates to reducing the development of a pre-capillary component of PH in a patient by at least 25%. In some embodiments, the method relates to reducing the development of a pre-capillary component of PH in a patient by at least 30%. In some embodiments, the method relates to reducing the development of a pre-capillary component of PH in a patient by at least 35%. In some embodiments, the method relates to reducing the development of a pre-capillary component of PH in a patient by at least 40%. In some embodiments, the method relates to reducing the development of a pre-capillary component of PH in a patient by at least 45%. In some embodiments, the method relates to reducing the development of a pre-capillary component of PH in a patient by at least 50%. In some embodiments, the method relates to reducing the development of a pre-capillary component of PH in a patient by at least 55%. In some embodiments, the method relates to reducing the development of a pre-capillary component of PH in a patient by at least 60%. In some embodiments, the method relates to reducing the development of a pre-capillary component of PH in a patient by at least 65%. In some embodiments, the method relates to reducing the development of a pre-capillary component of PH in a patient by at least 70%. In some embodiments, the method relates to reducing the development of a pre-capillary component of PH in a patient by at least 75%. In some embodiments, the method relates to reducing the development of a pre-capillary component of PH in a patient by at least 80%. In some embodiments, the method relates to reducing the development of a pre-capillary component of PH in a patient by at least 85%. In some embodiments, the method relates to reducing the development of a pre-capillary component of PH in a patient by at least 90%. In some embodiments, the method relates to reducing the development of a pre-capillary component of PH in a patient by at least 95%. In some embodiments, the method relates to reducing the development of a pre-capillary component of PH in a patient by at least 100%.

In some embodiments, sustained left atrial pressure in IpcPH has been shown to lead to the development of CpcPH. In certain aspects, the disclosure relates to methods of treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the method reduces the progression of IpcPH to CpcPH in a patient by at least 1% (e.g., 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100%. In some embodiments, the method relates to reducing the progression of IpcPH to CpcPH in a patient by at least 1%. In some embodiments, the method relates to reducing the progression of IpcPH to CpcPH in a patient by at least 2%. In some embodiments, the method relates to reducing the progression of IpcPH to CpcPH in a patient by at least 3%. In some embodiments, the method relates to reducing the progression of IpcPH to CpcPH in a patient by at least 4%. In some embodiments, the method relates to reducing the progression of IpcPH to CpcPH in a patient by at least 5%. In some embodiments, the method relates to reducing the progression of IpcPH to CpcPH in a patient by at least 10%. In some embodiments, the method relates to reducing the progression of IpcPH to CpcPH in a patient by at least 15%. In some embodiments, the method relates to reducing the progression of IpcPH to CpcPH in a patient by at least 20%. In some embodiments, the method relates to reducing the progression of IpcPH to CpcPH in a patient by at least 25%. In some embodiments, the method relates to reducing the progression of IpcPH to CpcPH in a patient by at least 30%. In some embodiments, the method relates to reducing the progression of IpcPH to CpcPH in a patient by at least 35%. In some embodiments, the method relates to reducing the progression of IpcPH to CpcPH in a patient by at least 40%. In some embodiments, the method relates to reducing the progression of IpcPH to CpcPH in a patient by at least 45%. In some embodiments, the method relates to reducing the progression of IpcPH to CpcPH in a patient by at least 50%. In some embodiments, the method relates to reducing the progression of IpcPH to CpcPH in a patient by at least 55%. In some embodiments, the method relates to reducing the progression of IpcPH to CpcPH in a patient by at least 60%. In some embodiments, the method relates to reducing the progression of IpcPH to CpcPH in a patient by at least 65%. In some embodiments, the method relates to reducing the progression of IpcPH to CpcPH in a patient by at least 70%. In some embodiments, the method relates to reducing the progression of IpcPH to CpcPH in a patient by at least 75%. In some embodiments, the method relates to reducing the progression of IpcPH to CpcPH in a patient by at least 80%. In some embodiments, the method relates to reducing the progression of IpcPH to CpcPH in a patient by at least 85%. In some embodiments, the method relates to reducing the progression of IpcPH to CpcPH in a patient by at least 90%. In some embodiments, the method relates to reducing the progression of IpcPH to CpcPH in a patient by at least 95%. In some embodiments, the method relates to reducing the progression of IpcPH to CpcPH in a patient by at least 100%.

Exercise Capacity (6 MWD and BDI)

In certain aspects, the disclosure relates to methods of increasing exercise capacity in a patient having PcPH (e.g., WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1). Any suitable measure of exercise capacity can be used. For example, exercise capacity in a 6-minute walk test (6 MWT), which measures how far the subject can walk in 6 minutes, i.e., the 6-minute walk distance (6 MWD), is frequently used to assess pulmonary hypertension severity and disease progression. In certain aspects, the Borg dyspnea index (BDI) may be used to measure exercise capacity. The BDI is a numerical scale for assessing perceived dyspnea (breathing discomfort). It measures the degree of breathlessness, for example, after completion of the 6 MWT, where a BDI of 0 indicates no breathlessness and 10 indicates maximum breathlessness. In some embodiments, the BDI is measured using the BORG CR10 scale.

In certain aspects, the disclosure relates to methods of treating, preventing, or reducing the progression rate and/or severity of PcPH (e.g., WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has a 6 MWD of less than 550 meters (e.g., a 6 MWD of less than 550, 500, 450, 440, 400, 380, 350, 300, 250, 200, or 150 meters). In some embodiments, the method relates to patient's having a 6 MWD of between 150 to 550 meters. In some embodiments, the method relates to patient's having a 6 MWD of between 100 to 500 meters. In some embodiments, the method relates to patient's having a 6 MWD of between 150 to 500 meters. In some embodiments, the method relates to patient's having a 6 MWD of at least 100 meters. In some embodiments, the method relates to patient's having a 6 MWD of greater than 150 meters. In some embodiments, the method relates to patient's having a 6 MWD of less than 550 meters. In some embodiments, the method relates to patient's having a 6 MWD of less than 500 meters. In some embodiments, the method relates to patient's having a 6 MWD of less than 450 meters. In some embodiments, the method relates to patient's having a 6 MWD of less than 440 meters. In some embodiments, the method relates to patient's having a 6 MWD of less than 400 meters. In some embodiments, the method relates to patient's having a 6 MWD of less than 380 meters. In some embodiments, the method relates to patient's having a 6 MWD of less than 350 meters. In some embodiments, the method relates to patient's having a 6 MWD of less than 300 meters. In some embodiments, the method relates to patient's having a 6 MWD of less than 250 meters. In some embodiments, the method relates to patient's having a 6 MWD of less than 200 meters. In some embodiments, the method relates to patient's having a 6 MWD of less than 150 meters. In some embodiments, the method relates to increasing the patient's 6 MWD to >380 meters. In some embodiments, the method relates to increasing the patient's 6 MWD to >440 meters. In some embodiments, the method relates to increasing the patient's 6 MWD to >500 meters. See, e.g., Galie N., et al Euro Heart J. (2016) 37, 67-119.

In some embodiments, the disclosure relates to methods of adjusting one or more measurements of exercise capacity in the PcPH (e.g., WHO Group 2 and/or Group 5 PH) patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to increasing the patient's 6 MWD by at least 10 meters. In some embodiments, the method relates to increasing the patient's 6 MWD by at least 20 meters. In some embodiments, the method relates to increasing the patient's 6 MWD by at least 25 meters. In some embodiments, the method relates to increasing the patient's 6 MWD by at least 30 meters. In some embodiments, the method relates to increasing the patient's 6 MWD by at least 40 meters. In some embodiments, the method relates to increasing the patient's 6 MWD by at least 50 meters. In some embodiments, the method relates to increasing the patient's 6 MWD by at least 60 meters. In some embodiments, the method relates to increasing the patient's 6 MWD by at least 70 meters. In some embodiments, the method relates to increasing the patient's 6 MWD by at least 80 meters. In some embodiments, the method relates to increasing the patient's 6 MWD by at least 90 meters. In some embodiments, the method relates to increasing the patient's 6 MWD by at least 100. In some embodiments, the method relates to increasing the patient's 6 MWD by at least 125. In some embodiments, the method relates to increasing the patient's 6 MWD by at least 150 meters. In some embodiments, the method relates to increasing the patient's 6 MWD by at least 175 meters. In some embodiments, the method relates to increasing the patient's 6 MWD by at least 200 meters. In some embodiments, the method relates to increasing the patient's 6 MWD by at least 250 meters. In some embodiments, the method relates to increasing the patient's 6 MWD by at least 300 meters. In some embodiments, the method relates to increasing the patient's 6 MWD by at least 400 meters. In some embodiments, the 6 MWD is tested after the patient has received 4 weeks of treatment utilizing an ActRII polypeptide disclosed herein. In some embodiments, the 6 MWD is tested after the patient has received 8 weeks of treatment utilizing an ActRII polypeptide disclosed herein. In some embodiments, the 6 MWD is tested after the patient has received 12 weeks of treatment utilizing an ActRII polypeptide disclosed herein. In some embodiments, the 6 MWD is tested after the patient has received 16 weeks of treatment utilizing an ActRII polypeptide disclosed herein. In some embodiments, the 6 MWD is tested after the patient has received 20 weeks of treatment utilizing an ActRII polypeptide disclosed herein. In some embodiments, the 6 MWD is tested after the patient has received 22 weeks of treatment utilizing an ActRII polypeptide disclosed herein. In some embodiments, the 6 MWD is tested after the patient has received 24 weeks of treatment utilizing an ActRII polypeptide disclosed herein. In some embodiments, the 6 MWD is tested after the patient has received 26 weeks of treatment utilizing an ActRII polypeptide disclosed herein. In some embodiments, the 6 MWD is tested after the patient has received 28 weeks of treatment utilizing an ActRII polypeptide disclosed herein. In some embodiments, the 6 MWD is tested after the patient has received 48 weeks of treatment utilizing an ActRII polypeptide disclosed herein.

In some embodiments, the disclosure relates to methods of adjusting one or more measurements of exercise capacity (e.g., BDI) in the PcPH (e.g., WHO Group 2 and/or Group 5 PH) patient toward a more normal level (e.g., normal as compared to healthy people of similar age and sex), comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to reducing the patient's BDI. In some embodiments, the method relates to lowering the patient's BDI by at least 0.5 index points. In some embodiments, the method relates to lowering the patient's BDI by at least 1 index points. In some embodiments, the method relates to lowering the patient's BDI by at least 1.5 index points. In some embodiments, the method relates to lowering the patient's BDI by at least 2 index points. In some embodiments, the method relates to lowering the patient's BDI by at least 2.5 index points In some embodiments, the method relates to lowering the patient's BDI by at least 3 index points. In some embodiments, the method relates to lowering the patient's BDI by at least 3.5 index points. In some embodiments, the method relates to lowering the patient's BDI by at least 4 index points. In some embodiments, the method relates to lowering the patient's BDI by at least 4.5 index points. In some embodiments, the method relates to lowering the patient's BDI by at least 5 index points. In some embodiments, the method relates to lowering the patient's BDI by at least 5.5 index points. In some embodiments, the method relates to lowering the patient's BDI by at least 6 index points. In some embodiments, the method relates to lowering the patient's BDI by at least 6.5 index points. In some embodiments, the method relates to lowering the patient's BDI by at least 7 index points. In some embodiments, the method relates to lowering the patient's BDI by at least 7.5 index points. In some embodiments, the method relates to lowering the patient's BDI by at least 8 index points. In some embodiments, the method relates to lowering the patient's BDI by at least 8.5 index points. In some embodiments, the method relates to lowering the patient's BDI by at least 9 index points. In some embodiments, the method relates to lowering the patient's BDI by at least 9.5 index points. In some embodiments, the method relates to lowering the patient's BDI by at least 3 index points. In some embodiments, the method relates to lowering the patient's BDI by at least 10 index points.

Echocardiography

There are numerous clinical presentation factors, echocardiography features, and other features that could be indicative of PcPH (e.g., WHO Group 2 and/or Group 5 PH). For instance, patients who are ≥65 years old are at higher risk for WHO Group 2 (also known as PH-LHD). In patients suspected of having PcPH (e.g., WHO Group 2 and/or Group 5 PH), an echocardiogram may be used to image the effects of PH on the heart and estimate the mPAP from continuous wave Doppler measurements. In some embodiments, an echocardiogram performed on a patient shows structural left heart abnormalities. In some embodiments, the structural left heart abnormality is a disease of the left heart valves. In some embodiments, the structural left heart abnormality is left atrium enlargement (e.g., >4.2 cm). In some embodiments, an electrocardiogram performed on a patient shows left ventricular hypertrophy (LVH) and/or left atrial hypertrophy/dilation (LAH). In some embodiments, an electrocardiogram performed on a patient shows atrial flutter/atrial fibrillation (AF/Afib). In some embodiments, an electrocardiogram performed on a patient shows left bundle branch block (LBBB). In some embodiments, an electrocardiogram performed on a patient shows the presence of Q waves. See, e.g., Galie N., et al Euro Heart J. (2016) 37, 67-119.

In a patient that has symptoms of left heart failure, an echocardiogram may be performed to evaluate various parameters. For instance, in some embodiments, an echocardiogram using Doppler performed on a patient may show indices of increased filling pressures and/or diastolic dysfunction (e.g., increased E/E' or >Type 2-3 mitral flow abnormality). In some embodiments, imaging (e.g. echocardiogram, CT scan, chest X-ray, or MRI) performed on a patient shows Kerley B lines. In some embodiments, imaging (e.g. echocardiogram, CT scan, chest X-ray, or MRI) performed on a patient shows pleural effusion. In some embodiments, imaging (e.g. echocardiogram, CT scan, chest X-ray, or MRI) performed on a patient shows pulmonary edema. In some embodiments, imaging (e.g., echocardiogram, CT scan, chest X-ray, or MRI) performed on a patient shows left atrium enlargement. Id.

Furthermore, in a patient that has features of metabolic syndrome, imaging (e.g. an echocardiogram) may be performed to evaluate various parameters. For instance, in some embodiments, an echocardiogram performed on a patient shows the absence of right ventricle dysfunction (e.g., IpcPH). In some embodiments, an echocardiogram performed on a patient shows the presence of right ventricle dysfunction (e.g., CpcPH). In some embodiments, an echocardiogram performed on a patient shows the absence of mid systolic notching of the pulmonary artery flow. In some embodiments, an echocardiogram performed on a patient shows the absence of pericardial effusion. In some embodiments, the patient has a history of heart disease (past or current). In some embodiments, the patient has persistent atrial fibrillation. Id. In some embodiments, an Echo Score or the TAPSE/systolic pulmonary arterial pressure ratio are used to differentiate Cpc-PH from Ipc-PH. In some embodiments, an integrative score of five echocardiographic parameters (RV/LV ratio, left ventricular eccentricity index (LVEI), E/E', RV forming apex, width and inspiratory collapse of IVC) as well as "notching" of the RV outflow tract Doppler envelope may be used to distinguish between precapillary PH (e.g., PAH) from post-capillary PH (e.g., WHO Group 2 and/or Group 5 PH).

In some embodiments, a patient has diastolic dysfunction. In some embodiments, the method improves diastolic dysfunction in the patient. In some embodiments, the improvement in diastolic dysfunction is an improvement in the E/E' ratio (a ratio of mitral inflow velocity (E) to mitral annular velocity (E')). In some embodiments, the improvement in diastolic dysfunction is an improvement in the isovolumic relaxation time (IVRT). In some embodiments, the improvement in the diastolic dysfunction is a lower RVSP. In some embodiments, the diastolic dysfunction results from one or more conditions selected from the group consisting of hypertension, diabetes, and advanced age.

Complications of PH

In certain aspects, the disclosure relates to methods of treating, preventing, or reducing the progression rate and/or severity of one or more complications of PcPH (e.g., WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method relates to treating, preventing, or reducing the progression rate and/or severity of cell proliferation in the pulmonary artery of a PcPH patient. In some embodiments, the method relates to treating, preventing, or reducing the progression rate and/or severity of smooth muscle and/or endothelial cells proliferation in the pulmonary artery of a PcPH patient. In some embodiments, the method relates to treating, preventing, or reducing the progression rate and/or severity of angiogenesis in the pulmonary artery of a PcPH patient. In some embodiments, the method relates to increasing physical activity of a patient having PcPH. In some embodiments, the method relates to treating, preventing, or reducing the progression rate and/or severity of dyspnea in a PcPH patient. In some embodiments, the method relates to treating, preventing, or reducing the progression rate and/or severity of chest pain in a PcPH patient. In some embodiments, the method relates to treating, preventing, or reducing the progression rate and/or severity of fatigue in a PcPH patient. In some embodiments, the method relates to treating, preventing, or reducing the progression rate and/or severity of fibrosis in a PcPH patient. In some embodiments, the fibrosis is selected from the group consisting of left ventricular fibrosis, right ventricular fibrosis, and pulmonary fibrosis. In some embodiments, the method relates to treating, preventing, or reducing the progression rate and/or severity of left ventricular fibrosis in a PcPH patient. In some embodiments, the method relates to treating, preventing, or reducing the progression rate and/or severity of right ventricular fibrosis in a PcPH patient. In some embodiments, the method relates to treating, preventing, or reducing the progression rate and/or severity of pulmonary fibrosis in a PcPH patient. In some embodiments, the method relates to decreasing the patient's fibrosis by least 1% (e.g., 1%, 5, 10, 15, 20, 25, 30, 35, 40, 45, 50, 55, 60, 65, 70, 75, 80, 85, 90, 95, or 100%). In some embodiments, the method relates to decreasing the patient's fibrosis by at least 1%. In some embodiments, the method relates to decreasing the patient's fibrosis by at least 5%. In some embodiments, the method relates to decreasing the patient's fibrosis by at least 10%. In some embodiments, the method relates to decreasing the patient's fibrosis by at least 15%. In some embodiments, the method relates to decreasing the patient's fibrosis by at least 20%. In some embodiments, the method relates to decreasing the patient's fibrosis by at least 25%. In some embodiments, the method relates to decreasing the patient's fibrosis by at least 30%. In some embodiments, the method relates to decreasing the patient's fibrosis by at least 35%. In some embodiments, the method relates to decreasing the patient's fibrosis by at least 40%. In some embodiments, the method relates to decreasing the patient's fibrosis by at least 45%. In some embodiments, the method relates to decreasing the patient's fibrosis by at least 50%. In some embodiments, the method relates to decreasing the patient's fibrosis by at least 55%. In some embodiments, the method relates to decreasing the patient's fibrosis by at least 60%. In some embodiments, the method relates to decreasing the patient's fibrosis by at least 65%. In some embodiments, the method relates to decreasing the patient's fibrosis by at least 70%. In some embodiments, the method relates to decreasing the patient's fibrosis by at least 75%. In some embodiments, the method relates to decreasing the patient's fibrosis by at least 80%. In some embodiments, the method relates to decreasing the patient's fibrosis by at least 85%. In some embodiments, the method relates to decreasing the patient's fibrosis by at least 90%. In some embodiments, the method relates to decreasing the patient's fibrosis by at least 95%. In some embodiments, the method relates to decreasing the patient's fibrosis by at least 100%.

In some embodiments, the method relates to treating, preventing, or reducing the progression rate and/or severity of pulmonary vascular remodeling in a PcPH patient. In some embodiments, the method relates to treating, preventing, or reducing the progression rate and/or severity of cardiac remodeling in a PcPH patient. In some embodiments, the method relates to treating, preventing, or reducing the progression rate and/or severity of left cardiac remodeling in a PcPH patient. In some embodiments, the method relates to treating, preventing, or reducing the progression rate and/or severity of right cardiac remodeling in a PcPH patient. In some embodiments, the method relates to treating, preventing, or reducing the progression rate and/or severity of right ventricular hypertrophy in a PcPH patient. In some embodiments, the method relates to treating, preventing, or reducing the progression rate and/or severity of left ventricular hypertrophy in a PcPH patient In some embodiments, the method relates to treating, preventing, or reducing the progression rate and/or severity of metabolic syndrome in a PcPH patient. In some embodiments, the method relates to treating, preventing, or reducing the progression rate and/or severity of left atrium dilation in a PcPH patient. In some embodiments, the method relates to treating, preventing, or reducing the progression rate and/or severity of an underlying condition (e.g., COPD, sleep apnea syndrome, CTEPH) in a PcPH patient.

Complications or Comorbidities and Combination Therapies

In some embodiments, the disclosure contemplates methods of treating one or more complications of PcPH (e.g., smooth muscle and/or endothelial cell proliferation in the pulmonary artery, angiogenesis in the pulmonary artery, dyspnea, chest pain, pulmonary vascular remodeling, cardiac remodeling, right ventricular hypertrophy, left ventricular hypertrophy, left atrium dilation, pulmonary fibrosis, need for lung and/or heart transplant, and need for atrial septostomy) comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the disclosure contemplates methods of preventing one or more complications of PcPH comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the disclosure contemplates methods of reducing the progression rate of one or more complications of PcPH comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the disclosure contemplates methods of reducing the severity of one or more complications of PcPH comprising administering to a patient in need thereof an effective amount of an ActRII polypeptide (e.g., an amino acid sequence that is at least 90% identical to an amino acid sequence corresponding to residues 30-110 of SEQ ID NO: 1).

In some embodiments, the disclosure contemplates methods of treating one or more comorbidities of PcPH (e.g., systemic hypertension, decreased renal function, diabetes mellitus, obesity, coronary artery disease (CAD), heart failure, and anemia) comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the method results in the improvement of one or more comorbidities of PcPH (e.g., systemic hypertension, decreased renal function, diabetes mellitus, obesity, coronary artery disease (CAD), heart failure, and anemia). In some embodiments, the one or more comorbidities of PcPH are improved indirectly (e.g., due to an improvement in the patient's PH).

In some embodiments, the disclosure contemplates methods of reducing the progression rate of PcPH (e.g., WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the disclosure contemplates methods of reducing the progression rate of one or more complications of PcPH (e.g., WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the disclosure contemplates methods of reducing the severity of PcPH (e.g., WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the disclosure contemplates methods of reducing the severity of one or more complications of PcPH (e.g., WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the disclosure contemplates method of reducing the need to initiate treatment with a known treatment for PcPH comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the disclosure contemplates a method of reducing the need to increase the dose of prostacyclin in a patient (e.g., increasing the dose by at least 10%) comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the disclosure contemplates a method of reducing the need for PcPH-specific hospitalization comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, PcPH-specific hospitalization is hospitalization of patient for at least 24 hours. In some embodiments, the disclosure contemplates a method of reducing the deterioration of PcPH comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, deterioration of PcPH comprises worsening in WHO functional class and/or a decrease of at least 15% in the 6 MWD of the patient.

Optionally, methods disclosed herein for treating, preventing, or reducing the progression rate and/or severity of PcPH (e.g., WHO Group 2 and/or Group 5 PH), particularly treating, preventing, or reducing the progression rate and/or severity of one or more complications of PcPH, may further comprise administering to the patient one or more supportive therapies or additional active agents for treating PcPH. For example, the patient also may be administered one or more supportive therapies or active agents selected from the group consisting of: nitrates, hydralazine, prostacyclin and derivatives thereof (e.g., epoprostenol, treprostinil, and iloprost); prostacyclin receptor agonists (e.g., selexipag); endothelin receptor antagonists (e.g., thelin, ambrisentan, macitentan, darusentan, and bosentan); calcium channel blockers (e.g., amlodipine, diltiazem, and nifedipine; anticoagulants (e.g., warfarin); diuretics; oxygen therapy; atrial septostomy; pulmonary thromboendarterectomy; phosphodiesterase type 5 inhibitors (e.g., sildenafil and tadalafil); activators of soluble guanylate cyclase (e.g., cinaciguat, vericiguat, and riociguat); ASK-1 inhibitors (e.g., CIIA; SCH79797; GS-4997; MSC2032964A; 3H-naphtho[1,2,3-de]quiniline-2,7-diones, NQDI-1; 2-thioxo-thiazolidines, 5-bromo-3-(4-oxo-2-thioxo-thiazolidine-5-ylidene)-1,3-dihydro-indol-2-one); NF-κB antagonists (e.g., dh404, CDDO-epoxide; 2.2-difluoropropionamide; C28 imidazole (CDDO-Im); 2-cyano-3,12-dioxoolean-1,9-dien-28-oic acid (CDDO); 3-Acetyloleanolic Acid; 3-Triflouroacetyloleanolic Acid; 28-Methyl-3-acetyloleanane; 28-Methyl-3-trifluoroacetyloleanane; 28-Methyloxyoleanolic Acid; SZC014; SCZ015; SZC017; PEGylated derivatives of oleanolic acid; 3-O-(beta-D-glucopyranosyl) oleanolic acid; 3-O-[beta-D-glucopyranosyl-(1-->3)-beta-D-glucopyranosyl]oleanolic acid; 3-0-[beta-D-glucopyranosyl-(1-->2)-beta-D-glucopyranosyl]oleanolic acid; 3-O-[beta-D-glucopyranosyl-(1-->3)-beta-D-glucopyranosyl]oleanolic acid 28-O-beta-D-glucopyranosyl ester; 3-O-[beta-D-glucopyranosyl-(1-->2)- beta-D-glucopyranosyl]oleanolic acid 28-O-beta-D-glucopyranosyl ester; 3-O-[a-L-rhamnopyranosyl-(1-->3)-beta-D-glucuronopyranosyl]oleanolic acid; 3-O-[alpha-L-rhamnopyranosyl-(1-->3)-beta-D-glucuronopyranosyl] oleanolic acid 28-O-beta-D-glucopyranosyl ester; 28-O-β-D-glucopyranosyl-oleanolic acid; 3-O-β-D-glucopyranosyl (1->3)-β-D-glucopyranosiduronic acid (CS1); oleanolic acid 3-O-β-D-glucopyranosyl (1->3)-β-D-glucopyranosiduronic acid (CS2); methyl 3,11-dioxoolean-12-en-28-olate (DIOXOL); $ZCVI_4$-2; Benzyl 3-dehydr-oxy-1,2,5-oxadiazolo[3',4':2,3]oleanolate), an LV assist device (LVAD), implantable cardioverter-defibrillator (ICD), valve replacement, valve repair, lung and/or heart transplantation. In some embodiments, the methods described herein may further comprise administering to the patient parental prostacyclin. In some embodiments, the methods described herein may further comprise administering to the patient one additional supportive therapy or additional active agent (i.e., double therapy) for treating PcPH. In some embodiments, the methods described herein may further comprise administering to the patient two additional supportive therapies or additional active agents (i.e., triple therapy) for treating PcPH. In some embodiments, the methods described herein may further comprise administering to the patient three additional supportive therapies or additional active agents (i.e., quadruple therapy) for treating PcPH.

In some embodiments, the methods described herein may further comprise administering to the patient an angiotensin antagonist (e.g., angiotensin receptor blocker, ARB). In some embodiments, a patient is further administered one or more ARBs selected from the group consisting of losartan, irbesartan, olmesartan, candesartan, valsartan, fimasartan, azilsartan, salprisartan, and telmisartan. In some embodiments, a patient is administered losartan. In some embodiments, a patient is administered irbesartan. In some embodiments, a patient is administered olmesartan. In some embodiments, a patient is administered candesartan. In some embodiments, a patient is administered valsartan. In some embodiments, a patient is administered fimasartan. In some embodiments, a patient is administered azilsartan. In some embodiments, a patient is administered salprisartan. In some embodiments, a patient is administered telmisartan. In some embodiments, the methods described herein may further comprise administering to the patient a neprilysin inhibitor and an angiotensin antagonist (e.g., sacubitril/valsartan; also known as LCZ696).

In some embodiments, the methods described herein may further comprise administering to the patient one or more ACE inhibitors. In some embodiments, the one or more ACE inhibitors are selected from the group consisting of benazepril, captopril, enalapril, lisinopril, perindopril, ramipril (e.g., ramipen), trandolapril, and zofenopril. In some embodiments, a patient is administered benazepril. In some embodiments, a patient is administered captopril. In some embodiments, a patient is administered enalapril. In some embodiments, a patient is administered lisinopril. In some embodiments, a patient is administered perindopril. In some embodiments, a patient is administered ramipril. In some embodiments, a patient is administered trandolapril. In some embodiments, a patient is administered zofenopril. In some embodiments, the methods described herein may further comprise administering to the patient an ARB and an ACE inhibitor. In some embodiments, an alternative approach to angiotensin antagonism is to combine an ACE inhibitor and/or ARB with an aldosterone antagonist.

In some embodiments, the methods described herein may further comprise administering to the patient one or more neprilysin inhibitors. In some embodiments, the one or more neprilysin inhibitors are selected from the group consisting of thiorphan, phosphoramidon, candoxatrilat, candoxatril, ecadotril, omapatrilat, LBQ657, and sacubitril. In some embodiments, a patient is administered thiorphan. In some embodiments, a patient is administered phosphoramidon. In some embodiments, a patient is administered candoxatrilat. In some embodiments, a patient is administered candoxatril. In some embodiments, a patient is administered ecadotril. In some embodiments, a patient is administered omapatrilat. In some embodiments, a patient is administered LBQ657. In some embodiments, a patient is administered sacubitril. In some embodiments, the methods described herein may further comprise administering to the patient a neprilysin inhibitor and an ARB (e.g., sacubitril/valsartan; also known as LCZ696).

In some embodiments, the methods described herein may further comprise administering to the patient an angiotensin receptor-neprilysin inhibitor (ARNI). In some embodiments, the ARNI is sacubitril/valsartan (Entresto®). In some embodiments, a patient is administered sacubitril/valsartan (Entresto®).

In some embodiments, the methods described herein may further comprise administering to the patient one or more beta-blockers. In some embodiments, the one or more beta-blockers are selected from the group consisting of bisoprolol, carvedilol, metoprolol succinate (CR/XL), and nebivolol. In some embodiments, a patient is administered bisoprolol. In some embodiments, a patient is administered carvedilol. In some embodiments, a patient is administered metoprolol succinate (CR/XL). In some embodiments, a patient is administered nebivolol.

In some embodiments, the methods described herein may further comprise administering to the patient one or more mineralocorticoid receptor antagonists (MRA). In some embodiments, the one or more MRA are selected from the group consisting of eplerenone and spironolactone. In some embodiments, a patient is administered eplerenone. In some embodiments, a patient is administered spironolactone.

In some embodiments, the methods described herein may further comprise administering to the patient one or more hyperpolarization-activated cyclic nucleotide-gated (HCN) channel blockers. In some embodiments, the one or more HCN are selected from the group consisting of ivabradine, ZD7288, cilobradine, zatebradine, alinidine, clonidine, falipamil, TH92:20, and YM758. In some embodiments, a patient is administered ivabradine. In some embodiments, a patient is administered ZD7288. In some embodiments, a patient is administered cilobradine. In some embodiments, a patient is administered zatebradine. In some embodiments, a patient is administered alinidine. In some embodiments, a patient is administered clonidine. In some embodiments, a patient is administered falipamil. In some embodiments, a patient is administered TH92:20. In some embodiments, a patient is administered YM758.

In some embodiments, the one or more supportive therapies or additional active agents for treating PcPH are administered prior to administration of the ActRII polypeptide. In some embodiments, the one or more supportive therapies or additional active agents for treating PcPH are administered in combination with the ActRII polypeptide. In some embodiments, the one or more supportive therapies or additional active agents for treating PcPH are administered after the administration of the ActRII polypeptide. As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

Transplant Free Survival

Lung and/or heart transplantation is a surgical treatment option for patients with PcPH, and is often recommended for patients who don't respond to less invasive therapies (e.g., vasodilator therapy). Generally, PcPH patients who receive lung and/or heart transplantation have Functional Class III or Class IV pulmonary hypertension in accordance with the World Health Organization's functional classification system for pulmonary hypertension.

In certain aspects, the disclosure relates to methods of treating, preventing, or reducing the progression rate and/or severity of PcPH comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the method increases the patient's transplant free survival by at least 1% (e.g., 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100%. In some embodiments, the method relates to increasing the patient's transplant free survival by at least 1%. In some embodiments, the method relates to increasing the patient's transplant free survival by at least 2%. In some embodiments, the method relates to increasing the patient's transplant free survival by at least 3%. In some embodiments, the method relates to increasing the patient's transplant free survival by at least 4%. In some embodiments, the method relates to increasing the patient's transplant free survival by at least 5%. In some embodiments, the method relates to increasing the patient's transplant free survival by at least 10%. In some embodiments, the method relates to increasing the patient's transplant free survival by at least 15%. In some embodiments, the method relates to increasing the patient's transplant free survival by at least 20%. In some embodiments, the method relates to increasing the patient's transplant free survival by at least 25%. In some embodiments, the method relates to increasing the patient's transplant free survival by at least 30%. In some embodiments, the method relates to increasing the patient's transplant free survival by at least 35%. In some embodiments, the method relates to increasing the patient's transplant free survival by at least 40%. In some embodiments, the method relates to increasing the patient's transplant free survival by at least 45%. In some embodiments, the method relates to increasing the patient's transplant free survival by at least 50%. In some embodiments, the method relates to increasing the patient's transplant free survival by at least 55%. In some embodiments, the method relates to increasing the patient's transplant free survival by at least 60%. In some embodiments, the method relates to increasing the patient's transplant free survival by at least 65%. In some embodiments, the method relates to increasing the patient's transplant free survival by at least 70%. In some embodiments, the method relates to increasing the patient's transplant free survival by at least 75%. In some embodiments, the method relates to increasing the patient's transplant free survival by at least 80%. In some embodiments, the method relates to increasing the patient's transplant free survival by at least 85%. In some embodiments, the method relates to increasing the patient's transplant free survival by at least 90%. In some embodiments, the method relates to increasing the patient's transplant free survival by at least 95%. In some embodiments, the method relates to increasing the patient's transplant free survival by at least 100%. In some embodiments, the method relates to increasing the patient's transplant free survival as compared to controls over 1 year. In some embodiments, the method relates to increasing the patient's transplant free survival as compared to controls over 2 years. In some embodiments, the method relates to increasing the patient's transplant free survival as compared to controls over 3 years. In some embodiments, the method relates to increasing the patient's transplant free survival as compared to controls over 4 years. In some embodiments, the method relates to increasing the patient's transplant free survival as compared to controls over 5 years. In some embodiments, the method relates to increasing the patient's transplant free survival as compared to controls over 6 years. In some embodiments, the method relates to increasing the patient's transplant free survival as compared to controls over 7 years.

Death

In certain aspects, the disclosure relates to methods of reducing the risk of death in patients with PcPH comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the method reduces the patient's risk of death by at least 1% (e.g., 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100%). In some embodiments, the method relates to reducing the patient's risk of death by at least 1%. In some embodiments, the method relates to reducing the patient's risk of death by at least 2%. In some embodiments, the method relates to reducing the patient's risk of death by at least 3%. In some embodiments, the method relates to reducing the patient's risk of death by at least 4%. In some embodiments, the method relates to reducing the patient's risk of death by at least 5%. In some embodiments, the method relates to reducing the patient's risk of death by at least 10%. In some embodiments, the method relates to reducing the patient's risk of death by at least 15%. In some embodiments, the method relates to reducing the patient's risk of death by at least 20%. In some embodiments, the method relates to reducing the patient's risk of death by at least 25%. In some embodiments, the method relates to reducing the patient's risk of death by at least 30%. In some embodiments, the method relates to reducing the patient's risk of death by at least 35%. In some embodiments, the method relates to reducing the patient's risk of death by at least 40%. In some embodiments, the method relates to reducing the patient's risk of death by at least 45%. In some embodiments, the method relates to reducing the patient's risk of death by at least 50%. In some embodiments, the method relates to reducing the patient's risk of death by at least 55%. In some embodiments, the method relates to reducing the patient's risk of death by at least 60%. In some embodiments, the method relates to reducing the patient's risk of death by at least 65%. In some embodiments, the method relates to reducing the patient's risk of death by at least 70%. In some embodiments, the method relates to reducing the patient's risk of death by at least 75%. In some embodiments, the method relates to reducing the patient's risk of death by at least 80%. In some embodiments, the method relates to reducing the patient's risk of death by at least 85%. In some embodiments, the method relates to reducing the patient's risk of death by at least 90%. In some embodiments, the method relates to reducing the patient's risk of death by at least 95%. In some embodiments, the method relates to reducing the patient's risk of death by at least 100%. In some embodiments, the method reduces the risk of hospitalization for one or more complications associated with PcPH.

Composite Clinical Endpoint

In certain aspects, the disclosure relates to methods of treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the method reduces the patient's composite clinical endpoint by at least 1% (e.g., 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100%). In some embodiments, the method relates to reducing the patient's composite clinical endpoint by at least 1%. In some embodiments, the method relates to reducing the patient's composite clinical endpoint by at least 2%. In some embodiments, the method relates to reducing the patient's composite clinical endpoint by at least 3%. In some embodiments, the method relates to reducing the patient's composite clinical endpoint by at least 4%. In some embodiments, the method relates to reducing the patient's composite clinical endpoint by at least 5%. In some embodiments, the method relates to reducing the patient's composite clinical endpoint by at least 10%. In some embodiments, the method relates to reducing the patient's composite clinical endpoint by at least 15%. In some embodiments, the method relates to reducing the patient's composite clinical endpoint by at least 20%. In some embodiments, the method relates to reducing the patient's composite clinical endpoint by at least 25%. In some embodiments, the method relates to reducing the patient's composite clinical endpoint by at least 30%. In some embodiments, the method relates to reducing the patient's composite clinical endpoint by at least 35%. In some embodiments, the method relates to reducing the patient's composite clinical endpoint by at least 40%. In some embodiments, the method relates to reducing the patient's composite clinical endpoint by at least 45%. In some embodiments, the method relates to reducing the patient's composite clinical endpoint by at least 50%. In some embodiments, the method relates to reducing the patient's composite clinical endpoint by at least 55%. In some embodiments, the method relates to reducing the patient's composite clinical endpoint by at least 60%. In some embodiments, the method relates to reducing the patient's composite clinical endpoint by at least 65%. In some embodiments, the method relates to reducing the patient's composite clinical endpoint by at least 70%. In some embodiments, the method relates to reducing the patient's composite clinical endpoint by at least 75%. In some embodiments, the method relates to reducing the patient's composite clinical endpoint by at least 80%. In some embodiments, the method relates to reducing the patient's composite clinical endpoint by at least 85%. In some embodiments, the method relates to reducing the patient's composite clinical endpoint by at least 90%. In some embodiments, the method relates to reducing the patient's composite clinical endpoint by at least 95%. In some embodiments, the method relates to reducing the patient's composite clinical endpoint by at least 100%. In some embodiments, the method reduces the risk of hospitalization for one or more complications associated with PcPH. In some embodiments, the composite clinical endpoint comprises one or more endpoints selected from the group consisting of clinical worsening, hospitalization, and death.

Functional Classes

PcPH (e.g., WHO Group 2 and Group 5 PH) at baseline can be mild, moderate or severe, as measured for example by World Health Organization (WHO) functional class, which is a measure of disease severity in patients with pulmonary hypertension. The WHO functional classification is an adaptation of the New York Heart Association (NYHA) system and is routinely used to qualitatively assess activity tolerance, for example in monitoring disease progression and response to treatment (Rubin (2004) Chest 126:7-10). Four functional classes are recognized in the WHO system: Class I: pulmonary hypertension without resulting limitation of physical activity; ordinary physical activity does not cause undue dyspnea or fatigue, chest pain or near syncope; Class II: pulmonary hypertension resulting in slight limitation of physical activity; patient comfortable at rest; ordinary physical activity causes undue dyspnea or fatigue, chest pain or near syncope; Class III: pulmonary hypertension resulting in marked limitation of physical activity; patient comfortable at rest; less than ordinary activity causes undue dyspnea or fatigue, chest pain or near syncope; Class IV: pulmonary hypertension resulting in inability to carry out any physical activity without symptoms; patient manifests signs of right-heart failure; dyspnea and/or fatigue may be present even at rest; discomfort is increased by any physical activity.

In certain aspects, the disclosure relates to methods of treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has Functional Class I, Functional Class II, Functional Class III, or Functional Class IV pulmonary hypertension as recognized by the WHO. In some embodiments, the method relates to a patient that has Functional Class I pulmonary hypertension as recognized by the WHO. In some embodiments, the method relates to a patient that has Functional Class II pulmonary hypertension as recognized by the WHO. In some embodiments, the method relates to a patient that has Functional Class III pulmonary hypertension as recognized by the WHO. In some embodiments, the method relates to a patient that has Functional Class IV pulmonary hypertension as recognized by the WHO. In some embodiments, the method relates to patients having Functional Class II or Class III pulmonary hypertension as recognized by the WHO. In some embodiments, the method relates to patients having Functional Class II, Class III, or Class IV pulmonary hypertension as recognized by the WHO. In some embodiments, the method relates to patients having Functional Class I, Class II, Class III, or Class IV pulmonary hypertension as recognized by the WHO. In some embodiments, the method delays clinical worsening of PcPH. In some embodiments, the method delays clinical worsening of PcPH in accordance with the WHO's functional classification system for pulmonary hypertension.

In some embodiments, the disclosure relates to methods of preventing or reducing pulmonary hypertension Functional Class progression comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the reduction in Functional Class progression is a delay in Functional Class progression. In some embodiments, the method relates to preventing or decreasing pulmonary hypertension functional class progression as recognized by the WHO. In some embodiments, the disclosure relates to methods of promoting or increasing pulmonary hypertension Functional Class regression in a PcPH patient comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has Functional Class I, Functional Class II, Functional Class III, or Functional Class IV pulmonary hypertension as recognized by the WHO. In some embodiments, the method relates to preventing or delaying patient progression from Functional Class I pulmonary hypertension to Functional Class II pulmonary hypertension as recognized by the WHO. In some embodiments, the method relates to promoting patient regression from Functional Class II pulmonary hypertension to Functional Class I pulmonary hypertension as recognized by the WHO. In some embodiments, the method relates to preventing or delaying patient progression from Functional Class II pulmonary hypertension to Functional Class III pulmonary hypertension as recognized by the WHO. In some embodiments, the method relates to promoting patient regression from Functional Class III pulmonary hypertension to Functional Class II pulmonary hypertension as recognized by the WHO. In some embodiments, the method relates to promoting patient regression from Functional Class III pulmonary hypertension to Functional Class I pulmonary hypertension as recognized by the WHO. In some embodiments, the method relates to preventing or delaying patient progression from Functional Class III pulmonary hypertension to Functional Class IV pulmonary hypertension as recognized by the WHO. In some embodiments, the method relates to promoting patient regression from Functional Class IV pulmonary hypertension to Functional Class III pulmonary hypertension as recognized by the WHO. In some embodiments, the method relates to promoting patient regression from Functional Class IV pulmonary hypertension to Functional Class II pulmonary hypertension as recognized by the WHO. In some embodiments, the method relates to promoting patient regression from Functional Class IV pulmonary hypertension to Functional Class I pulmonary hypertension as recognized by the WHO.

The New York Heart Association (NYHA) functional classification (Table 3) has been used to describe the severity of symptoms and exercise intolerance in patients with pulmonary hypertension. The NYHA functional classification system provides a rapid assessment of patients' functional status in everyday clinical practice and is a well-established means of predicting prognosis. The four functional classes recognized by the NYHA functional classification system are shown in Table 3.

TABLE 3

New York Heart Association (NYHA) functional classification of pulmonary hypertension based on severity of symptoms and physical activity

| | |
|---|---|
| Class I | No limitation of physical activity. Ordinary physical activity does not cause undue breathlessness, fatigue, or palpitations. |
| Class II | Slight limitation of physical activity. Comfortable at rest, but ordinary physical activity results in undue breathlessness, fatigue, or palpitations. |
| Class III | Marked limitation of physical activity. Comfortable at rest, but less than ordinary physical activity results in undue breathlessness, fatigue, or palpitations. |
| Class IV | Unable to carry on any physical activity without discomfort. Symptoms at rest can be present If any physical activity is undertaken, discomfort is increased. |

In certain aspects, the disclosure relates to methods of treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has Functional Class I, Functional Class II, Functional Class III, or Functional Class IV pulmonary hypertension as recognized by the NYHA.

In some embodiments, the method relates to a patient that has Functional Class I pulmonary hypertension as recognized by the NYHA. In some embodiments, a patient with Functional Class I pulmonary hypertension as recognized by the NYHA has no limitation of physical activity. In some embodiments, a patient with Functional Class I pulmonary hypertension as recognized by the NYHA experiences physical activity that does not cause undue breathlessness, fatigue, and/or palpitations. In some embodiments, the method relates to a patient that has Functional Class II pulmonary hypertension as recognized by the NYHA. In some embodiments, a patient with Functional Class II pulmonary hypertension as recognized by the NYHA has slight limitation of physical activity. In some embodiments, a patient with Functional Class II pulmonary hypertension as recognized by the NYHA experiences ordinary physical activity resulting in undue breathlessness, fatigue, or palpitations. In some embodiments, the method relates to a patient that has Functional Class III pulmonary hypertension as recognized by the NYHA. In some embodiments, a patient with Functional Class III pulmonary hypertension as recognized by the NYHA has marked limitation of physical activity. In some embodiments, a patient with Functional Class III pulmonary hypertension as recognized by the NYHA experiences less than ordinary physical activity resulting in undue breathlessness, fatigue, or palpitations. In some embodiments, the method relates to a patient that has Functional Class IV pulmonary hypertension as recognized by the NYHA. In some embodiments, a patient with Functional Class IV pulmonary hypertension as recognized by the NYHA is unable to carry on any physical activity without discomfort. In some embodiments, a patient with Functional Class IV pulmonary hypertension as recognized by the NYHA experiences symptoms at rest, as well as when any physical activity is undertaken, discomfort is increased. In some embodiments, the method relates to patients having Functional Class II or Class III pulmonary hypertension as recognized by the NYHA. In some embodiments, the method relates to patients having Functional Class II, Class III, or Class IV pulmonary hypertension as recognized by the NYHA. In some embodiments, the method relates to patients having Functional Class I, Class II, Class III, or Class IV pulmonary hypertension as recognized by the NYHA. In some embodiments, the method delays clinical worsening of PcPH. In some embodiments, the method delays clinical worsening of PcPH in accordance with the NYHA's functional classification system for pulmonary hypertension.

In some embodiments, the disclosure relates to methods of preventing or reducing pulmonary hypertension Functional Class progression comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the reduction in Functional Class progression is a delay in Functional Class progression. In some embodiments, the method relates to preventing or decreasing pulmonary hypertension functional class progression as recognized by the NYHA. In some embodiments, the disclosure relates to methods of promoting or increasing pulmonary hypertension Functional Class regression in a PcPH patient comprising administering to a patient in need thereof an effective amount of an ActRII polypeptide (e.g., an amino acid sequence that is at least 90% identical to an amino acid sequence corresponding to residues 30-110 of SEQ ID NO: 1), wherein the patient has Functional Class I, Functional Class II, Functional Class III, or Functional Class IV pulmonary hypertension as recognized by the NYHA. In some embodiments, the method relates to preventing or delaying patient progression from Functional Class I pulmonary hypertension to Functional Class II pulmonary hypertension as recognized by the NYHA. In some embodiments, the method relates to promoting patient regression from Functional Class II pulmonary hypertension to Functional Class I pulmonary hypertension as recognized by the NYHA. In some embodiments, the method relates to preventing or delaying patient progression from Functional Class II pulmonary hypertension to Functional Class III pulmonary hypertension as recognized by the NYHA. In some embodiments, the method relates to promoting patient regression from Functional Class III pulmonary hypertension to Functional Class II pulmonary hypertension as recognized by the NYHA. In some embodiments, the method relates to promoting patient regression from Functional Class III pulmonary hypertension to Functional Class I pulmonary hypertension as recognized by the NYHA. In some embodiments, the method relates to preventing or delaying patient progression from Functional Class III pulmonary hypertension to Functional Class IV pulmonary hypertension as recognized by the NYHA. In some embodiments, the method relates to promoting patient regression from Functional Class IV pulmonary hypertension to Functional Class III pulmonary hypertension as recognized by the NYHA. In some embodiments, the method relates to promoting patient regression from Functional Class IV pulmonary hypertension to Functional Class II pulmonary hypertension as recognized by the NYHA. In some embodiments, the method relates to promoting patient regression from Functional Class IV pulmonary hypertension to Functional Class I pulmonary hypertension as recognized by the NYHA.

In some embodiments, functional class regression is tested after the patient has received 4 weeks of treatment utilizing an ActRII polypeptide disclosed herein. In some embodiments, functional class regression is tested after the patient has received 8 weeks of treatment utilizing an ActRII polypeptide disclosed herein. In some embodiments, functional class regression is tested after the patient has received 12 weeks of treatment utilizing an ActRII polypeptide disclosed herein. In some embodiments, functional class regression is tested after the patient has received 16 weeks of treatment utilizing an ActRII polypeptide disclosed herein. In some embodiments, functional class regression is tested after the patient has received 20 weeks of treatment utilizing an ActRII polypeptide disclosed herein. In some embodiments, functional class regression is tested after the patient has received 22 weeks of treatment utilizing an ActRII polypeptide disclosed herein. In some embodiments, functional class regression is tested after the patient has received 24 weeks of treatment utilizing an ActRII polypeptide disclosed herein. In some embodiments, functional class regression is tested after the patient has received 26 weeks of treatment utilizing an ActRII polypeptide disclosed herein. In some embodiments, functional class regression is tested after the patient has received 28 weeks of treatment utilizing an ActRII polypeptide disclosed herein. In some embodiments, functional class regression is tested after the patient has received 48 weeks of treatment utilizing an ActRII polypeptide disclosed herein.

Sustained Therapeutic Effect

In certain aspects, the disclosure relates to methods of treating, preventing, or reducing the progression rate and/or severity of PcPH in a sustained manner comprising administering to a patient in need thereof an effective amount of an ActRII polypeptide (e.g., an amino acid sequence that is at least 90% identical to an amino acid sequence corresponding to residues 30-110 of SEQ ID NO: 1). In some embodiments, the sustained manner comprises a persistent therapeutic effect following the reduction in administration of an ActRII polypeptide described herein. In some embodiments, the sustained manner comprises a persistent therapeutic effect following the withdrawal of administration of an ActRII polypeptide described herein. In some embodiments, the persistent therapeutic effect relates to maintaining functional or hematologic measurements over time. In some embodiments, the persistent therapeutic effect is measured as a sustained reduction in PVR. In some embodiments, the patient's PVR level does not increase for at least 1 week to at least 12 weeks following withdrawal of an ActRII polypeptide treatment described herein. In some embodiments, the patient's PVR level does not increase for at least 1 week following withdrawal of an ActRII polypeptide treatment described herein. In some embodiments, the patient's PVR level does not increase for at least 2 weeks following withdrawal of an ActRII polypeptide treatment described herein. In some embodiments, the patient's PVR level does not increase for at least 3 weeks following withdrawal of an ActRII polypeptide treatment described herein. In some embodiments, the patient's PVR level does not increase for at least 4 weeks following withdrawal of an ActRII polypeptide treatment described herein. In some embodiments, the patient's PVR level does not increase for at least 5 weeks following withdrawal of an ActRII polypeptide treatment described herein. In some embodiments, the patient's PVR level does not increase for at least 6 weeks following withdrawal of an ActRII polypeptide treatment described herein. In some embodiments, the patient's PVR level does not increase for at least 1 month to at least 6 months following withdrawal of an ActRII polypeptide treatment described herein.

In certain aspects, the disclosure relates to methods of treating or preventing cardiopulmonary remodeling associated with PcPH in a patient, comprising administering to a patient in need thereof an effective amount of an ActRII polypeptide, wherein said method slows down cardiac remodeling and/or reverses cardiac remodeling. In some embodiments, the reversal is a sustained reversal. In some embodiments, the cardiac remodeling is left cardiac remodeling. In some embodiments, the cardiac remodeling is right cardiac remodeling. In some embodiments, the cardiac remodeling is ventricle remodeling. In some embodiments, the ventricle remodeling is left ventricular remodeling. In some embodiments, the ventricle remodeling is right ventricular remodeling. In some embodiments, the cardiac remodeling is ventricular dilation. In some embodiments, the method decreases interventricular septal end diastole. In some embodiments, the method decreases posterior wall end diastole.

In some embodiments, echocardiographic measurements may be used to assess the persistent therapeutic effect. In some embodiments, the echocardiographic measurements include, but are not limited to, RV fractional area change (RVFAC), sPAP, tricuspid annular systolic velocity (TASV), and Tei index. In some embodiments, a patient treated with an ActRII polypeptide disclosed herein shows a persistent therapeutic effect. In some embodiments, the persistent therapeutic effect results in decreased intrusion of the ventral wall into the left ventricle. In some embodiments, the persistent therapeutic effect results in an increase in right ventricular fractional area change (RVFAC).

Known Treatments for PcPH

There is no known cure for PcPH (e.g., WHO Group 2 and/or Group 5 PH); current methods of treatment focus on prolonging patient lifespan and enhancing patient quality of life. This is usually associated with good exercise capacity, good right ventricle function, and a low mortality risk (e.g., bringing the patient to and/or keeping the patient in WHO Functional Class I or Functional Class II). Current methods of treatment of PcPH may include administration of: vasodilators such as prostacyclin, epoprostenol, and sildenafil; endothelin receptor antagonists such as bosentan; calcium channel blockers such as amlodipine, diltiazem, and nifedipine; anticoagulants such as warfarin; and diuretics. Treatment of PcPH has also been carried out using oxygen therapy, atrial septostomy, pulmonary thromboendarterectomy, and lung and/or heart transplantation. Each of these methods, however, suffers from one or multiple drawbacks which may include lack of effectiveness, serious side effects, low patient compliance, and high cost. In certain aspects, the method relate to treating, preventing, or reducing the progression rate and/or severity of PcPH (e.g., treating, preventing, or reducing the progression rate and/or severity of one or more complications of PcPH in WHO Group 2 and/or Group 5 PH) comprising administering to a patient in need thereof an effective amount of an ActRII polypeptide (e.g., an amino acid sequence that is at least 90% identical to an amino acid sequence corresponding to residues 30-110 of SEQ ID NO: 1) in combination with one or more additional active agents and/or supportive therapies for treating PcPH (e.g., vasodilators such as prostacyclin, epoprostenol, and sildenafil; endothelin receptor antagonists such as bosentan; calcium channel blockers such as amlodipine, diltiazem, and nifedipine; anticoagulants such as warfarin; diuretics; oxygen therapy; atrial septostomy; pulmonary thromboendarterectomy: LVAD; implantable cardioverter-defibrillator (ICD); valve replacement; valve repair; and lung and/or heart transplantation); bardoxolone methyl or a derivative thereof; oleanolic acid or derivative thereof.

Measuring Hematologic Parameters in a Patient

In certain embodiments, the present disclosure provides methods for managing a patient that has been treated with, or is a candidate to be treated with, one or more one or more ActRII polypeptides of the disclosure (e.g., an amino acid sequence that is at least 90% identical to an amino acid sequence corresponding to residues 30-110 of SEQ ID NO: 1) by measuring one or more hematologic parameters in the patient. The hematologic parameters may be used to evaluate appropriate dosing for a patient who is a candidate to be treated with one or more ActRII polypeptides of the present disclosure, to monitor the hematologic parameters during treatment, to evaluate whether to adjust the dosage during treatment with one or more ActRII polypeptides of the disclosure, and/or to evaluate an appropriate maintenance dose of one or more ActRII polypeptides of the disclosure. If one or more of the hematologic parameters are outside the normal level, dosing with one or more ActRII polypeptides may be reduced, delayed or terminated.

Hematologic parameters that may be measured in accordance with the methods provided herein include, for example, red blood cell levels, blood pressure, iron stores, and other agents found in bodily fluids that correlate with increased red blood cell levels, using art recognized methods. In other embodiments, hematologic parameters such as white blood cell levels, platelet levels, and neutrophil levels may be measured using art recognized methods. Such parameters may be determined using a blood sample from a patient. Increases in red blood cell levels, hemoglobin levels, and/or hematocrit levels may cause increases in blood pressure. Decreases in white blood cell levels, platelet levels, and/or neutrophil levels may indicate a need to decrease, delay, or discontinue treatment of the administration of one or more ActRII polypeptides of the disclosure.

In one embodiment, if one or more hematologic parameters are outside the normal range or on the high side of normal in a patient who is a candidate to be treated with one or more ActRII polypeptides, then onset of administration of the one or more ActRII polypeptides of the disclosure may be delayed until the hematologic parameters have returned to a normal or acceptable level either naturally or via therapeutic intervention. For example, if a candidate patient is hypertensive or pre-hypertensive, then the patient may be treated with a blood pressure lowering agent in order to reduce the patient's blood pressure. Any blood pressure lowering agent appropriate for the individual patient's condition may be used including, for example, diuretics, adrenergic inhibitors (including alpha blockers and beta blockers), vasodilators, calcium channel blockers, angiotensin-converting enzyme (ACE) inhibitors, or angiotensin II receptor blockers. Blood pressure may alternatively be treated using a diet and exercise regimen. Similarly, if a candidate patient has iron stores that are lower than normal, or on the low side of normal, then the patient may be treated with an appropriate regimen of diet and/or iron supplements until the patient's iron stores have returned to a normal or acceptable level. For patients having higher than normal red blood cell levels and/or hemoglobin levels (e.g., hemoglobin levels >16.0 g/dL or hemoglobin levels >18.0 g/dL), then administration of the one or more ActRII polypeptides of the disclosure may be delayed or reduced until the levels have returned to a normal or acceptable level. In some embodiments, a normal or acceptable level of hemoglobin includes patients with hemoglobin levels between 8-15 g/dl. In some embodiments, a normal or acceptable level of hemoglobin includes patients with hemoglobin levels of <18 g/dl. In some embodiments, a normal or acceptable level of hemoglobin increase over time includes patients whose hemoglobin levels increase less than 2 g/dL over the first period of time in treatment. In some embodiments, the first period of time is 3 weeks. For patients having lower than normal white blood cell counts (e.g., leukopenia; white blood cell count $<3000/mm^3$ or $<3.0\times10^9/L$ (Grade 2)), then administration of the one or more ActRII polypeptides of the disclosure may be delayed or reduced until the levels have returned to a normal or acceptable level. For patients having lower than normal white blood cell counts (e.g., leukopenia; white blood cell count $<2000/mm^3$ or $<2.0\times10^9/L$ (Grade 3)), then administration of the one or more ActRII polypeptides of the disclosure may be delayed or reduced until the levels have returned to a normal or acceptable level. For patients having lower than normal platelet counts (e.g., thrombocytopenia; platelet count $<75,000/mm^3$ or $<75.0\times10^9/L$ (Grade 2)), then administration of the one or more ActRII polypeptides of the disclosure may be delayed or reduced until the levels have returned to a normal or acceptable level. For patients having lower than normal platelet counts (e.g., thrombocytopenia; platelet count $<50,000/mm^3$ or $<50.0\times10^9/L$ (Grade 3)), then administration of the one or more ActRII polypeptides of the disclosure may be delayed or reduced until the levels have returned to a normal or acceptable level. For patients having lower than normal neutrophil counts (e.g., neutropenia; neutrophil count $<1500/mm^3$ or $<1.5\times10^9/L$ (Grade 2)), then administration of the one or more ActRII polypeptides of the disclosure may be delayed or reduced until the levels have returned to a normal or acceptable level. For patients having lower than normal neutrophil counts (e.g., neutropenia; neutrophil count $<1000/mm^3$ or $<1.0\times10^9/L$ (Grade 3)), then administration of the one or more ActRII polypeptides of the disclosure may be delayed or reduced until the levels have returned to a normal or acceptable level.

In certain embodiments, if one or more hematologic parameters are outside the normal range or on the high side of normal in a patient who is a candidate to be treated with one or more ActRII polypeptides, then the onset of administration may not be delayed. However, the dosage amount or frequency of dosing of the one or more ActRII polypeptides of the disclosure may be set at an amount that would reduce the risk of an unacceptable increase in the hematologic parameters arising upon administration of the one or more ActRII polypeptides of the disclosure. Alternatively, a therapeutic regimen may be developed for the patient that combines one or more ActRII polypeptides with a therapeutic agent that addresses the undesirable level of the hematologic parameter. For example, if the patient has elevated blood pressure, then a therapeutic regimen may be designed involving administration of one or more ActRII polypeptides and a blood pressure lowering agent. For a patient having lower than desired iron stores, a therapeutic regimen may be developed involving one or more ActRII polypeptides of the disclosure and iron supplementation.

In one embodiment, baseline parameter(s) for one or more hematologic parameters may be established for a patient who is a candidate to be treated with one or more ActRII polypeptides of the disclosure and an appropriate dosing regimen established for that patient based on the baseline value(s). Alternatively, established baseline parameters based on a patient's medical history could be used to inform an appropriate ActRII polypeptide dosing regimen for a patient. For example, if a healthy patient has an established baseline blood pressure reading that is above the defined normal range it may not be necessary to bring the patient's blood pressure into the range that is considered normal for the general population prior to treatment with the one or more ActRII polypeptides of the disclosure. A patient's baseline values for one or more hematologic parameters prior to treatment with one or more ActRII polypeptides of the disclosure may also be used as the relevant comparative values for monitoring any changes to the hematologic parameters during treatment with the one or more ActRII polypeptides of the disclosure.

In certain embodiments, one or more hematologic parameters are measured in patients who are being treated with one or more ActRII polypeptides. The hematologic parameters may be used to monitor the patient during treatment and permit adjustment or termination of the dosing with the one or more ActRII polypeptides of the disclosure or additional dosing with another therapeutic agent. For example, if administration of one or more ActRII polypeptides results in an increase in blood pressure, red blood cell level, or hemoglobin level, or a reduction in iron stores, white blood cell count, platelet count, or absolute neutrophil count, then the dose of the one or more ActRII polypeptides of the disclosure may be reduced in amount or frequency in order to decrease the effects of the one or more ActRII polypeptides of the disclosure on the one or more hematologic parameters. If administration of one or more ActRII polypeptides results in a change in one or more hematologic parameters that is adverse to the patient, then the dosing of the one or more ActRII polypeptides of the disclosure may be terminated either temporarily, until the hematologic parameter(s) return to an acceptable level, or permanently. Similarly, if one or more hematologic parameters are not brought within an acceptable range after reducing the dose or frequency of administration of the one or more ActRII polypeptides of the disclosure, then the dosing may be terminated. As an alternative, or in addition to, reducing or terminating the dosing with the one or more ActRII polypeptides of the disclosure, the patient may be dosed with an additional therapeutic agent that addresses the undesirable level in the hematologic parameter(s), such as, for example, a blood pressure lowering agent or an iron supplement. For example, if a patient being treated with one or more ActRII polypeptides has elevated blood pressure, then dosing with the one or more ActRII polypeptides of the disclosure may continue at the same level and a blood-pressure-lowering agent is added to the treatment regimen, dosing with the one or more antagonist of the disclosure may be reduced (e.g., in amount and/or frequency) and a blood-pressure-lowering agent is added to the treatment regimen, or dosing with the one or more antagonist of the disclosure may be terminated and the patient may be treated with a blood-pressure-lowering agent.

Measuring Various Parameters Over Time

In certain embodiments, one or more of the measurements of pulmonary hypertension (e.g., PcPH) described herein can be measured over various periods of treatment time. In some embodiments, one or more of the measurements of pulmonary hypertension described herein is measured after the patient has received 4 weeks of treatment utilizing an ActRII polypeptide disclosed herein. In some embodiments, one or more of the measurements of pulmonary hypertension described herein is measured after the patient has received 8 weeks of treatment utilizing an ActRII polypeptide disclosed herein. In some embodiments, one or more of the measurements of pulmonary hypertension described herein is measured after the patient has received 12 weeks of treatment utilizing an ActRII polypeptide disclosed herein. In some embodiments, one or more of the measurements of pulmonary hypertension described herein is measured after the patient has received 16 weeks of treatment utilizing an ActRII polypeptide disclosed herein. In some embodiments, one or more of the measurements of pulmonary hypertension described herein is measured after the patient has received 20 weeks of treatment utilizing an ActRII polypeptide disclosed herein. In some embodiments, one or more of the measurements of pulmonary hypertension described herein is measured after the patient has received 22 weeks of treatment utilizing an ActRII polypeptide disclosed herein. In some embodiments, one or more of the measurements of pulmonary hypertension described herein is measured after the patient has received 24 weeks of treatment utilizing an ActRII polypeptide disclosed herein. In some embodiments, one or more of the measurements of pulmonary hypertension described herein is measured after the patient has received 26 weeks of treatment utilizing an ActRII polypeptide disclosed herein. In some embodiments, one or more of the measurements of pulmonary hypertension described herein is measured after the patient has received 28 weeks of treatment utilizing an ActRII polypeptide disclosed herein. In some embodiments, one or more of the measurements of pulmonary hypertension described herein is measured after the patient has received 48 weeks of treatment utilizing an ActRII polypeptide disclosed herein.

5. Pharmaceutical Compositions & Modes of Administration

In certain embodiments, the therapeutic methods of the disclosure include administering the composition systemically, or locally as an implant or device. When administered, the therapeutic composition for use in this disclosure is in a substantially pyrogen-free, or pyrogen-free, physiologically acceptable form. Therapeutically useful agents other than the ActRII polypeptides which may also optionally be included in the composition as described above, may be administered simultaneously or sequentially with the subject compounds in the methods disclosed herein.

Typically, protein therapeutic agents disclosed herein will be administered parentally, and particularly intravenously or subcutaneously. Pharmaceutical compositions suitable for parenteral administration may comprise one or more ActRII polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. The formulations can be presented in unit-dose or multi-dose sealed containers, such as ampules and vials, and can be stored in a freeze-dried (lyophilized) condition requiring only the addition of a sterile liquid excipient, for example, water, for injections, immediately prior to use. Extemporaneous injection solutions and suspensions can be prepared from sterile powders, granules, and tablets of the kind described herein.

The compositions and formulations may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Further, the composition may be encapsulated or injected in a form for delivery to a target tissue site. In certain embodiments, compositions of the present invention may include a matrix capable of delivering one or more therapeutic compounds (e.g., ActRII polypeptides) to a target tissue site, providing a structure for the developing tissue and optimally capable of being resorbed into the body. For example, the matrix may provide slow release of the ActRII polypeptide. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalcium phosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability.

In certain embodiments, methods of the invention can be administered for orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof, and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject compounds of the disclosure (e.g., ActRII polypeptides). The various factors include, but are not limited to, the patient's age, sex, and diet, the severity disease, time of administration, and other clinical factors. Optionally, the dosage may vary with the type of matrix used in the reconstitution and the types of compounds in the composition.

In some embodiments, a patient's hematologic parameters can be monitored by periodic assessments in order to determine if they have higher than normal red blood cell levels and/or hemoglobin levels (e.g., hemoglobin levels >16.0 g/dL or hemoglobin levels >18.0 g/dL). In some embodiments, patient's having higher than normal red blood cell levels and/or hemoglobin levels may receive a delayed or reduced dose until the levels have returned to a normal or acceptable level.

The probability of a patient having hemoglobin levels greater than 18 g/dL or increases in hemoglobin of greater than 2 g/dL may be higher during initial treatment with an ActRII polypeptide. In certain embodiments, a dosing regimen can be used to prevent, ameliorate, or decrease the adverse changes in hemoglobin levels. In some embodiments, ActRII polypeptides of the disclosure are administered using a dosing regimen. In some embodiments, the method comprises administering a dosing regimen of a therapeutically effective amount of an ActRII polypeptide as disclosed herein to a patient, comprising a first dose of between 0.1 mg/kg and 1.0 mg/kg of said polypeptide for a first period of time, and a second dose of between 0.1 mg/kg and 1.0 mg/kg of said polypeptide subsequently administered for a second period of time. In some embodiments, the method comprises administering a dosing regimen of therapeutically effective amount of an ActRII polypeptide as disclosed herein to a patient, comprising a first dose of between 0.1 mg/kg and 1.0 mg/kg of said polypeptide for a first period of time, a second dose of between 0.1 mg/kg and 1.0 mg/kg of said polypeptide administered for a second period of time, and a third dose of between 0.1 mg/kg and 1.0 mg/kg of said polypeptide subsequently administered for a third period of time. In some embodiments, the first dose of ActRII polypeptide is administered to a patient in an amount from about 0.2 mg/kg to about 0.4 mg/kg. In some embodiments, the first dose of ActRII polypeptide is administered to a patient at a dose of 0.3 mg/kg. In some embodiments, the second dose of ActRII polypeptide is administered to a patient in an amount from about 0.5 mg/kg to about 0.8 mg/kg. In some embodiments, the second dose of ActRII polypeptide is administered to a patient at a dose of 0.7 mg/kg. In some embodiments, the third dose of ActRII polypeptide is administered to a patient in an amount from about 0.2 mg/kg to about 0.4 mg/kg. In some embodiments, the third dose of ActRII polypeptide is administered to a patient at a dose of 0.3 mg/kg.

In some embodiments, the dosing regimen comprises administering a first dose of ActRII polypeptide to a patient in an amount of 0.3 mg/kg followed by administration of a second dose of ActRII polypeptide to the patient in an amount of 0.7 mg/kg. In some embodiments, the dosing regimen comprises administering a first dose of ActRII polypeptide to a patient in an amount of 0.3 mg/kg, administering a second dose of ActRII polypeptide to the patient in an amount of 0.7 mg/kg, and administering a third dose of ActRII polypeptide to the patient in an amount of 0.3 mg/kg. In some embodiments, the second dose exceeds the first dose. In some embodiments, the first dose exceeds the second dose. In some embodiments, the third dose exceeds the second dose. In some embodiments, the second dose exceeds the third dose. In some embodiments, the first period of time is at least 3 weeks. In some embodiments, the second period of time is at least 3 weeks. In some embodiments, the third period of time is at least 3 weeks. In some embodiments, the second period of time is at least 21 weeks. In some embodiments, the second period of time is at least 45 weeks. In some embodiments, the second period of time exceeds the first period of time. In some embodiments, the third period of time exceeds the first period of time. In some embodiments, the third period of time exceeds the second period of time.

In some embodiments, the change in dosing between the first dose and the second dose is determined by the attending physician considering various factors (e.g., hemoglobin levels). In some embodiments, the change in dosing between the second dose and the third dose is determined by the attending physician considering various factors (e.g., hemoglobin levels). In some embodiments, the various factors include, but are not limited to, the patient's change in hematologic parameters over a period of time. In some embodiments, a patient's hematologic parameters are monitored in order to determine if they have higher than normal red blood cell levels and/or hemoglobin levels (e.g., hemoglobin levels >16.0 g/dL or hemoglobin levels >18.0 g/dL). In some embodiments, a patient's hematologic parameters are monitored in order to determine if they have a higher than normal increase in hemoglobin levels over a period of time (e.g., hemoglobin level increase of >2 g/dL in less than 3 weeks). In some embodiments, the patient's dose of an ActRII polypeptide as disclosed herein will be decreased (e.g., decrease in dose from 0.7 mg/kg to 0.3 mg/kg) if one or more of the patient's hematologic parameters before or during treatment is abnormal. In some embodiments, the patient's dose of an ActRII polypeptide as disclosed herein will be maintained (e.g., maintained at 0.3 mg/kg or 0.7 mg/kg) if one or more of the patient's hematologic parameters before or during treatment is abnormal.

In some embodiments, the dosing regimen prevents, ameliorates, or decreases adverse effects of the ActRII polypeptide. In some embodiments, administration of an ActRII polypeptide in accordance with the dosage regimen as provided herein results in decreased adverse side effects. In some embodiments, administration of an ActRII polypeptide in accordance with the dosage regimen as provided herein decreases the probability of having hemoglobin levels greater than 18 g/dL during the first period of time. In some embodiments, administration of an ActRII polypeptide in accordance with the dosage regimen as provided herein decreases the probability of having hemoglobin levels greater than 18 g/dL in the first 3 weeks of treatment. In some embodiments, administration of an ActRII polypeptide in accordance with the dosage regimen as provided herein decreases the probability of increasing hemoglobin levels by greater than 2 g/dL during the first period of time. In some embodiments, administration of an ActRII polypeptide in accordance with the dosage regimen as provided herein decreases the probability of increasing hemoglobin levels by greater than 2 g/dL in the first 3 weeks of treatment.

In some embodiments, ActRII polypeptides of the disclosure are administered at a dosing range of 0.1 mg/kg to 2.0 mg/kg. In some embodiments, ActRII polypeptides of the disclosure are administered at 0.1 mg/kg. In some embodiments, ActRII polypeptides of the disclosure are administered at 0.2 mg/kg. In some embodiments, ActRII polypeptides of the disclosure are administered at 0.3 mg/kg. In some embodiments, ActRII polypeptides of the disclosure are administered at 0.4 mg/kg. In some embodiments, ActRII polypeptides of the disclosure are administered at 0.5 mg/kg. In some embodiments, ActRII polypeptides of the disclosure are administered at 0.6 mg/kg. In some embodiments, ActRII polypeptides of the disclosure are administered at 0.7 mg/kg. In some embodiments, ActRII polypeptides of the disclosure are administered at 0.8 mg/kg. In some embodiments, ActRII polypeptides of the disclosure are administered at 0.9 mg/kg. In some embodiments, ActRII polypeptides of the disclosure are administered at 1.0 mg/kg. In some embodiments, ActRII polypeptides of the disclosure are administered at 1.1 mg/kg. In some embodiments, ActRII polypeptides of the disclosure are administered at 1.2 mg/kg. In some embodiments, ActRII polypeptides of the disclosure are administered at 1.3 mg/kg. In some embodiments, ActRII polypeptides of the disclosure are administered at 1.4 mg/kg. In some embodiments, ActRII polypeptides of the disclosure are administered at 1.5 mg/kg. In some embodiments, ActRII polypeptides of the disclosure are administered at 1.6 mg/kg. In some embodiments, ActRII polypeptides of the disclosure are administered at 1.7 mg/kg. In some embodiments, ActRII polypeptides of the disclosure are administered at 1.8 mg/kg. In some embodiments, ActRII polypeptides of the disclosure are administered at 1.9 mg/kg. In some embodiments, ActRII polypeptides of the disclosure are administered at 2.0 mg/kg.

In certain embodiments, ActRII polypeptides of the disclosure are administered once a day. In certain embodiments, ActRII polypeptides of the disclosure are administered twice a day. In certain embodiments, ActRII polypeptides of the disclosure are administered once a week. In certain embodiments, ActRII polypeptides of the disclosure are administered twice a week. In certain embodiments, ActRII polypeptides of the disclosure are administered three times a week. In certain embodiments, ActRII polypeptides of the disclosure are administered every two weeks. In certain embodiments, ActRII polypeptides of the disclosure are administered every three weeks. In certain embodiments, ActRII polypeptides of the disclosure are administered every four weeks. In certain embodiments, ActRII polypeptides of the disclosure are administered every month.

In certain embodiments, the present invention also provides gene therapy for the in vivo production of ActRII polypeptides. Such therapy would achieve its therapeutic effect by introduction of the ActRII polypeptide polynucleotide sequences into cells or tissues having the disorders as listed above. Delivery of ActRII polypeptide polynucleotide sequences can be achieved using a recombinant expression vector such as a chimeric virus or a colloidal dispersion system. Preferred for therapeutic delivery of ActRII polypeptide polynucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the ActRII polypeptide. In a preferred embodiment, the vector is targeted to bone or cartilage.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for ActRII polypeptide polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

The disclosure provides formulations that may be varied to include acids and bases to adjust the pH; and buffering agents to keep the pH within a narrow range.

6. Kits

The present disclosure provides a kit comprising a lyophilized polypeptide and an injection device. In certain embodiments, the lyophilized polypeptide comprises an ActRII polypeptide (e.g., a polypeptide that is at least 70%, 75%, 80%, 85%, 86%, 87%, 88%, 89%, 90%, 91%, 92%, 93%, 94%, 95%, 96%, 97%, 98%, 99%, or 100% identical to amino acids 30-110 of SEQ ID NO: 1), or fragments, functional variants, or modified forms thereof. In certain embodiments, the lyophilized polypeptide binds to one or more ligands selected from the group consisting of activin A, activin B, and GDF11. In certain such embodiments, the lyophilized polypeptide further binds to one or more ligands selected from the group consisting of BMP10, GDF8, and BMP6. In certain embodiments, the lyophilized polypeptide binds to activin and/or GDF11.

In some embodiments, the lyophilized polypeptide comprises a polypeptide that comprises, consists essentially of, or consists of an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to a portion of a polypeptide beginning at a residue corresponding to any one of amino acids 21-30 (e.g., beginning at any one of amino acids 21, 22, 23, 24, 25, 26, 27, 28, 29, or 30) of SEQ ID NO: 1 and ending at a position corresponding to any one amino acids 110-135 (e.g., ending at any one of amino acids 110, 111, 112, 113, 114, 115, 116, 117, 118, 119, 120, 121, 122, 123, 124, 125, 126, 127, 128, 129, 130, 131, 132, 133, 134, or 135) of SEQ ID NO: 1. In certain such embodiments, the polypeptide comprises an amino acid sequence that is least 90%, 95%, or 99% identical to an amino acid sequence corresponding to residues 30-110 of SEQ ID NO: 1, wherein the polypeptide binds to activin and/or GDF11. In certain embodiments, the polypeptide comprises the amino acid sequence corresponding to residues 30-110 of SEQ ID NO: 1. In other embodiments, the polypeptide consists of the amino acid sequence corresponding to residues 30-110 of SEQ ID NO: 1. In certain embodiments, the polypeptide is a polypeptide comprising an amino acid sequence that is at least 90%, 95%, or 99% identical to the amino acid sequence corresponding to residues 21-135 of SEQ ID NO: 1. In certain embodiments, the polypeptide comprises the amino acid sequence corresponding to residues 21-135 of SEQ ID NO: 1. In other embodiments, the polypeptide consists of the amino acid sequence corresponding to residues 21-135 of SEQ ID NO: 1.

In some embodiments, the lyophilized polypeptide comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of SEQ ID NO: 2. In certain embodiments, the polypeptide consists essentially of the amino acid sequence of SEQ ID NO: 2. In other embodiments, the polypeptide consists of the amino acid sequence of SEQ ID NO: 2.

In some embodiments, the lyophilized polypeptide comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of SEQ ID NO: 3. In certain embodiments, the polypeptide consists of the amino acid sequence of SEQ ID NO: 3. In other embodiments, the polypeptide consists of the amino acid sequence of SEQ ID NO: 3.

In certain embodiments of the foregoing, the lyophilized polypeptide comprises a fusion protein further comprising an Fc domain of an immunoglobulin. In certain such embodiments, the Fc domain of the immunoglobulin is an Fc domain of an IgG1 immunoglobulin. In other embodiments, the fusion protein further comprises a linker domain positioned between the polypeptide domain and the Fc domain of the immunoglobulin. In certain embodiments, the linker domain is selected from the group consisting of: TGGG (SEQ ID NO: 20), TGGGG (SEQ ID NO: 18), SGGGG (SEQ ID NO: 19), GGGGS (SEQ ID NO: 22), GGG, GGGG (SEQ ID NO: 17), and SGGG (SEQ ID NO: 21). In certain embodiments, the linker domain comprises TGGG (SEQ ID NO: 20).

In certain embodiments, the lyophilized polypeptide comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of SEQ ID NO: 23. In certain embodiments, the polypeptide consists of the amino acid sequence of SEQ ID NO: 23. In other embodiments, the polypeptide consists of the amino acid sequence of SEQ ID NO: 23.

In certain embodiments, the lyophilized polypeptide comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of SEQ ID NO: 30. In certain embodiments, the polypeptide consists of the amino acid sequence of SEQ ID NO: 30. In other embodiments, the polypeptide consists of the amino acid sequence of SEQ ID NO: 30.

In certain embodiments, the lyophilized polypeptide comprises an amino acid sequence that is at least 70%, 75%, 80%, 85%, 86%, 87%, 88%, 89%, 90%, 91%, 92%, 93%, 94%, 95%, 96%, 97%, 98%, 99%, or 100% identical to the amino acid sequence of SEQ ID NO: 41. In certain embodiments, the polypeptide consists of the amino acid sequence of SEQ ID NO: 41.

In other embodiments, the polypeptide consists of the amino acid sequence of SEQ ID NO: 41.

In certain embodiments, the lyophilized polypeptide is part of a homodimer protein complex.

In certain embodiments, the polypeptide is glycosylated.

The present disclosure provides a kit comprising a sterile powder comprising a lyophilized polypeptide as disclosed herein and an injection device. In some embodiments of the kits disclosed herein, the sterile powder comprising a lyophilized polypeptide is pre-filled in one or more containers, such as one or more vials [FIG. 21 (1)].

In certain embodiments, the pH range for the sterile powder comprising a lyophilized polypeptide is from 7 to 8.

In some embodiments, the sterile powder comprising a lyophilized polypeptide further comprises a buffering agent. In some embodiments, the buffering agent may be added in an amount of at least 10 mM. In some embodiments, the buffering agent may be added in an amount in the range of between about 10 mM to about 200 mM. In some embodiments, the buffering agent comprises citric acid monohydrate and/or trisodium citrate dehydrate.

In some embodiments, the sterile powder comprising a lyophilized polypeptide further comprises a surfactant. In some embodiments, the surfactant comprises a polysorbate. In some embodiments, the surfactant comprises polysorbate 80.

In some embodiments, the sterile powder comprising a lyophilized polypeptide further comprises a lyoprotectant. In some embodiments, the lyoprotectant comprises a sugar, such as disaccharides (e.g, sucrose). In some embodiments, the lyoprotectant comprises sucrose, trehalose, mannitol, polyvinylpyrrolidone (PVP), dextrose, and/or glycine. In some embodiments, the lyoprotectant comprises sucrose. In some embodiments, the sterile powder comprises the lyoprotectant and lyophilized polypeptide in a weight ratio of at least 1:1 lyophilized polypeptide to lyoprotectant. In some embodiments, the sterile powder comprises the lyoprotectant and lyophilized polypeptide in a weight ratio of from 1:1 to 1:10 lyophilized polypeptide to lyoprotectant. In some embodiments, the sterile powder comprises the lyoprotectant and lyophilized polypeptide in a weight ratio of 1:1, 1:2, 1:3, 1:4, 1:5, 1:6, 1:7, 1:8, 1:9, or 1:10 lyophilized polypeptide to lyoprotectant. In some embodiments, the sterile powder comprises the lyoprotectant and lyophilized polypeptide in a weight ratio of 1:6 lyophilized polypeptide to lyoprotectant. In certain embodiments of the foregoing, the sterile powder comprises lyoprotectant in an amount sufficient to stabilize the lyophilized polypeptide.

Figure 21:
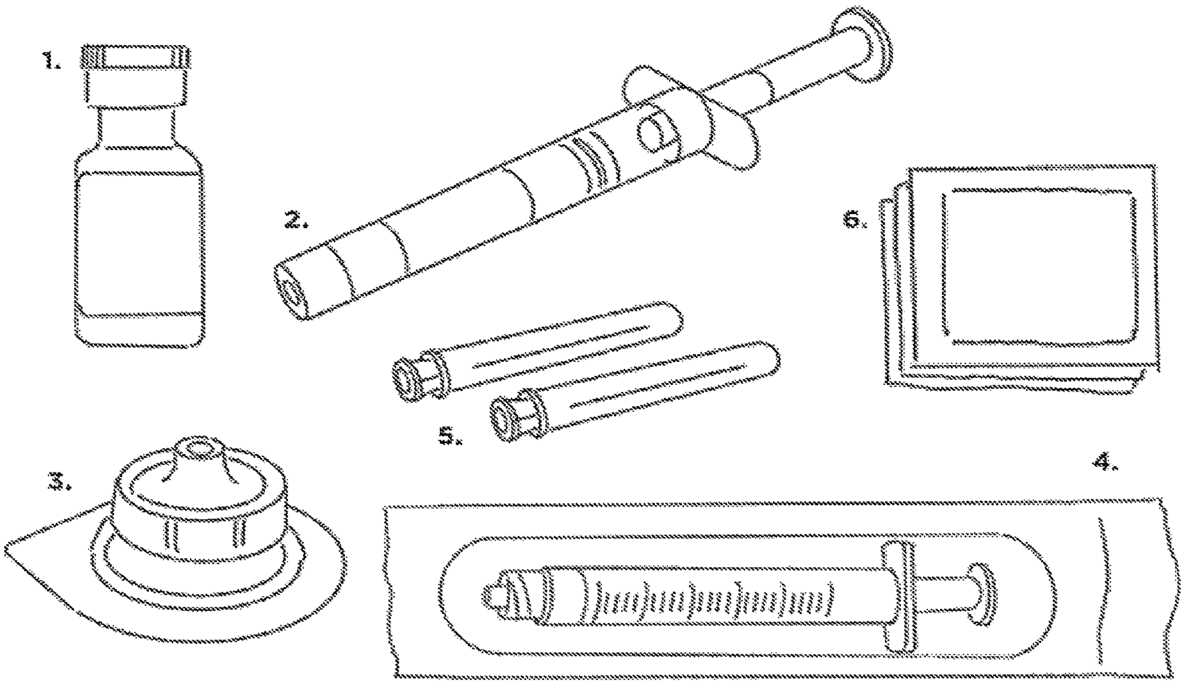
FIG. 21 shows components of a kit comprising a lyophilized polypeptide and an injection device. A vial (1) holds lyophilized polypeptide, reconstituted sterile injectable solution, or sterile injectable solution. A prefilled syringe (2) containing a reconstitution solution is used to reconstitute lyophilized polypeptide from (1) into a sterile injectable solution. A vial adapter (3) couples the vial (1) to the pre-filled syringe (2) via attachment to the vial at one end, and attachment to the pre-filled syringe at an opposite end. A syringe (4) and needle (5) are provided for administration of sterile injectable solution. Swab wipes (6) are provided for sterilization of individual kit components.
Figure 22:
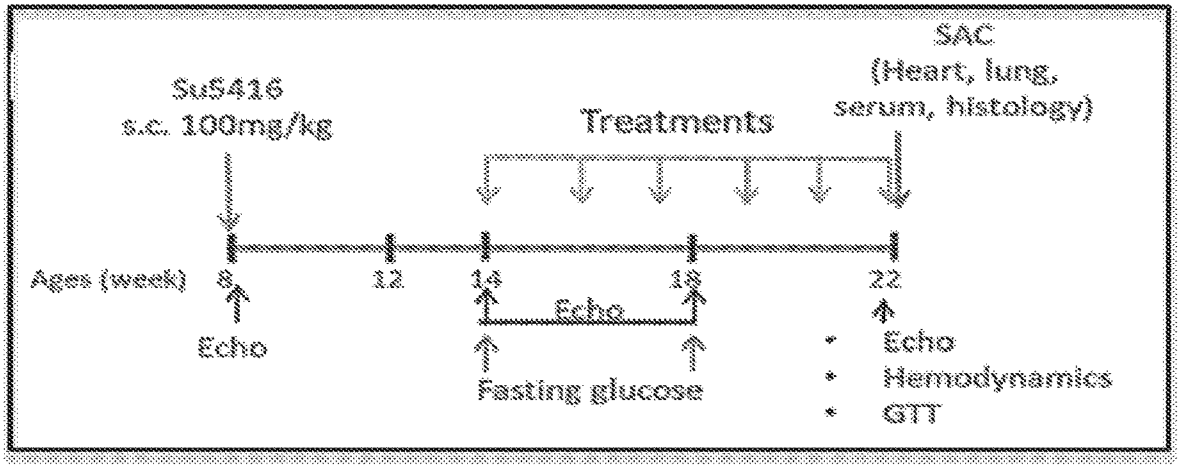
FIGS. 22-25 show that treatment with an ActRIIA-mFc fusion protein improves diastolic dysfunction in a rat model of left ventricular diastolic dysfunction (also referred to as HEpEF) group 2 (subgroup 2.2) pulmonary hypertension (PH). The experimental strategy used to test the preventative effects of ActRIIA-mFc in the rat model of HEpEF is shown in FIG. 22.

In certain embodiments of the kits disclosed herein, the injection device comprises a syringe [FIG. 21 (2)]. In certain such embodiments, the syringe is pre-filled with a reconstitution solution. In some embodiments, the reconstitution solution comprises a pharmaceutically acceptable carrier and/or excipient. In some embodiments, the pharmaceutically acceptable carrier comprises aqueous solutions such as water, physiologically buffered saline, or other solvents or vehicles such as glycols, glycerol, oils or injectable organic esters. In some embodiments, the pharmaceutically acceptable excipient comprises a pharmaceutically acceptable excipient selected from calcium phosphates, calcium carbonates, calcium sulfates, halites, metallic oxides, sugars, sugar alcohols, starch, glycols, povidones, mineral hydrocarbons, acrylic polymers, fatty alcohols, mineral stearates, glycerin, and/or lipids. In certain embodiments, the reconstitution solution comprises pharmaceutically acceptable sterile isotonic aqueous or nonaqueous solutions, dispersions, suspensions or emulsions. In certain such embodiments, the reconstitution solution comprises antioxidants, buffers, bacteriostats, and/or solutes which render the formulation isotonic with the blood of the intended recipient. In other embodiments, the reconstitution solution comprises suspending or thickening agents.

In certain embodiments of the kits disclosed herein, the kit further comprises a vial adapter [FIG. 21 (3)]. In some embodiments, the vial pre-filled with sterile powder comprising a lyophilized polypeptide attaches to one end of the vial adapter. In some embodiments, the syringe pre-filled with a reconstitution solution as disclosed herein attaches to an end of the vial adapter. In some embodiments, the syringe pre-filled with a reconstitution solution as disclosed herein and the vial pre-filled with sterile powder comprising a lyophilized polypeptide are attached to opposite ends of the vial adapter. In some embodiments, the reconstitution solution is transferred from the pre-filled syringe to the vial. In some embodiments, transfer of the reconstitution solution to the vial pre-filled with sterile powder comprising a lyophilized polypeptide reconstitutes the lyophilized polypeptide into a sterile injectable solution. In some embodiments, the lyophilized polypeptide is reconstituted into a sterile injectable solution. In some embodiments, the lyophilized polypeptide is reconstituted into a sterile injectable solution prior to use.

In other embodiments of the kits disclosed herein, the kit further comprises a pump apparatus. In certain embodiments, the pump apparatus comprises an electromechanical pumping assembly. In certain embodiments, the pump apparatus comprises a reservoir for holding a sterile injectable solution. In certain embodiments, the reservoir holds 1 mL of sterile injectable solution. In certain embodiments, the pump apparatus comprises one or more vials or cartridges comprising a sterile injectable solution. In certain embodiments, the vials or cartridges are prefilled with sterile injectable solution. In certain embodiments, the vials or cartridges comprise sterile injectable solution reconstituted from a lyophilized polypeptide. In certain embodiments, the reservoir is coupled to the vial or cartridge. In certain embodiments, the vial or cartridge holds 1-20 mL of sterile injectable solution. In certain embodiments, the electromechanical pumping assembly comprises a pump chamber. In certain embodiments, the electromechanical pumping assembly is coupled to the reservoir. In certain embodiments, the sterile injectable solution is received from the reservoir into the pump chamber. In some embodiments, the electromechanical pumping assembly comprises a plunger that is disposed such that sterile injectable solution in the pump chamber is in direct contact with the plunger. In certain embodiments, a sterile injectable solution is received from the reservoir into the pump chamber during a first pumping phase, and is delivered from the pump chamber to a subject during a second pumping phase. In certain embodiments, the electromechanical pumping assembly comprises control circuitry. In certain embodiments, control circuitry drives the plunger to (a) draw the sterile injectable solution into the pump chamber during the first pumping phase and (b) deliver the sterile injectable solution from the pump chamber in a plurality of discrete motions of the plunger during the second pumping phase, thereby delivering the therapeutic substance to the subject in a plurality of controlled and discrete dosages throughout the second pumping phase. In certain embodiments, a cycle of alternating the first and second pumping phases may be repeated until a desired dose is administered. In certain embodiments, the pump apparatus is coupled to a wearable patch. In certain embodiments, the pump apparatus is a wearable pump apparatus. In some embodiments, the pump apparatus administers a dose every 3 weeks. In some embodiments, the pump apparatus administers the dose via subcutaneous injection The present disclosure provides a kit used for reconstituting a lyophilized polypeptide into a sterile injectable solution. In certain embodiments, the resulting sterile injectable solution is useful in the methods disclosed herein.

In certain embodiments of the kits disclosed herein, the kit further comprises an injectable device for use in administering the sterile injectable solution parenterally [FIG. 21 (1, 2, 3, 4, and 5)]. In some embodiments, the sterile injectable solution is administered via subcutaneous injection. In some embodiments, the sterile injectable solution is administered via intradermal injection. In some embodiments, the sterile injectable solution is administered via intramuscular injection. In some embodiments, the sterile injectable solution is administered via intravenous injection. In some embodiments, the sterile injectable solution is self-administered. In some embodiments, the sterile injectable solution comprises a therapeutically effective dose. In some embodiments, the therapeutically effective dose comprises a weight based dose. In some embodiments, the weight based dose is 0.3 mg/kg. In some embodiments, the weight based dose is 0.7 mg/kg.

In some embodiments of the kits disclosed herein, the kit further comprises one or more vials or cartridges containing the lyophilized polypeptide. In some embodiments, the kit comprises at least two vials or cartridges containing the lyophilized polypeptide. In some embodiments, the kit comprises at least three vials or cartridges containing the lyophilized polypeptide. In some embodiments, the two vials can contain the same or different amounts of the lyophilized polypeptide. In some embodiments, the vials or cartridges comprise a vial or cartridge containing between 25 mg to 60 mg of lyophilized polypeptide. In some embodiments, at least one of the vials or cartridges comprise a vial or cartridge containing 60 mg of lyophilized polypeptide. In some embodiments, at least one of the vials or cartridges comprise a vial or cartridge containing 45 mg of lyophilized polypeptide. In some embodiments, at least one of the vials or cartridges comprise a vial or cartridge containing 30 mg of lyophilized polypeptide. In some embodiments, at least one of the vials or cartridges comprise a vial or cartridge containing 25 mg of lyophilized polypeptide. In some embodiments, a first vial or cartridge contains 45 mg of lyophilized polypeptide and a second vial or cartridge contains 60 mg of lyophilized polypeptide. In some embodiments, a first vial or cartridge contains 30 mg of lyophilized polypeptide and a second vial or cartridge contains 60 mg of lyophilized polypeptide. In some embodiments, a first vial or cartridge contains 30 mg of lyophilized polypeptide, a second vial or cartridge contains 45 mg of lyophilized polypeptide, and a third vial or cartridge contains 60 mg of lyophilized polypeptide. In some embodiments, a first vial or cartridge contains 25 mg of lyophilized polypeptide, a second vial or cartridge contains 45 mg of lyophilized polypeptide, and a third vial or cartridge contains 60 mg of lyophilized polypeptide. In some embodiments, the one or more vials or cartridges are refrigerated at 2-8° C.

7. Sequences

```
Human ActRIIB precursor protein sequence
                                        (SEQ ID NO: 39)
MTAPWVALALLWGSLCAGSGRGEAETRECIYYNANWELERTNQSGLERCE

GEQDKRLHCYASWRNSSGTIELVKKGCWLDDFNCYDRQECVATEENPQVY

FCCCEGNFCNERFTHLPEAGGPEVTYEPPPTAPTLLTVLAYSLLPIGGLS

LIVLLAFWMYRHRKPPYGHVDIHEDPGPPPPSPLVGLKPLQLLEIKARGR

FGCVWKAQLMNDFVAVKIFPLQDKQSWQSEREIFSTPGMKHENLLQFIAA

EKRGSNLEVELWLITAFHDKGSLTDYLKGNIITWNELCHVAETMSRGLSY

LHEDVPWCRGEGHKPSIAHRDFKSKNVLLKSDLTAVLADFGLAVRFEPGK

PPGDTHGQVGTRRYMAPEVLEGAINFQRDAFLRIDMYAMGLVLWELVSRC
```

-continued

```
KAADGPVDEYMLPFEEEIGQHPSLEELQEVVVHKKMRPTIKDHWLKHPGL

AQLCVTIEECWDHDAEARLSAGCVEERVSLIRRSVNGTTSDCLVSLVTSV

TNVDLPPKESSI

Processed (mature) extracellular ActRIIB poly-
peptide sequence
                                        (SEQ ID NO: 31)
GRGEAETRECIYYNANWELERTNQSGLERCEGEQDKRLHCYASWRNSSGT

IELVKKGCWLDDFNCYDRQECVATEENPQVYFCCCEGNFCNERFTHLPEA

GGPEVTYEPPPTAPT

Processed (mature) extracellular ActRIIB poly-
peptide sequence with the "tail" deleted (a Δ15
sequence)
                                        (SEQ ID NO: 40)
GRGEAETRECIYYNANWELERTNQSGLERCEGEQDKRLHCYASWRNSSGT

IELVKKGCWLDDFNCYDRQECVATEENPQVYFCCCEGNFCNERFTHLPEA
```

8. Exemplification

The disclosure above will be more readily understood by reference to the following examples, which are included merely for purposes of illustration of certain embodiments of the present invention, and are not intended to be limiting.

Example 1: ActRIIA-Fc Fusion Proteins

A soluble ActRII fusion protein was constructed that has the extracellular domain of human ActRIIA fused to a human or mouse Fc domain with a minimal linker in between. The constructs are referred to as ActRIIA-hFc and ActRIIA-mFc, respectively.

```
ActRIIA-hFc is shown below as purified from CHO
cell lines (SEQ ID NO: 23):
ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

EVTQPTSNPVTPKPPTGGGTHTCPPCPAPELLGGPSVFLFPPKPKDTLMI

SRTPEVTCVVVDVSHEDPEVKFNWYVDGVEVHNAKTKPREEQYNSTYRVV

SVLTVLHQDWLNGKEYKCKVSNKALPVPIEKTISKAKGQPREPQVYTLPP

SREEMTKNQVSLTCLVKGFYPSDIAVEWESNGQPENNYKTTPPVLDSDGS

FFLYSKLTVDKSRWQQGNVFSCSVMHEALHNHYTQKSLSLSPGK

An additional ActRIIA-hFc lacking the C-terminal
lysine is shown below as purified from CHO cell
lines (SEQ ID NO: 41):
ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

EVTQPTSNPVTPKPPTGGGTHTCPPCPAPELLGGPSVFLFPPKPKDTLMI

SRTPEVTCVVVDVSHEDPEVKFNWYVDGVEVHNAKTKPREEQYNSTYRVV

SVLTVLHQDWLNGKEYKCKVSNKALPVPIEKTISKAKGQPREPQVYTLPP

SREEMTKNQVSLTCLVKGFYPSDIAVEWESNGQPENNYKTTPPVLDSDGS

FFLYSKLTVDKSRWQQGNVFSCSVMHEALHNHYTQKSLSLSPG
```

The ActRIIA-hFc and ActRIIA-mFc proteins were expressed in CHO cell lines. Three different leader sequences were considered:

```
(i) Honey bee mellitin (HBML):
                                   (SEQ ID NO: 24)
MKFLVNVALVFMVVYISYIYA

(ii) Tissue plasminogen activator (TPA):
                                   (SEQ ID NO: 25)
MDAMKRGLCCVLLLCGAVFVSP

(iii) Native:
                                   (SEQ ID NO: 26)
MGAAAKLAFAVFLISCSSGA.
```

The selected form employs the TPA leader and has the following unprocessed amino acid sequence:

```
                                                  (SEQ ID NO: 27)
MDAMKRGLCCVLLLCGAVFVSPGAAILGRSETQECLFFNANWEKDRTNQ

TGVEPCYGDKDKRRHCFATWKNISGSIEIVKQGCWLDDINCYDRTDCVE

KKDSPEVYFCCCEGNMCNEKFSYFPEMEVTQPTSNPVTPKPPTGGGTHT

CPPCPAPELLGGPSVFLFPPKPKDTLMISRTPEVTCVVVDVSHEDPEVK

FNWYVDGVEVHNAKTKPREEQYNSTYRVVSVLTVLHQDWLNGKEYKCKV

SNKALPVPIEKTISKAKGQPREPQVYTLPPSREEMTKNQVSLTCLVKGF

YPSDIAVEWESNGQPENNYKTTPPVLDSDGSFFLYSKLTVDKSRWQQGN

VFSCSVMHEALHNHYTQKSLSLSPGK
```

This polypeptide is encoded by the following nucleic acid sequence:

```
                                                  (SEQ ID NO: 28)
ATGGATGCAATGAAGAGAGGGCTCTGCTGTGTGCTGCTGCTGTGTGGAG

CAGTCTTCGTTTCGCCCGGCGCCGCTATACTTGGTAGATCAGAAACTCA

GGAGTGTCTTTTTTTAATGCTAATTGGGAAAAAGACAGAACCAATCAAA

CTGGTGTTGAACCGTGTTATGGTGACAAAGATAAACGGCGGCATTGTTT

TGCTACCTGGAAGAATATTTCTGGTTCCATTGAATAGTGAAACAAGGTT

GTTGGCTGGATGATATCAACTGCTATGACAGGACTGATTGTGTAGAAAA

AAAAGACAGCCCTGAAGTATATTTCTGTTGCTGTGAGGGCAATATGTGT

AATGAAAAGTTTTCTTATTTTCCGGAGATGGAAGTCACACAGCCCACTT

CAAATCCAGTTACACCTAAGCCACCCACCGGTGGTGGAACTCACACATG

CCCACCGTGCCCAGCACCTGAACTCCTGGGGGGACCGTCAGTCTTCCTC

TTCCCCCCAAAACCCAAGGACACCCTCATGATCTCCCGGACCCCTGAGG

TCACATGCGTGGTGGTGGACGTGAGCCACGAAGACCCTGAGGTCAAGTT

CAACTGGTACGTGGACGGCGTGGAGGTGCATAATGCCAAGACAAAGCCG

CGGGAGGAGCAGTACAACAGCACGTACCGTGTGGTCAGCGTCCTCACCG

TCCTGCACCAGGACTGGCTGAATGGCAAGGAGTACAAGTGCAAGGTCTC

CAACAAAGCCCTCCCAGTCCCCATCGAGAAAACCATCTCCAAAGCCAAA

GGGCAGCCCCGAGAACCACAGGTGTACACCCTGCCCCCATCCCGGGAGG

AGATGACCAAGAACCAGGTCAGCCTGACCTGCCTGGTCAAAGGCTTCTA

TCCCAGCGACATCGCCGTGGAGTGGGAGAGCAATGGGCAGCCGGAGAAC
```

-continued

```
AACTACAAGACCACGCCTCCCGTGCTGGACTCCGACGGCTCCTTCTTCC

TCTATAGCAAGCTCACCGTGGACAAGAGCAGGTGGCAGCAGGGGAACGT

CTTCTCATGCTCCGTGATGCATGAGGCTCTGCACAACCACTACACGCAG

AAGAGCCTCTCCCTGTCTCCGGGTAAATGAGAATTC
```

Both ActRIIA-hFc and ActRIIA-mFc were remarkably amenable to recombinant expression. As shown in FIG. 4, the protein was purified as a single, well-defined peak of protein. N-terminal sequencing revealed a single sequence of -ILGRSETQE (SEQ ID NO: 29). Purification could be achieved by a series of column chromatography steps, including, for example, three or more of the following, in any order: protein A chromatography, Q sepharose chromatography, phenylsepharose chromatography, size exclusion chromatography, and cation exchange chromatography. The purification could be completed with viral filtration and buffer exchange. The ActRIIA-hFc protein was purified to a purity of >98% as determined by size exclusion chromatography and >95% as determined by SDS PAGE.

ActRIIA-hFc and ActRIIA-mFc showed a high affinity for ligands. GDF11 or activin A were immobilized on a Biacore™ CM5 chip using standard amine-coupling procedure. ActRIIA-hFc and ActRIIA-mFc proteins were loaded onto the system, and binding was measured. ActRIIA-hFc bound to activin with a dissociation constant ($K_D$) of $5\times10^{-12}$ and bound to GDF11 with a $K_D$ of $9.96\times10^{-9}$. See FIG. 5. Using a similar binding assay, ActRIIA-hFc was determined to have high to moderate affinity for other TGF-beta superfamily ligands including, for example, activin B, GDF8, BMP6, and BMP10. ActRIIA-mFc behaved similarly.

The ActRIIA-hFc was very stable in pharmacokinetic studies. Rats were dosed with 1 mg/kg, 3 mg/kg, or 10 mg/kg of ActRIIA-hFc protein, and plasma levels of the protein were measured at 24, 48, 72, 144 and 168 hours. In a separate study, rats were dosed at 1 mg/kg, 10 mg/kg, or 30 mg/kg. In rats, ActRIIA-hFc had an 11-14 day serum half-life, and circulating levels of the drug were quite high after two weeks (11 g/ml, 110 g/ml, or 304 g/ml for initial administrations of 1 mg/kg, 10 mg/kg, or 30 mg/kg, respectively.) In cynomolgus monkeys, the plasma half-life was substantially greater than 14 days, and circulating levels of the drug were 25 g/ml, 304 g/ml, or 1440 g/ml for initial administrations of 1 mg/kg, 10 mg/kg, or 30 mg/kg, respectively.

Example 2: Characterization of an ActRIIA-hFc Protein

ActRIIA-hFc fusion protein was expressed in stably transfected CHO-DUKX B11 cells from a pAID4 vector (SV40 or/enhancer, CMV promoter), using a tissue plasminogen leader sequence of SEQ ID NO: 25. The protein, purified as described above in Example 1, had a sequence of SEQ ID NO: 23. The Fc portion is a human IgG1 Fc sequence, as shown in SEQ ID NO: 23. Protein analysis reveals that the ActRIIA-hFc fusion protein is formed as a homodimer with disulfide bonding.

The CHO-cell-expressed material has a higher affinity for activin B ligand than that reported for an ActRIIA-hFc fusion protein expressed in human 293 cells [see, del Re et al. (2004) J Biol Chem. 279(51):53126-53135]. Additionally, the use of the TPA leader sequence provided greater production than other leader sequences and, unlike ActRIIA-Fc expressed with a native leader, provided a highly pure N-terminal sequence. Use of the native leader sequence resulted in two major species of ActRIIA-Fc, each having a different N-terminal sequence.

Example 3: Alternative ActRIIA-Fc Proteins

A variety of ActRIIA variants that may be used according to the methods described herein are described in the International Patent Application published as WO2006/012627 (see e.g., pp. 55-58), incorporated herein by reference in its entirety. An alternative construct may have a deletion of the C-terminal tail (the final 15 amino acids of the extracellular domain of ActRIIA). The sequence for such a construct is presented below (Fc portion underlined) (SEQ ID NO: 30):

```
ILGRSETQECLFFNANWEKDRTNQTGVEPCYGDKDKRRHCFATWKNISG

SIEIVKQGCWLDDINCYDRTDCVEKKDSPEVYFCCCEGNMCNEKFSYFP

EMTGGGTHTCPPCPAPELLGGPSVFLFPPKPKDTLMISRTPEVTCVVVD

VSHEDPEVKFNWYVDGVEVHNAKTKPREEQYNSTYRVVSVLTVLHQDWL

NGKEYKCKVSNKALPVPIEKTISKAKGQPREPQVYTLPPSREEMTKNQV

SLTCLVKGFYPSDIAVEWESNGQPENNYKTTPPVLDSDGSFFLYSKLTV

DKSRWQQGNVFSCSVMHEALHNHYTQKSLSLSPGK
```

Example 4: Effects of an ActRIIA-mFc on Group 2 Pulmonary Hypertension in a Transverse Aortic Constriction (TAC) Induced PH Mouse Model The effects of an ActRIIA-mFc fusion protein (ActRIIA-mFc homodimer as described in Example 1) was examined in a mouse model of left ventricular systolic dysfunction (also referred to as HErEF) of pulmonary hypertension (PH). In this model, C57BL/6 mice underwent transverse aortic constriction (TAC) to induce left heart failure, and right heart and pulmonary remodeling. See, e.g., Xiong P Y, et al. Hypertension 2018, 71(1):34-55 and Chen Y, et al. Hypertension 2012, 59(6):1170-1178.

Twenty-six C57/B6 male mice (10 wks old) underwent TAC surgery and ten age-matched animals underwent a mock surgical procedure (Sham) at day 0. Two weeks after the surgery, TAC-PH mice were randomized into two groups. i) fourteen mice were injected subcutaneously with vehicle control (phosphate buffered saline (PBS)), twice weekly for 4 weeks starting from day 14 after surgery, "TAC-PH/PBS"; and a ii) twelve mice were injected subcutaneously with ActRIIA-mFc at a dose of 10 mg/kg twice weekly for 4 weeks starting from day 14 after TAC surgery, "TAC-PH/ActRII-mFc". At the end of the study, echocardiography and pressure-volume catheter were performed to measure left and right ventricular remodeling and functional changes before animals were euthanized for heart and lung collection. Hearts and lungs of each mouse were weighed, fixed in 10% formalin, embedded in paraffin, and sectioned for Masson's trichrome stain to assess fibrosis.

Prior to euthanasia, in vivo cardiac function was assessed by transthoracic echocardiography (Acuson P300, 18 MHz transducer; Siemens) in conscious mice. From left ventricle (LV) short axis view, M-mode echocardiogram was acquired to measure left ventricle end diastolic diameter (LVEDD), and left ventricle end systolic diameter (LVESD). Fractional shortening (FS) was calculated from the end-diastolic diameter (EDD) and end-systolic diameter (ESD) using the following equation: FS=100%×[(EDD−ESD)/EDD]. Early diastolic filling peak velocity (E), early diastolic mitral annular velocity (E'), and isovolumetric relaxation time (IVRT) were measured from the medial or septal wall at the mitral valve level from tissue Doppler image. LV diastolic function was assessed by measuring the E/E' ratio and IVRT. Three to five beats were averaged for each mouse measurement. Tricuspid annular plane systolic excursion (TAPSE), a parameter of global right ventricular function, was also measured.

On day 42, mice were anesthetized by an intraperitoneal injection of ketamine/xylazine (100/5 mg/kg) to evaluate left and right ventricular function by Millar pressure-volume conductance catheter. The respiration was supported by a small animal ventilator. Thoracotomy was made through 4-5 intercostal space, and the heart was exposed. A pressure-volume catheter (1.0-Fr, PVR-1035, Millar Instruments, Houston, TX, USA) was inserted into the left ventricle and right ventricle from the apex. Ventricular pressure and volume were calculated with LabChart 7 software. Stroke work, ejection fraction, maximum and minimum rate of pressure development (+dp/dtm, −dp/dtm) were derived.

Figure 10:
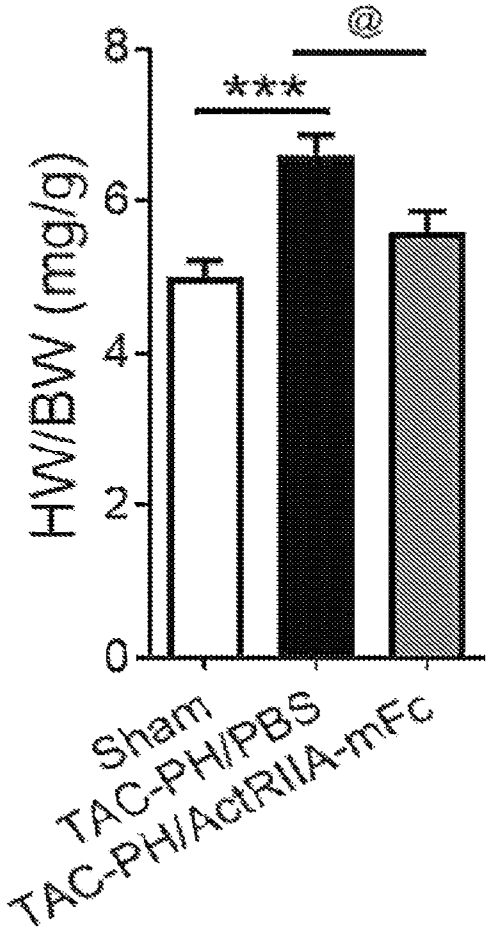
FIGS. 10-14 shows the therapeutic effect of ActRIIA-mFc in a TAC-PH model based on endpoints for left ventricle function. Twenty-six C57/B6 male mice (10 wks old) underwent TAC pulmonary hypertension surgery (TAC-PH) and ten age-matched animals underwent a mock surgical procedure (Sham) at day 0. Two weeks after the surgery, TAC-PH mice were randomized into two groups. i) fourteen mice were injected subcutaneously with vehicle control (phosphate buffered saline (PBS)), twice weekly for 4 weeks starting from day 14 after surgery, “TAC-PH/PBS”; and a ii) twelve mice were injected subcutaneously with ActRIIA-mFc at a dose of 10 mg/kg twice weekly for 4 weeks starting from day 14 after TAC surgery, “TAC-PH/ActRIIA-mFc”.
Figure 11:
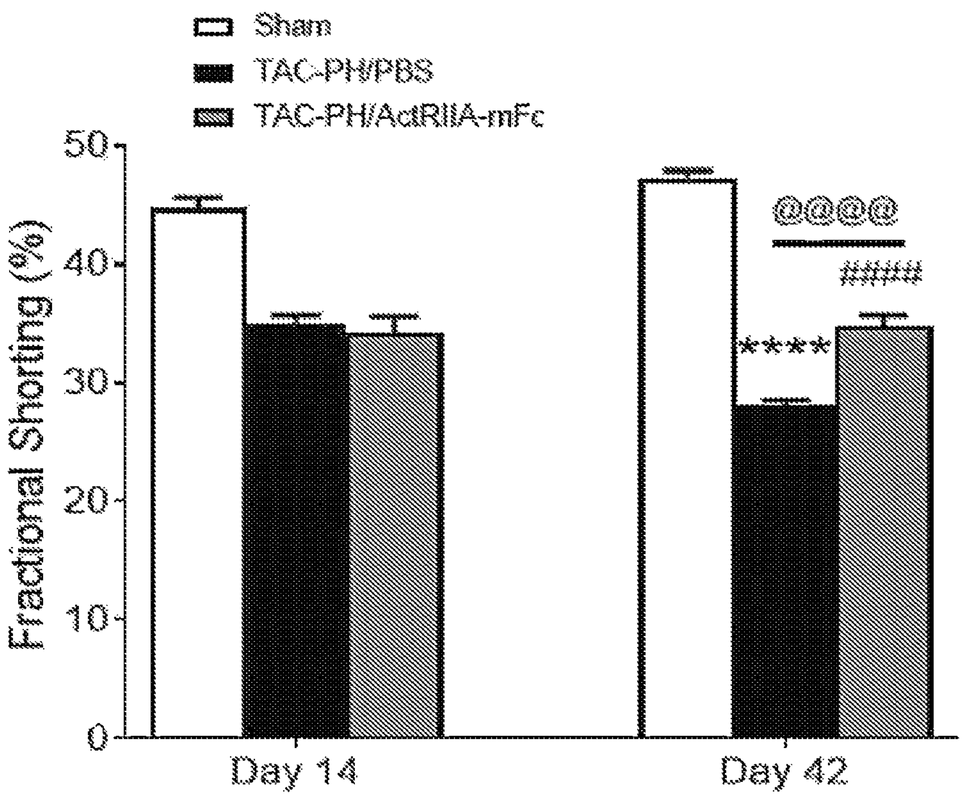
Figure 12:
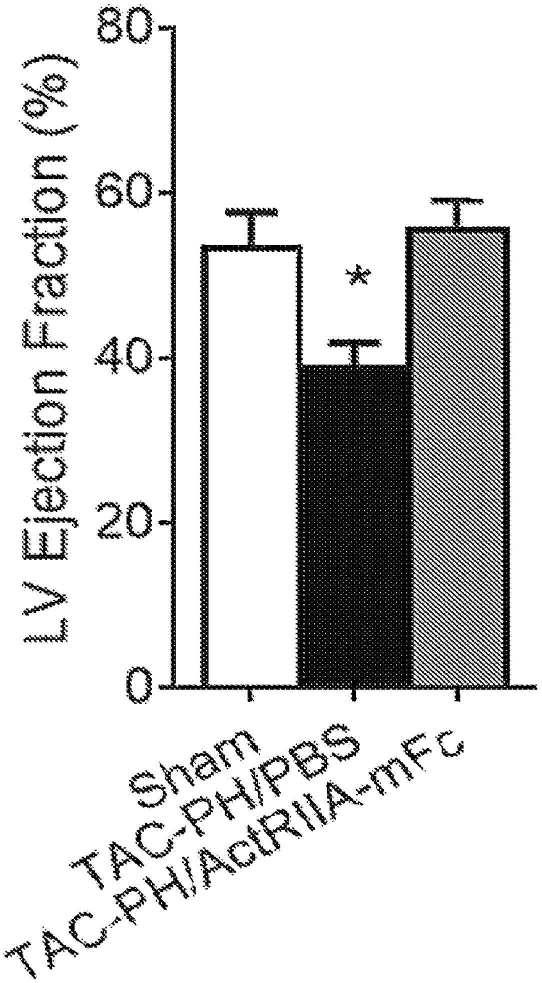
Figure 13:
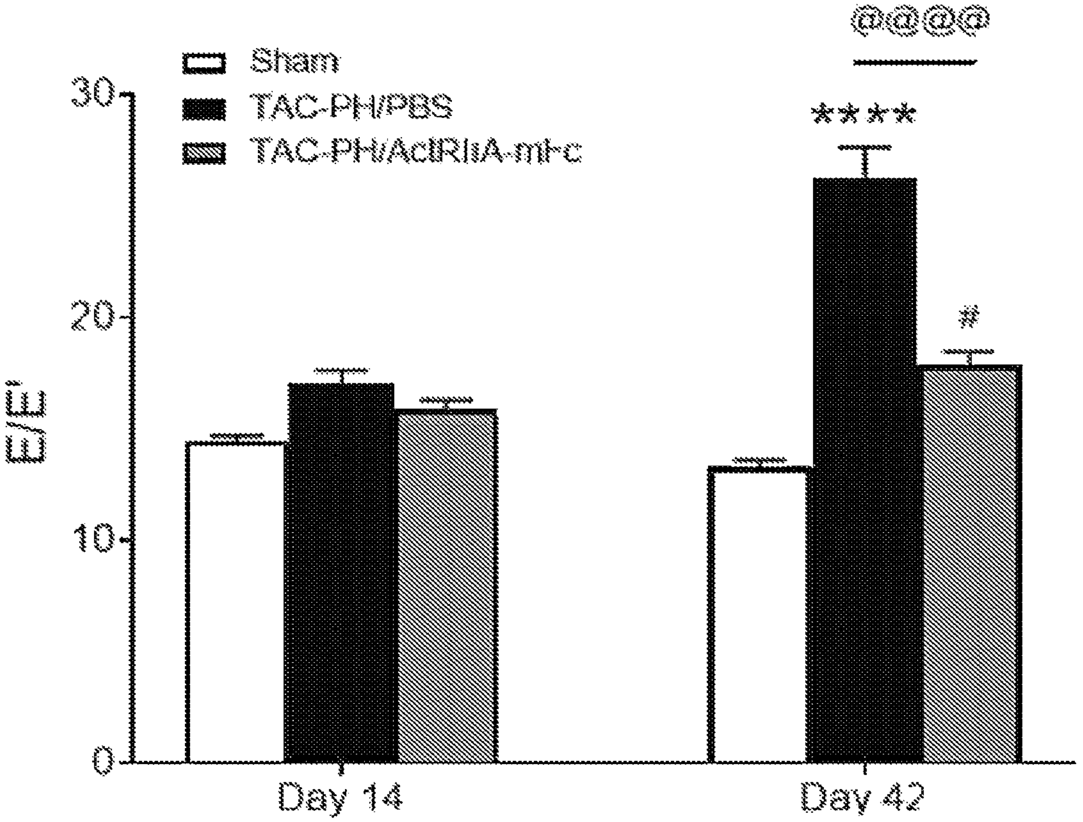

Compared to Sham control animals, TAC-PH mice in the PBS treatment group (TAC-PH/PBS) on day 42 were observed to have increased heart weight (HW/BW) (FIG. 10), reduced FS (FIG. 11), reduced LV ejection fraction (FIG. 12), increased E/E' ratio (FIG. 13), and increased IVRT (FIG. 14), indicating cardiac hypertrophy and left heart failure. TAC mice also increased right ventricle free wall thickness (RVFWT) (FIG. 15), decreased TAPSE (FIG. 16), increased right ventricle (RV) stroke work (FIG. 17), and increased minimum rate of pressure development in RV ($-dp/dT_{min}$) (FIG. 18) compared to Sham control mice, suggesting the RV remodeling and RV dysfunction. In addition, increased lung weight (LW/TL) (FIG. 19) and lung fibrosis (FIG. 20) were observed in TAC-PH/PBS mice, indicating lung remodeling caused by TAC-induced left heart failure.

Figure 14:
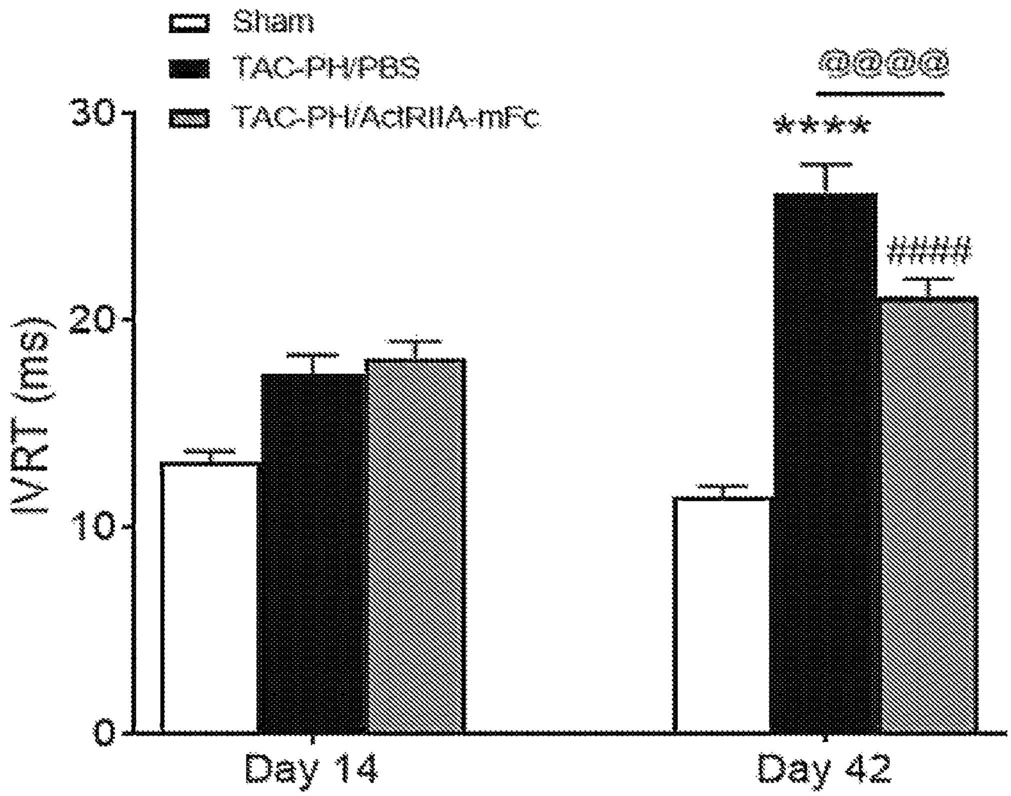
Figure 15:
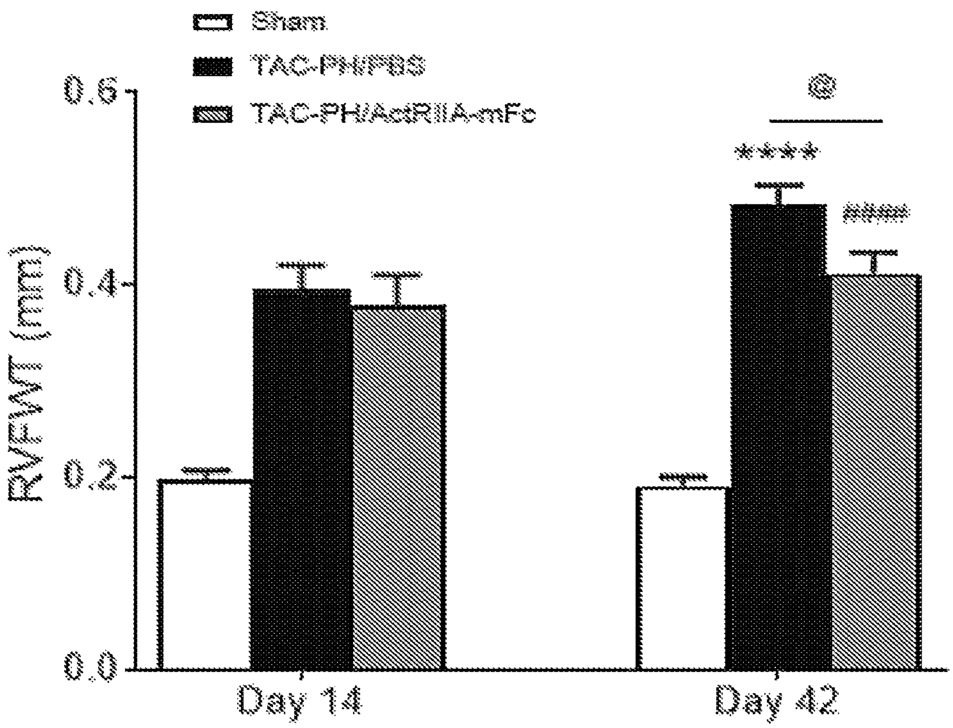
FIGS. 15-18 show the therapeutic effect of ActRIIA-mFc in a TAC-PH model based on endpoints for right ventricle function. Twenty-six C57/B6 male mice (10 wks old) underwent TAC pulmonary hypertension surgery (TAC-PH) and ten age-matched animals underwent a mock surgical procedure (Sham) at day 0. Two weeks after the surgery, TAC-PH mice were randomized into two groups. i) fourteen mice were injected subcutaneously with vehicle control (phosphate buffered saline (PBS)), twice weekly for 4 weeks starting from day 14 after surgery, “TAC-PH/PBS”; and a ii) twelve mice were injected subcutaneously with ActRIIA-mFc at a dose of 10 mg/kg twice weekly for 4 weeks starting from day 14 after TAC surgery, “TAC-PH/ActRIIA-mFc”.
Figure 16:
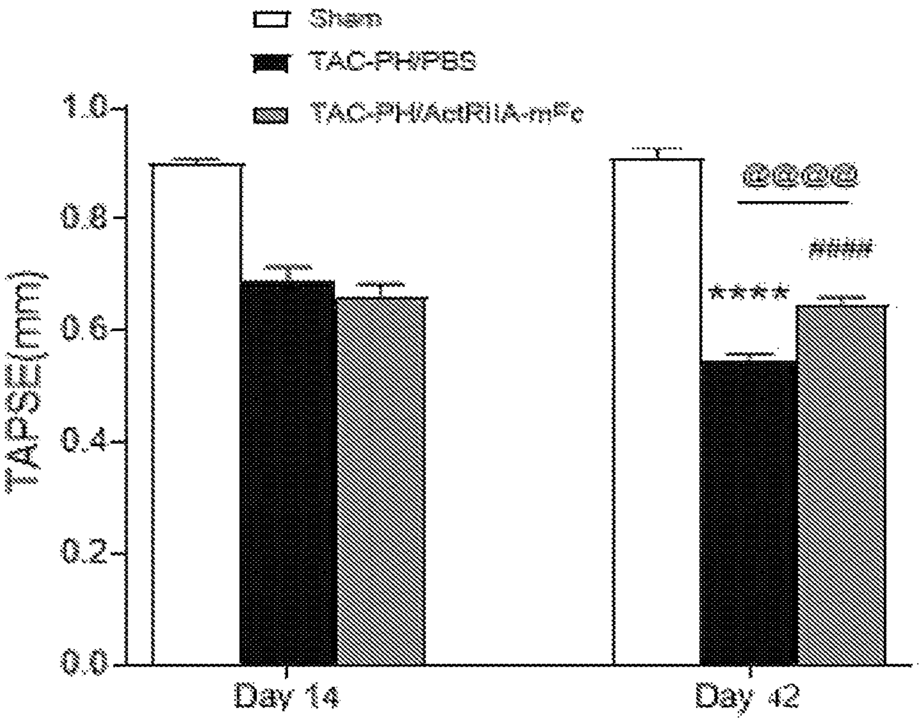
Figure 17:
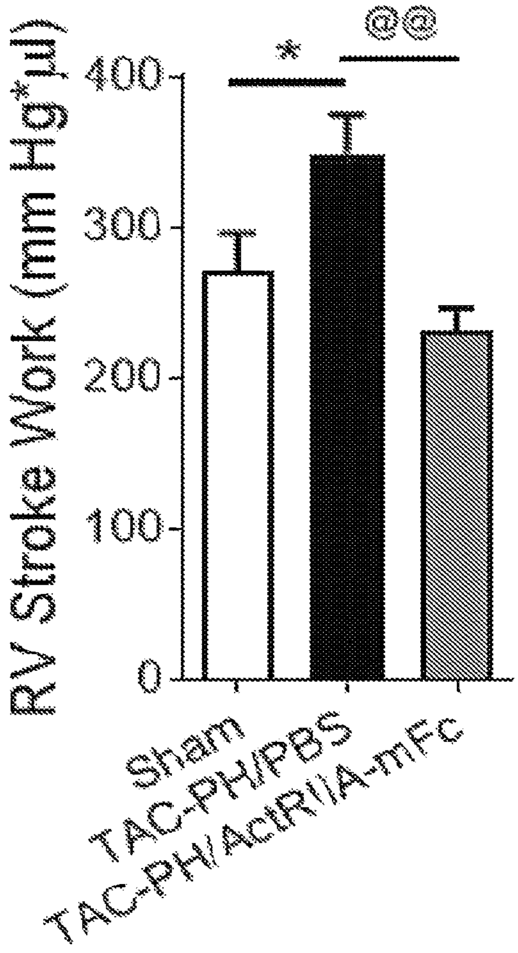
Figure 18:
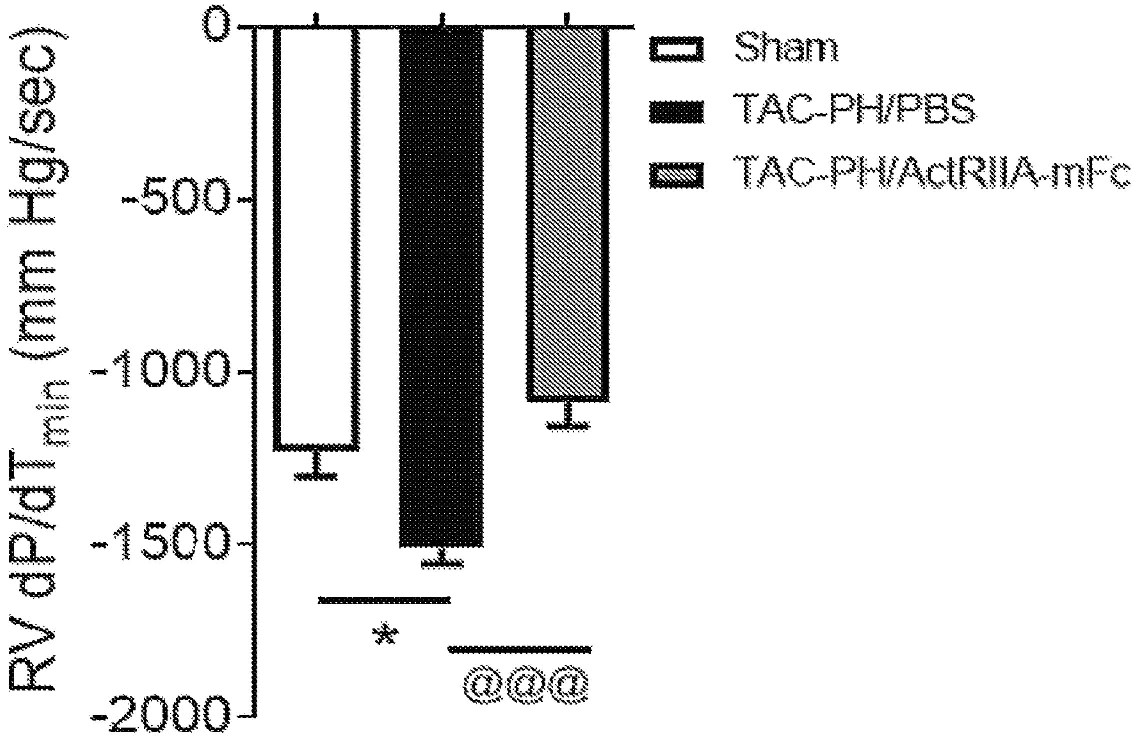
Figure 19:
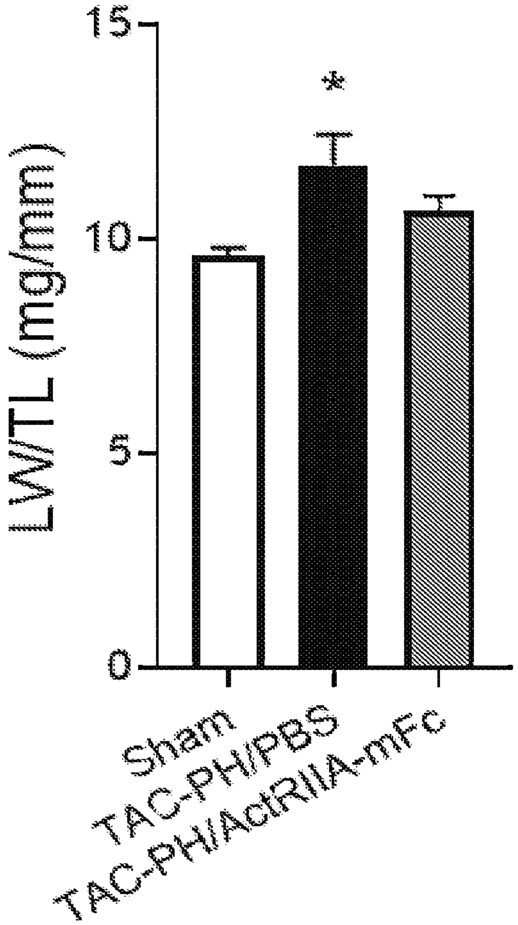
FIGS. 19 and 20 show the therapeutic effect of ActRIIA-mFc in a TAC-PH model based on endpoints for lung remodeling. Twenty-six C57/B6 male mice (10 wks old) underwent TAC pulmonary hypertension surgery (TAC-PH) and ten age-matched animals underwent a mock surgical procedure (Sham) at day 0. Two weeks after the surgery, TAC-PH mice were randomized into two groups. i) fourteen mice were injected subcutaneously with vehicle control (phosphate buffered saline (PBS)), twice weekly for 4 weeks starting from day 14 after surgery, “TAC-PH/PBS”; and a ii) twelve mice were injected subcutaneously with ActRIIA-mFc at a dose of 10 mg/kg twice weekly for 4 weeks starting from day 14 after TAC surgery, “TAC-PH/ActRIIA-mFc”.
Figure 20:
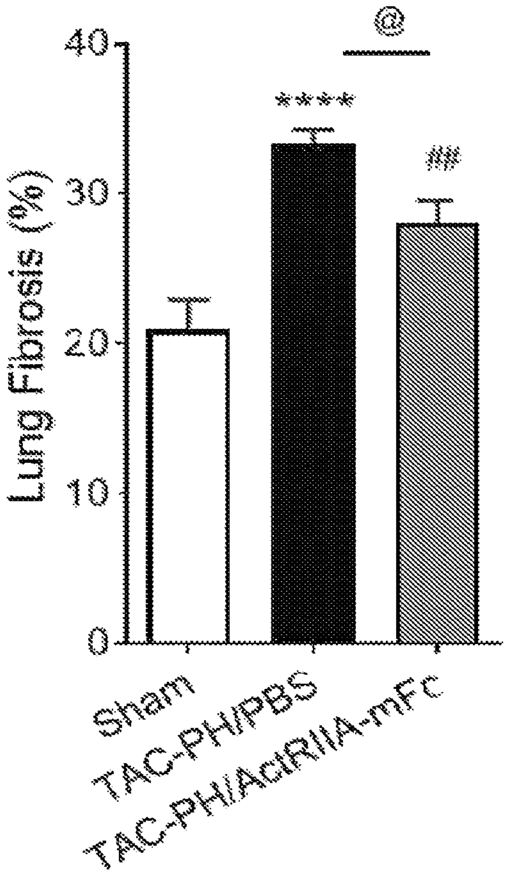

As shown in FIGS. 10-20, ActRIIA-mFc treatment (TAC-PH/ActRIIA-mFc) relative to PBS treatment (TAC-PH/PBS) on day 42 significantly reduced cardiac hypertrophy (FIG. 10), elevated FS (FIG. 11), restored LV ejection fraction (FIG. 12), reduced E/E' ratio (FIG. 13), and reduced IVRT (FIG. 14). ActRIIA-mFc treatment (TAC-PH/ActRIIA-mFc) relative to PBS treatment (TAC-PH/PBS) on day 42 also significantly reduced elevated RVFWT (FIG. 15), increased reduced TAPSE (FIG. 16), reduced elevated RV stroke work (FIG. 17), and decreased increased RV $-dp/dT_{min}$ (FIG. 18). ActRIIA-mFc treatment (TAC-PH/ActRII-mFc) relative to PBS treatment (TAC-PH/PBS) on day 42 decreased lung weight (FIG. 19) and significantly reduced lung fibrosis (FIG. 20).

Together, these data demonstrate that ActRIIA-mFc is effective in ameliorating various complications of Group 2 PH in a left heart failure-induced PH model (TAC-PH). In particular, ActRIIA-mFc had a significant effect in reducing cardiac hypertrophy, improving cardiac function, improving right heart remodeling and function, and reducing pulmonary remodeling and fibrosis.

Example 5: Effects of an ActRIIA-mFc on Group 2 Pulmonary Hypertension in an HFpEF Induced PH Rat Model The effects of an ActRIIA-mFc fusion protein (ActRIIA-mFc homodimer as described in Example 1) was examined in a rat model of left ventricular diastolic dysfunction (also referred to as HEpEF) group 2 (subgroup 2.2) pulmonary hypertension (PH). In this model, ZSF1-$Lepr^{fa}Lepr^{cp}$/Crl rats were challenged with semaxanib to induce HFpEF-PH (1).

Forty ZSF1 $Lepr^{fa}Lepr^{cp}$/Crl male mice (8 wks old) and five lean rats were subcutaneously administered with a single dose of semaxanib (100 mg/kg) at day 0, and five lean rats were included as normal control. Six weeks after semaxanib (SU5416) treatment, Thirty-six ZSF1 $Lepr^{fa}Lepr^{cp}$/Crl rats were randomized into four groups: i) nine rats were injected subcutaneously with vehicle control (phosphate buffered saline (PBS)), twice weekly for 8 weeks starting from day 42 after semaxanib treatment, "ZSF1-SU/PBS"; a ii) ten rats were injected subcutaneously with ActRIIA-mFc at a dose of 1 mg/kg twice weekly for 8 weeks starting from day 42 after semaxanib treatment, "ZSF1-SU/ActRIIA-mFc 1 mpk"; a iii) nine rats were injected subcutaneously with ActRIIA-mFc at a dose of 3 mg/kg twice weekly for 8 weeks starting from day 42 after semaxanib treatment, "ZSF1-SU/ActRIIA-mFc 3 mpk"; and a iv) eight rats were injected subcutaneously with ActRIIA-mFc at a dose of 10 mg/kg twice weekly for 8 weeks starting from day 42 after semaxanib treatment, "ZSF1-SU/ActRIIA-mFc 10 mpk". At the end of the study, echocardiography and pressure-volume catheter were performed to measure left and right ventricular remodeling and functional changes before animals were euthanized for heart and lung collection. Hearts and lungs of each rat were weighed, fixed in 10% formalin, embedded in paraffin, and sectioned for Masson's trichrome stain to assess fibrosis. Serum and urine samples were collected at the end of the study.

Rats were fasted overnight to measure fasting blood glucose levels at week 14 (before treatments started), week 18 (4 weeks after treatments), and week 22, and oral glucose tolerance test was performed at week 22. Blood glucose levels were measured with a glucometer after bleeding tail vein with a 27 G needle. To prepare oral glucose tolerance test, 40% glucose stock solution run through a filter to sterilize it. After fasting overnight, rat body weight was measured. Blood glucose level was detected. Then 40% glucose solution was administered via oral gavage according to body weight (2 g/kg). Blood glucose levels were measured at 30, 60, 90, 120 minutes.

Prior to euthanization, in vivo cardiac function was assessed by transthoracic echocardiography (Acuson P300, 18 MHz linear transducer; Siemens) in lightly anesthetized rats as described(2). From left ventricle short axis view, M-mode echocardiogram was acquired to measure interventricular septal thickness at end diastole (IVSd), left ventricular posterior wall thickness at end diastole (LVPWd), left ventricular end diastolic diameter (LVEDD), and left ventricular end systolic diameter (LVESD). Left ventricular mass (LVM) was assessed by the equation: $1.05\ [(LVEDD+LVPTD+IVSd)^3-LVEDD^3]$. Early diastolic filling peak velocity (E), early diastolic mitral annular velocity (E'), and isovolumetric relaxation time (IVRT) were measured from the medial or septal wall at the mitral valve level from tissue Doppler image. LV diastolic function was assessed by measuring the E/E' ratio and IVRT. Pulmonary arterial acceleration time (PAAT), a parameter of right ventricular function, was also measured.

Fourteen weeks after semaxanib treatment, rats were anesthetized with ketamine (100 mg/kg) and xylazine (5 mg/kg) at the end of the experiment to evaluate cardiac and pulmonary hemodynamics. The respiration was supported by a small animal ventilator. Thoracotomy was made through 4-5 intercostal space, and the heart was exposed. A pressure-volume catheter (2.0-Fr, SPR-869, Millar Instruments, Houston, TX, USA) was be inserted into the left ventricle and right ventricle from the apex. Ventricular pressure and volume were calculated with LabChart 7 software. Stroke work, ejection fraction, and cardiac output were derived. After finishing left ventricular measurements, the catheter was advanced to the aorta, arterial blood systolic and diastolic pressure was detected. Then the catheter returned to the left ventricle and changed the direction laterally to enter the left atrium. Similarly, right atrial pressure was measured by moving the catheter from the right ventricle into atrium. To measure pulmonary arterial pressure, the sternum was cross-sectioned at the second inter-rib space. The right ventricular outflow tract was exposed. A hole was made with 27 G needle, and then the catheter was inserted into the right ventricular outflow tract and advanced into the pulmonary artery.

Figure 23:
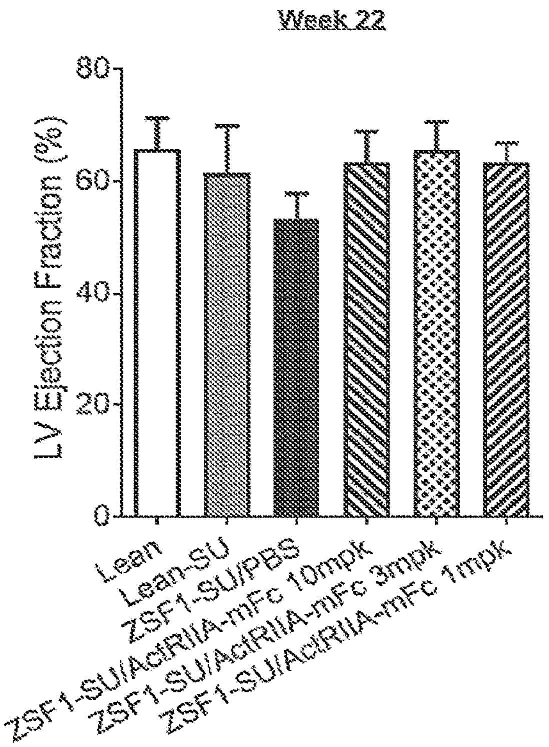
Figure 24:
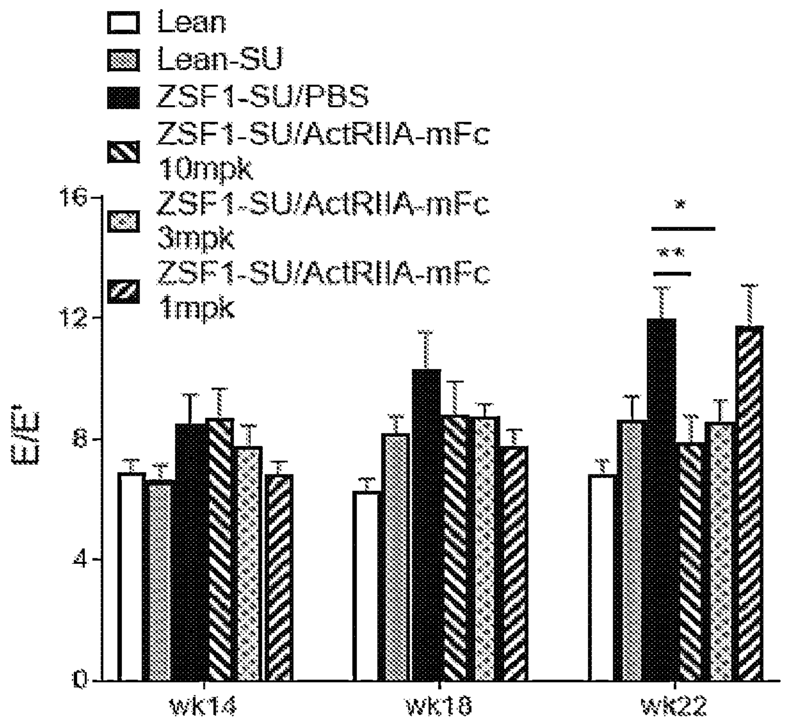
Figure 29:
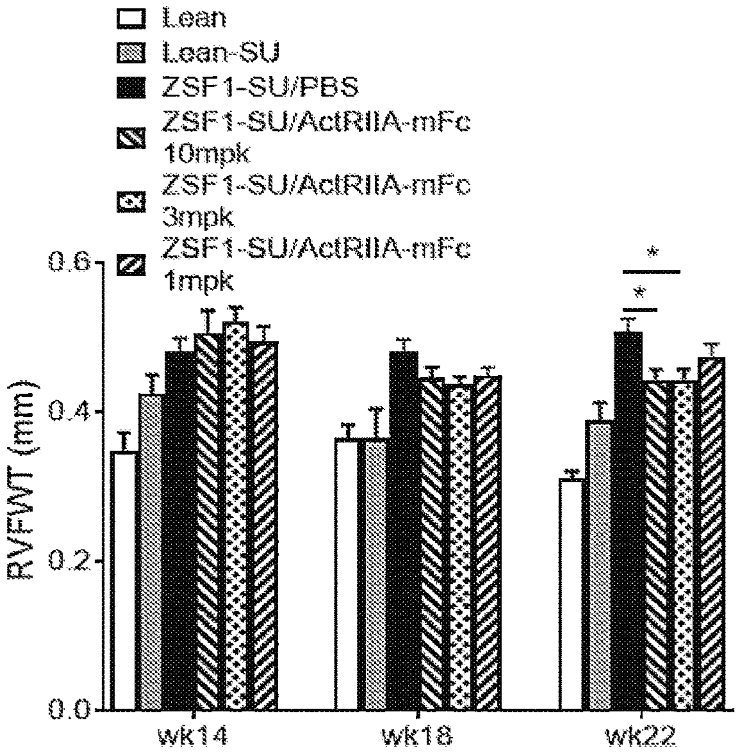
FIGS. 29-31 show that treatment with an ActRIIA-mFc fusion protein reduces right ventricular systolic pressure (RVSP) and improves right ventricular function in a rat model of left ventricular diastolic dysfunction (also referred to as HEpEF) group 2 (subgroup 2.2) pulmonary hypertension (PH).
Figure 30:
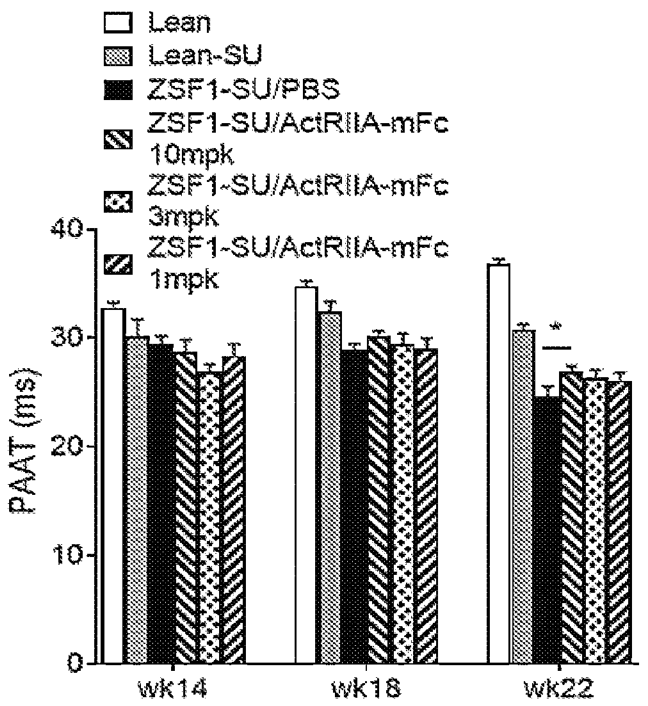

Compared to lean control animals, ZSF1-SU rats in the PBS treatment group (ZSF1-SU/PBS) 14-weeks after semaxanib treatment were observed to have increased heart weight (HW/TL) (FIG. 26), increased IVSd (FIG. 27), and increased LVM (FIG. 28), preserved LV ejection fraction (FIG. 23), increased E/E' ratio (FIG. 24), increased IVRT (FIG. 25), indicating cardiac hypertrophy and left ventricular diastolic dysfunction. ZSF1 rats also increased right ventricle free wall thickness (RVFWT) (FIG. 29), decreased PAAT (FIG. 30), and increased RVSP (FIG. 31), compared to lean control rats, suggesting the pulmonary hypertension and RV remodeling. In addition, increased fibrosis in LV, RV and lung (FIGS. 32-34) was observed in ZSF1-SU/PBS rats.

Figure 25:
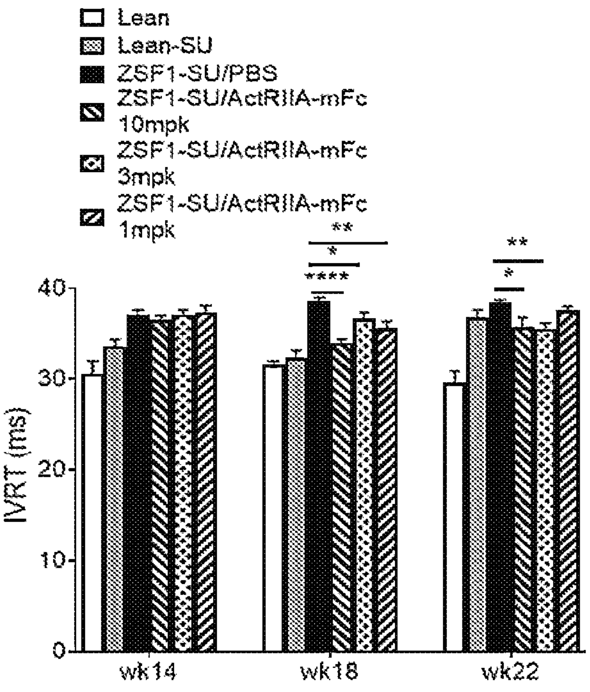
Figure 26:
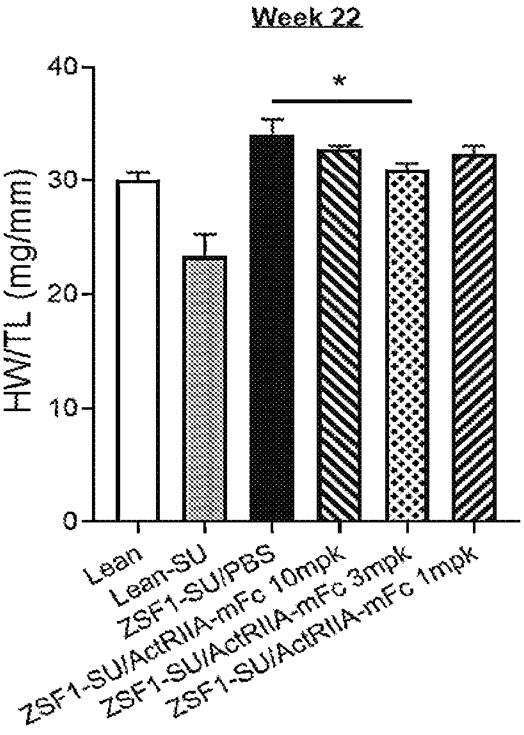
FIGS. 26-28 show that treatment with an ActRIIA-mFc fusion protein reduces left heart remodeling in a rat model of left ventricular diastolic dysfunction (also referred to as HEpEF) group 2 (subgroup 2.2) pulmonary hypertension (PH).
Figure 27:
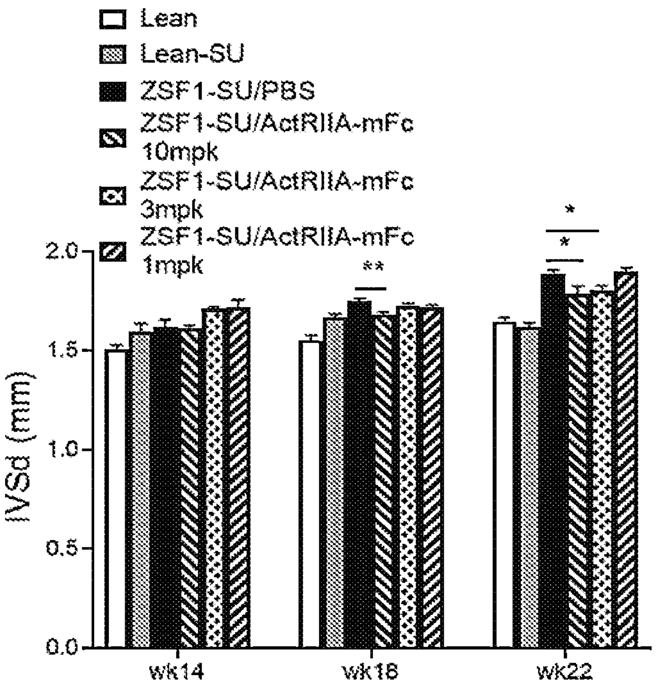
Figure 28:
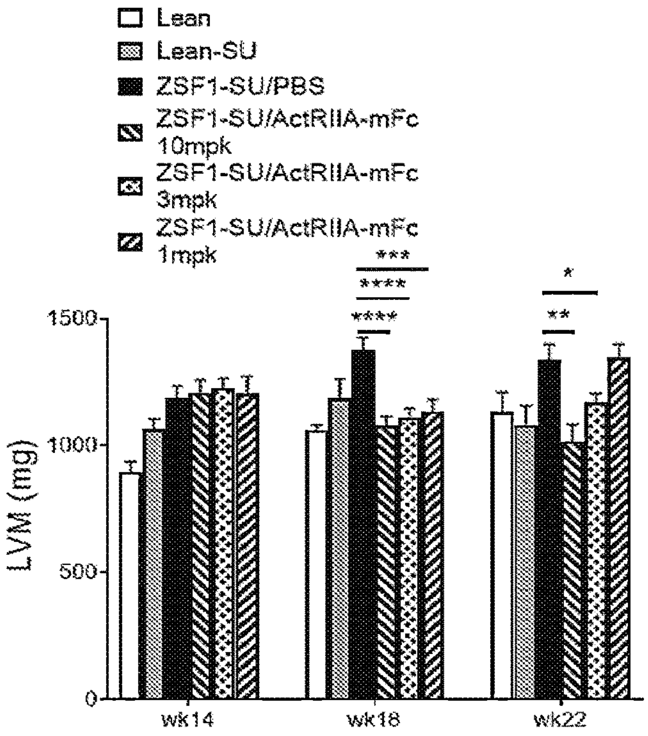
Figure 31:
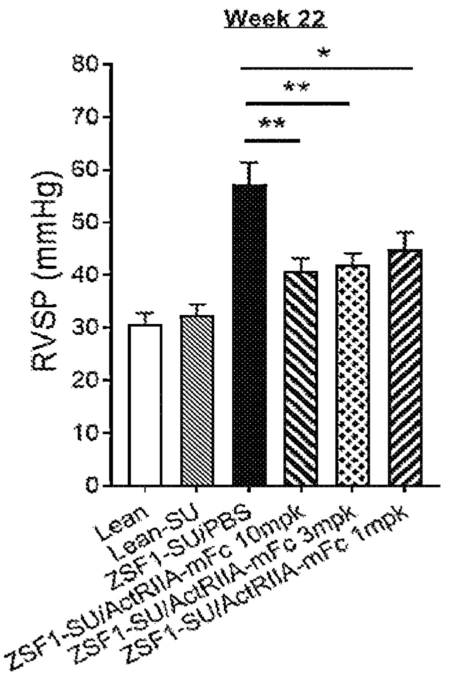
Figure 32:
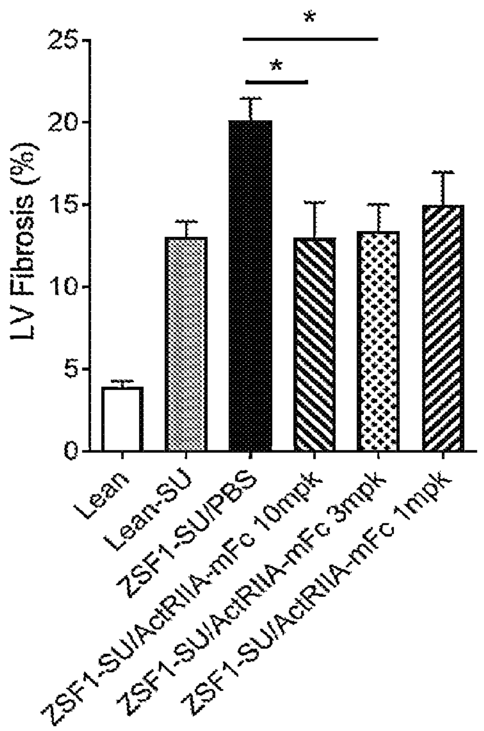
FIGS. 32-34 show that treatment with an ActRIIA-mFc fusion protein significantly reduced the fibrosis in LV, RV and lung in a rat model of left ventricular diastolic dysfunction (also referred to as HEpEF) group 2 (subgroup 2.2) pulmonary hypertension (PH).
Figure 33:
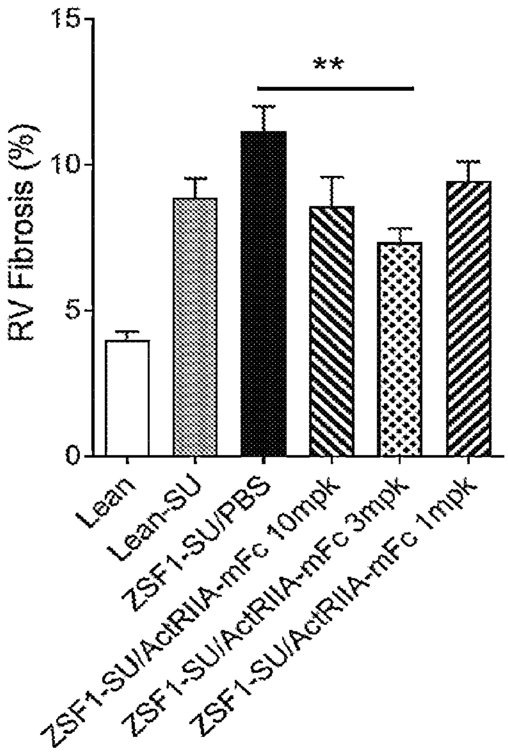
Figure 34:
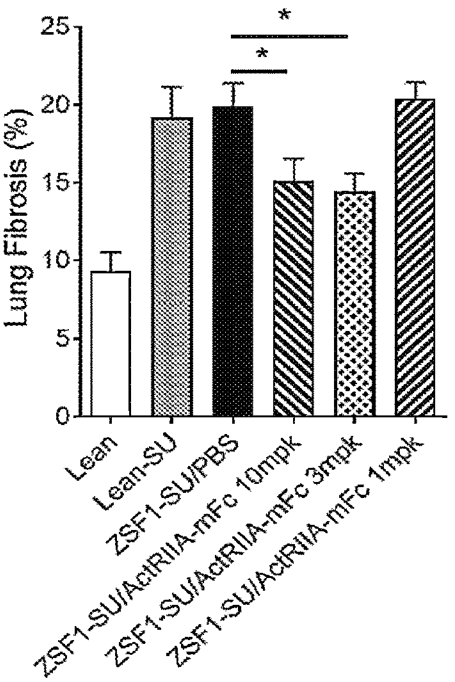
Figure 35:
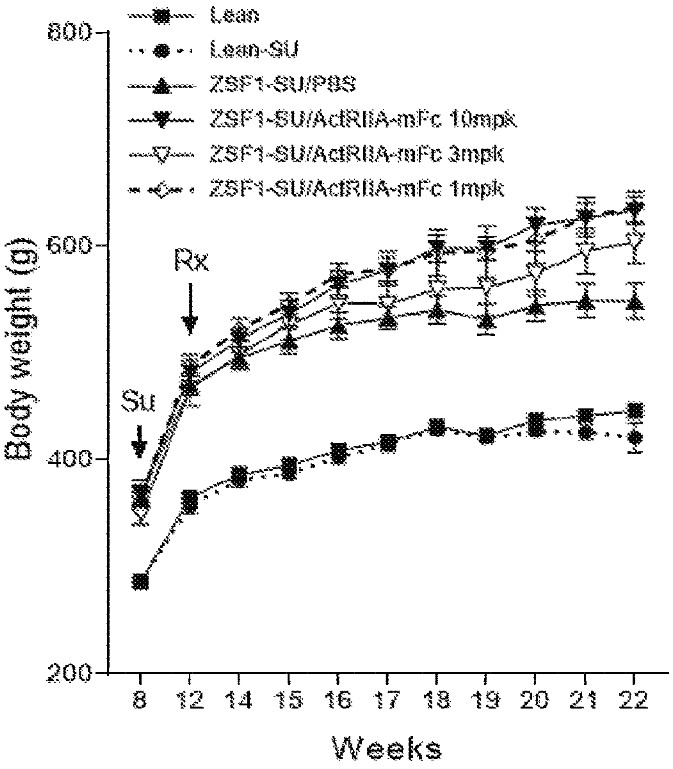
FIGS. 35-38 show that treatment with an ActRIIA-mFc fusion protein significantly improves hyperglycemia and glucose intolerance in a rat model of left ventricular diastolic dysfunction (also referred to as HEpEF) group 2 (subgroup 2.2) pulmonary hypertension (PH).

As shown in FIGS. 26 to 28, ActRIIA-mFc treatment (ZSF1-SU/ActRIIA-mFc) relative to PBS treatment (ZSF1-SU/PBS) both at 3 mpk and 10 mpk significantly reduced left heart remodeling (FIGS. 26-28), and reduced E/E' ratio (FIG. 24), and decreased IVRT (FIG. 25). ActRIIA-mFc treatment (ZSF1-SU/ActRIIA-mFc) relative to PBS treatment (ZSF1-SU/PBS) both at 3 mpk and 10 mpk also significantly reduced elevated RVFWT (FIG. 29), reduced PAAT (FIG. 30), and reduced elevated RVSP (FIG. 31). ActRIIA-mFc treatment (ZSF1-SU/ActRIIA-mFc) relative to PBS treatment (ZSF1-SU/PBS) also significantly reduced the increased fibrosis in LV, RV and lung (FIGS. 32-34).

Figure 36:
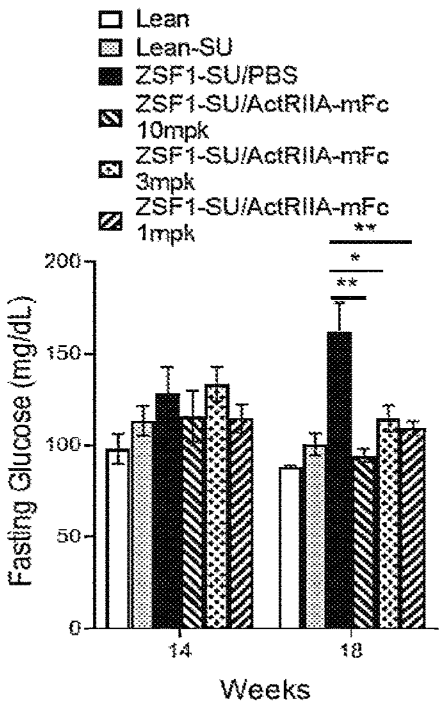
Figure 37:
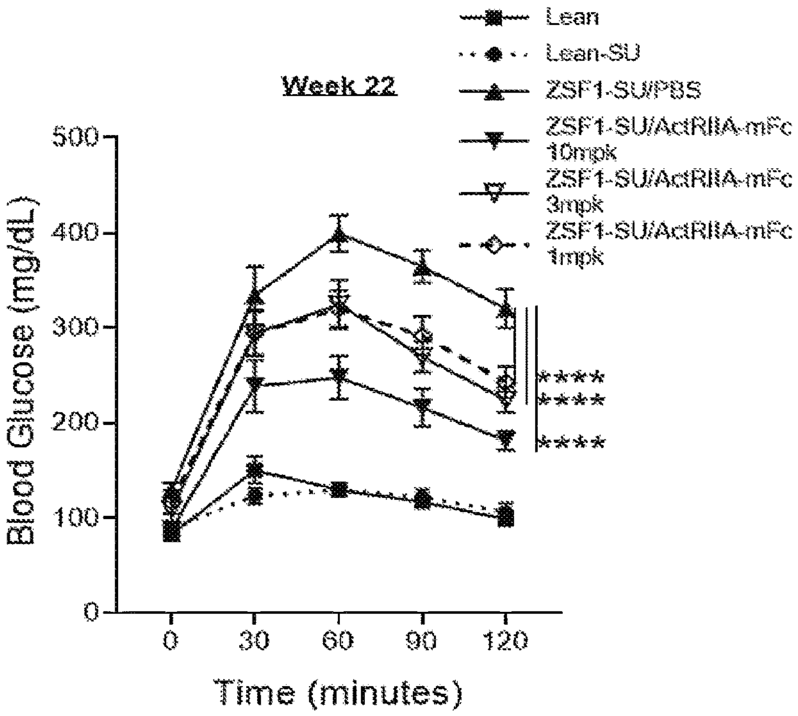
Figure 38:
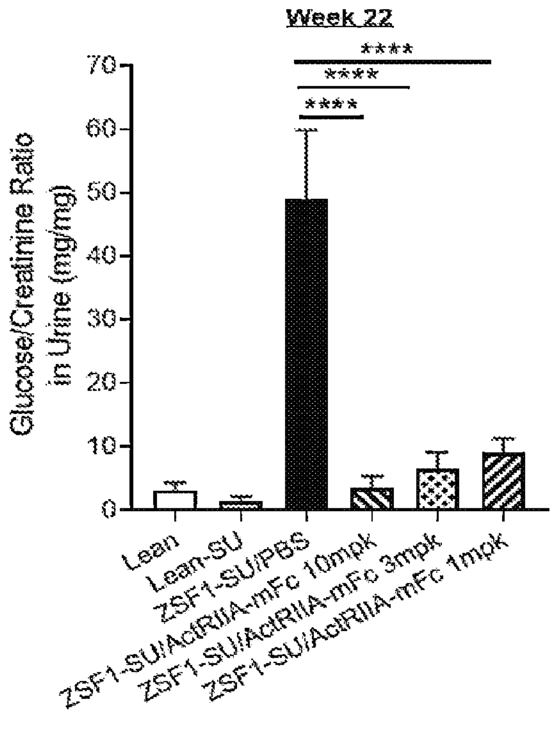
Figure 39:
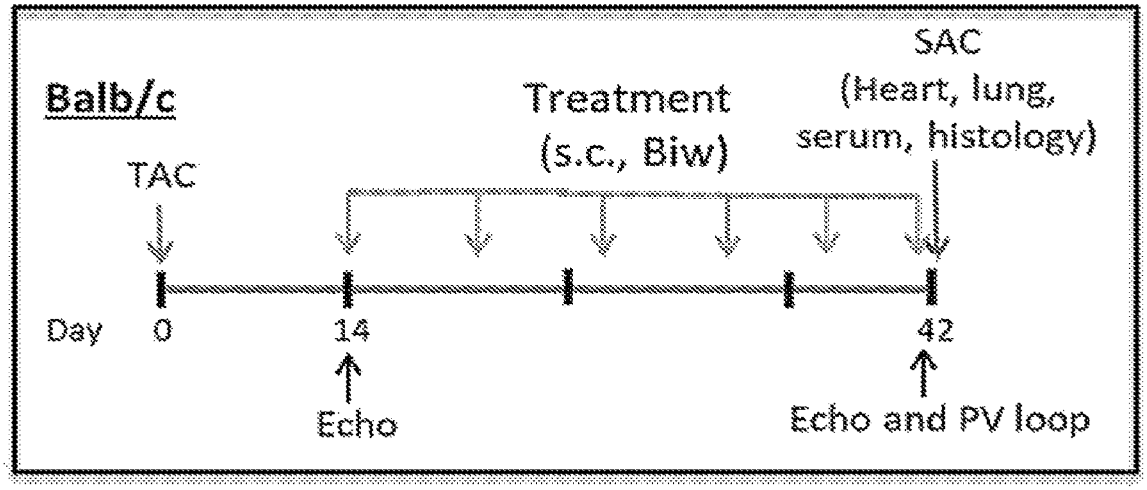
FIGS. 39-43 show that treatment with an ActRIIA-mFc fusion protein inhibits cardiac remodeling and improves LV function in a mouse model of PH due to heart failure with reduced LVEF (also referred to as HErEF) group 2 (subgroup 2.1) pulmonary hypertension (PH) and valvular heart disease (subgroup 2.3). The experimental strategy used to test the preventative effects of ActRIIA-mFc in the rat model of HErEF is shown in FIG. 39.

In addition, compared to lean control animals, ZSF1-SU rats in the PBS treatment group (ZSF1-SU/PBS) had elevated fasting blood glucose level and increased glucose level in urine, accompanied by glucose intolerance. ActRIIA-mFc treatment (ZSF1-SU/ActRIIA-mFc) relative to PBS treatment (ZSF1-SU/PBS) at 1 mpk, 3 mpk and 10 mpk significantly reduced fasting blood glucose, decreased glucose level in urine, and improved glucose tolerance (FIGS. 36-38).

Together, these data demonstrate that ActRIIA-mFc is effective in ameliorating various complications of Group 2 PH in a left heart failure-induced PH model (HFpEF-PH). In particular, ActRIIA-mFc had a significant effect in reducing cardiac hypertrophy, improving diastolic function, improving right heart remodeling and function, decreasing pulmonary hypertension, and reducing cardiac and pulmonary remodeling and fibrosis. Furthermore, ActRIIA-mFc had a robust effect in reducing glucose levels and improving glucose tolerance. The data indicate that other ActRII antagonists, particularly ones having activities similar to ActRIIA-mFc, may be useful in the treatment of Group 2 PH, particularly in preventing or reducing the severity various complications of Group 2 PH.

Example 6: Effects of an ActRIIA-hFc Polypeptide in Patients with Cpc-PH Due to HFpEF The effects of an ActRIIA-hFc fusion protein (SEQ ID NO: 23 as described in Example 1) are examined in a double-blind, randomized, placebo-controlled study to evaluate the effects of the ActRIIA-hFc fusion protein versus placebo for the treatment of combined pre- and postcapillary pulmonary hypertension (Cpc-PH) due to heart failure with preserved ejection fraction (HFpEF).

Patients and Trial Design

Eligible patients will have confirmed Cpc-PH due to HFpEF, Functional Class II or III as assessed by the NYHA. Additionally, eligible patients are between 18 to 85 years of age and have a six minute walk distance greater than 100 meters repeated twice during screening and both values within 15% of each other, calculated from the highest value. Patients may be receiving stable medications for heart failure or any underlying condition for at least 30 days before and throughout the study. A planned interim analysis will occur when approximately 15 participants in each of the three treatment groups have completed 24 weeks on the study. Sensitivity analysis will be performed to account for any differences in background therapy. All patients will provide informed consent.

Initially, approximately 90 eligible patients will be randomly assigned in a 1:1:1 ratio to one of three treatment groups: (1) placebo; (2) ActRIIA-hFc fusion protein 0.3 mg/kg; or (3) ActRIIA-hFc fusion protein 0.3 mg/kg then escalating to 0.7 mg/kg. ActRIIA-hFc fusion protein or placebo (saline) will be given by subcutaneous injection every 21 days for a total of 24 weeks. Safety and efficacy will be assessed at screening and every 3 weeks for 24 weeks. See, e.g., Table 4 below. Adverse events are recorded from screening until the end of primary treatment study visit, 8 weeks after the last dose of study drug. An interim analysis will occur when approximately 15 participants in each of the 3 treatment groups have completed 24 weeks of treatment in the placebo-controlled treatment period.

Participants who have not discontinued early from the placebo-controlled treatment period and have had the 24-week PVR assessment will continue into the 18-month extension period and will be treated as follows: Placebo participants will be re-randomized in a 1:1 ratio to one of the two ActRIIA-hFc fusion protein treatment groups utilized in the placebo-controlled treatment period to receive either (1) ActRIIA-hFc fusion protein SC at a dose level of 0.3 mg/kg every 21 days for up to 18 months in the Extension Period or (2) ActRIIA-hFc fusion protein SC at a starting dose of 0.3 mg/kg plus background therapy, then escalate to 0.7 mg/kg at Visit 12 and every 21 days for up to 18 months in the Extension Period.

TABLE 4

| Efficacy Endpoints | |
|---|---|
| Type | End points |
| Primary end point | Change in pulmonary vascular resistance from baseline to 24 weeks |
| Key secondary end point | Change in 6-minute walk distance from baseline to 24 weeks |
| Other secondary end points | • Clinical Worsening<br>○ Number of Clinical Worsening events, defined as follows, at 24 and 48 weeks:<br>- The occurrence of any 1 of the following clinical worsening events: hospitalization due to a cardiopulmonary indication (a non-elective hospitalization lasting at least 24 hours in duration caused by clinical conditions directly related to PH and/or heart failure), administration of IV diuretics, death (all causes), decrease in 6MWD > 15% from Baseline (or the subject was too ill to walk, and the cause was directly related to the disease under study) at 2 consecutive visits on different days (except Week 24)<br>○ Number of Participants with first Clinical Worsening event, defined as above, at 24 and 48 weeks<br>○ Time to Clinical Worsening, defined as above<br>• Change in dyspnea score (assessed by Borg CR10 scale ®) at Week 24 from baseline<br>• Change in hemodynamic and ECHO parameters, including but not limited to mPAP, PCWP, TAPSE, RVFAC, and LVEF at 24 weeks from baseline<br>• Change in NT-proBNP at 24 weeks from baseline<br>• Change in NYHA FC at 24 weeks from baseline<br>• Change in 6MWD at 48 weeks from baseline<br>• Change in hemodynamic and ECHO parameters, including but not limited to PVR, mPAP, PCWP, TAPSE, RVFAC, and LVEF, at 48 weeks from baseline<br>• Change in NT-proBNP at 48 weeks from baseline<br>• Change in NYHA FC at 48 weeks from baseline<br>• Change in PVR, 6MWD and NYHA FC at week 48 from baseline in the extension in the Placebo-Crossed treatment group<br>• Change in PVR, 6MWD and NYHA FC from week 24 to week 48 in the extension in the Placebo-Crossed treatment group |
| Exploratory end points | Placebo-Controlled Treatment and Extension Periods<br>• Changes in Kansas City Cardiomyopathy Questionnaire (KCCQ) and EQ-5D-5L scores<br>• Change from baseline in disease-related biomarkers at 24 weeks and 48 weeks<br>• Correlation of clinical efficacy vs. genetic phenotype |

Example 7: Effects of an ActRIIA-mFc on Group 2 Pulmonary Hypertension in a Transverse Aortic Constriction (TAC) Induced PH Mouse Model The effects of an ActRIIA-mFc fusion protein (ActRIIA-mFc homodimer as described in Example 1) was examined in a mouse model of left ventricular systolic dysfunction (also referred to as HErEF) of pulmonary hypertension (PH) and valvular heart disease. In this model, BALB/cJ mice underwent transverse aortic constriction (TAC) to induce left heart failure, and right heart and pulmonary remodeling. See, e.g., Xiong P Y, et al. Hypertension 2018, 71(1):34-55 and Chen Y, et al. Hypertension 2012, 59(6):1170-1178.

Forty-four BALB/cJ male mice (10 wks old) underwent TAC surgery and fourteen age-matched animals underwent a mock surgical procedure (Sham) at day 0. Two weeks after the surgery, TAC-PH mice were randomized into three groups. i) fourteen mice were injected subcutaneously with vehicle control (phosphate buffered saline (PBS)), twice weekly for 4 weeks starting from day 14 after surgery, "TAC PBS"; ii) fifteen mice were injected subcutaneously with ActRIIA-mFc at a dose of 3 mg/kg twice weekly for 4 weeks starting from day 14 after TAC surgery, "TAC ActRIIA-mFc 3 mpk"; and iii) fifteen mice were injected subcutaneously with ActRIIA-mFc at a dose of 10 mg/kg twice weekly for 4 weeks starting from day 14 after TAC surgery, "TAC ActRIIA-mFc 10 mpk." At the end of the study, echocardiography and pressure-volume catheter were performed to measure left and right ventricular remodeling and functional changes before animals were euthanized for heart and lung collection. Hearts and lungs of each mouse were weighed, fixed in 10% formalin, embedded in paraffin, and sectioned for Masson's trichrome stain to assess fibrosis.

Prior to euthanasia, in vivo cardiac function was assessed by transthoracic echocardiography (Acuson P300, 18 MHz transducer; Siemens) in conscious mice. From left ventricle (LV) short axis view, M-mode echocardiogram was acquired to measure left ventricle end diastolic diameter (LVEDD), and left ventricle end systolic diameter (LVESD). Fractional shortening (FS) was calculated from the end-diastolic diameter (EDD) and end-systolic diameter (ESD) using the following equation: FS=100%×[(EDD−ESD)/EDD]. Early diastolic filling peak velocity (E), early diastolic mitral annular velocity (E'), and isovolumetric relaxation time (IVRT) were measured from the medial or septal wall at the mitral valve level from tissue Doppler image. LV diastolic function was assessed by measuring the E/E' ratio and IVRT. Three to five beats were averaged for each mouse measurement. RV free wall thickness (RVFWT) was measured using M-mode in a modified parasternal long-axis view through the aortic valve. Pulmonary artery acceleration time (PAAT) was measured as the time from start to peak velocity of blood flow in the lumen of the main pulmonary artery distal to the pulmonary valve as obtained from the pulse-wave doppler recording.

On day 42, mice were anesthetized by an intraperitoneal injection of ketamine/xylazine (100/5 mg/kg) to evaluate left and right ventricular function by Millar pressure-volume conductance catheter. The respiration was supported by a small animal ventilator. Thoracotomy was made through 4-5 intercostal space, and the heart was exposed. A pressure-volume catheter (1.0-Fr, PVR-1035, Millar Instruments, Houston, TX, USA) was inserted into the left ventricle and right ventricle from the apex. Ventricular pressure and volume were calculated with LabChart 7 software. Ejection fraction was derived. Afterwards, animals were euthanized for heart and lung collection. Cardiac hypertrophy was measured by heart weight (HW) normalized by tibial length (TL). Left ventricle (LV), right ventricle (RV) and lung of each mouse were separated, fixed in 10% formalin, embedded in paraffin, and sectioned for Masson's trichrome stain to assess fibrosis. Serum and urine samples were collected at the end of the study.

Figure 40:
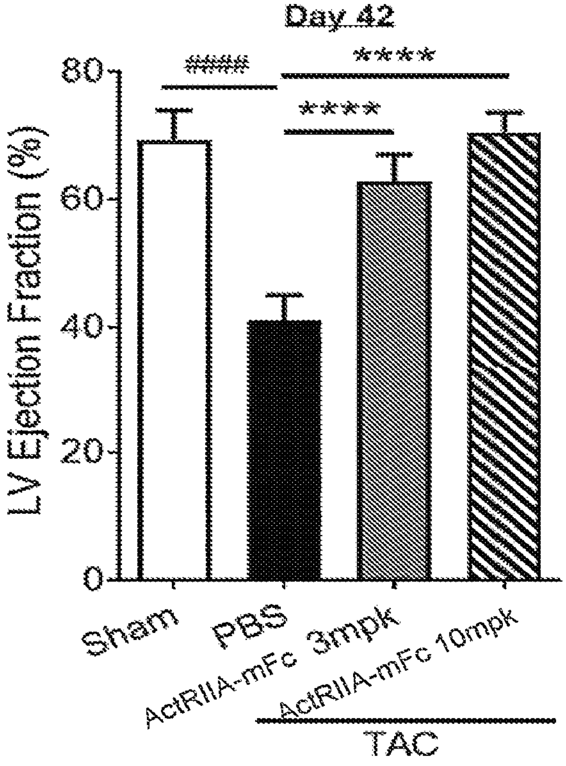
Figure 41:
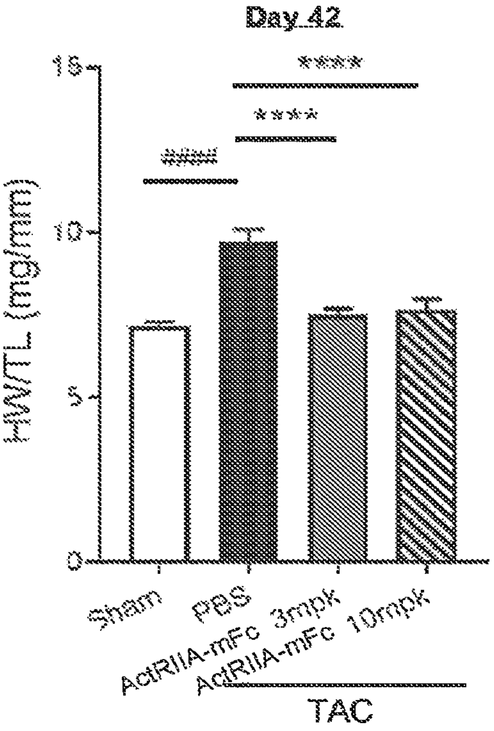
Figure 42:
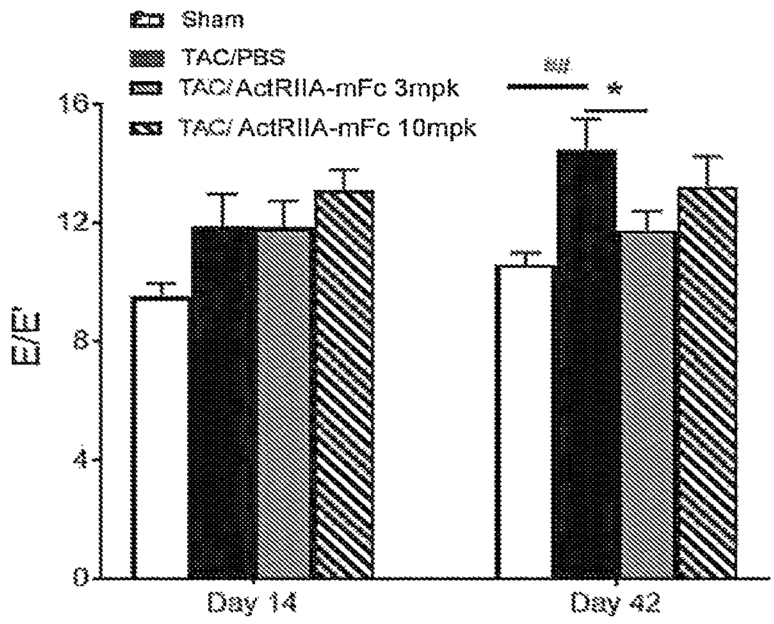

Compared to Sham control animals, TAC-PH mice in the PBS treatment group (TAC PBS) on day 42 were observed to have decreased left ventricle ejection fraction (FIG. 40), increased heart weight (HW/TL) (FIG. 41), increased E/E' ratio (FIG. 42), increased isovolumic relaxation time (IVRT) (FIG. 43), and increased left ventricle fibrosis (FIG. 47), indicating cardiac hypertrophy and left heart failure. TAC mice also had increased right ventricle free wall thickness (RVFWT) (FIG. 45), decreased PAAT (FIG. 46), and increased right ventricle fibrosis (FIG. 48) compared to Sham control mice, suggesting the RV remodeling and RV dysfunction. In addition, increased RVSP (FIG. 44) and increased lung fibrosis (FIG. 49) were observed in TAC-PH/PBS mice, indicating pulmonary hypertension and lung remodeling caused by TAC-induced left heart failure.

Figure 43:
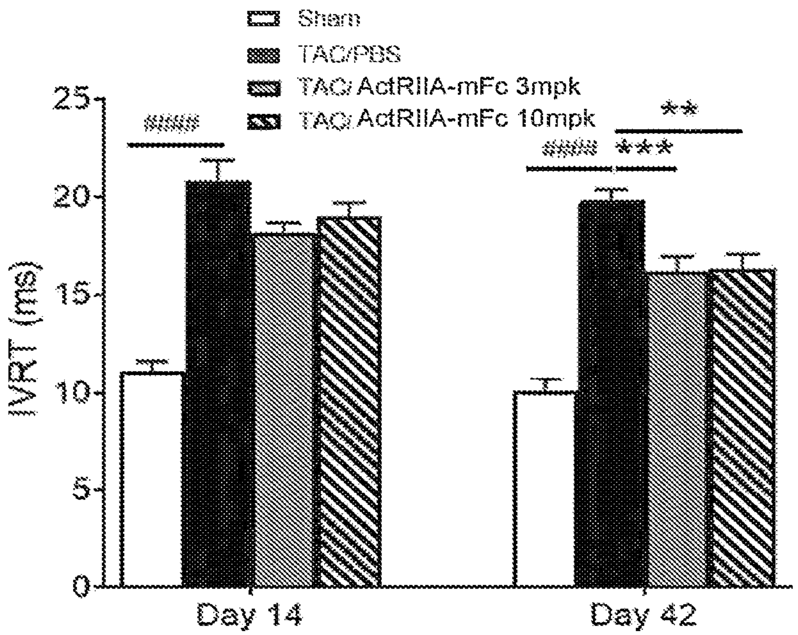
Figure 44:
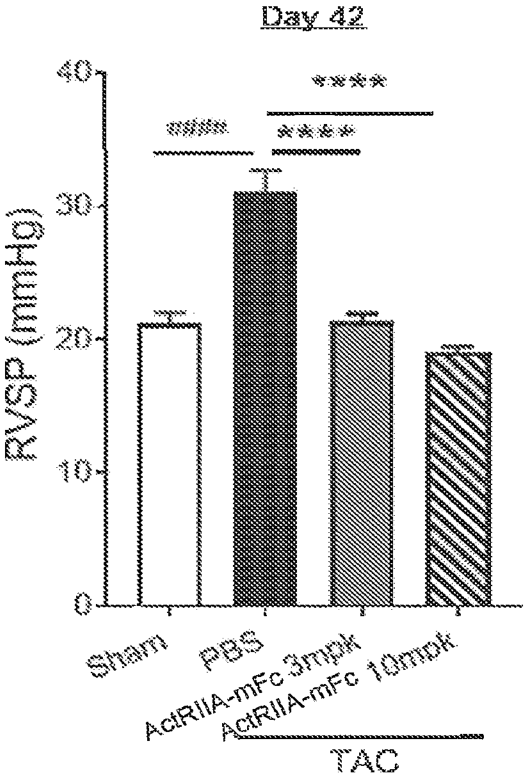
FIGS. 44-46 show the therapeutic effect of ActRIIA-mFc in a TAC-PH model based on endpoints for right ventricle function.
Figure 45:
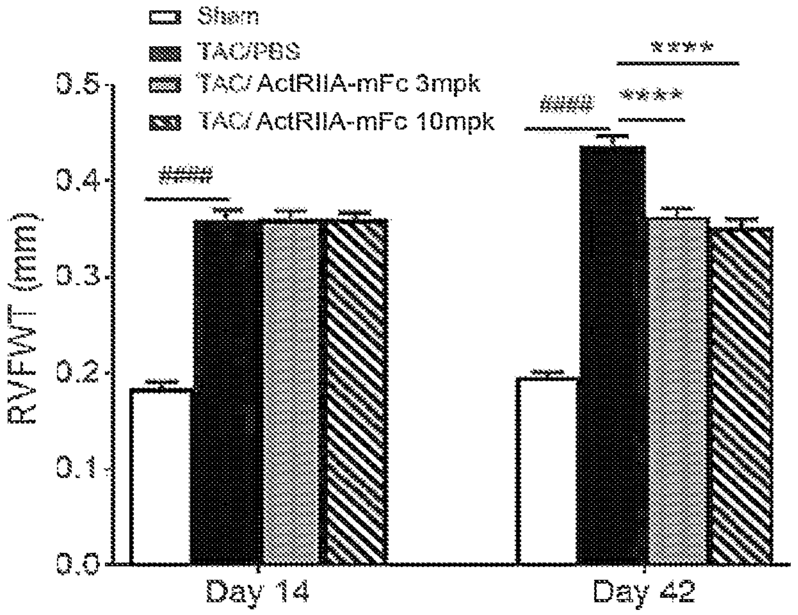
Figure 46:
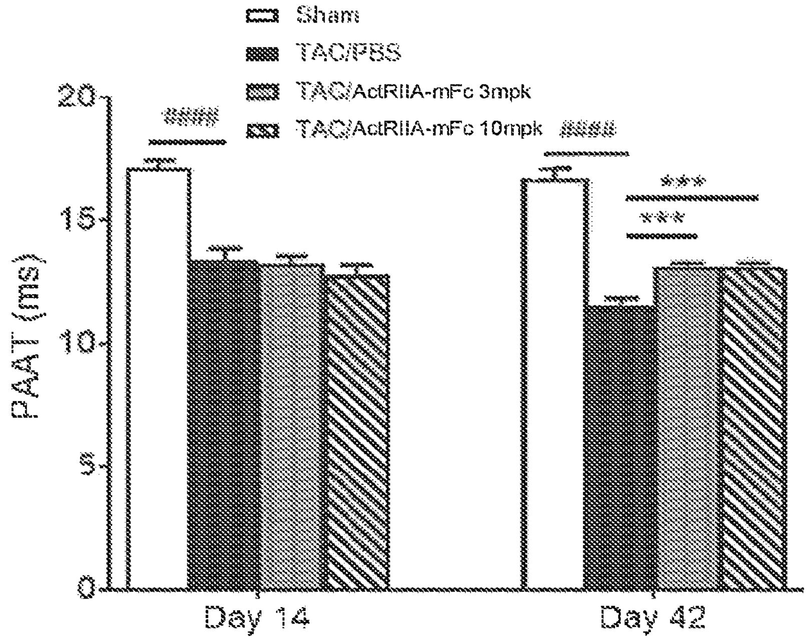
Figure 47:
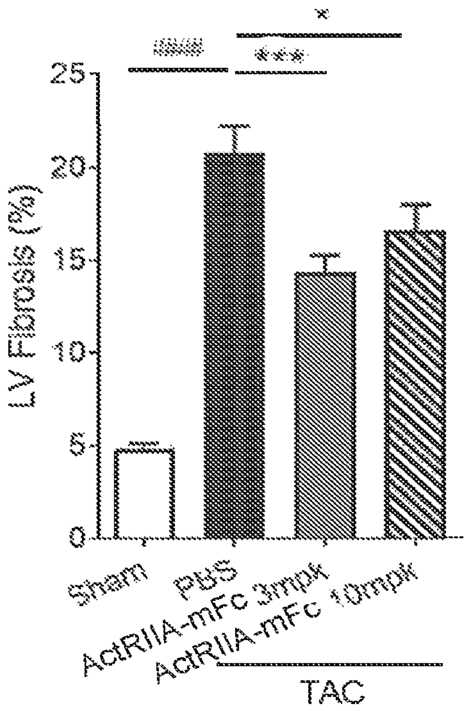
FIGS. 47-49 show the therapeutic effect of ActRIIA-mFc in a TAC-PH model based on endpoints for fibrosis in the left ventricle (LV), right ventricle (RV), and lung.
Figure 48:
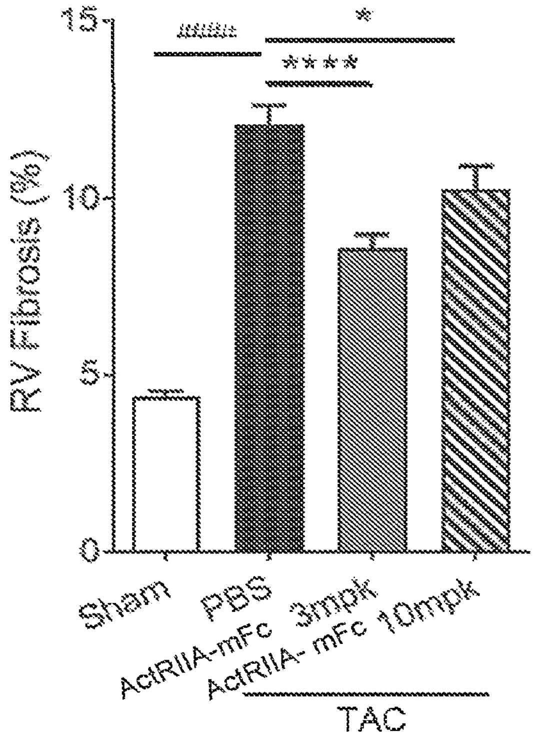
Figure 49:
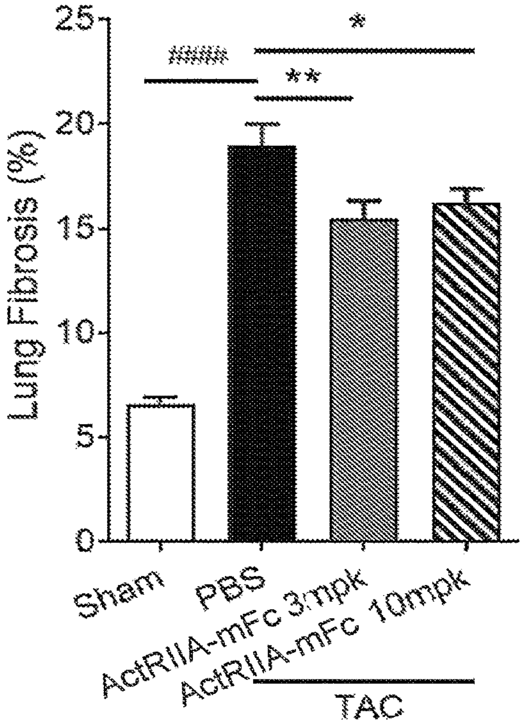
Figure 50:
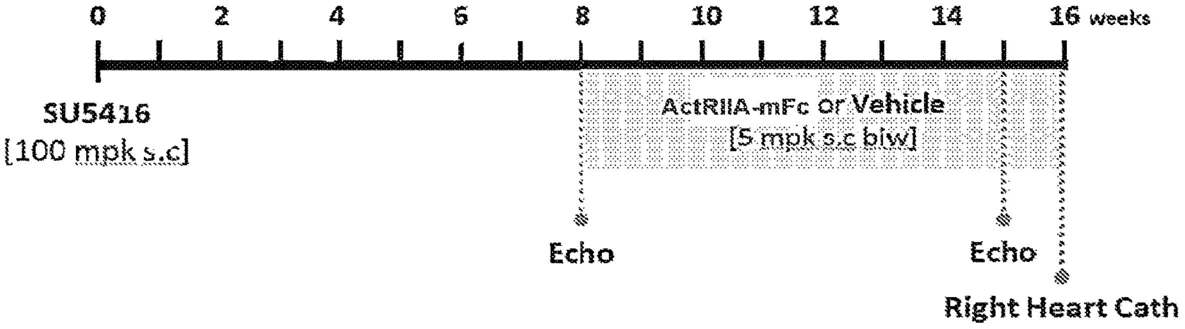
FIGS. 50-55 show that treatment with an ActRIIA-mFc fusion protein reduces right ventricular systolic pressure (RVSP) and improves cardiopulmonary function in a rat model of left ventricular diastolic dysfunction (also referred to as HEpEF) group 2 (subgroup 2.2) pulmonary hypertension (PH). The experimental strategy used to test the preventative effects of an ActRIIA-mFc fusion protein in the rat model of HEpEF is shown in FIG. 50.

As shown in FIGS. 40-49, ActRIIA-mFc treatment (TAC ActRIIA-mFc 3 mpk or TAC ActRIIA-mFc 10 mpk) relative to PBS treatment (TAC PBS) on day 42 significantly reduced cardiac hypertrophy (FIG. 41), restored LV ejection fraction (FIG. 40), reduced E/E' ratio at 3 mpk (FIG. 42), and reduced IVRT (FIG. 43). ActRIIA-mFc treatment (TAC ActRIIA-mFc 3 mpk or TAC ActRIIA-mFc 10 mpk) relative to PBS treatment (TAC PBS) on day 42 also significantly reduced elevated RVFWT (FIG. 45), reduced RVSP (FIG. 44), (FIG. 45), and increased PAAT (FIG. 46). ActRIIA-mFc treatment (TAC ActRIIA-mFc 3 mpk or TAC ActRIIA-mFc 10 mpk) relative to PBS treatment (TAC PBS) on day 42 significantly reduced lung fibrosis (FIG. 49), LV fibrosis (FIG. 47), and RV fibrosis (FIG. 48).

Together, these data demonstrate that ActRIIA-mFc is effective in ameliorating various complications of Group 2 PH in a left heart failure-induced PH model (TAC PH). In particular, ActRIIA-mFc had a significant effect in reducing cardiac hypertrophy, improving cardiac function, improving right heart remodeling and function, improving LV function, and reducing pulmonary remodeling and fibrosis.

Example 8: Effects of an ActRIIA-mFc on Group 2 Pulmonary Hypertension in an HFpEF Induced PH Rat Model The effects of an ActRIIA-mFc fusion protein (ActRIIA-mFc homodimer as described in Example 1) was examined in a rat model of left ventricular diastolic dysfunction (also referred to as HFpEF) group 2 (subgroup 2.2) pulmonary hypertension (PH). In this model, ZSF1-$Lepr^{fa}Lepr^{cp}$/Crl rats were challenged with semaxanib (SU5416) to induce HFpEF-PH.

Twenty ZSF1 $Lepr^{fa}Lepr^{cp}$/Crl male mice (8 wks old) and ten lean rats were subcutaneously administered with a single dose of semaxanib (100 mg/kg) at day 0, and ten lean rats were included as normal control. Eight weeks after semaxanib (SU5416) treatment, twenty ZSF1 $Lepr^{fa}Lepr^{cp}$/Crl rats were randomized into two groups: i) ten rats were injected subcutaneously with vehicle control (phosphate buffered saline (PBS)), twice weekly for 8 weeks starting from day 64 after semaxanib treatment, "Obese ZSF1 Veh"; and ii) ten rats were injected subcutaneously with ActRIIA-mFc at a dose of 5 mpk twice weekly for 8 weeks starting from day 64 after semaxanib treatment, "Obese ZSF1 ActRIIA-mFc." At the end of the study, echocardiography and pressure-volume catheter were performed to measure left and right ventricular remodeling and functional changes before animals were euthanized for heart and lung collection.

Prior to euthanization, in vivo cardiac function was assessed by transthoracic echocardiography (Acuson P300, 18 MHz linear transducer; Siemens) in lightly anesthetized rats as described. Echocardiographic assessments were conducted at week 8 (before therapy with ActRIIA-mFc or vehicle) and week 15 (after therapy) in each rat. From left ventricle short axis view, M-mode echocardiogram was acquired to measure interventricular septal thickness at end diastole (IVSd), left ventricular posterior wall thickness at end diastole (LVPWd), left ventricular end diastolic diameter (LVEDD), and left ventricular end systolic diameter (LVESD). Left ventricular mass (LVM) was assessed by the equation: 1.05 $[(LVEDD+LVPTD+IVSd)^3-LVEDD^3]$. Early diastolic filling peak velocity (E), early diastolic mitral annular velocity (E'), and isovolumetric relaxation time (IVRT) were measured from the medial or septal wall at the mitral valve level from tissue Doppler image. LV diastolic function was assessed by measuring the E/E' ratio and IVRT. Pulmonary arterial acceleration time (PAAT), a parameter of right ventricular function, was measured. Tricuspid annular plane systolic excursion (TAPSE), a parameter of global right ventricular function, was also measured. RV free wall thickness (RVFWT) was measured using M-mode in a modified parasternal long-axis view through the aortic valve. Pulmonary artery acceleration time (PAAT) was measured as the time from start to peak velocity of blood flow in the lumen of the main pulmonary artery distal to the pulmonary valve as obtained from the pulse-wave doppler recording.

Sixteen weeks after semaxanib treatment, rats were anesthetized with ketamine (100 mg/kg) and xylazine (5 mg/kg) at the end of the experiment to evaluate cardiac and pulmonary hemodynamics. The respiration was supported by a small animal ventilator. Thoracotomy was made through 4-5 intercostal space, and the heart was exposed. A pressure-volume catheter (2.0-Fr, SPR-869, Millar Instruments, Houston, TX, USA) was inserted into the left ventricle and right ventricle from the apex. Ventricular pressure and volume were calculated with LabChart 7 software. Stroke work, ejection fraction, and cardiac output were derived. After finishing left ventricular measurements, the catheter was advanced to the aorta, arterial blood systolic and diastolic pressure was detected. Then the catheter returned to the left ventricle and changed the direction laterally to enter the left atrium. Similarly, right atrial pressure was measured by moving the catheter from the right ventricle into atrium. To measure pulmonary arterial pressure, the sternum was cross-sectioned at the second inter-rib space. The right ventricular outflow tract was exposed. A hole was made with 27 G needle, and then the catheter was inserted into the right ventricular outflow tract and advanced into the pulmonary artery.

Figure 53:
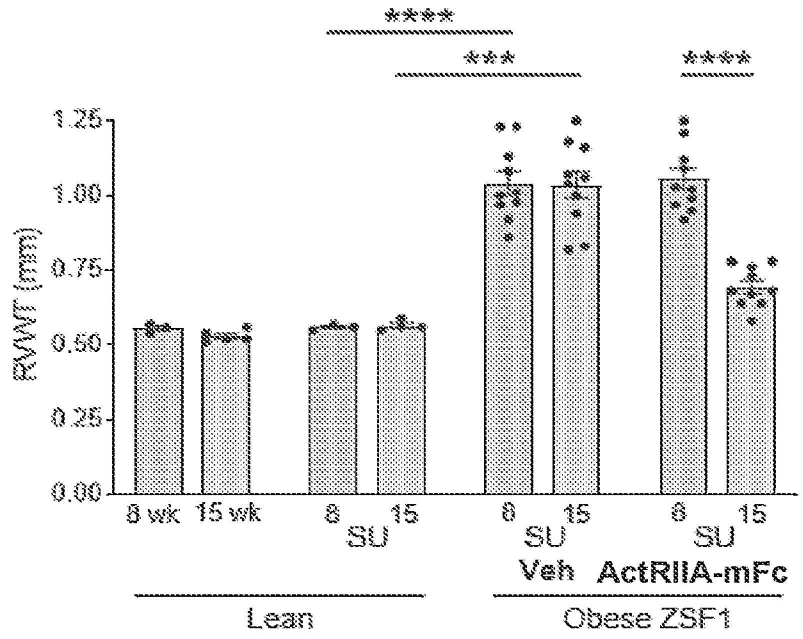
Figure 54:
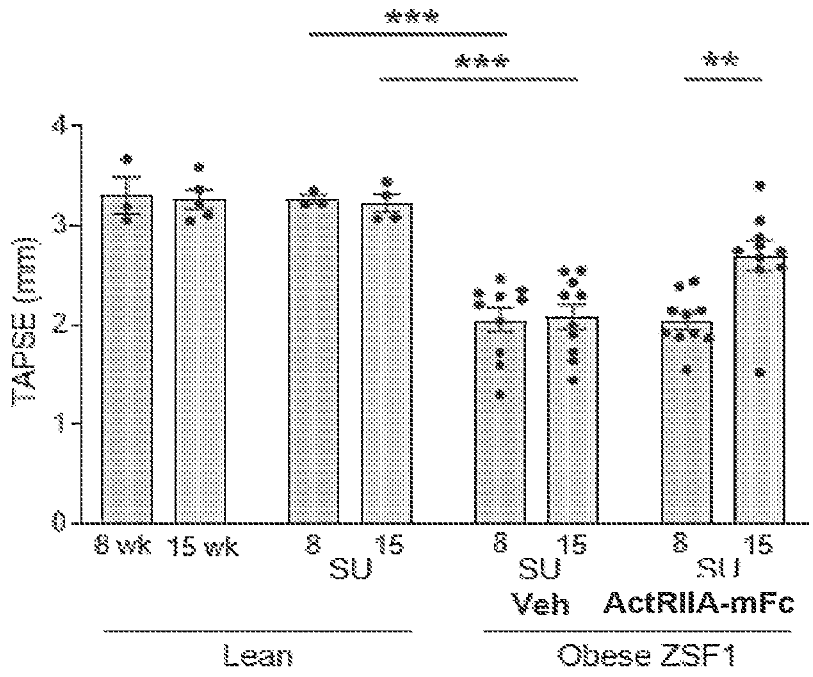
Figure 55:
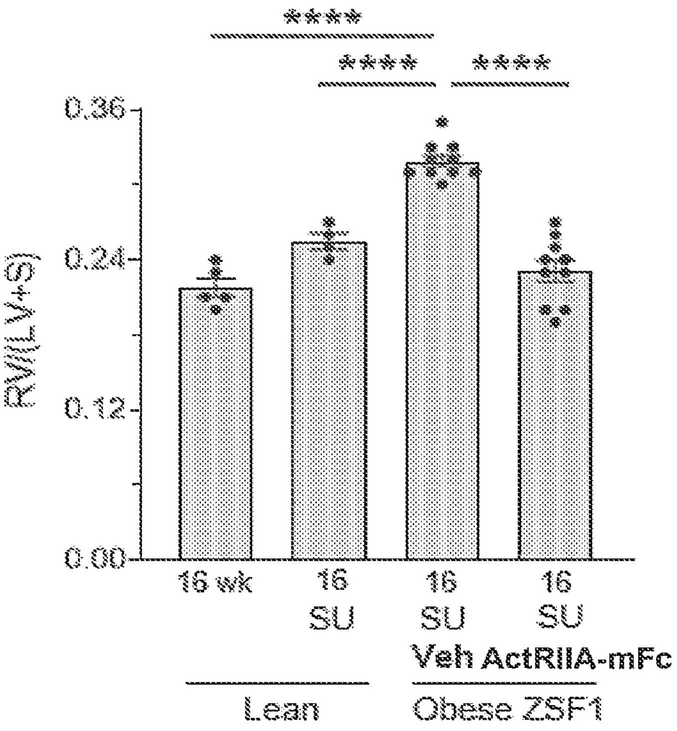

Compared to lean control animals, Obese ZSF1-SU rats in the PBS treatment group (Obese ZSF1 SU/Veh) 16-weeks after semaxanib treatment were observed to have decreased pulmonary artery acceleration time (PAAT) (FIG. 51), increased RVSP (FIG. 52), increased right ventricle free wall thickness (RVFWT) (FIG. 53), decreased tricuspid annular plane systolic excursion (TAPSE) (FIG. 54), and increased Fulton Index, calculated as the ratio of right ventricular weight (RV) to weight of the combined left ventricle and septum (LV+S) (FIG. 55).

Figure 51:
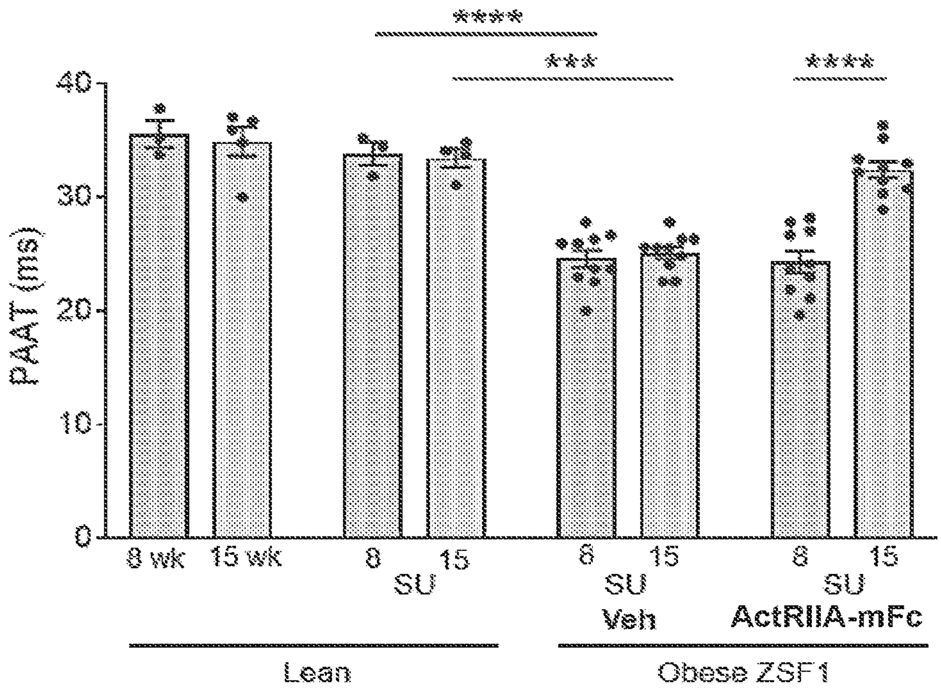
Figure 52:
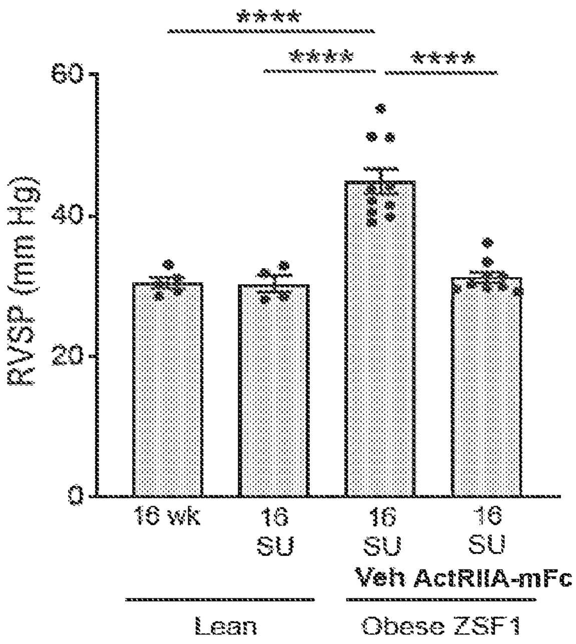

As shown in FIGS. 51 and 52, ActRIIA-mFc treatment (Obese ZSF1-SU/ActRIIA-mFc) relative to PBS treatment (Obese ZSF1-SU/Veh) at 5 mpk normalized cardiopulmonary function as shown by the significantly increased PAAT (FIG. 51) and significantly reduced right ventricular systolic pressure (RVSP) (FIG. 52). ActRIIA-mFc treatment (Obese ZSF1-SU/ActRIIA-mFc) relative to PBS treatment (Obese ZSF1-SU/Veh) at 5 mpk also normalized right ventricular structure and function as shown by the significantly reduced elevated RVWT (FIG. 53), increased TAPSE (FIG. 54), and the decreased Fulton index (FIG. 55).

Together, these data demonstrate that ActRIIA-mFc is effective in ameliorating various complications of Group 2 PH in a left heart failure-induced PH model (HFpEF-PH). In particular, ActRIIA-mFc had a significant effect in normalizing cardiopulmonary function and in normalizing right ventricular structure and function.

SEQUENCE LISTING

```
Sequence total quantity: 43
SEQ ID NO: 1            moltype = AA  length = 513
FEATURE                 Location/Qualifiers
source                  1..513
                        mol_type = protein
                        organism = Homo sapiens
SEQUENCE: 1
MGAAAKLAFA VFLISCSSGA ILGRSETQEC LFFNANWEKD RTNQTGVEPC YGDKDKRRHC  60
FATWKNISGS IEIVKQGCWL DDINCYDRTD CVEKKDSPEV YFCCCEGNMC NEKFSYFPEM  120
EVTQPTSNPV TPKPPYYNIL LYSLVPLMLI AGIVICAFWV YRHHKMAYPP VLVPTQDPGP  180
PPPSPLLGLK PLQLLEVKAR GRFGCVWKAQ LLNEYVAVKI FPIQDKQSWQ NEYEVYSLPG  240
MKHENILQFI GAEKRGTSVD VDLWLITAFH EKGSLSDFLK ANVVSWNELC HIAETMARGL  300
AYLHEDIPGL KDGHKPAISH RDIKSKNVLL KNNLTACIAD FGLALKFEAG KSAGDTHGQV  360
GTRRYMAPEV LEGAINFQRD AFLRIDMYAM GLVLWELASR CTAADGPVDE YMLPFEEEIG  420
QHPSLEDMQE VVVHKKKRPV LRDYWQKHAG MAMLCETIEE CWDHDAEARL SAGCVGERIT  480
QMQRLTNIIT TEDIVTVVTM VTNVDFPPKE SSL                                513

SEQ ID NO: 2            moltype = AA  length = 115
FEATURE                 Location/Qualifiers
source                  1..115
                        mol_type = protein
                        organism = Homo sapiens
SEQUENCE: 2
ILGRSETQEC LFFNANWEKD RTNQTGVEPC YGDKDKRRHC FATWKNISGS IEIVKQGCWL  60
DDINCYDRTD CVEKKDSPEV YFCCCEGNMC NEKFSYFPEM EVTQPTSNPV TPKPP        115
```

-continued

```
SEQ ID NO: 3            moltype = AA  length = 100
FEATURE                 Location/Qualifiers
REGION                  1..100
                        note = Description of Artificial Sequence: Synthetic
                         polypeptide
source                  1..100
                        mol_type = protein
                        organism = synthetic construct
SEQUENCE: 3
ILGRSETQEC LFFNANWEKD RTNQTGVEPC YGDKDKRRHC FATWKNISGS IEIVKQGCWL  60
DDINCYDRTD CVEKKDSPEV YFCCCEGNMC NEKFSYFPEM                        100

SEQ ID NO: 4            moltype = DNA  length = 1539
FEATURE                 Location/Qualifiers
source                  1..1539
                        mol_type = unassigned DNA
                        organism = Homo sapiens
SEQUENCE: 4
atgggagctg ctgcaaagtt ggcgtttgcc gtctttctta tctcctgttc ttcaggtgct  60
atacttggta gatcagaaac tcaggagtgt cttttcttta atgctaattg ggaaaaagac  120
agaaccaatc aaactggtgt tgaaccgtgt tatggtgaca aagataaacg gcggcattgt  180
tttgctacct ggaagaatat ttctggttcc attgaaatag tgaaacaagg ttgttggctg  240
gatgatatca actgctatga caggactgat tgtgtagaaa aaaaagacag ccctgaagta  300
tatttttgtt gctgtgaggg caatatgtgt aatgaaaagt tttcttattt tccggagatg  360
gaagtcacac agcccacttc aaatccagtt acacctaagc caccctatta caacatcctg  420
ctctattcct tggtgccact tatgttaatt gcggggattg tcatttgtgc attttgggtg  480
tacaggcatc acaagatggc ctaccctcct gtacttgttc caactcaaga cccaggacca  540
cccccacctt ctccattact aggtttgaaa ccactgcagt tattagaagt gaaagcaagg  600
ggaagatttg gttgtgtctg gaaagcccag ttgcttaacg aatatgtggc tgtcaaaata  660
tttccaatac aggacaaaca gtcatggcaa aatgaatacg aagtctacag tttgcctgga  720
atgaagcatg agaacatatt acagttcatt ggtgcagaaa aacgaggcac cagtgttgat  780
gtggatcttt ggctgatcac agcatttcat gaaaagggtt cactatcaga ctttcttaag  840
gctaatgtgg tctcttggaa tgaactgtgt catattgcag aaaccatggc tagaggattg  900
gcatatttac atgaggatat acctggccta aaagatggcc acaaacctgc catatctcac  960
agggacatca aaagtaaaaa tgtgctgttg aaaaacaacc tgacagcttg cattgctgac  1020
tttgggttgg ccttaaaatt tgaggctggc aagtctgcag gcgataccca tggacaggtt  1080
ggtacccgga ggtacatggc tccagaggta ttagagggtg ctataaactt ccaaagggat  1140
gcatttttga ggatagatat gtatgccatg ggattagtcc tatgggaact ggcttctcgc  1200
tgtactgctg cagatggacc tgtagatgaa tacatgttgc catttgagga ggaaattggc  1260
cagcatccat ctcttgaaga catgcaggaa gttgttgtgc ataaaaaaaa gaggcctgtt  1320
ttaagagatt attggcagaa acatgctgga atggcaatgc tctgtgaaac cattgaagaa  1380
tgttgggatc acgacgcaga agccaggtta tcagctggat gtgtaggtga aagaattacc  1440
cagatgcaga gactaacaaa tattattacc acagaggaca ttgtaacagt ggtcacaatg  1500
gtgacaaatg ttgactttcc tcccaaagaa tctagtcta                         1539

SEQ ID NO: 5            moltype = DNA  length = 345
FEATURE                 Location/Qualifiers
source                  1..345
                        mol_type = unassigned DNA
                        organism = Homo sapiens
SEQUENCE: 5
atacttggta gatcagaaac tcaggagtgt cttttcttta atgctaattg ggaaaaagac  60
agaaccaatc aaactggtgt tgaaccgtgt tatggtgaca aagataaacg gcggcattgt  120
tttgctacct ggaagaatat ttctggttcc attgaaatag tgaaacaagg ttgttggctg  180
gatgatatca actgctatga caggactgat tgtgtagaaa aaaaagacag ccctgaagta  240
tatttttgtt gctgtgaggg caatatgtgt aatgaaaagt tttcttattt tccggagatg  300
gaagtcacac agcccacttc aaatccagtt acacctaagc caccc                  345

SEQ ID NO: 6            moltype = AA  length = 115
FEATURE                 Location/Qualifiers
source                  1..115
                        mol_type = protein
                        organism = Homo sapiens
SEQUENCE: 6
ILGRSETQEC LFFNANWEKD RTNQTGVEPC YGDKDKRRHC FATWKNISGS IEIVKQGCWL  60
DDINCYDRTD CVEKKDSPEV YFCCCEGNMC NEKFSYFPEM EVTQPTSNPV TPKPP       115

SEQ ID NO: 7            moltype = AA  length = 115
FEATURE                 Location/Qualifiers
source                  1..115
                        mol_type = protein
                        organism = Ovis aries
SEQUENCE: 7
ILGRSETQEC IFYNANWERD RTNRTGVESC YGDKDKRRHC FATWKNISGS IEIVKQGCWL  60
DDINCYDRTD CIEKKDSPEV YFCCCEGNMC NERFSYFPEM EVTQPTSNPV TPKPP       115

SEQ ID NO: 8            moltype = AA  length = 115
FEATURE                 Location/Qualifiers
REGION                  1..115
```

-continued

```
                        note = Description of Unknown: Mole ActRIIA sequence
source                  1..115
                        mol_type = protein
                        organism = unidentified
SEQUENCE: 8
ILGRSETQEC LFFNANWERD RTNQTGVEPC YGDKDKRRHC FATWKNISGS IEIVKQGCWL  60
DDINCYDRTD CIEKKDSPEV YFCCCEGNMC NEKFSYFPEM EVTQPTSNPV TPKAP       115

SEQ ID NO: 9            moltype = AA  length = 115
FEATURE                 Location/Qualifiers
source                  1..115
                        mol_type = protein
                        organism = Mus sp.
SEQUENCE: 9
ILGRSETQEC LFFNANWERD RTNQTGVEPC YGDKDKRRHC FATWKNISGS IEIVKQGCWL  60
DDINCYDRTD CIEKKDSPEV YFCCCEGNMC NEKFSYFPEM EVTQPTSNPV TPKPP       115

SEQ ID NO: 10           moltype = AA  length = 115
FEATURE                 Location/Qualifiers
source                  1..115
                        mol_type = protein
                        organism = Gallus gallus
SEQUENCE: 10
ILGRSETQEC IYYNANWEKD KTNRSGIEPC YGDKDKRRHC FATWKNISGS IEIVKQGCWL  60
DDINCYDRND CIEKKDSPEV FFCCCEGNMC NERFFYFPEM EVTQPTSNPV TPKPP       115

SEQ ID NO: 11           moltype = AA  length = 225
FEATURE                 Location/Qualifiers
source                  1..225
                        mol_type = protein
                        organism = Homo sapiens
SEQUENCE: 11
THTCPPCPAP ELLGGPSVFL FPPKPKDTLM ISRTPEVTCV VVDVSHEDPE VKFNWYVDGV  60
EVHNAKTKPR EEQYNSTYRV VSVLTVLHQD WLNGKEYKCK VSNKALPAPI EKTISKAKGQ  120
PREPQVYTLP PSREEMTKNQ VSLTCLVKGF YPSDIAVEWE SNGQPENNYK TTPPVLDSDG  180
SFFLYSKLTV DKSRWQQGNV FSCSVMHEAL HNHYTQKSLS LSPGK                  225

SEQ ID NO: 12           moltype = AA  length = 223
FEATURE                 Location/Qualifiers
source                  1..223
                        mol_type = protein
                        organism = Homo sapiens
SEQUENCE: 12
VECPPCPAPP VAGPSVFLFP PKPKDTLMIS RTPEVTCVVV DVSHEDPEVQ FNWYVDGVEV  60
HNAKTKPREE QFNSTFRVVS VLTVVHQDWL NGKEYKCKVS NKGLPAPIEK TISKTKGQPR  120
EPQVYTLPPS REEMTKNQVS LTCLVKGFYP SDIAVEWESN GQPENNYKTT PPMLDSDGSF  180
FLYSKLTVDK SRWQQGNVFS CSVMHEALHN HYTQKSLSLS PGK                    223

SEQ ID NO: 13           moltype = AA  length = 232
FEATURE                 Location/Qualifiers
source                  1..232
                        mol_type = protein
                        organism = Homo sapiens
SEQUENCE: 13
EPKSCDTPPP CPRCPAPELL GGPSVFLFPP KPKDTLMISR TPEVTCVVVD VSHEDPEVQF  60
KWYVDGVEVH NAKTKPREEQ YNSTFRVVSV LTVLHQDWLN GKEYKCKVSN KALPAPIEKT  120
ISKTKGQPRE PQVYTLPPSR EEMTKNQVSL TCLVKGFYPS DIAVEWESSG QPENNYNTTP  180
PMLDSDGSFF LYSKLTVDKS RWQQGNIFSC SVMHEALHNR FTQKSLSLSP GK          232

SEQ ID NO: 14           moltype = AA  length = 279
FEATURE                 Location/Qualifiers
source                  1..279
                        mol_type = protein
                        organism = Homo sapiens
SEQUENCE: 14
ELKTPLGDTT HTCPRCPEPK SCDTPPPCPR CPEPKSCDTP PPCPRCPEPK SCDTPPPCPR  60
CPAPELLGGP SVFLFPPKPK DTLMISRTPE VTCVVVDVSH EDPEVQFKWY VDGVEVHNAK  120
TKPREEQYNS TFRVVSVLTV LHQDWLNGKE YKCKVSNKAL PAPIEKTISK TKGQPREPQV  180
YTLPPSREEM TKNQVSLTCL VKGFYPSDIA VEWESSGQPE NNYNTTPPML DSDGSFFLYS  240
KLTVDKSRWQ QGNIFSCSVM HEALHNRFTQ KSLSLSPGK                        279

SEQ ID NO: 15           moltype = AA  length = 229
FEATURE                 Location/Qualifiers
source                  1..229
                        mol_type = protein
                        organism = Homo sapiens
SEQUENCE: 15
ESKYGPPCPS CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
```

-continued

```
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGK              229

SEQ ID NO: 16          moltype =   length =
SEQUENCE: 16
000

SEQ ID NO: 17          moltype = AA  length = 4
FEATURE                Location/Qualifiers
REGION                 1..4
                       note = Description of Artificial Sequence: Synthetic peptide
source                 1..4
                       mol_type = protein
                       organism = synthetic construct
SEQUENCE: 17
GGGG                                                                4

SEQ ID NO: 18          moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 18
TGGGG                                                               5

SEQ ID NO: 19          moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 19
SGGGG                                                               5

SEQ ID NO: 20          moltype = AA  length = 4
FEATURE                Location/Qualifiers
REGION                 1..4
                       note = Description of Artificial Sequence: Synthetic peptide
source                 1..4
                       mol_type = protein
                       organism = synthetic construct
SEQUENCE: 20
TGGG                                                                4

SEQ ID NO: 21          moltype = AA  length = 4
FEATURE                Location/Qualifiers
REGION                 1..4
                       note = Description of Artificial Sequence: Synthetic peptide
source                 1..4
                       mol_type = protein
                       organism = synthetic construct
SEQUENCE: 21
SGGG                                                                4

SEQ ID NO: 22          moltype = AA  length = 5
FEATURE                Location/Qualifiers
REGION                 1..5
                       note = Description of Artificial Sequence: Synthetic peptide
source                 1..5
                       mol_type = protein
                       organism = synthetic construct
SEQUENCE: 22
GGGGS                                                               5

SEQ ID NO: 23          moltype = AA  length = 344
FEATURE                Location/Qualifiers
REGION                 1..344
                       note = Description of Artificial Sequence: Synthetic
                        polypeptide
source                 1..344
                       mol_type = protein
                       organism = synthetic construct
SEQUENCE: 23
ILGRSETQEC LFFNANWEKD RTNQTGVEPC YGDKDKRRHC FATWKNISGS IEIVKQGCWL  60
DDINCYDRTD CVEKKDSPEV YFCCCEGNMC NEKFSYFPEM EVTQPTSNPV TPKPPTGGGT  120
HTCPPCPAPE LLGGPSVFLF PPKPKDTLMI SRTPEVTCVV VDVSHEDPEV KFNWYVDGVE  180
```

-continued

```
VHNAKTKPRE EQYNSTYRVV SVLTVLHQDW LNGKEYKCKV SNKALPVPIE KTISKAKGQP  240
REPQVYTLPP SREEMTKNQV SLTCLVKGFY PSDIAVEWES NGQPENNYKT TPPVLDSDGS  300
FFLYSKLTVD KSRWQQGNVF SCSVMHEALH NHYTQKSLSL SPGK                   344

SEQ ID NO: 24          moltype = AA  length = 21
FEATURE                Location/Qualifiers
source                 1..21
                       mol_type = protein
                       organism = Apis sp.
SEQUENCE: 24
MKFLVNVALV FMVVYISYIY A                                            21

SEQ ID NO: 25          moltype = AA  length = 22
FEATURE                Location/Qualifiers
REGION                 1..22
                       note = Description of Unknown: TPA leader sequence
source                 1..22
                       mol_type = protein
                       organism = unidentified
SEQUENCE: 25
MDAMKRGLCC VLLLCGAVFV SP                                           22

SEQ ID NO: 26          moltype = AA  length = 20
FEATURE                Location/Qualifiers
REGION                 1..20
                       note = Description of Unknown: Activin receptor type 2A
                        leader sequence
source                 1..20
                       mol_type = protein
                       organism = unidentified
SEQUENCE: 26
MGAAAKLAFA VFLISCSSGA                                              20

SEQ ID NO: 27          moltype = AA  length = 369
FEATURE                Location/Qualifiers
REGION                 1..369
                       note = Description of Artificial Sequence: Synthetic
                        polypeptide
source                 1..369
                       mol_type = protein
                       organism = synthetic construct
SEQUENCE: 27
MDAMKRGLCC VLLLCGAVFV SPGAAILGRS ETQECLFFNA NWEKDRTNQT GVEPCYGDKD  60
KRRHCFATWK NISGSIEIVK QGCWLDDINC YDRTDCVEKK DSPEVYFCCC EGNMCNEKFS  120
YFPEMEVTQP TSNPVTPKPP TGGGTHTCPP CPAPELLGGP SVFLFPPKPK DTLMISRTPE  180
VTCVVVDVSH EDPEVKFNWY VDGVEVHNAK TKPREEQYNS TYRVVSVLTV LHQDWLNGKE  240
YKCKVSNKAL PVPIEKTISK AKGQPREPQV YTLPPSREEM TKNQVSLTCL VKGFYPSDIA  300
VEWESNGQPE NNYKTTPPVL DSDGSFFLYS KLTVDKSRWQ QGNVFSCSVM HEALHNHYTQ  360
KSLSLSPGK                                                          369

SEQ ID NO: 28          moltype = DNA  length = 1114
FEATURE                Location/Qualifiers
misc_feature           1..1114
                       note = Description of Artificial Sequence: Synthetic
                        polynucleotide
source                 1..1114
                       mol_type = other DNA
                       organism = synthetic construct
SEQUENCE: 28
atggatgcaa tgaagagagg gctctgctgt gtgctgctgc tgtgtggagc agtcttcgtt  60
tcgcccggcg ccgctatact tggtagatca gaaactcagg agtgtctttt tttaatgcta  120
attgggaaaa agacagaacc aatcaaactg gtgttgaacc gtgttatggt gacaaagata  180
aacggcggca ttgttttgct acctggaaga atatttctgg ttccattgaa tagtgaaaca  240
aggttgttgg ctggatgata tcaactgcta tgacaggact gattgtgtag aaaaaaaaga  300
cagccctgaa gtatatttct gttgctgtga gggcaatatg tgtaatgaaa agttttctta  360
ttttccggag atggaagtca cacagcccac ttcaaatcca gttacaccta agccacccac  420
cggtggtgga actcacacat gcccaccgtg cccagcacct gaactcctgg ggggaccgtc  480
agtcttcctc ttccccccaa aacccaagga caccctcatg atctcccgga cccctgaggt  540
cacatgcgtg gtggtggacg tgagccacga agaccctgag gtcaagttca actggtacgt  600
ggacggcgtg gaggtgcata atgccaagac aaagccgcgg gaggagcagt acaacagcac  660
gtaccgtgtg gtcagcgtcc tcaccgtcct gcaccaggac tggctgaatg gcaaggagta  720
caagtgcaag gtctccaaca aagccctccc agtccccatc gagaaaacca tctccaaagc  780
caaagggcag ccccgagaac cacaggtgta caccctgccc ccatcccggg aggagatgac  840
caagaaccag gtcagcctga cctgcctggt caaaggcttc tatcccagcg acatcgccgt  900
ggagtgggag agcaatgggc agccggagaa caactacaag accacgcctc ccgtgctgga  960
ctccgacggc tccttcttcc tctatagcaa gctcaccgtg gacaagagca ggtggcagca  1020
ggggaacgtc ttctcatgct ccgtgatgca tgaggctctg cacaaccact acacgcagaa  1080
gagcctctcc ctgtctccgg gtaaatgaga attc                              1114
```

-continued

```
SEQ ID NO: 29          moltype = AA  length = 9
FEATURE                Location/Qualifiers
REGION                 1..9
                       note = Description of Artificial Sequence: Synthetic peptide
source                 1..9
                       mol_type = protein
                       organism = synthetic construct
SEQUENCE: 29
ILGRSETQE                                                         9

SEQ ID NO: 30          moltype = AA  length = 329
FEATURE                Location/Qualifiers
REGION                 1..329
                       note = Description of Artificial Sequence: Synthetic
                        polypeptide
source                 1..329
                       mol_type = protein
                       organism = synthetic construct
SEQUENCE: 30
ILGRSETQEC LFFNANWEKD RTNQTGVEPC YGDKDKRRHC FATWKNISGS IEIVKQGCWL  60
DDINCYDRTD CVEKKDSPEV YFCCCEGNMC NEKFSYFPEM TGGGTHTCPP CPAPELLGGP  120
SVFLFPPKPK DTLMISRTPE VTCVVVDVSH EDPEVKFNWY VDGVEVHNAK TKPREEQYNS  180
TYRVVSVLTV LHQDWLNGKE YKCKVSNKAL PVPIEKTISK AKGQPREPQV YTLPPSREEM  240
TKNQVSLTCL VKGFYPSDIA VEWESNGQPE NNYKTTPPVL DSDGSFFLYS KLTVDKSRWQ  300
QGNVFSCSVM HEALHNHYTQ KSLSLSPGK                                   329

SEQ ID NO: 31          moltype = AA  length = 115
FEATURE                Location/Qualifiers
source                 1..115
                       mol_type = protein
                       organism = Homo sapiens
SEQUENCE: 31
GRGEAETREC IYYNANWELE RTNQSGLERC EGEQDKRLHC YASWRNSSGT IELVKKGCWL  60
DDFNCYDRQE CVATEENPQV YFCCCEGNFC NERFTHLPEA GGPEVTYEPP PTAPT       115

SEQ ID NO: 32          moltype = AA  length = 225
FEATURE                Location/Qualifiers
source                 1..225
                       mol_type = protein
                       organism = Homo sapiens
SEQUENCE: 32
THTCPPCPAP ELLGGPSVFL FPPKPKDTLM ISRTPEVTCV VVDVSHEDPE VKFNWYVDGV  60
EVHNAKTKPR EEQYNSTYRV VSVLTVLHQD WLNGKEYKCK VSNKALPAPI EKTISKAKGQ  120
PREPQVYTLP PSREEMTKNQ VSLTCLVKGF YPSDIAVEWE SNGQPENNYK TTPPVLDSDG  180
SFFLYSKLTV DKSRWQQGNV FSCSVMHEAL HNHYTQKSLS LSPGK                 225

SEQ ID NO: 33          moltype = AA  length = 223
FEATURE                Location/Qualifiers
source                 1..223
                       mol_type = protein
                       organism = Homo sapiens
SEQUENCE: 33
VECPPCPAPP VAGPSVFLFP PKPKDTLMIS RTPEVTCVVV DVSHEDPEVQ FNWYVDGVEV  60
HNAKTKPREE QFNSTFRVVS VLTVVHQDWL NGKEYKCKVS NKGLPAPIEK TISKTKGQPR  120
EPQVYTLPPS REEMTKNQVS LTCLVKGFYP SDIAVEWESN GQPENNYKTT PPMLDSDGSF  180
FLYSKLTVDK SRWQQGNVFS CSVMHEALHN HYTQKSLSLS PGK                   223

SEQ ID NO: 34          moltype = AA  length = 232
FEATURE                Location/Qualifiers
source                 1..232
                       mol_type = protein
                       organism = Homo sapiens
SEQUENCE: 34
EPKSCDTPPP CPRCPAPELL GGPSVFLFPP KPKDTLMISR TPEVTCVVVD VSHEDPEVQF  60
KWYVDGVEVH NAKTKPREEQ YNSTFRVVSV LTVLHQDWLN GKEYKCKVSN KALPAPIEKT  120
ISKTKGQPRE PQVYTLPPSR EEMTKNQVSL TCLVKGFYPS DIAVEWESSG QPENNYNTTP  180
PMLDSDGSFF LYSKLTVDKS RWQQGNIFSC SVMHEALHNR FTQKSLSLSP GK         232

SEQ ID NO: 35          moltype = AA  length = 229
FEATURE                Location/Qualifiers
source                 1..229
                       mol_type = protein
                       organism = Homo sapiens
SEQUENCE: 35
ESKYGPPCPS CPAPEFLGGP SVFLFPPKPK DTLMISRTPE VTCVVVDVSQ EDPEVQFNWY  60
VDGVEVHNAK TKPREEQFNS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGK              229
```

-continued

```
SEQ ID NO: 36          moltype = AA  length = 115
FEATURE                Location/Qualifiers
source                 1..115
                       mol_type = protein
                       organism = Bos taurus
SEQUENCE: 36
ILGRSETQEC IFYNANWERD RTNRTGVESC YGDKDKRRHC FATWKNISGS IEIVKQGCWL  60
DDINCYDRTD CIEKKDSPEV YFCCCEGNMC NERFSYFPEM EVTQPTSNPV TPKPP       115

SEQ ID NO: 37          moltype = AA  length = 115
FEATURE                Location/Qualifiers
source                 1..115
                       mol_type = protein
                       organism = Tyto alba
SEQUENCE: 37
ILGRSETQEC IYYNANWEKD KTNRSGIEPC YGDKDKRRHC FATWKNISGS IEIVKQGCWL  60
DDINCYDRND CIEKKDSPEV FFCCCEGNMC NERFFYFPEM EVTQPTSNPV TPKPP       115

SEQ ID NO: 38          moltype = AA  length = 115
FEATURE                Location/Qualifiers
source                 1..115
                       mol_type = protein
                       organism = Myotis davidii
SEQUENCE: 38
ILGRSETQEC IFYNANWERD KTNRTGVELC YGDKDKRRHC FATWKNISGS IEIVKQGCWL  60
DDINCYDRTD CIEKKDSPEV YFCCCEGNMC NERFSYFPEM EVTQPTSNPV TPKPP       115

SEQ ID NO: 39          moltype = AA  length = 512
FEATURE                Location/Qualifiers
source                 1..512
                       mol_type = protein
                       organism = Homo sapiens
SEQUENCE: 39
MTAPWVALAL LWGSLCAGSG RGEAETRECI YYNANWELER TNQSGLERCE GEQDKRLHCY  60
ASWRNSSGTI ELVKKGCWLD DFNCYDRQEC VATEENPQVY FCCCEGNFCN ERFTHLPEAG  120
GPEVTYEPPP TAPTLLTVLA YSLLPIGGLS LIVLLAFWMY RHRKPPYGHV DIHEDPGPPP  180
PSPLVGLKPL QLLEIKARGR FGCVWKAQLM NDFVAVKIFP LQDKQSWQSE REIFSTPGMK  240
HENLLQFIAA EKRGSNLEVE LWLITAFHDK GSLTDYLKGN IITWNELCHV AETMSRGLSY  300
LHEDVPWCRG EGHKPSIAHR DFKSKNVLLK SDLTAVLADF GLAVRFEPGK PPGDTHGQVG  360
TRRYMAPEVL EGAINFQRDA FLRIDMYAMG LVLWELVSRC KAADGPVDEY MLPFEEEIGQ  420
HPSLEELQEV VVHKKMRPTI KDHWLKHPGL AQLCVTIEEC WDHDAEARLS AGCVEERVSL  480
IRRSVNGTTS DCLVSLVTSV TNVDLPPKES SI                                512

SEQ ID NO: 40          moltype = AA  length = 100
FEATURE                Location/Qualifiers
REGION                 1..100
                       note = Description of Artificial Sequence: Synthetic
                        polypeptide
source                 1..100
                       mol_type = protein
                       organism = synthetic construct
SEQUENCE: 40
GRGEAETREC IYYNANWELE RTNQSGLERC EGEQDKRLHC YASWRNSSGT IELVKKGCWL  60
DDFNCYDRQE CVATEENPQV YFCCCEGNFC NERFTHLPEA                        100

SEQ ID NO: 41          moltype = AA  length = 343
FEATURE                Location/Qualifiers
REGION                 1..343
                       note = Description of Artificial Sequence: Synthetic
                        polypeptide
source                 1..343
                       mol_type = protein
                       organism = synthetic construct
SEQUENCE: 41
ILGRSETQEC LFFNANWEKD RTNQTGVEPC YGDKDKRRHC FATWKNISGS IEIVKQGCWL  60
DDINCYDRTD CVEKKDSPEV YFCCCEGNMC NEKFSYFPEM EVTQPTSNPV TPKPPTGGGT  120
HTCPPCPAPE LLGGPSVFLF PPKPKDTLMI SRTPEVTCVV VDVSHEDPEV KFNWYVDGVE  180
VHNAKTKPRE EQYNSTYRVV SVLTVLHQDW LNGKEYKCKV SNKALPVPIE KTISKAKGQP  240
REPQVYTLPP SREEMTKNQV SLTCLVKGFY PSDIAVEWES NGQPENNYKT TPPVLDSDGS  300
FFLYSKLTVD KSRWQQGNVF SCSVMHEALH NHYTQKSLSL SPG                    343

SEQ ID NO: 42          moltype = AA  length = 116
FEATURE                Location/Qualifiers
source                 1..116
                       mol_type = protein
                       organism = Homo sapiens
SEQUENCE: 42
ILGRSETQEC LFFNANWEKD RTNQTGVEPC YGDKDKRRHC FATWKNISGS IEIVKQGCWL  60
DDINCYDRTD CVEKKDSPEV YFCCCEGNMC NEKFSYFPEM EVTQPTSNPV TPKPPT      116
```

-continued

```
SEQ ID NO: 43            moltype = AA  length = 6
FEATURE                  Location/Qualifiers
REGION                   1..6
                         note = Description of Artificial Sequence: Synthetic 6xHis
                          tag
source                   1..6
                         mol_type = protein
                         organism = synthetic construct
SEQUENCE: 43
HHHHHH                                                                6
```

We claim:

1. A method of treating combined pre- and postcapillary pulmonary hypertension (Cpc-PH) due to heart failure with preserved ejection fraction (HFpEF) in a apatient, comprising administering to the patient an effective amount of a fusion protein comprising:

(i) an ActRII polypeptide comprising the amino acid sequence of SEQ ID NO: 2;

(ii) an Fc domain comprising an amino acid sequence that is at least 95% identical to the amino acid sequence of SEQ ID NO: 32; and (iii) a linker domain positioned between the ActRII polypeptide and the Fc domain.

2. The method of claim 1, wherein the patient has a pulmonary vascular resistance (PVR) greater than 2 Woods Units.

3. The method of claim 1, wherein the Fc domain comprises an amino acid sequence that is at least 99% identical to the amino acid sequence of SEQ ID NO: 32.

4. The method of claim 3, wherein the Fc domain comprises the amino acid sequence of SEQ ID NO: 32.

5. The method of claim 3, wherein the linker domain is selected from the group consisting of: TGGG (SEQ ID NO: 20), TGGGG (SEQ ID NO: 18), SGGGG (SEQ ID NO: 19), GGGGS (SEQ ID NO: 22), GGGG (SEQ ID NO: 17), and SGGG (SEQ ID NO: 21).

6. The method of claim 5, wherein the linker domain comprises SEQ ID NO: 20.

7. The method of claim 1, wherein the fusion protein comprises an amino acid sequence that is at least 95% identical to the amino acid sequence of SEQ ID NOs: 23 or 41.

8. The method of claim 7, wherein the fusion protein comprises an amino acid sequence that is at least 99% identical to the amino acid sequence of SEQ ID NO: 23.

9. The method of claim 8, wherein the fusion protein comprises the amino acid sequence of SEQ ID NO: 23.

10. The method of claim 7, wherein the fusion protein comprises an amino acid sequence that is at least 99% identical to the amino acid sequence of SEQ ID NO: 41.

11. The method of claim 10, wherein the fusion protein comprises the amino acid sequence of SEQ ID NO: 41.

12. The method of claim 1, wherein the patient has Group 2 pulmonary hypertension as recognized by the World Health Organization (WHO).

13. The method of claim 1, wherein the patient has a pulmonary vascular resistance (PVR) greater than or equal to 3 Wood Units.

14. The method of claim 13 wherein the method reduces the PVR in the patient.

15. The method of claim 14, wherein the method reduces the PVR in the patient by at least 10%.

16. The method of claim 1, wherein the patient has preserved left ventricular ejection fraction.

17. The method of claim 16, wherein the preserved left ventricular ejection fraction is greater than 45%.

18. The method of claim 1, wherein the method increases the patient's 6-minute walk distance.

19. The method of claim 18, wherein the method increases the patient's 6-minute walk distance by at least 10 meters.

20. The method of claim 1, wherein the method delays clinical worsening of post-capillary pulmonary hypertension (PcPH).

21. The method of claim 20, wherein the method delays clinical worsening of PcPH in accordance with the World Health Organization's functional classification system for pulmonary hypertension.

22. The method of claim 21, wherein the method delays clinical worsening of PcPH in accordance with the New York Heart Association's functional classification system for pulmonary hypertension.

* * * * *